US012454518B2

(12) United States Patent
Fischer et al.

(10) Patent No.: US 12,454,518 B2
(45) Date of Patent: Oct. 28, 2025

(54) SUBSTITUTED N-(2-(2,6-DIOXOPIPERIDIN-3-YL)-1,3-DIOXOISOINDOLIN-5-YL) ARYLSULFONAMIDE ANALOGS AS MODULATORS OF CEREBLON PROTEIN

(71) Applicant: ST. JUDE CHILDREN'S RESEARCH HOSPITAL, INC., Memphis, TN (US)

(72) Inventors: Marcus Fischer, Memphis, TN (US); Fatemeh Keramatnia, Memphis, TN (US); Kevin Mcgowan, Memphis, TN (US); Jaeki Min, Memphis, TN (US); Gisele A. Nishiguchi, Memphis, TN (US); Jeanine Price, Memphis, TN (US); Zoran Rankovic, Memphis, TN (US); Sourav Das, Memphis, TN (US); Charles G. Mullighan, Memphis, TN (US); Yunchao Chang, Memphis, TN (US)

(73) Assignee: St. Jude Children's Research Hospital, Inc., Memphis, TN (US)

( * ) Notice: Subject to any disclaimer, the term of this patent is extended or adjusted under 35 U.S.C. 154(b) by 0 days.

(21) Appl. No.: 17/740,148

(22) Filed: May 9, 2022

(65) Prior Publication Data

US 2022/0274948 A1 Sep. 1, 2022

Related U.S. Application Data

(63) Continuation of application No. PCT/US2021/051648, filed on Sep. 23, 2021.

(60) Provisional application No. 63/082,365, filed on Sep. 23, 2020.

(51) Int. Cl.

| | |
|---|---|
| ***C07D 401/04*** | (2006.01) |
| ***A61K 31/45*** | (2006.01) |
| ***A61K 45/06*** | (2006.01) |
| ***A61P 35/00*** | (2006.01) |
| ***A61P 35/02*** | (2006.01) |
| ***C07D 405/14*** | (2006.01) |
| ***C07D 409/14*** | (2006.01) |
| ***C07D 413/14*** | (2006.01) |

(52) U.S. Cl.

CPC ............ *C07D 401/04* (2013.01); *A61K 31/45* (2013.01); *A61K 45/06* (2013.01); *A61P 35/00* (2018.01); *A61P 35/02* (2018.01); *C07D 405/14* (2013.01); *C07D 409/14* (2013.01); *C07D 413/14* (2013.01)

(58) Field of Classification Search

CPC .. C07D 401/04; C07D 405/14; C07D 409/14; C07D 413/14; A61P 35/00; A61P 35/02; A61K 31/45

See application file for complete search history.

(56) References Cited

U.S. PATENT DOCUMENTS

| | | | |
|---|---|---|---|
| 7,576,104 | B2 | 8/2009 | Robarge et al. |
| 8,481,568 | B2 | 7/2013 | Muller et al. |
| 9,801,868 | B2 | 10/2017 | Muller et al. |
| 11,021,457 | B2 | 6/2021 | Yao et al. |
| 11,311,609 | B2 | 4/2022 | Bradner et al. |
| 2003/0045552 | A1 | 3/2003 | Robarge et al. |
| 2005/0222124 | A1 | 10/2005 | Bromidge et al. |
| 2009/0286986 | A1 | 11/2009 | Robarge et al. |
| 2013/0079306 | A1 | 3/2013 | Uchida et al. |
| 2014/0314752 | A1 | 10/2014 | Lopez-Girona et al. |
| 2015/0005303 | A1 | 1/2015 | Muller et al. |
| 2017/0088538 | A1 | 3/2017 | Muller et al. |
| 2018/0099940 | A1 | 4/2018 | Crew et al. |
| 2018/0179183 | A1 | 6/2018 | Crew et al. |
| 2018/0215731 | A1 | 8/2018 | Crew et al. |
| 2019/0021689 | A1 | 1/2019 | Hirose et al. |
| 2019/0062309 | A1 | 2/2019 | Beckwith et al. |
| 2019/0322647 | A1 | 10/2019 | Alexander et al. |
| 2019/0388429 | A1 | 12/2019 | Schafer et al. |
| 2020/0339704 | A1 | 10/2020 | Bradner et al. |
| 2023/0271966 | A1 | 8/2023 | Anderson et al. |

FOREIGN PATENT DOCUMENTS

| | | | |
|---|---|---|---|
| CN | 101578277 | A | 11/2009 |
| CN | 108929307 | A | 3/2020 |
| JP | 2001-507341 | A | 6/2001 |
| KR | 10-2009-0060314 | A | 6/2009 |

(Continued)

OTHER PUBLICATIONS

Golub et al., Science, vol. 286, Oct. 15, 1999, pp. 531-537.*

Hu, Shengquan, et al. "Design, synthesis and biological evaluation of Lenalidomide derivatives as tumor angiogenesis inhibitor", Bioorganic & medicinal chemistry letters, 27.17 (2017): 4075-4081.

Helm, et al. "On the correlation of cereblon binding, fluorination and antiangiogenic properties of irnrnunornodulatory drugs," Biochemical and Biophysical Research Communications 534 (2021), all enclosed pages cited.

Naccache, et al., "Patterns of Nonelectrolyte Permeability in Human Red Blood Cell Membrane," The Journal of General Physiology, vol. 62, 1973, all enclosed pages cited.

(Continued)

*Primary Examiner* — Sarah Pihonak

(74) *Attorney, Agent, or Firm* — Ballard Spahr LLP

(57) ABSTRACT

In one aspect, the disclosure relates to substituted N-(2-(2,6-dioxopiperidinyl-3-yl)-1,3-dioxoisoindolin-5-yl)arylsulfo namide analogs that useful as modulators of cereblon (CRBN) activity, methods of making same, pharmaceutical compositions comprising same, and methods of treating various clinical conditions and disorders using same, e.g., a disorder of uncontrolled cellular proliferation, such as a cancer, which may be associated with cereblon protein dysfunction and/or a GSPT1 dysfunction. In various further aspects, the disclosed compounds can selectively modulate the degradation of GSPT1 protein, i.e., the disclosed compounds can act as GSPT1 degraders. This abstract is intended as a scanning tool for purposes of searching in the particular art and is not intended to be limiting of the present disclosure.

29 Claims, 8 Drawing Sheets

Specification includes a Sequence Listing.

(56) References Cited

FOREIGN PATENT DOCUMENTS

| | | | |
|---|---|---|---|
| KR | 20090060314 | A | 6/2009 |
| KR | 10-2018-0005174 | A | 1/2018 |
| KR | 10-2018-0095094 | A | 8/2018 |
| KR | 10-2019-0015300 | A | 2/2019 |
| KR | 10-2019-0044499 | A | 4/2019 |
| WO | 98/026773 | A1 | 6/1998 |
| WO | 1998/026773 | A1 | 6/1998 |
| WO | 2008/027542 | A2 | 3/2008 |
| WO | 2016007848 | | 7/2015 |
| WO | 2016/007848 | A1 | 1/2016 |
| WO | 2017120422 | | 1/2017 |
| WO | 2018071606 | | 10/2017 |
| WO | 2018071606 | A1 | 4/2018 |
| WO | 2019038717 | A1 | 2/2019 |
| WO | 2019148055 | A1 | 8/2019 |
| WO | 2020118098 | | 12/2019 |
| WO | 2020006262 | A1 | 1/2020 |
| WO | 2020014489 | A2 | 1/2020 |
| WO | 2020/118098 | A1 | 7/2020 |
| WO | 2022066734 | | 9/2021 |
| WO | 2022066880 | | 9/2021 |
| WO | 2022/066835 | A1 | 3/2022 |

OTHER PUBLICATIONS (Nishiguchi, G et al.) Identification of Potent, Selective, and Orally Bioavailable Small-Molecule GSPT1/2 Degraders from a Focused Library of Cereblon Modulators. Journal of Medicinal Chemistry. Jun. 10, 2021, Epub May 27, 2021, vol. 64, No. 11; pp. 7296-7311; DOI: 10.1021/acs.jmedchem.0c01313.

* cited by examiner

| Route | Dose (mg/Kg) | $T_{1/2}$ (h) | CL (mL/min/kg) | Vss (L/Kg) | %F |
|---|---|---|---|---|---|
| IV | 3 | 3.44 | 0.46 | 0.15 | - |
| PO | 10 | - | - | - | 84 |

SEQUENCE LISTING

<160> NUMBER OF SEQ ID NOS: 8

<210> SEQ ID NO 1
<211> LENGTH: 43
<212> TYPE: DNA
<213> ORGANISM: Homo sapiens

<400> SEQUENCE: 1
ttttgacacc agtctgccga catcacatac agtatgtaat tta 43

<210> SEQ ID NO 2
<211> LENGTH: 42
<212> TYPE: DNA
<213> ORGANISM: Homo sapiens

<400> SEQUENCE: 2
ttttgacacc agtctgcgac atcacataca gtatgtaatt ta 42

<210> SEQ ID NO 3
<211> LENGTH: 44
<212> TYPE: DNA
<213> ORGANISM: Homo sapiens

<400> SEQUENCE: 3
ttttgacacc agtcttgccg acatcacata cagtatgtaa ttta 44

<210> SEQ ID NO 4
<211> LENGTH: 42
<212> TYPE: DNA
<213> ORGANISM: Homo sapiens

<400> SEQUENCE: 4
ttttgacacc agtcgccgac atcacataca gtatgtaatt ta 42

<210> SEQ ID NO 5
<211> LENGTH: 42
<212> TYPE: DNA
<213> ORGANISM: Homo sapiens

<400> SEQUENCE: 5
ttttgacacc agctgccgac atcacataca gtatgtaatt ta 42

<210> SEQ ID NO 6
<211> LENGTH: 23
<212> TYPE: DNA
<213> ORGANISM: Homo sapiens

<400> SEQUENCE: 6
gcagagagtg aggaagaaga tga 23

<210> SEQ ID NO 7
<211> LENGTH: 20
<212> TYPE: DNA
<213> ORGANISM: Homo sapiens

<400> SEQUENCE: 7
gcccatgtcc tcatccacaa 20

-continued

<210> SEQ ID NO 8
<211> LENGTH: 20
<212> TYPE: RNA
<213> ORGANISM: Homo sapiens

<400> SEQUENCE: 8
uguaugugau gucggcagac 20

SUBSTITUTED N-(2-(2,6-DIOXOPIPERIDIN-3-YL)-1,3-DIOXOISOINDOLIN-5-YL) ARYLSULFONAMIDE ANALOGS AS MODULATORS OF CEREBLON PROTEIN

CROSS-REFERENCE TO RELATED APPLICATIONS

This Application is a Continuation of PCT Application No. PCT/US2021/051648, filed Sep. 23, 2021, where the PCT claims priority to, and the benefit of U.S. Provisional Application No. 63/082,365, filed on Sep. 23, 2020, both of which are incorporated herein by reference in their entireties.

REFERENCE TO A SEQUENCE LISTING SUBMITTED AS A TEXT FILE VIA EFS-WEB

The Sequence Listing submitted Nov. 4, 2021 as an Annex C/ST.25 text file named "2021-11-04_Sequence-_Listing_STJUDE-00005-U-PCT-01_ST25.txt," created on Nov. 4, 2021, and having a size 1,589 bytes is hereby incorporated by reference pursuant to 37 C.F.R. § 1.52(e)(5). The sequence listing filing does not go beyond the disclosure in the international application as originally filed.

BACKGROUND

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). A tremendous demand exists for new methods, treatments, and compositions that can be used to treat patients with cancer.

Protein degradation plays a role in various cellular functions, i.e. the concentrations of regulatory proteins are adjusted through degradation into small peptides to maintain health and productivity of the cells. Cereblon is a protein that forms an E3 ubiquitin ligase complex, which ubiquinates various other proteins. Specifically targeting protein degradation offers a tantalizing prospect of targeting currently undruggable oncoproteins such as transcription factors and chimeric fusion oncoproteins.

Despite advances in research directed to clinical amelioration of cancer, there is still a scarcity of compounds that are both potent, efficacious, and selective modulators of protein degradation, e.g., potent and selective modulation of cereblon. These needs and other needs are satisfied by the present disclosure.

SUMMARY

In accordance with the purpose(s) of the disclosure, as embodied and broadly described herein, the disclosure, in one aspect, relates to substituted N-(2-(2,6-dioxopiperidinyl-3-yl)-1,3-dioxoisoindolin-5-yl)arylsulfonamide analogs that useful as modulators of cereblon (CRBN) activity, methods of making same, pharmaceutical compositions comprising same, and methods of treating various clinical conditions and disorders using same, e.g., a disorder of uncontrolled cellular proliferation, such as a cancer, which may be associated with cereblon protein dysfunction. In various further aspects, the disclosed compounds can act to selectively modulate the degradation of GSPT1 protein, i.e., the disclosed compounds can act as GSPT1 degraders. In a further aspect, the disclosed compounds shown selectively for GSPT1 degradation over IKZF1 degradation by at least 5-fold.

Disclosed are compounds having a structure represented by a formula:

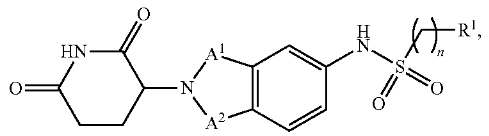

wherein n is an integer selected from 0, 1, and 2; wherein each of $A^1$ and $A^2$ is independently selected from —(C═O)— and —$CH_2$—, provided that at least one of $A^1$ and $A^2$ is —(C═O)—; wherein $R^1$ is selected from: (a) a 5- to 10-membered aryl or heteroaryl optionally substituted with a group selected from halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl; and (b) a 5- to 10-membered cycloalkyl optionally substituted with a group selected from halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl; or a pharmaceutically acceptable salt thereof.

Also disclosed are compounds having a structure represented by a formula:

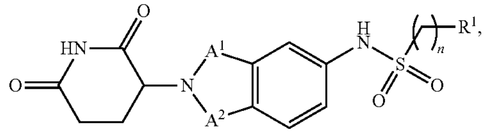

wherein n is an integer selected from 0, 1, and 2; wherein each of $A^1$ and $A^2$ is independently selected from —(C═O)— and —$CH_2$—, provided that at least one of $A^1$ and $A^2$ is —(C═O)—; wherein $R^1$ is selected from: (a) a 5- to 10-membered aryl or heteroaryl optionally substituted with a group selected from halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl; and (b) a 5- to 10-membered cycloalkyl optionally substituted with a group selected from halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl; or a pharmaceutically acceptable salt thereof; provided that the compound is not a compound having a structure:

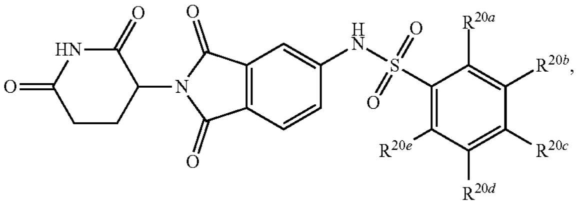

wherein $R^{20a}$ is selected from bromo, methyl, —$CF_3$, and —$OCF_3$; and wherein each of $R^{20b}$, $R^{20c}$, $R^{20d}$, and $R_{20e}$ is independently selected from hydrogen, halogen, and methyl; or a pharmaceutically acceptable salt thereof; and a compound having a structure represented by a formula:

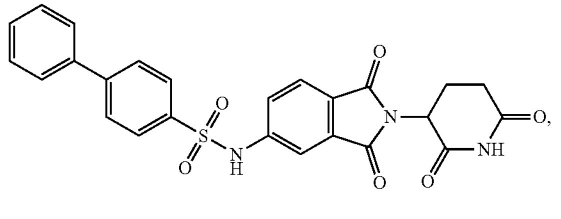 [SMILES: O=C1CCC(N2C(=O)c3ccc(NS(=O)(=O)c4ccc(-c5ccccc5)cc4)cc3C2=O)C(=O)N1]

or a pharmaceutically acceptable salt thereof.

Also disclosed are compounds having a structure represented by a formula:

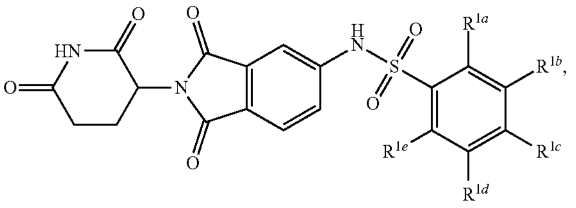

wherein $R^{1a}$ is selected from bromo, methyl, —$CF_3$, and —$OCF_3$; and wherein each of $R^{1b}$, $R^{1c}$, $R^{1d}$, and $R^{1e}$ is independently selected from hydrogen, halogen, and methyl; or a pharmaceutically acceptable salt thereof.

Also disclosed are compounds having a structure represented by a formula:

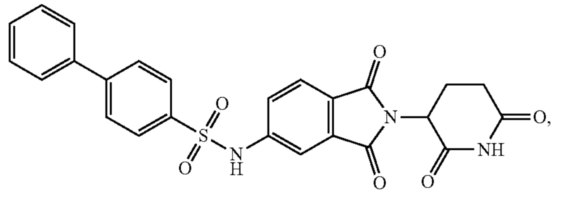 [SMILES: O=C1CCC(N2C(=O)c3ccc(NS(=O)(=O)c4ccc(-c5ccccc5)cc4)cc3C2=O)C(=O)N1]

or a pharmaceutically acceptable salt thereof.

Also disclosed are pharmaceutical compositions comprising a therapeutically effective amount of one or more disclosed compounds, or pharmaceutically acceptable salt thereof, and a pharmaceutically acceptable carrier.

Also disclosed are methods for the treatment of a disorder of uncontrolled cellular proliferation in a mammal comprising the step of administering to the mammal a therapeutically effective amount of at least one disclosed compound or pharmaceutically acceptable salt thereof, or at least one disclosed pharmaceutical composition.

Also disclosed are methods for modulating of cereblon activity in a mammal comprising the step of administering to the mammal a therapeutically effective amount of at least one disclosed compound or pharmaceutically acceptable salt thereof, or at least one disclosed pharmaceutical composition.

Also disclosed are methods for modulating of cereblon activity in at least one cell, comprising the step of contacting the at least one cell with an effective amount of at least one disclosed compound, or a pharmaceutically acceptable salt thereof; or at least one disclosed pharmaceutical composition.

Also disclosed are methods for modulating of GSPT1 activity in a mammal comprising the step of administering to the mammal a therapeutically effective amount of at least one disclosed compound or pharmaceutically acceptable salt thereof, or at least one disclosed pharmaceutical composition.

Also disclosed are methods for modulating of GSPT1 activity in at least one cell, comprising the step of contacting the at least one cell with an effective amount of at least one disclosed compound, or a pharmaceutically acceptable salt thereof; or at least one disclosed pharmaceutical composition.

Also disclosed are uses of a disclosed compound, or a pharmaceutically acceptable salt thereof; a disclosed product of making, or a pharmaceutically acceptable salt thereof; or a disclosed pharmaceutical composition.

Also disclosed are uses of a disclosed compound, or a pharmaceutically acceptable salt thereof, in the manufacture of a medicament for the treatment of a disorder associated with a cereblon protein dysfunction in a mammal.

Also disclosed are uses of a disclosed compound, or a pharmaceutically acceptable salt thereof, in the manufacture of a medicament for the treatment of a disorder associated with a GSPT1 dysfunction in a mammal.

Also disclosed are uses of a disclosed compound, or a pharmaceutically acceptable salt thereof, in the manufacture of a medicament for the treatment of a disorder associated with a cellular proliferation dysfunction in a mammal, e.g., to inhibit cellular proliferation in a cancer cell, in a mammal comprising combining at least one disclosed compound, or a pharmaceutically acceptable salt thereof with a pharmaceutically acceptable carrier or diluent.

Also disclosed are methods for the manufacture of a medicament to modulate the cereblon protein in a mammal comprising combining at least one disclosed compound, or a pharmaceutically acceptable salt thereof with a pharmaceutically acceptable carrier or diluent.

Also disclosed are methods for the manufacture of a medicament to modulate the degradation of GSPT1 in a mammal comprising combining at least one disclosed compound, or a pharmaceutically acceptable salt thereof with a pharmaceutically acceptable carrier or diluent.

Also disclosed are methods for the manufacture of a medicament to inhibit cellular proliferation, e.g., to inhibit cellular proliferation in a cancer cell, in a mammal comprising combining at least one disclosed compound, or a pharmaceutically acceptable salt thereof with a pharmaceutically acceptable carrier or diluent.

Also disclosed are kits comprising at least one disclosed compound, or a pharmaceutically acceptable salt thereof; or at least one disclosed pharmaceutical composition; and one or more of: (a) at least one agent known to increase cereblon activity; (b) at least one agent known to decrease cereblon activity; (c) at least one agent known to increase GSPT1 activity; (d) at least one agent known to decrease GSPT1 activity; (e) at least one agent known to increase cellular proliferation; (f) at least one agent known to decrease cellular proliferation; (g) at least one agent known to treat a disorder associated with cereblon activity; (h) at least one agent known to treat a disorder associated with GSPT1 activity; (i) at least one agent known to treat a disorder of uncontrolled cellular proliferation; and/or (j) instructions for treating a disorder of uncontrolled cellular proliferation.

Also disclosed are kits comprising at least one disclosed compound, or a pharmaceutically acceptable salt thereof; or at least one disclosed pharmaceutical composition; and one or more of: (a) at least one agent known to increase cereblon activity; (b) at least one agent known to decrease cereblon activity; (c) at least one agent known to increase cellular proliferation; (d) at least one agent known to decrease cellular proliferation; (e) at least one agent known to treat a disorder associated with cereblon activity; (f) at least one agent known to treat a disorder of uncontrolled cellular proliferation; and/or (g) instructions for treating a disorder of uncontrolled cellular proliferation.

Also disclosed are kits comprising at least one disclosed compound, or a pharmaceutically acceptable salt thereof; or at least one disclosed pharmaceutical composition; and one or more of: (a) at least one agent known to increase GSPT1 activity; (b) at least one agent known to decrease GSPT1 activity; (c) at least one agent known to increase cellular proliferation; (d) at least one agent known to decrease cellular proliferation; (e) at least one agent known to treat a disorder associated with GSPT1 activity; (f) at least one agent known to treat a disorder of uncontrolled cellular proliferation; and/or (g) instructions for treating a disorder of uncontrolled cellular proliferation.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 2A shows the effect of the treatment with increasing concentrations of compounds 1 and 5 over 3 days on viability of MV4-11 cells in absence and presence of lenalidomide (10 μM). FIG. 2B shows the effect of the treatment with increasing concentrations of compounds 1 and 5 over 3 days on viability of wild-type MV4-11 cells versus $CRBN^{-/-}$ MV4-11 cells.

FIG. 3A shows data obtained for treatment of MV4-11 cells for 4 hours with compound 1. FIG. 3B shows data obtained for treatment of MV4-11 cells for 4 hours with compound 5. FIG. 3C shows data obtained for treatment of MV4-11 cells for 24 hours with compound 1. FIG. 3D shows data obtained for treatment of MV4-11 cells for 24 hours with compound 5. Degradation values were calculated using quantified band intensities from immunoblots and DC50 values calculated based on the average of at least two independent experiments.

FIG. 9A shows data obtained for treatment of MV4-11 cells for 4 hours with compound CC-90009. FIG. 9B shows data obtained for treatment of MV4-11 cells for 24 hours with compound CC-90009.

Figure 1:
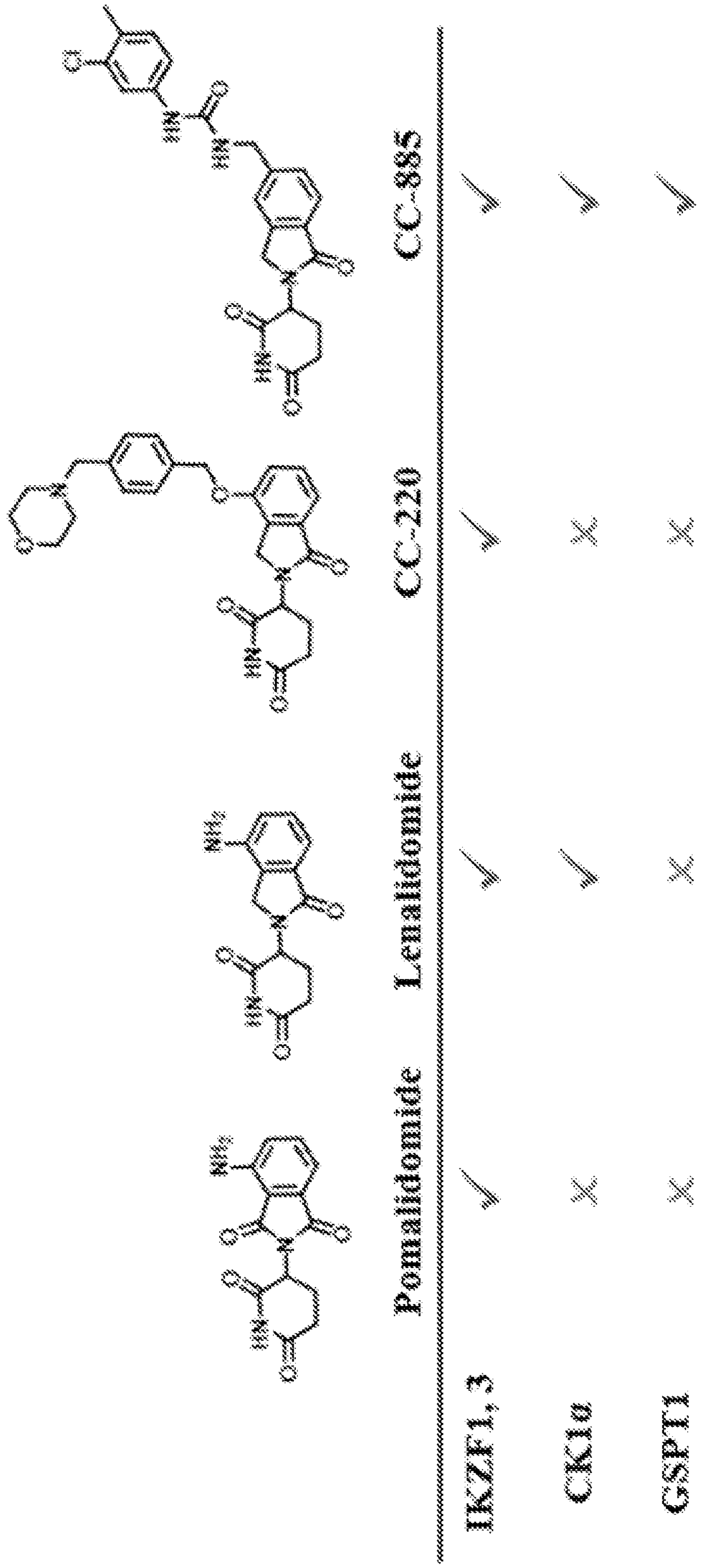
FIG. 1 shows prior art thalidomide analogues that induce degradation of distinct disease-relevant proteins. Checkmarks indicate targets degraded by their respective IMiDs.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior disclosure. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Aspects of the present disclosure will employ, unless otherwise indicated, techniques of molecular biology, microbiology, organic chemistry, biochemistry, physiology, cell biology, blood vessel biology, and the like, which are within the skill of the art. Such techniques are explained fully in the literature.

Prior to describing the various aspects of the present disclosure, the following definitions are provided and should be used unless otherwise indicated. Additional terms may be defined elsewhere in the present disclosure.

A. Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used herein, the term "and/or" includes any and all combinations of one or more of the associated listed items. Expressions such as "at least one of," when preceding a list of elements, modify the entire list of elements and do not modify the individual elements of the list.

As used in the specification and the appended claims, the singular forms "a," "an" and "the" include plural referents unless the context clearly dictates otherwise. Thus, for example, reference to "a compound," "a substituent group," or "a cancer," including, but not limited to, two or more such compounds, substituent groups, or cancers, including combinations of compounds, substituent groups, or cancers.

Reference to "a/an" chemical compound, protein, and antibody each refers to one or more molecules of the chemical compound, protein, and antibody rather than being limited to a single molecule of the chemical compound, protein, and antibody. Furthermore, the one or more molecules may or may not be identical, so long as they fall under the category of the chemical compound, protein, and antibody. Thus, for example, "an" antibody is interpreted to include one or more antibody molecules of the antibody, where the antibody molecules may or may not be identical (e.g., different isotypes and/or different antigen binding sites as may be found in a polyclonal antibody).

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10"

is also disclosed. Ranges can be expressed herein as from “about” one particular value, and/or to “about” another particular value. Similarly, when values are expressed as approximations, by use of the antecedent “about,” it will be understood that the particular value forms a further aspect. For example, if the value “about 10” is disclosed, then “10” is also disclosed.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase “x to y” includes the range from ‘x’ to ‘y’ as well as the range greater than ‘x’ and less than ‘y’. The range can also be expressed as an upper limit, e.g. ‘about x, y, z, or less’ and should be interpreted to include the specific ranges of ‘about x’, ‘about y’, and ‘about z’ as well as the ranges of ‘less than x’, less than y', and ‘less than z’. Likewise, the phrase ‘about x, y, z, or greater’ should be interpreted to include the specific ranges of ‘about x’, ‘about y’, and ‘about z’ as well as the ranges of ‘greater than x’, greater than y', and ‘greater than z’. In addition, the phrase “about ‘x’ to ‘y’”, where ‘x’ and ‘y’ are numerical values, includes “about ‘x’ to about ‘y’”.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of “about 0.1% to 5%” should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, “about,” “approximately,” “substantially,” and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms “about,” “approximate,” “at or about,” and “substantially” can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is “about,” “approximate,” or “at or about” whether or not expressly stated to be such. It is understood that where “about,” “approximate,” or “at or about” is used before a quantitative value, the parameter also includes the specific quantitative value itself, unless specifically stated otherwise.

As used herein, the terms “optional” or “optionally” means that the subsequently described event or circumstance can or cannot occur, and that the description includes instances where said event or circumstance occurs and instances where it does not.

As used herein, “cereblon” and “CRBN” can be used interchangeably, and refer to an protein encoded by the CRBN gene in humans with a cytogenetic location of 3p26.2 and a molecular location of base pairs 3,148,489 to 3,179, 716 on chromosome 3 (UCSC Genome Browser on Human December 2013 (GRCh38/hg38) Assembly). The gene structure in humans comprises 11 exons. CRBN is a substrate recognition component of a DCX (DDB1-CUL4-X-box) E3 protein ligase complex that mediates the ubiquitination and subsequent proteasomal degradation of target proteins. The DCX (DDB1-CUL4-X-box) E3 protein ligase complex is composed at least of CRBN, CUL4A, DDB1, and RBX1. The CRBN protein has two isoforms produced by alternative splicing: Isoform 1 has 442 amino acids and a molecular weight of 50,546 Da; and Isoform 2 has 441 amino acids and a molecular weight of 50,475 Da.

As used herein, “CC-220” refers to a compound having CAS #1323403-33-3; an IUPAC name of (S)-3-(4-((4-(morpholinomethyl)benzyl)oxy)-1-oxoisoindolin-2-yl)piperidine-2,6-dione; and a structure given by the formula:

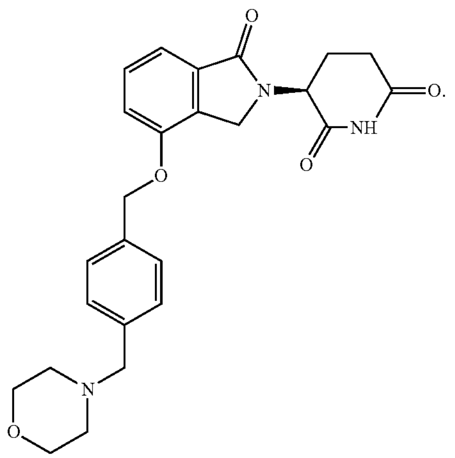 [SMILES: O=C1CC[C@H](N2Cc3c(OCc4ccc(CN5CCOCC5)cc4)cccc3C2=O)C(=O)N1]

As used herein, “CC-885” refers to a compound having CAS #1010100-07-8; an IUPAC name of N-(3-chloro-4-methylphenyl)-N'-[[2-(2,6-dioxo-3-piperidinyl)-2,3-dihydro-1-oxo-1H-isoindol-5-yl]methyl]-urea; and a structure given by the formula:

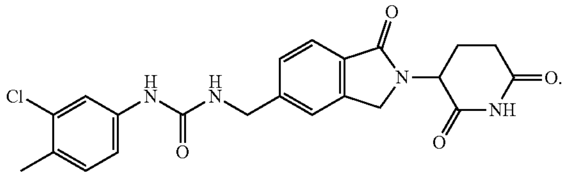 [SMILES: Cc1ccc(NC(=O)NCc2ccc3c(c2)CN(C2CCC(=O)NC2=O)C3=O)cc1Cl]

As used herein, "CC-90009" refers to a compound having CAS #1860875-51-9; an IUPAC name of 2-(4-chlorophenyl)-N-((2-(2,6-dioxopiperidin-3-yl)-1-oxoisoindolin-5-Amethyl)-2,2-difluoroacetamide; and a structure given by the formula:

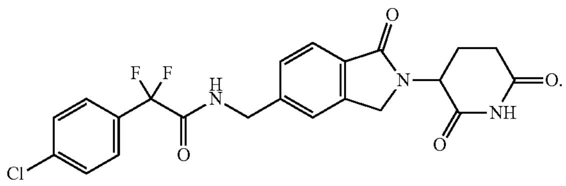 [SMILES: O=C1CCC(N2Cc3cc(CNC(=O)C(F)(F)c4ccc(Cl)cc4)ccc3C2=O)C(=O)N1]

As used herein, "administering" can refer to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratym panic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, "therapeutic agent" can refer to any substance, compound, molecule, and the like, which can be biologically active or otherwise can induce a pharmacologic, immunogenic, biologic and/or physiologic effect on a subject to which it is administered to by local and/or systemic action. A therapeutic agent can be a primary active agent, or in other words, the component(s) of a composition to which the whole or part of the effect of the composition is attributed. A therapeutic agent can be a secondary therapeutic agent, or in other words, the component(s) of a composition to which an additional part and/or other effect of the composition is attributed. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, "attached" can refer to covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, π-π interactions, cation-π interactions, anion-π interactions, polar π-interactions, and hydrophobic effects.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and juvenile subjects, whether male or female, are intended to be covered. In one aspect, the subject is a mammal. A patient refers to a subject afflicted with a disease or disorder. The term "patient" includes human and veterinary subjects.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as a disorder of uncontrolled cellular, e.g., a cancer such as acute leukemia or a medulloblastoma. The effect can be therapeutic in terms of a partial or complete cure of a disease, condition, symptom or adverse effect attributed to the disease, disorder, or condition. The term "treatment" as used herein can include any treatment of a disorder of uncontrolled cellular, e.g., a cancer such as acute leukemia or a medulloblastoma, in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

As used herein, "effective amount" can refer to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function.

As used herein, the term "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the disclosure (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound and/or pharmaceutical composition, for example, can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The term "pharmaceutically acceptable" describes a material that is not biologically or otherwise undesirable, i.e., without causing an unacceptable level of undesirable biological effects or interacting in a deleterious manner.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

The term "pharmaceutically acceptable ester" refers to esters of compounds of the present disclosure which hydrolyze in vivo and include those that break down readily in the human body to leave the parent compound or a salt thereof. Examples of pharmaceutically acceptable, non-toxic esters of the present disclosure include C 1-to-C 6 alkyl esters and C 5-to-C 7 cycloalkyl esters, although C 1-to-C 4 alkyl esters are preferred. Esters of disclosed compounds can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" refers to non-toxic amides of the present disclosure derived from ammonia, primary C 1-to-C 6 alkyl amines and secondary C 1-to-C 6 dialkyl amines. In the case of secondary amines, the amine can also be in the form of a 5- or 6-membered heterocycle containing one nitrogen atom. Amides derived from ammonia, C 1-to-C 3 alkyl primary amides and C 1-to-C 2 dialkyl secondary amides are preferred. Amides of disclosed compounds can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the present disclosure in the form of a pharmaceutically acceptable prodrug.

The term "pharmaceutically acceptable prodrug" or "prodrug" represents those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present disclosure can be rapidly transformed in vivo to a parent compound having a structure of a disclosed compound, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, nomenclature for compounds, including organic compounds, can be given using common names, IUPAC, IUBMB, or CAS recommendations for nomenclature. When one or more stereochemical features are present, Cahn-lngold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

Reference to "a" chemical compound refers to one or more molecules of the chemical compound rather than being limited to a single molecule of the chemical compound. Furthermore, the one or more molecules may or may not be identical, so long as they fall under the category of the chemical compound. Thus, for example, "a" chemical compound is interpreted to include one or more molecules of the chemical, where the molecules may or may not be identical (e.g., different isotopic ratios, enantiomers, and the like).

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

The term "contacting" as used herein refers to bringing a disclosed compound or pharmaceutical composition in proximity to a cell, a target protein, or other biological entity together in such a manner that the disclosed compound or pharmaceutical composition can affect the activity of the a cell, target protein, or other biological entity, either directly; i.e., by interacting with the cell, target protein, or other biological entity itself, or indirectly; i.e., by interacting with another molecule, co-factor, factor, or protein on which the activity of the cell, target protein, or other biological entity itself is dependent.

As used herein, the term "effective amount" refers to an amount that is sufficient to achieve the desired modification of a physical property of the composition or material. For example, an "effective amount" of a disclosed compound or pharmaceutical composition refers to an amount that is sufficient to achieve the desired degree of modulation of a target, e.g. modulation of cereblon protein, or a desired amelioration or improvement in a clinical condition, e.g. remission of a cancer. The specific level in terms of amount, e.g., milligrams, or concentration, e.g., micromolar, of a disclosed compound or pharmaceutical composition required as an effective amount will depend upon a variety of factors the route of administration or contacting with the target, the severity of a clinical condition, the desired degree of modulation, and the like.

As used herein, the terms "optional" or "optionally" means that the subsequently described event or circumstance can or cannot occur, and that the description includes instances where said event or circumstance occurs and instances where it does not.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described; that is, an alkoxy can be a polyether such as $—OA^1\text{-}OA^2$ or $—OA^1—(OA^2)_a—OA^3$, where "a" is an integer of from 1 to 200 and $A^1$, $A^2$, and $A^3$ are alkyl and/or cycloalkyl groups.

The terms "amine" or "amino" as used herein are represented by the formula $—NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is $—NH_2$.

The term "alkylamino" as used herein is represented by the formula —NH(-alkyl) and $—N(\text{-alkyl})_2$, where alkyl is a described herein. Representative examples include, but are not limited to, methylamino group, ethylamino group, propylamino group, isopropylamino group, butylamino group, isobutylamino group, (sec-butyl)amino group, (tert-butyl) amino group, pentylamino group, isopentylamino group, (tert-pentyl)amino group, hexylamino group, dimethylamino group, diethylamino group, dipropylamino group, diisopropylamino group, dibutylamino group, diisobutylamino group, di(sec-butyl)amino group, di(tert-butyl) amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula $—(A^1O\text{-}A^2O)_a—$, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "hydroxyl" or "hydroxy" as used herein is represented by the formula —OH.

The term "thiol" as used herein is represented by the formula —SH.

The term "azide" or "azido" as used herein is represented by the formula $—N_3$.

The term "nitro" as used herein is represented by the formula $—NO_2$.

The term "nitrile" or "cyano" as used herein is represented by the formula —CN.

The terms "halo," "halogen" or "halide," as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl" as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "carbonyl" as used herein is represented by the formula —C(O)—. Throughout this specification "C(O)" or C═O is a short hand notation for a carbonyl group.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The term "heterocycle" as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

"$R^1$," "$R^2$," "$R^3$," . . . "Re," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. In is also contemplated that, in certain aspects, unless expressly indicated to the contrary, individual substituents can be further optionally substituted (i.e., further substituted or unsubstituted).

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more $—OCH_2CH_2O—$ units in the polyester, regardless of whether ethylene glycol was used to prepare the polyester. Similarly, a sebacic acid residue in a polyester refers to one or more $—CO(CH_2)_8CO—$ moieties in the polyester, regardless of whether the residue is obtained by reacting sebacic acid or an ester thereof to obtain the polyester.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

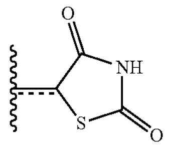

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present disclosure unless it is indicated to the contrary elsewhere herein.

The term "stable," as used herein, refers to compounds that are not substantially altered when subjected to conditions to allow for their production, detection, and, in certain aspects, their recovery, purification, and use for one or more of the purposes disclosed herein.

Compounds described herein can contain one or more double bonds and, thus, potentially give rise to cis/trans (E/Z) isomers, as well as other conformational isomers. Unless stated to the contrary, the disclosure includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present disclosure includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and I or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the disclosure include isotopes of hydrogen, carbon, nitrogen, oxygen, sulfur, fluorine and chlorine, such as $^{2}H$, $^{3}H$, $^{13}C$, $^{14}C$, $^{15}N$, $^{18}O$, $^{17}O$, $^{35}S$, $^{18}F$, and $^{36}Cl$, respectively. Compounds further comprise prodrugs thereof and pharmaceutically acceptable salts of said compounds or of said prodrugs which contain the aforementioned isotopes and/or other isotopes of other atoms are within the scope of this disclosure. Certain isotopically-labeled compounds of the present disclosure, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present disclosure and prodrugs thereof can generally be prepared by carrying out the procedures below, by substituting a readily available isotopically labeled reagent for a non-isotopically labeled reagent.

The compounds described in the disclosure can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the disclosure to form solvates and hydrates. Unless stated to the contrary, the disclosure includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

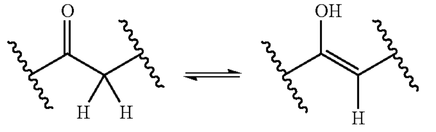

keto form enol form

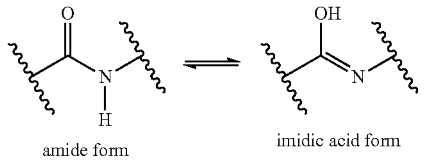

amide form imidic acid form

Likewise, amides with an N-hydrogen can exist in an equilibrium of the amide form and the imidic acid form. Unless stated to the contrary, the disclosure includes all such possible tautomers.

It is known that chemical substances form solids which are present in different states of order which are termed polymorphic forms or modifications. The different modifications of a polymorphic substance can differ greatly in their physical properties. The compounds according to the disclosure can be present in different polymorphic forms, with it being possible for particular modifications to be metastable. Unless stated to the contrary, the disclosure includes all such possible polymorphic forms.

In some aspects, a structure of a compound can be represented by a formula:

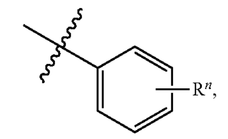

which is understood to be equivalent to a formula:

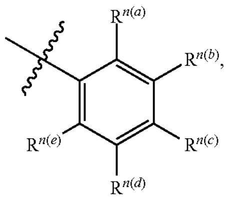

wherein n is typically an integer. That is, $R^n$ is understood to represent five independent substituents, $R^{n(a)}$, $R^{n(b)}$, $R^{n(c)}$, $R^{n(d)}$, and $R^{n(e)}$. By "independent substituents," it is meant that each R substituent can be independently defined. For example, if in one instance $R^{n(a)}$ is halogen, then $R^{n(b)}$ is not necessarily halogen in that instance.

Unless otherwise specified, temperatures referred to herein are based on atmospheric pressure (i.e. one atmosphere).

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the disclosure. Thus, if there are a variety of additional steps that can be performed it is understood that each of these additional steps can be performed with any specific embodiment or combination of embodiments of the methods of the disclosure.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Abbreviations used herein throughout: ADME, absorption, distribution, metabolism, excretion; AL, acute leukemia; AlogP, lipophilicity; CK1α, casein kinase 1α; CL, clearance; CRBN, cereblon; F, bioavailability; GSPT1, G1 to S phase transition 1; HBA, hydrogen-bond acceptors; HBD, hydrogen-bond donors; IMiDs, immunomodulatory drugs; IKZF, Ikaros family zinc finger; IV, intravenous; LCMS, liquid chromatography mass spectrometry; MB, medulloblastoma; MG, molecular glue; MW, molecular weight; PPB, plasma protein binding; PK, pharmacokinetics; PROTAC, proteolysis taragეting chimera(s); PSA, polar surface area; SBDD, structure-based drug design; SAR, structure-activity relationships; TMT, tandem mass tag; and TPD, targeted protein degradation.

Described herein are substituted N-(2-(2,6-dioxopiperidinyl-3-yl)-1,3-dioxoisoindolin-5-yl)arylsulfonamide analogs as modulators of cereblon protein that have therapeutic or clinical utility. Also described herein are methods of synthesizing the substituted N-(2-(2,6-dioxopiperidinyl-3-yl)-1,3-dioxoisoindolin-5-yl)arylsulfonamide analogs. Also described herein are methods of administering the substituted N-(2-(2,6-dioxopiperidinyl-3-yl)-1,3-dioxoisoindolin-5-yl)arylsulfonamide analogs to a subject in need thereof. In some aspects, the subject can have a disorder of uncontrolled cellular proliferation, e.g., a cancer. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

B. Biological Context

Targeted Protein Degradation (TPD) is a novel chemical biology approach with potential profound effects on fundamental biology and drug discovery research by uncovering opportunities towards drugging undruggable targets (see Refs. 1-2). The TPD paradigm includes two main approaches of differing molecular design that generate small molecules with a similar proteasome dependent mechanism of action, namely Proteolysis Targeting Chimeras (PROTACs; see Refs. 3-4) and Molecular Glues (MGs; see Refs. 5-8). MGs are small molecules capable of binding to an E3 ligase and altering its surface and specificity, leading to the recruitment, ubiquitination, and subsequent degradation of substrates that are normally not targeted by the ligase (neosubstrates). Recognition of the neosubstrate is governed by a protein-ligase surface interaction (a structural degron motif) and does not require a ligandable pocket. This provides a revolutionary opportunity to degrade hitherto undruggable targets, such as fusion oncoproteins and transcription factors (see Refs. 9-10) Immunomodulatory drugs (IMiDs), thalidomide and its close analogs pomalidomide and lenalidomide, are the "original" molecular glues providing the mechanistic and clinical validation of this approach (see Refs. 7 and 11)

Interestingly, despite high molecular structural similarity, IMiDs display different protein degradation profiles. Both lenalidomide and pomalidomide degrade the transcription factors IKZF1/3 but only lenalidomide induces degradation of CSNK1A[1] (CK1α), illustrating how a small change in molecular structure can significantly alter the specificity for the neosubstrate (FIG. 1; see Ref. 12). Moreover, diversification around the IMiDs scaffold has been shown to influence the potency and kinetics of neosubstrate degradation (exemplified by CC-220, which is 10-fold more potent in cells than lenalidomide; see Ref. 13) or specificity, leading to the discovery of novel neosubstrates, as demonstrated by the GSPT1 (G1 to S phase transition 1) degrader CC-885 developed by Celgene (FIG. 1; see Ref. 14). These chemical modifications lead to considerable changes in cellular responses, creating new clinical translation opportunities.

For IMiDs and closely related analogues, an expanding number of neosubstrates containing the common C2H2 zinc finger recognition degron motif have been discovered (IKZF2/4, SALL4, RNF166, ZFP91, ZNF692, ZNF276, ZNF653 and ZNF827; see Refs. 11 and 15). Each IMiD was shown to display distinct patterns of substrate specificity, supporting the notion that neosubstrate diversity can be modulated by structural alterations of the ligand and is not limited to traditionally known targets. It also suggests that achieving selective protein degradation is a challenge and that understanding the structural basis of how ligand modification alters the interaction of the neosubstrate at the cereblon (CRBN) interface is important (Ref. 16). Several recently reported studies showed how simple structural modifications can result in an unexpected conversion of a PROTAC into a GSPT1 molecular glue degrader (see Refs. 17-18).

In high-risk cancers like childhood acute leukemia (AL) and medulloblastoma (MB), aberrant activation, dysregulation and/or mutation of C2H2 zinc finger transcription factors are prevalent, with limited targeted treatments. Representative examples include ZNF384 fusion oncoproteins observed in lineage ambiguous acute leukemia, 19 IKZF1 mutations in acute lymphoblastic leukemia (ALL; see Ref. 20), deregulated MECOM in high-risk acute myeloid leukemia (AML) and enhancer-hijacking dependent activation of GFI1, GFI1B, and PRDM6 in high-risk group 3 and group 4 MB subgroups (see Refs. 21-24).

Small molecule degraders, often referred to as molecular glues, offer the tantalizing prospect of targeting currently undruggable oncoproteins such as transcription factors and chimeric fusion oncoproteins. The present disclosure relates to methods and uses of small molecule degraders that modulate CRBN protein and show high anti-proliferative activity.

C. Compounds

In one aspect, the disclosure relates to potent modulators of CRBN protein, and provide a new approach to targeting previously undruggable oncoproteins, e.g., GSPT1. In a further aspect, the disclosed compounds are potent and selective GSPT1 degraders displaying up to 30-fold selectivity over IKZF1 degradation with high oral bioavailability in mouse. Without wishing to be bound by a particular theory, it is believed that the disclosed compounds have chemical features for CRBN engagement while maximizing the 3-dimensionality of chemical diversity displayed at the CRBN substrate binding surface.

More specifically, in one aspect, the present disclosure relates to compounds having a structure represented by a formula:

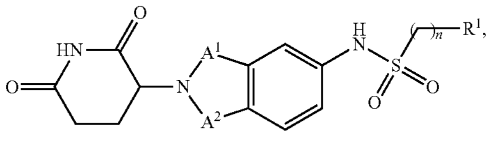

wherein n is an integer selected from 0, 1, and 2; wherein each of $A^1$ and $A^2$ is independently selected from —(C═O)— and —$CH_2$—, provided that at least one of $A^1$ and $A^2$ is —(C═O)—; wherein $R^1$ is selected from: (a) a 5- to 10-membered aryl or heteroaryl optionally substituted with a group selected from halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl; and (b) a 5- to 10-membered cycloalkyl optionally substituted with a group selected from halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl; or a pharmaceutically acceptable salt thereof. In the various structures disclosed herein, the substituent groups as derined herein throughout, including as disclosed in the claims.

In a further aspect, the disclosure relates to compounds having a structure represented by a formula:

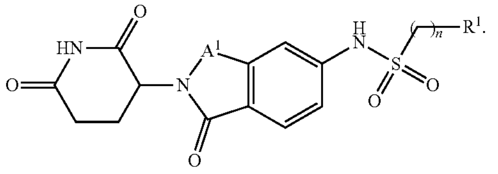

In a further aspect, the disclosure relates to compounds having a structure represented by a formula:

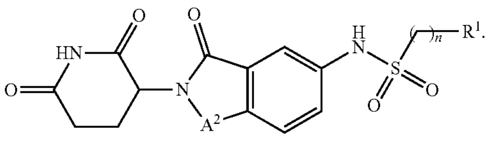

In a further aspect, the disclosure relates to compounds having a structure represented by a formula:

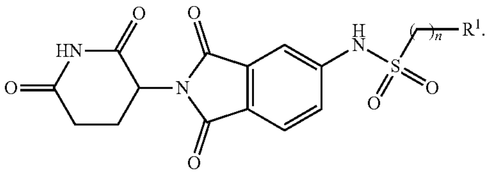

In a further aspect, the disclosure relates to compounds having a structure represented by a formula:

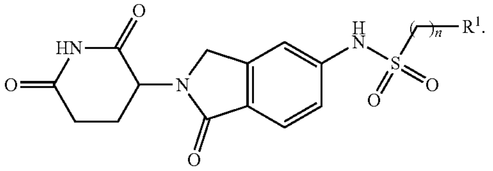

In a further aspect, the disclosure relates to compounds having a structure represented by a formula:

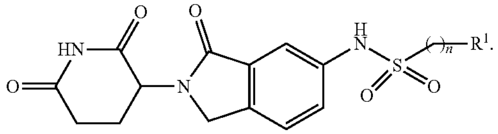

In a further aspect, the disclosure relates to compounds having a structure represented by a formula:

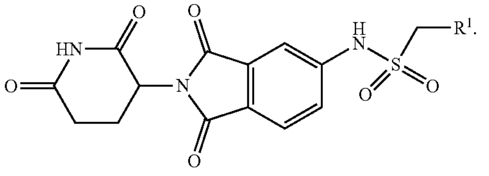

In a further aspect, the disclosure relates to compounds having a structure represented by a formula:

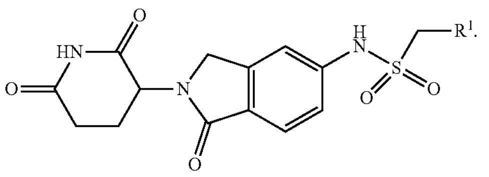

In a further aspect, the disclosure relates to compounds having a structure represented by a formula:

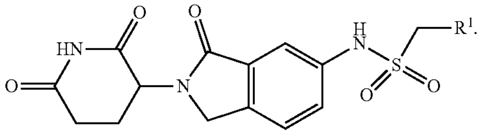

In a further aspect, the disclosure relates to compounds having a structure represented by a formula:

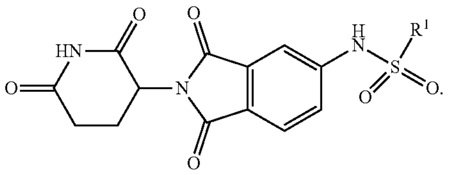

In a further aspect, the disclosure relates to compounds having a structure represented by a formula:

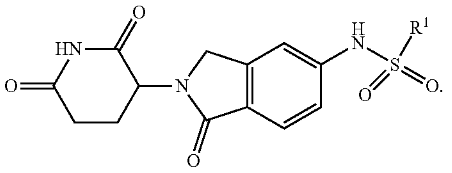

In a further aspect, the disclosure relates to compounds having a structure represented by a formula:

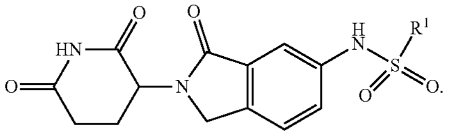

In a further aspect, $Ar^1$ is a 5-membered heteroaryl optionally substituted with a group selected from halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl.

In a further aspect, $Ar^1$ is selected from: (a) a 5-membered heteroaryl having one heteroatom and substituent groups $R^{11}$, $R^{12}$, and $R^{13}$; and wherein each of $R^{11}$, $R^{12}$, and $R^{13}$ is independently selected from hydrogen, halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-03 haloalkyl), C3-C8 cycloalkyl, C1-C6 alkyl, and phenyl; and (b) a 5-membered heteroaryl having two heteroatoms and substituent groups $R^{11}$, $R^{12}$, and $R^{13}$; and wherein each of $R^{11}$, $R^{12}$, and $R^{13}$ is independently selected from hydrogen, halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl.

In a further aspect, $Cy^1$ is a 5- to 10-membered cycloalkyl optionally substituted with a 1, 2, 3, 4, or 5 groups independently selected from halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl. In a still further aspect, Cy' is selected from cyclobutyl, cyclopentyl, cyclohexyl, and cycloheptyl optionally substituted with a 1, 2, 3, 4, or 5 groups independently selected from halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl.

In a further aspect, the disclosure relates to compounds having a structure represented by a formula:

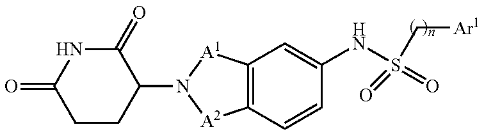

or

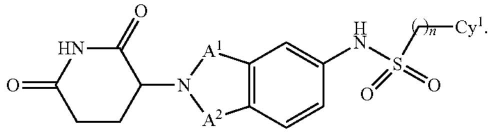

In a further aspect, the disclosure relates to compounds having a structure represented by a formula:

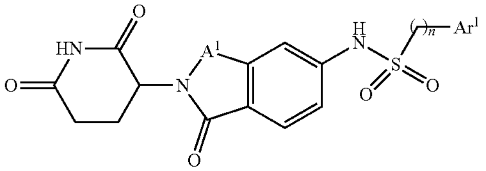

or

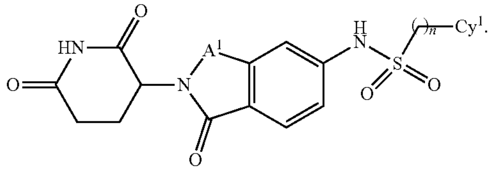

In a further aspect, the disclosure relates to compounds having a structure represented by a formula:

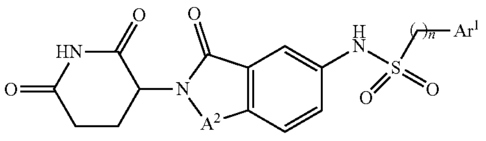

or

-continued

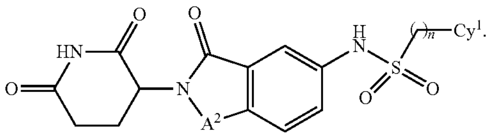

In a further aspect, the disclosure relates to compounds having a structure represented by a formula:

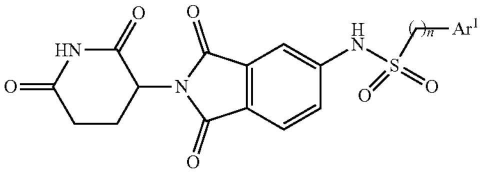

or

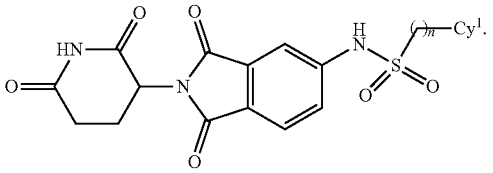

In a further aspect, the disclosure relates to compounds having a structure represented by a formula:

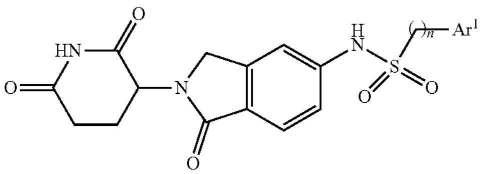

or

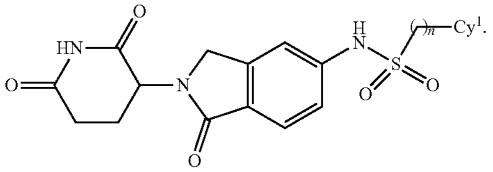

In a further aspect, the disclosure relates to compounds having a structure represented by a formula:

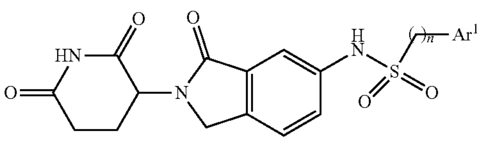

or

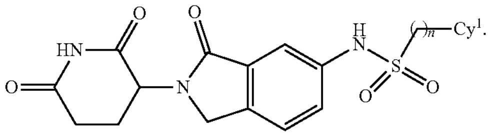

In a further aspect, the disclosure relates to compounds having a structure represented by a formula:

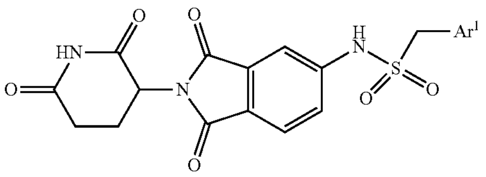

or

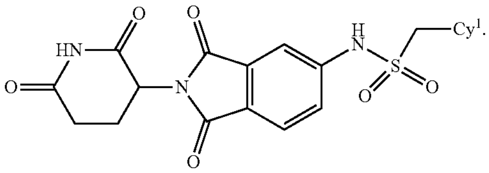

In a further aspect, the disclosure relates to compounds having a structure represented by a formula:

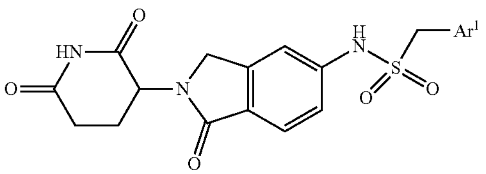

or

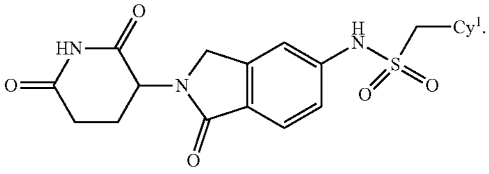

In a further aspect, the disclosure relates to compounds having a structure represented by a formula:

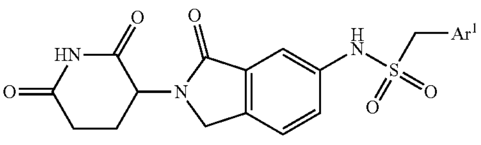

or

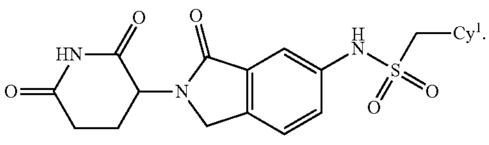

In a further aspect, the disclosure relates to compounds having a structure represented by a formula:

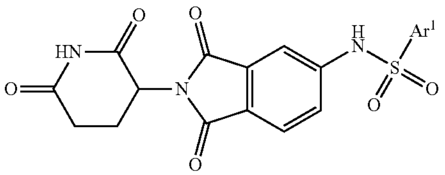

or

-continued

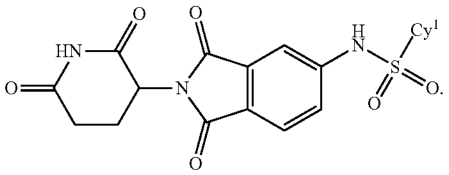

In a further aspect, the disclosure relates to compounds having a structure represented by a formula:

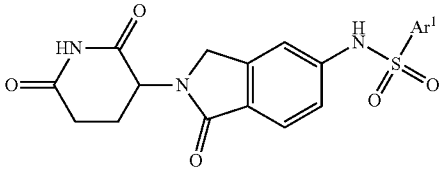

or

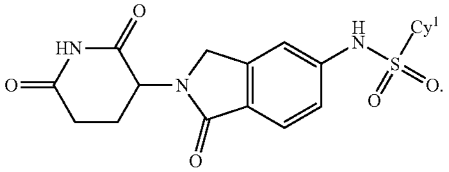

In a further aspect, the disclosure relates to compounds having a structure represented by a formula:

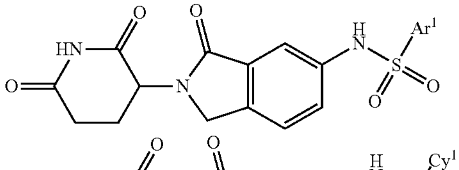

or

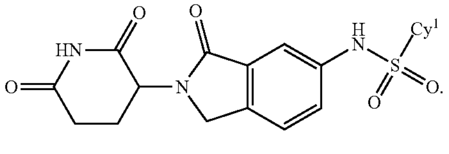

In a further aspect, the disclosure relates to compounds having a structure represented by a formula:

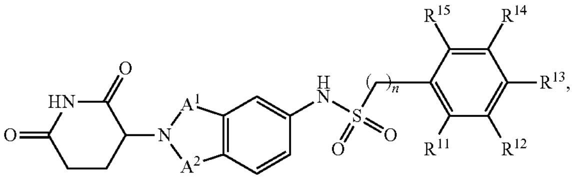

wherein n is an integer selected from 0, 1, and 2; wherein each of $A^1$ and $A^2$ is independently selected from —(C═O)— and —$CH_2$—, provided that at least one of $A^1$ and $A^2$ is —(C═O)—; wherein each of $R^{11}$, $R^{12}$, $R^{13}$, $R^{14}$, and $R^{15}$ is independently selected from hydrogen, halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl; or a pharmaceutically acceptable salt thereof.

In a further aspect, the disclosure relates to compounds having a structure represented by a formula:

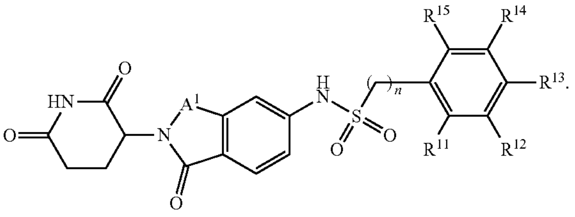

In a further aspect, the disclosure relates to compounds having a structure represented by a formula:

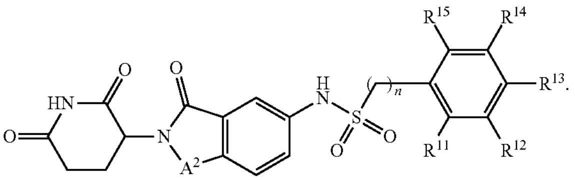

In a further aspect, the disclosure relates to compounds having a structure represented by a formula:

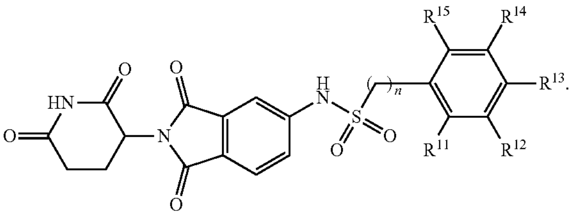

In a further aspect, the disclosure relates to compounds having a structure represented by a formula:

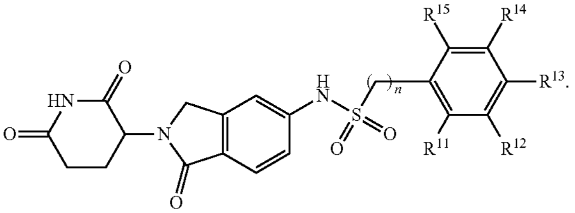

In a further aspect, the disclosure relates to compounds having a structure represented by a formula:

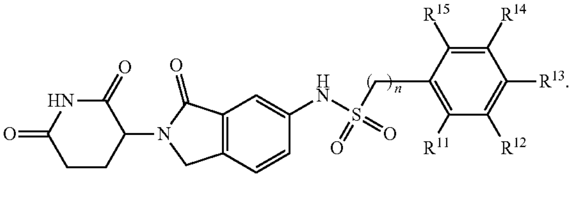

In a further aspect, the disclosure relates to compounds having a structure represented by a formula:

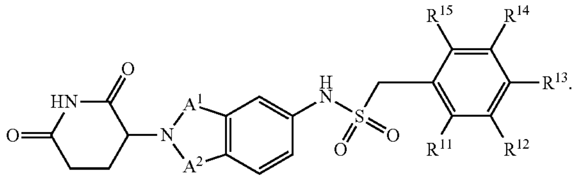

In a further aspect, the disclosure relates to compounds having a structure represented by a formula:

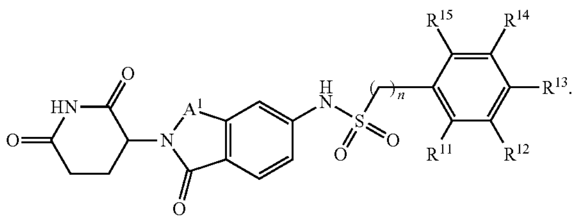

In a further aspect, the disclosure relates to compounds having a structure represented by a formula:

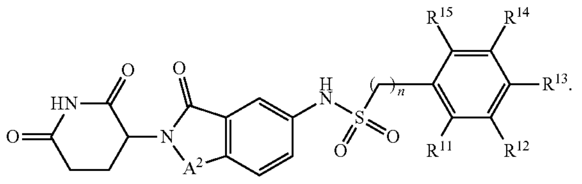

In a further aspect, the disclosure relates to compounds having a structure represented by a formula:

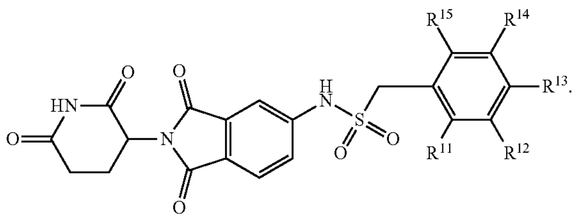

In a further aspect, the disclosure relates to compounds having a structure represented by a formula:

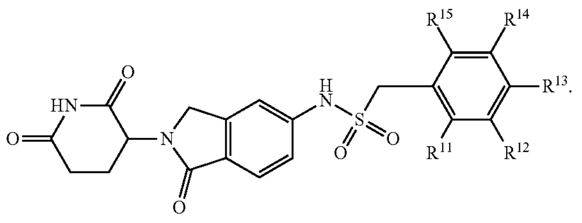

In a further aspect, the disclosure relates to compounds having a structure represented by a formula:

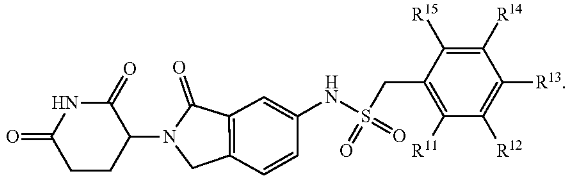

In a further aspect, the disclosure relates to compounds having a structure represented by a formula:

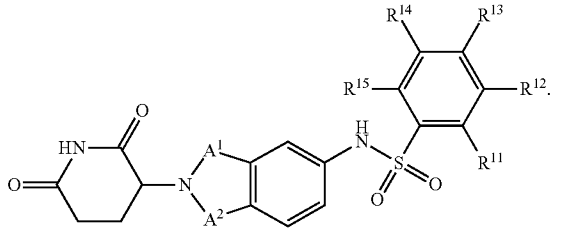

In a further aspect, the disclosure relates to compounds having a structure represented by a formula:

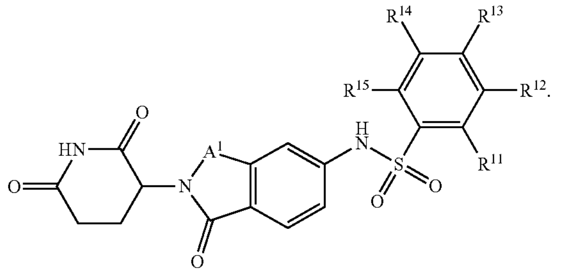

In a further aspect, the disclosure relates to compounds having a structure represented by a formula:

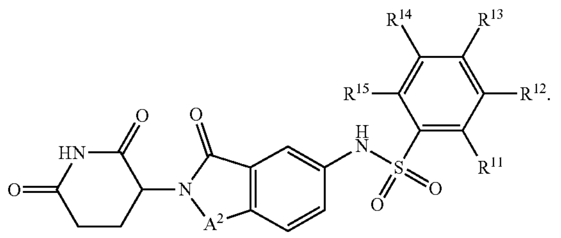

In a further aspect, the disclosure relates to compounds having a structure represented by a formula:

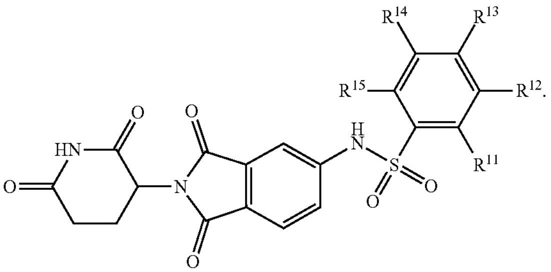
In a further aspect, the disclosure relates to compounds having a structure represented by a formula:
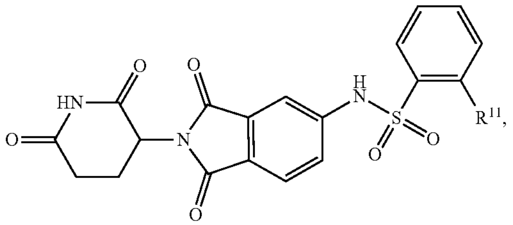
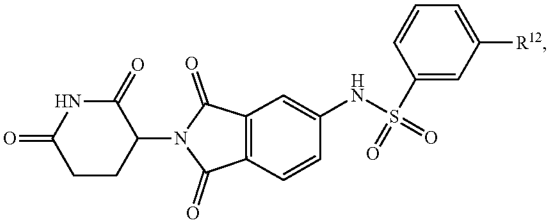
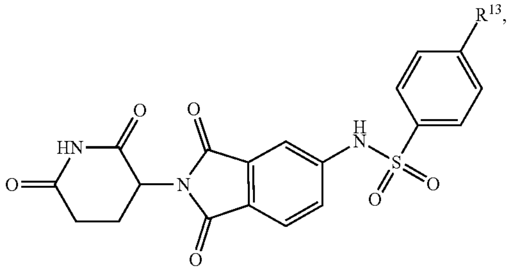
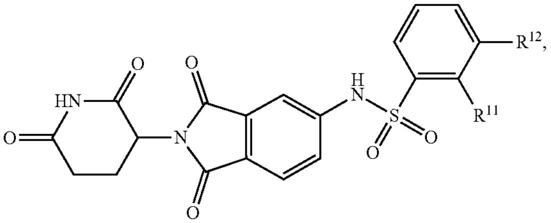
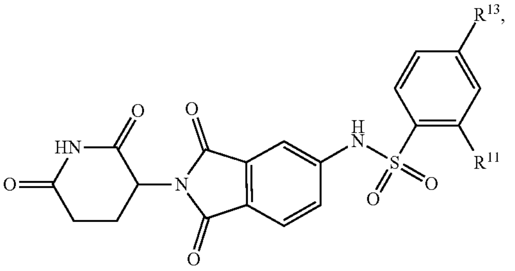
or
-continued
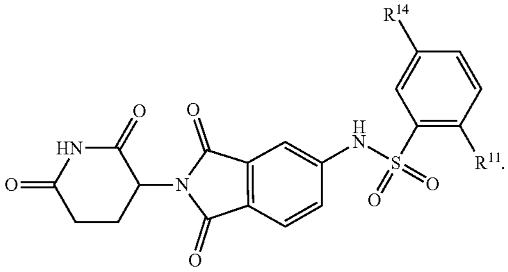
In a further aspect, the disclosure relates to compounds having a structure represented by a formula:
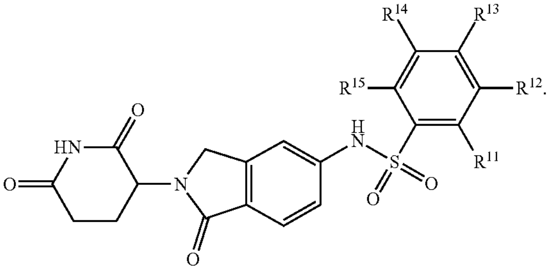
In a further aspect, the disclosure relates to compounds having a structure represented by a formula:
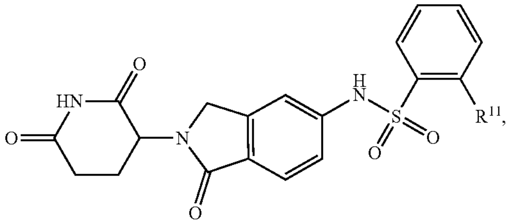
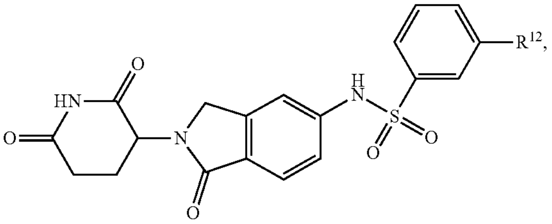
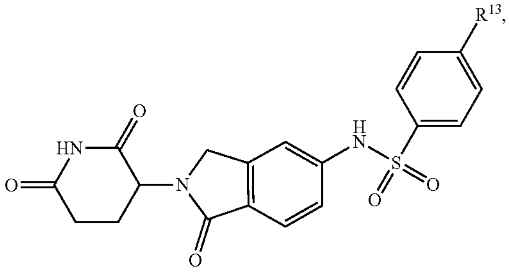

-continued
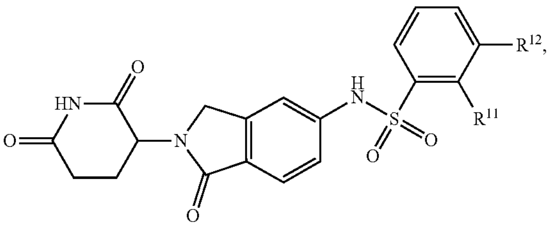
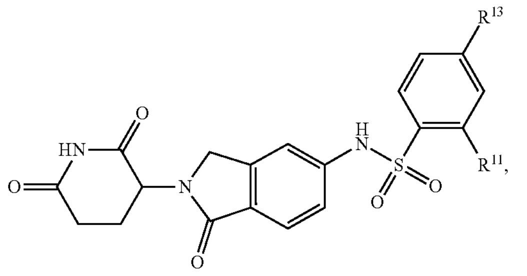
or
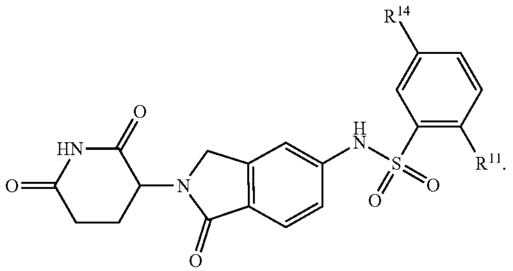
In a further aspect, the disclosure relates to compounds having a structure represented by a formula:
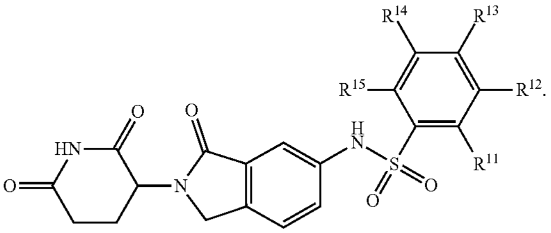
In a further aspect, the disclosure relates to compounds having a structure represented by a formula:
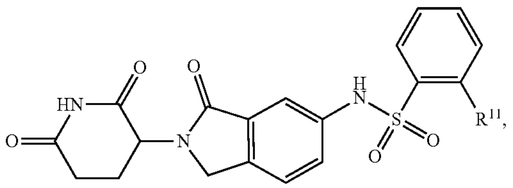
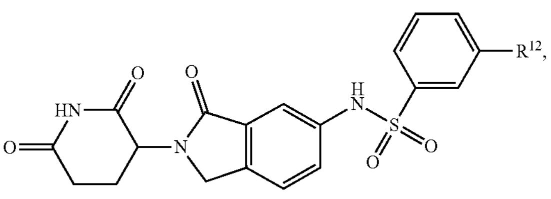
-continued
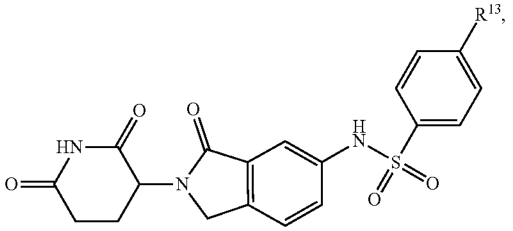
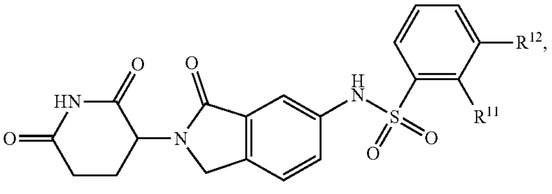
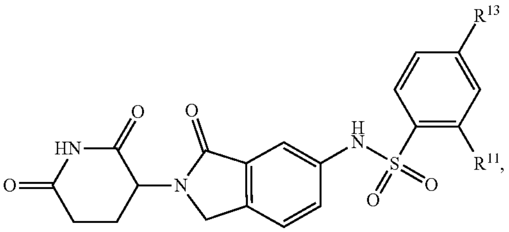
or
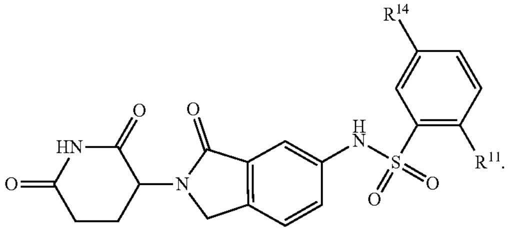
In a further aspect, a disclosed compound has a structure given by:
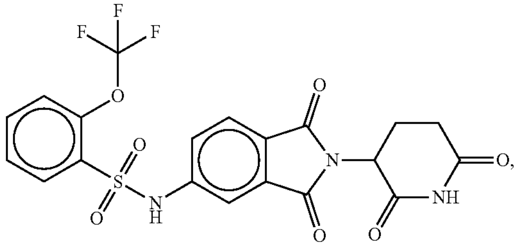
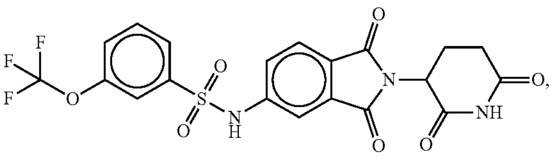
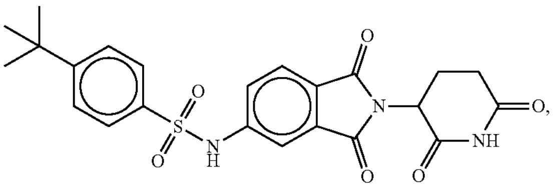

-continued
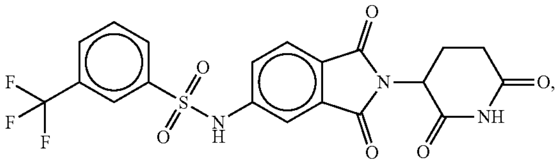,
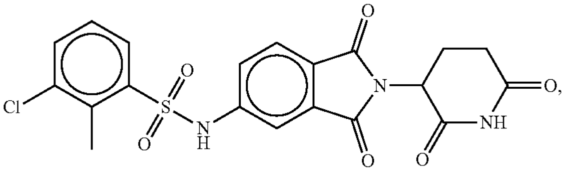,
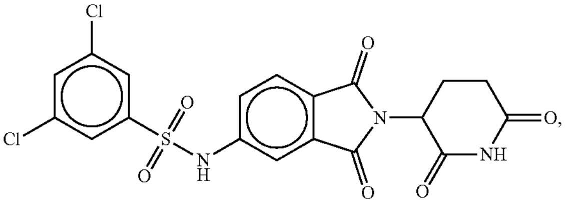,
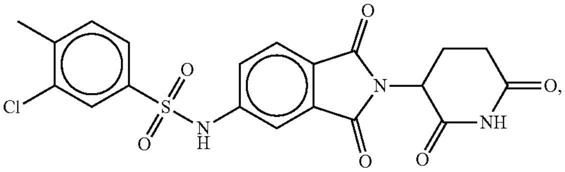,
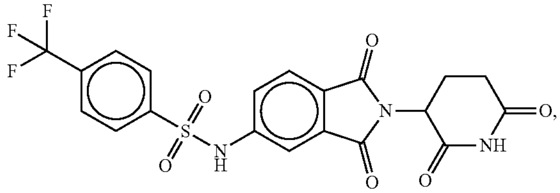,
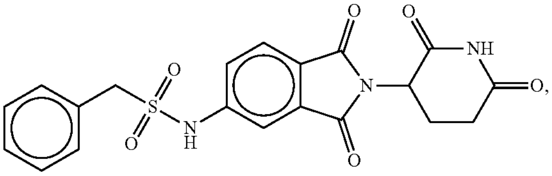,
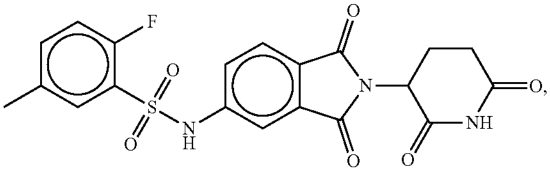,
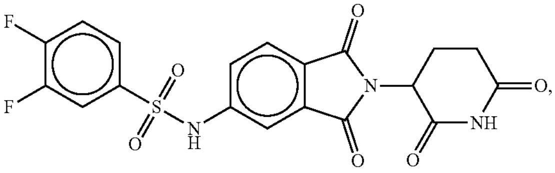,
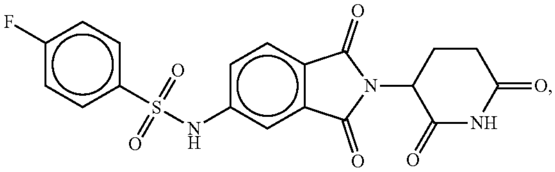,
-continued
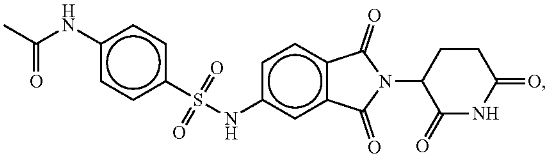,
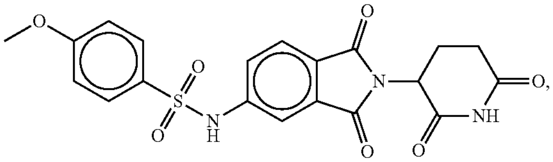,
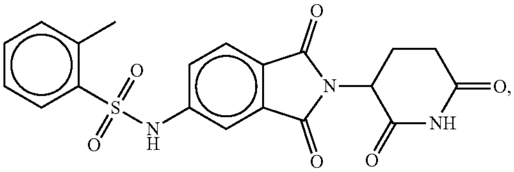,
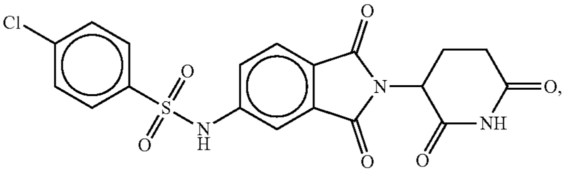,
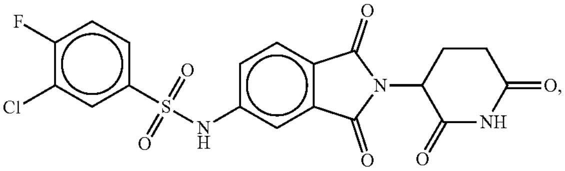,
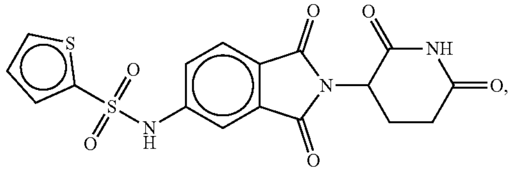,
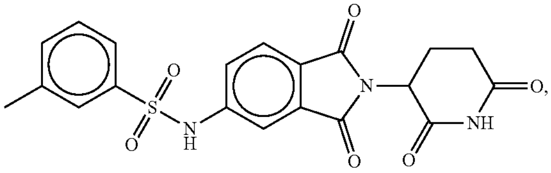,
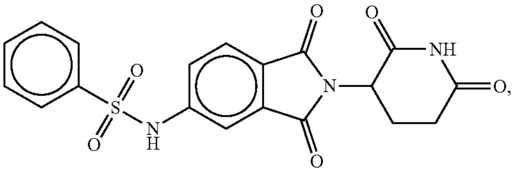,
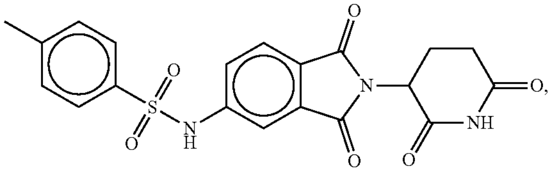,
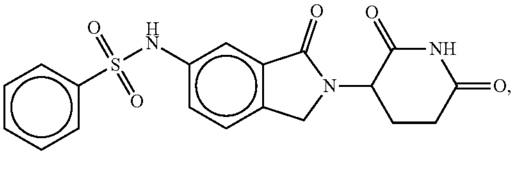, -continued
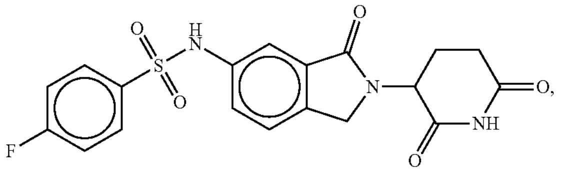
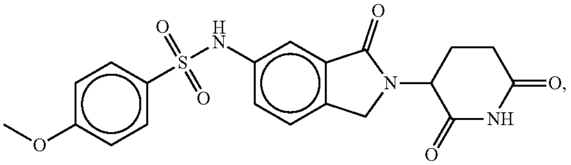
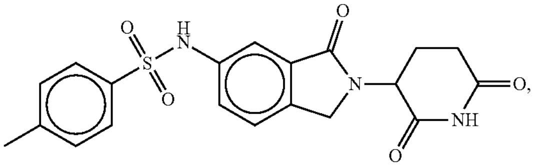
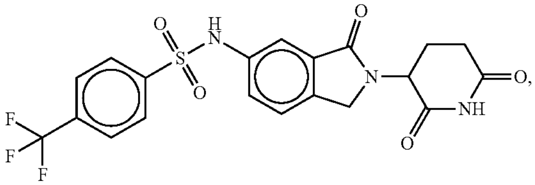
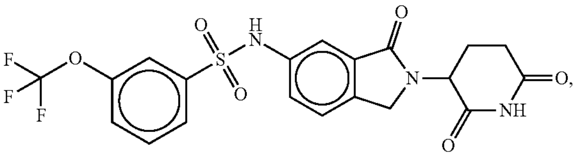
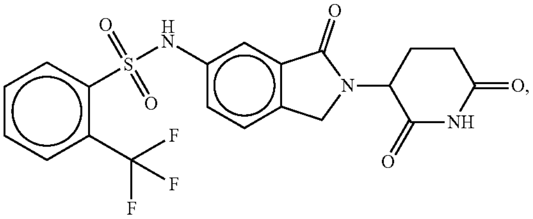
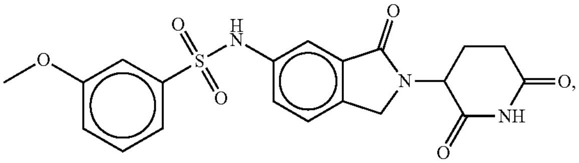
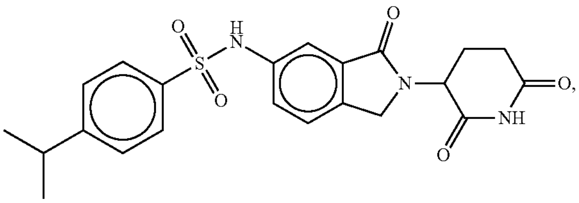
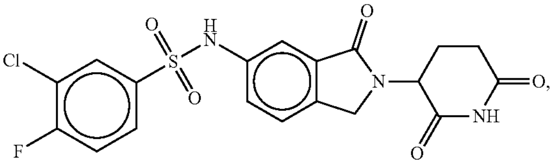
-continued
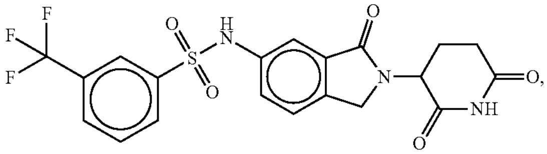
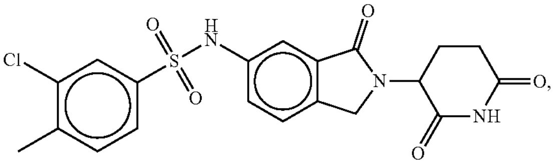
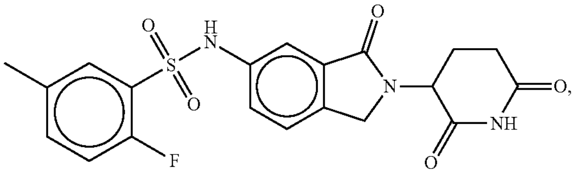
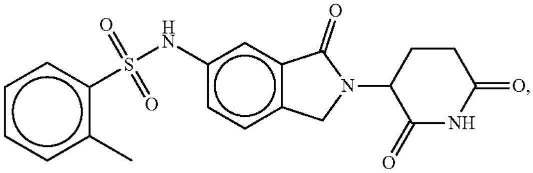
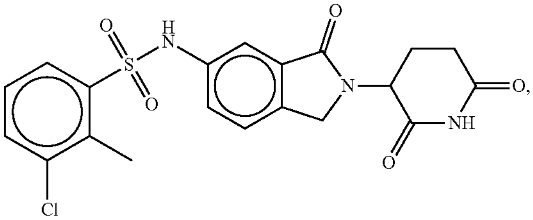
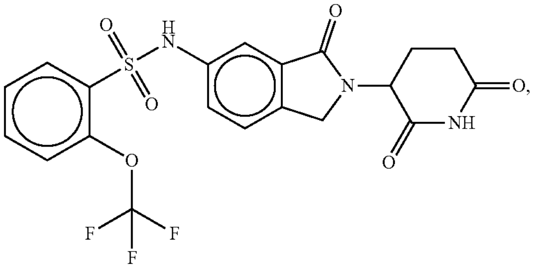
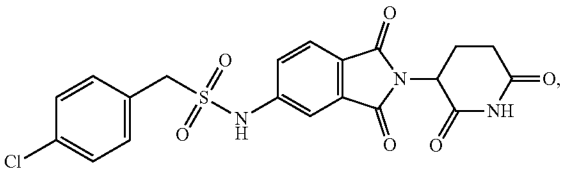
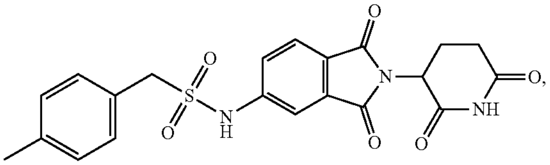
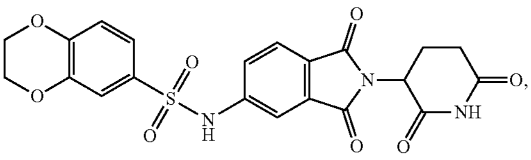

-continued
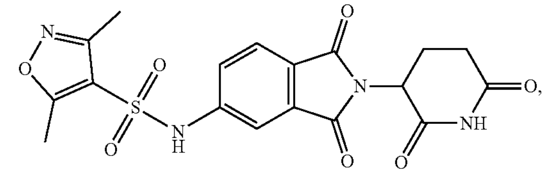
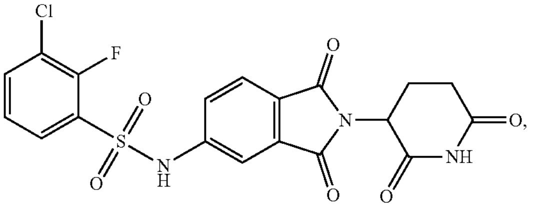
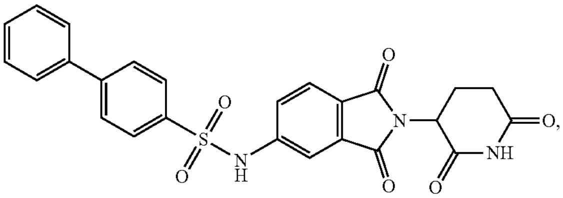
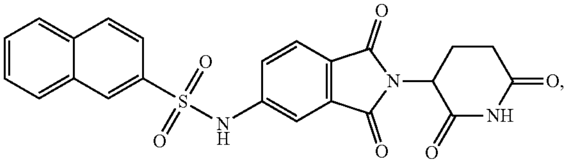
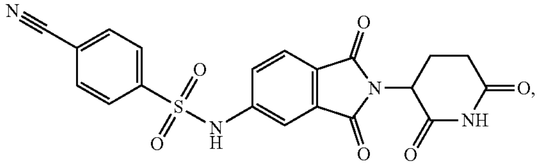
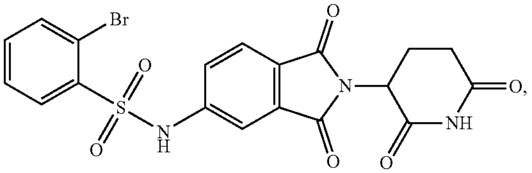
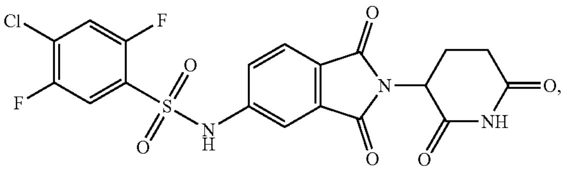
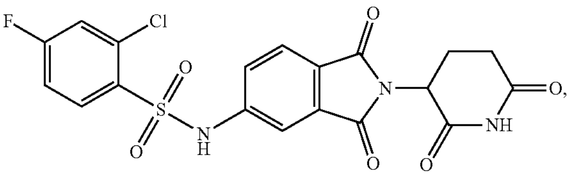
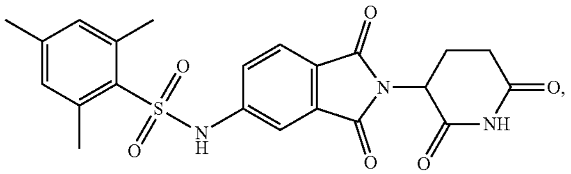
-continued
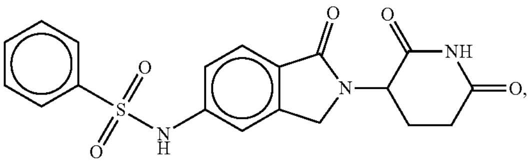
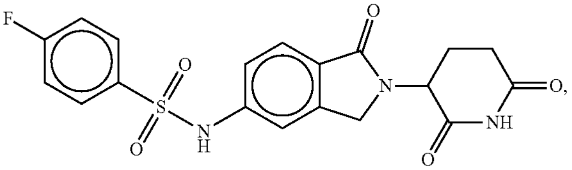
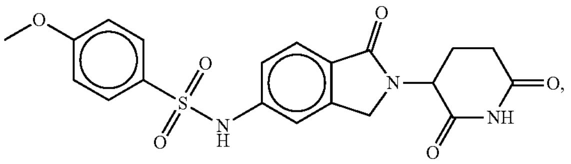
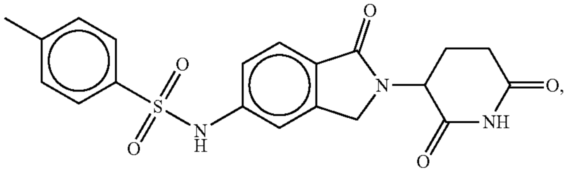
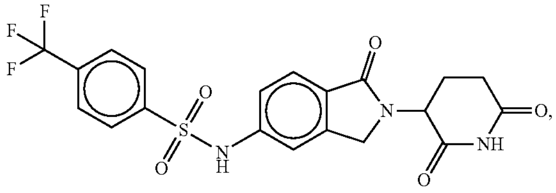
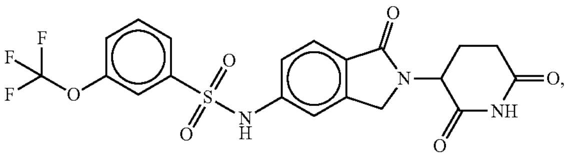
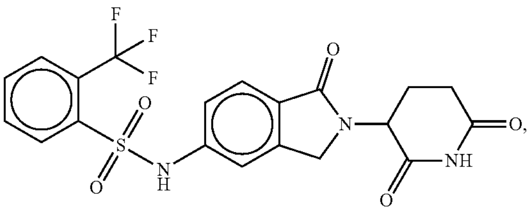
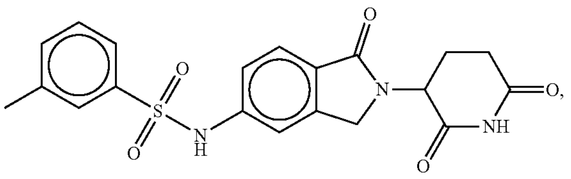
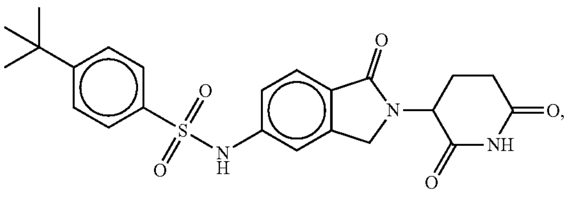

-continued
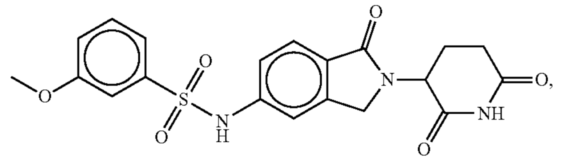
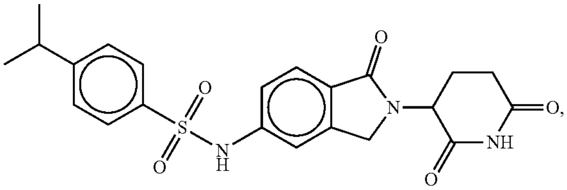
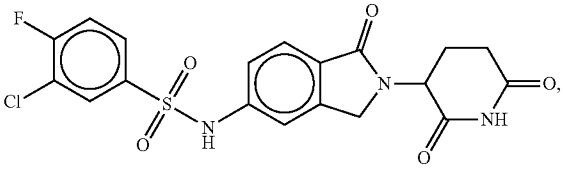
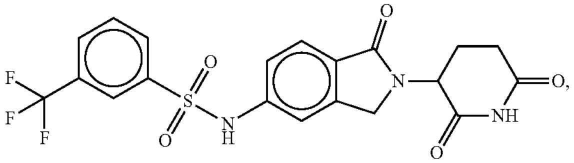
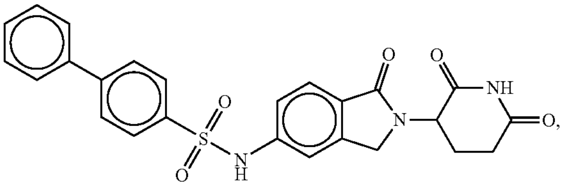
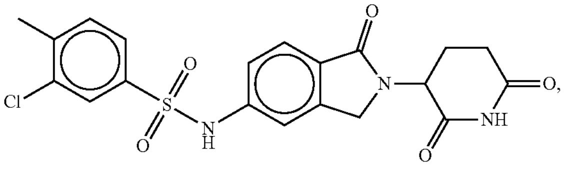
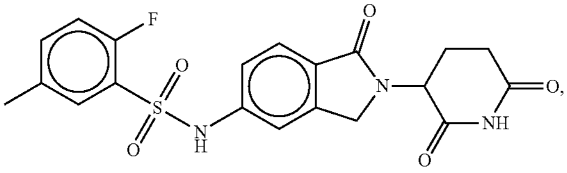
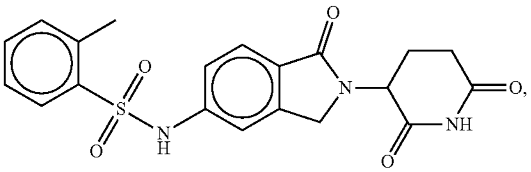
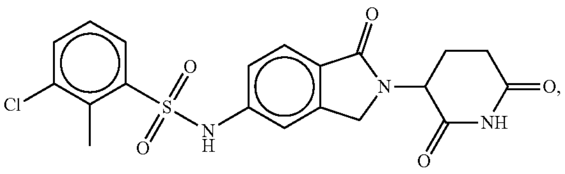
-continued
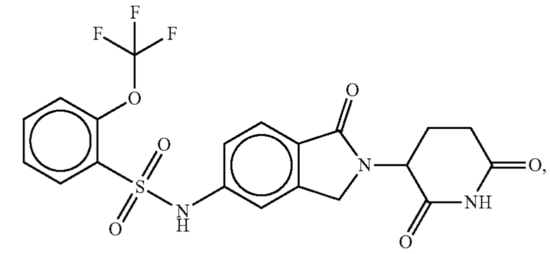
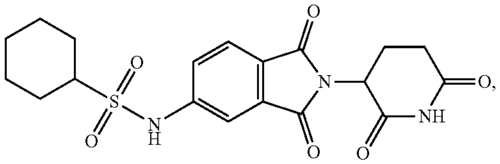
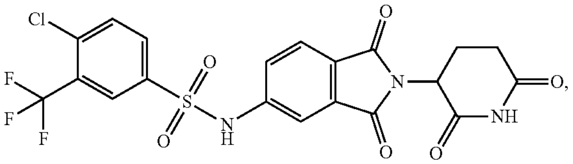
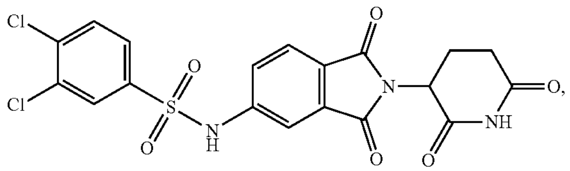
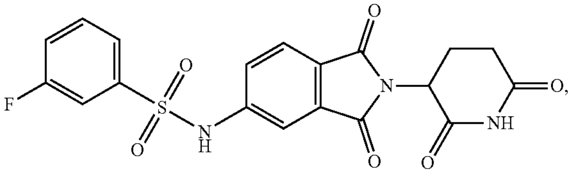
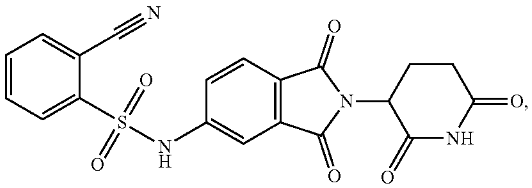
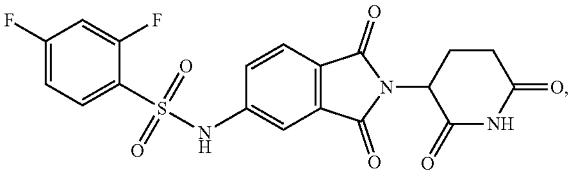
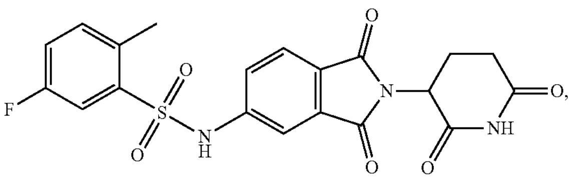
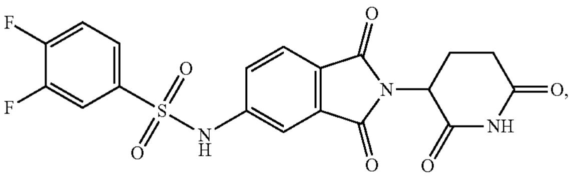

-continued
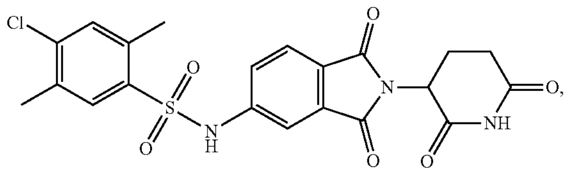
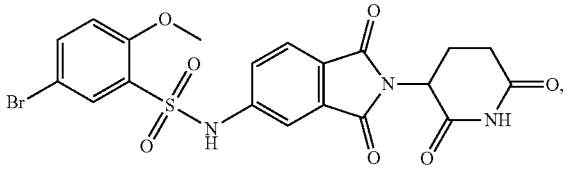
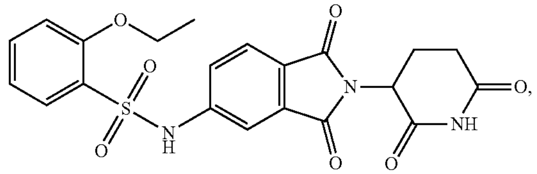
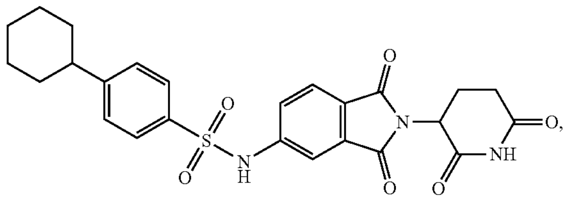
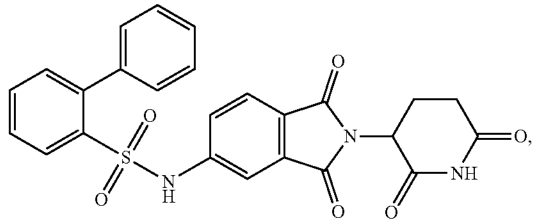
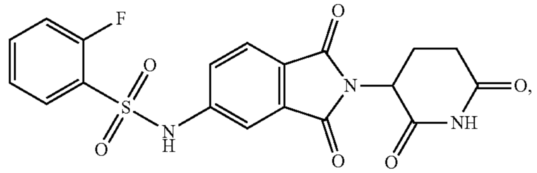
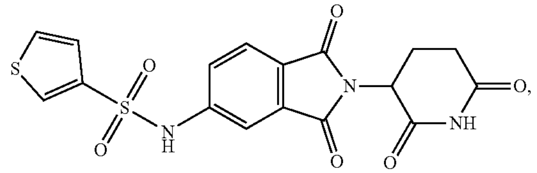
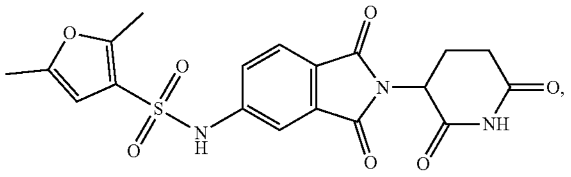
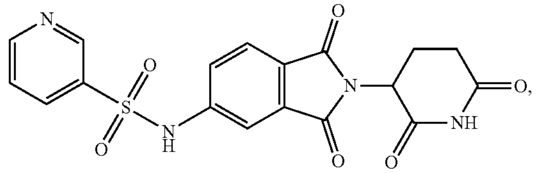
-continued
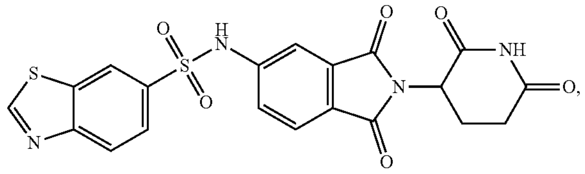
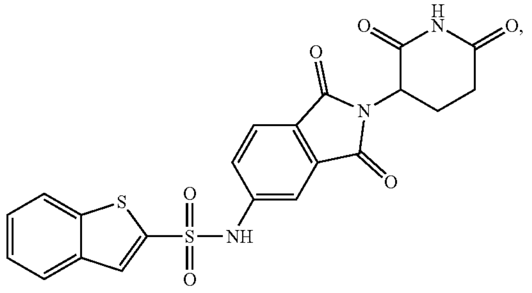
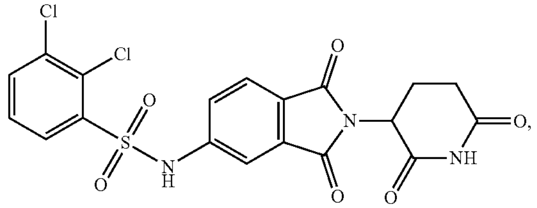
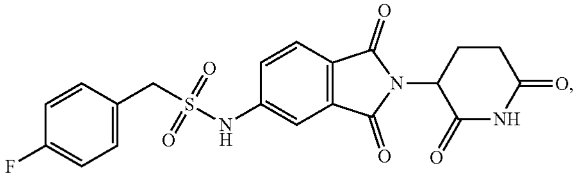
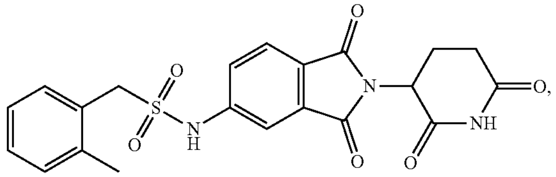
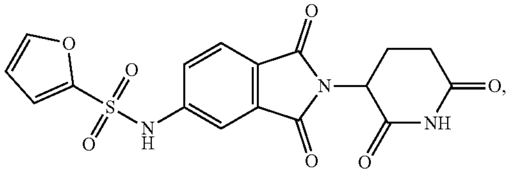
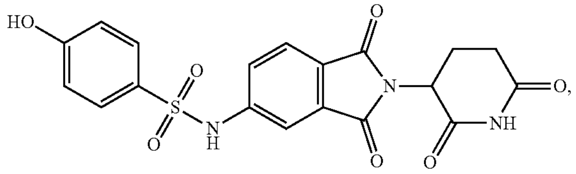
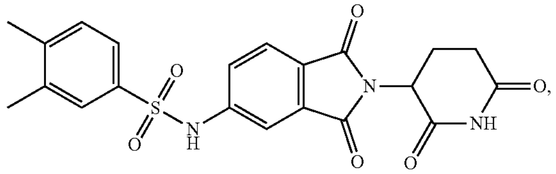
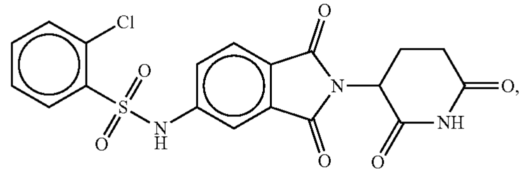

-continued
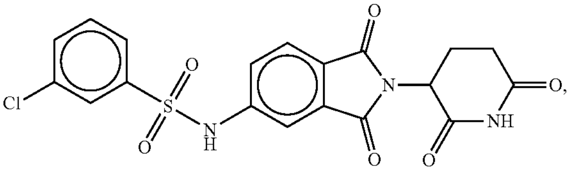
,
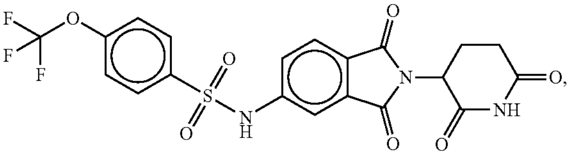
,
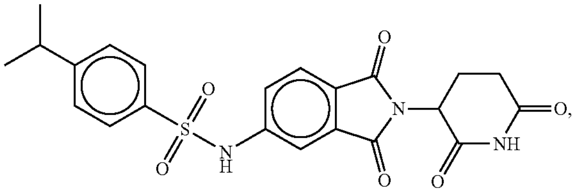
,
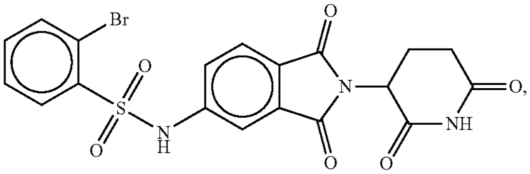
,
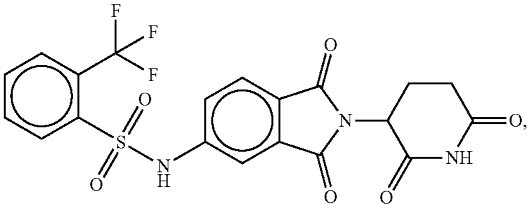
,
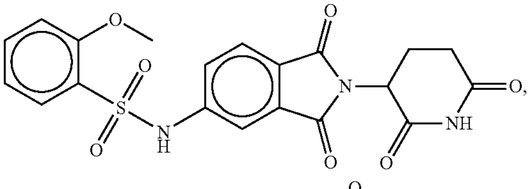
,
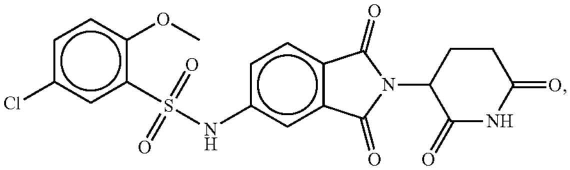
,
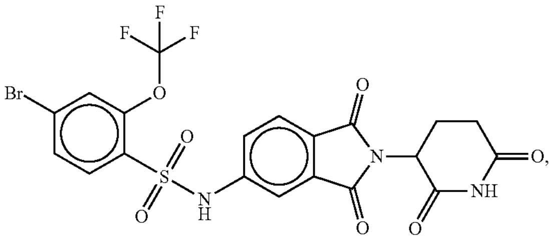
, or
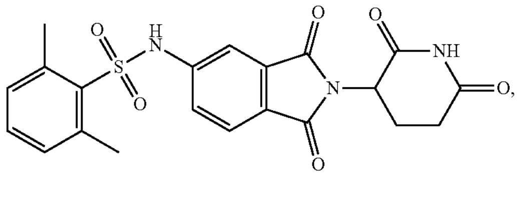
,
or a subgroup thereof.
In a further aspect, a disclosed compound has a structure given by:
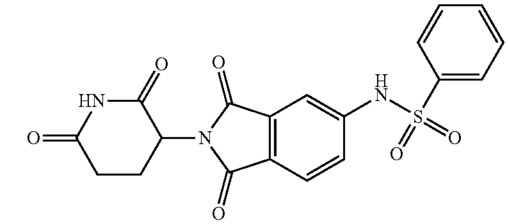
,
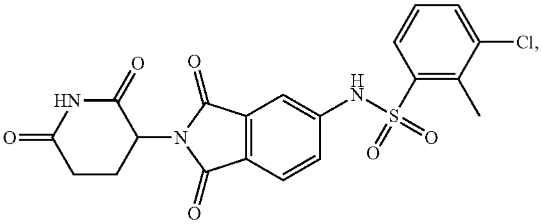
,
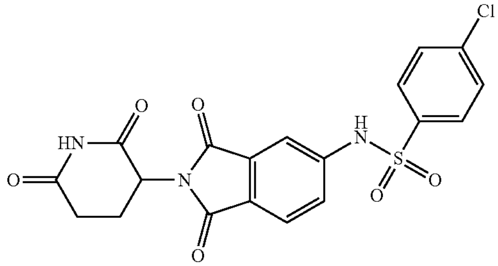
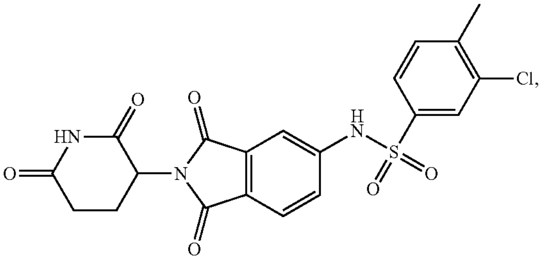
,
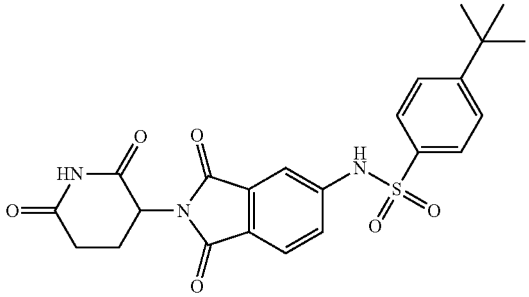
,
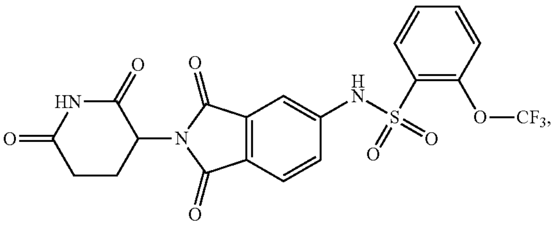
, -continued
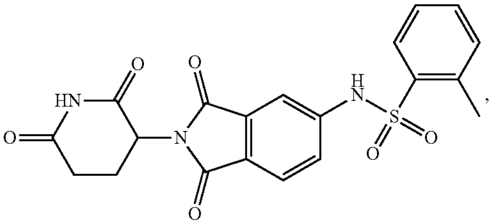
, or
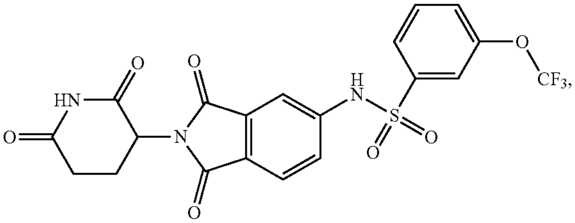
or a subgroup thereof.
In a further aspect, a disclosed compound has a structure given by:
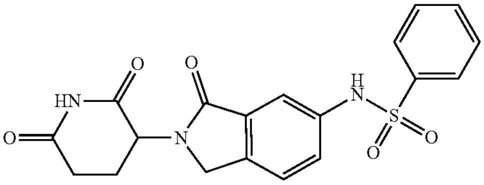
,
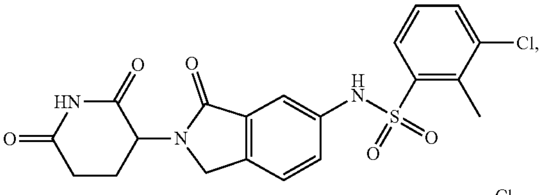
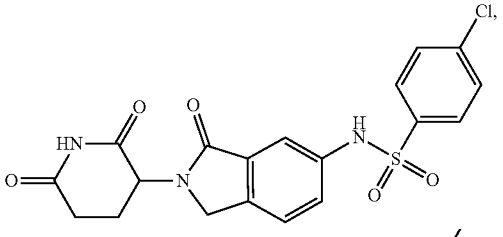
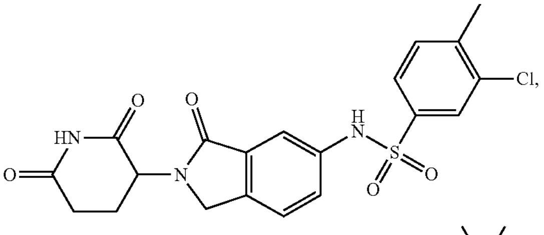
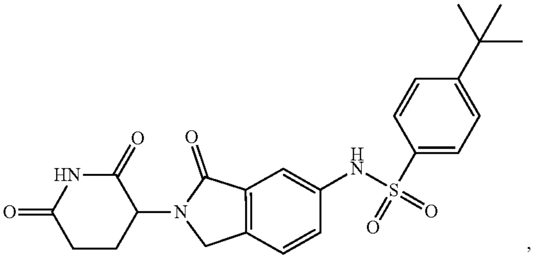
,
-continued
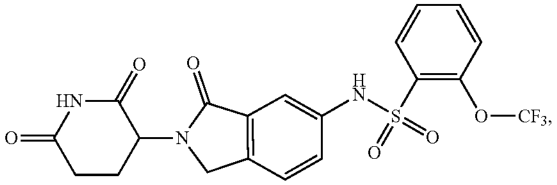
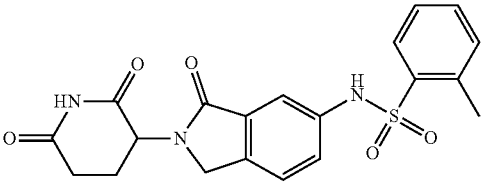
,
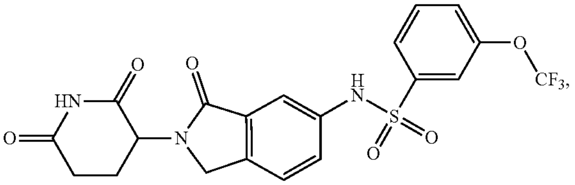
or a subgroup thereof.
In a further aspect, a disclosed compound has a structure given by:
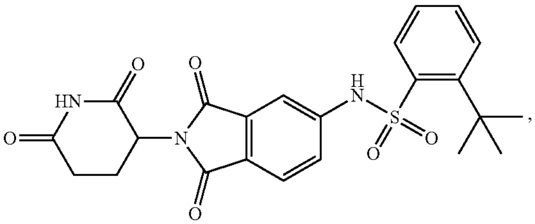
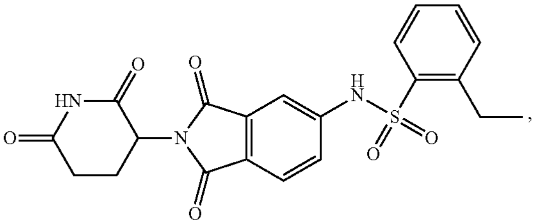
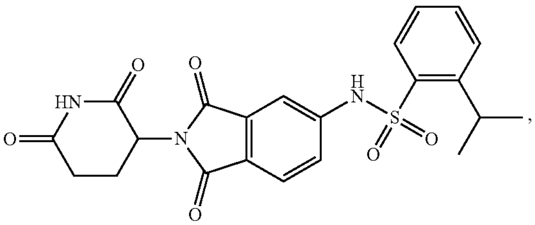
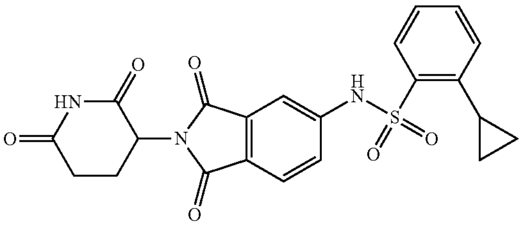
, -continued
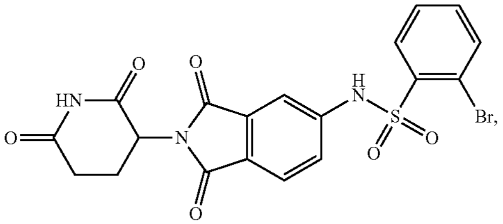
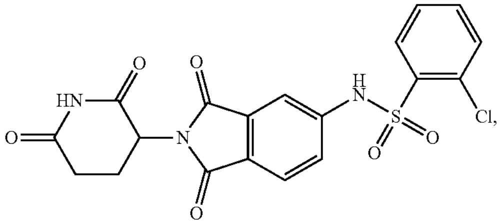
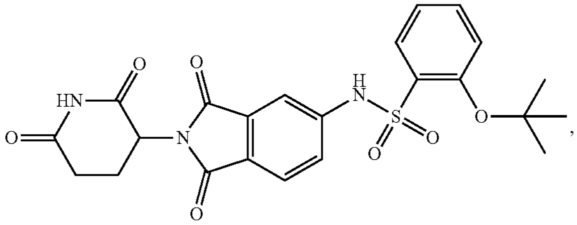
,
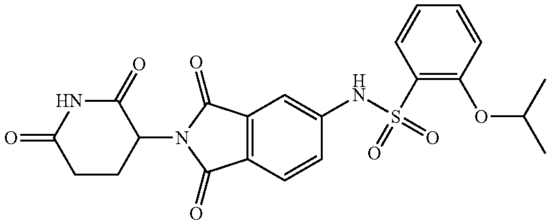
,
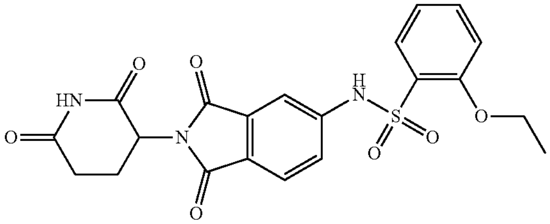
,
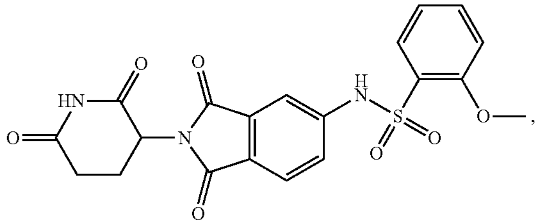
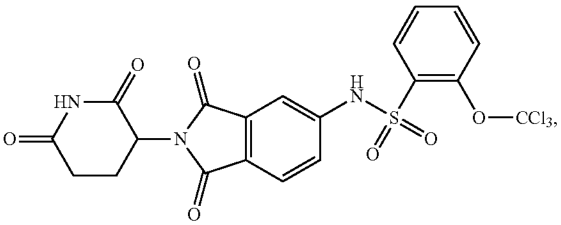
-continued
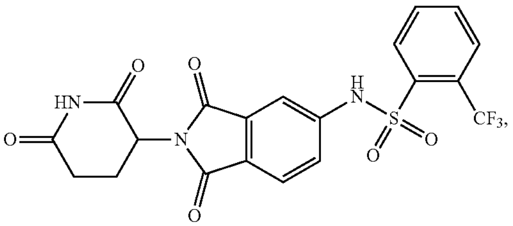
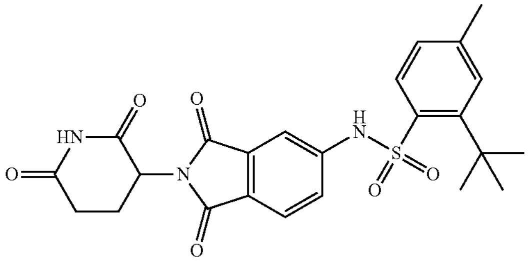
,
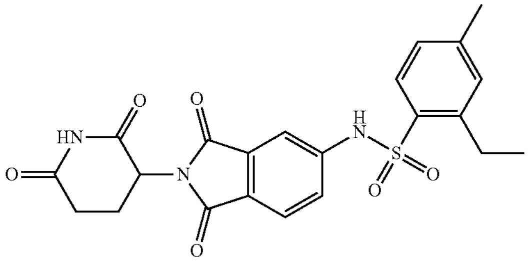
,
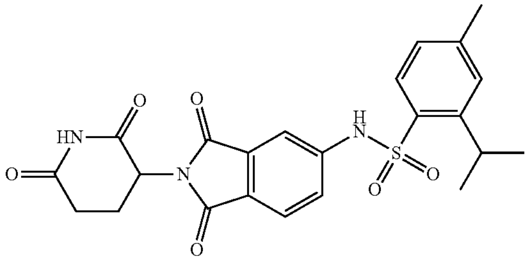
,
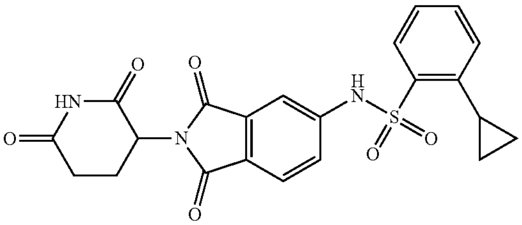
,
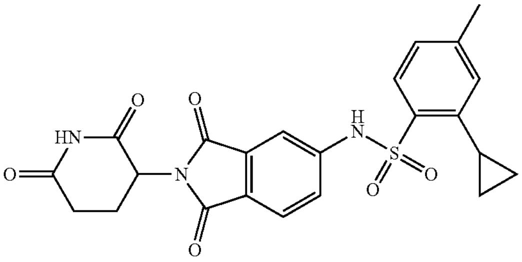
, -continued

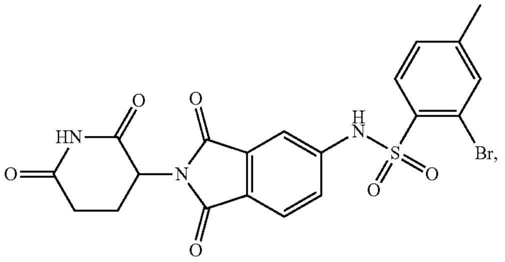

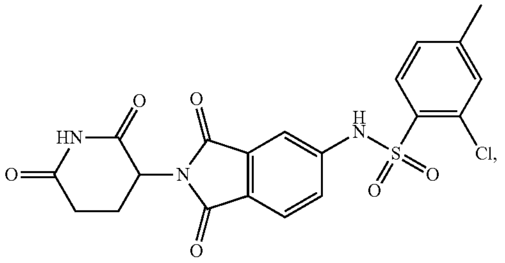

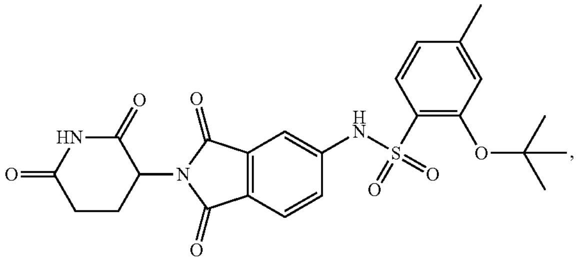

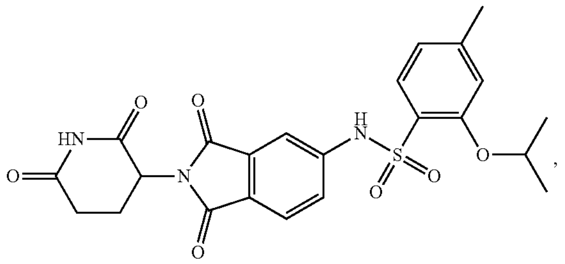

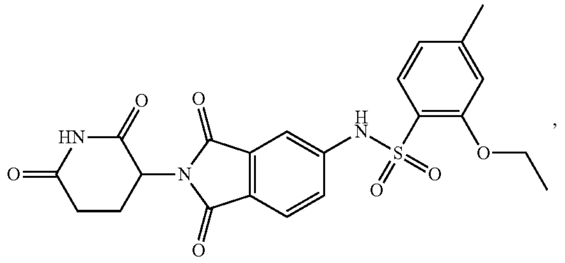

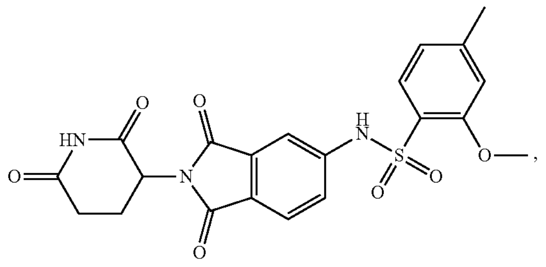

-continued

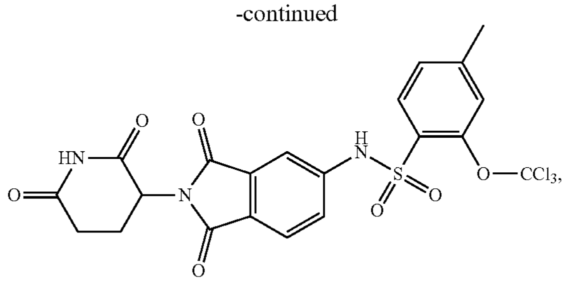

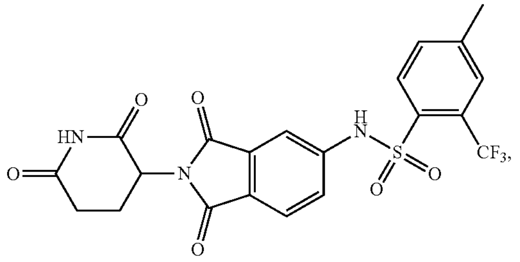

or

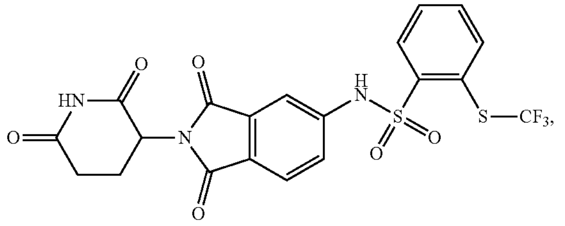

or a subgroup thereof.

In various aspects, it is contemplated herein that the disclosed compounds further comprise their biosteric equivalents. The term "bioisosteric equivalent" refers to compounds or groups that possess near equal molecular shapes and volumes, approximately the same distribution of electrons, and which exhibit similar physical and biological properties. Examples of such equivalents are: (i) fluorine vs. hydrogen, (ii) oxo vs. thia, (iii) hydroxyl vs. amide, (iv) carbonyl vs. oxime, (v) carboxylate vs. tetrazole. Examples of such bioisosteric replacements can be found in the literature and examples of such are: (i) Burger A, *Relation of chemical structure and biological activity*; in Medicinal Chemistry Third ed., Burger A, ed.; Wiley-Interscience; New York, 1970, 64-80; (ii) Burger, A.; "Isosterism and bioisosterism in drug design"; *Prog. Drug Res.* 1991, 37, 287-371; (iii) Burger A, "Isosterism and bioanalogy in drug design", *Med. Chem. Res.* 1994, 4, 89-92; (iv) Clark R D, Ferguson A M, Cramer R D, "Bioisosterism and molecular diversity", Perspect. *Drug Discovery Des.* 1998, 9/10/11, 213-224; (v) Koyanagi T, Haga T, "Bioisosterism in agrochemicals", *ACS Symp.* Ser. 1995, 584, 15-24; (vi) Kubinyi H, "Molecular similarities. Part 1. Chemical structure and biological activity", *Pharm. Unserer Zeit* 1998, 27, 92-106; (vii) Lipinski C A.; "Bioisosterism in drug design"; *Annu. Rep. Med. Chem.* 1986, 21, 283-91; (viii) Patani G A, LaVoie E J, "Bioisosterism: A rational approach in drug design", *Chem. Rev.* (Washington, D.C.) 1996, 96, 3147-3176; (ix) Soskic V, Joksimovic J, "Bioisosteric approach in the design of new dopaminergic/serotonergic ligands", *Curr. Med. Chem.* 1998, 5, 493-512 (x) Thornber C W, "Isosterism and molecular modification in drug design", *Chem. Soc. Rev.* 1979, 8, 563-80.

In further aspects, bioisosteres are atoms, ions, or molecules in which the peripheral layers of electrons can be considered substantially identical. The term bioisostere is usually used to mean a portion of an overall molecule, as opposed to the entire molecule itself. Bioisosteric replacement involves using one bioisostere to replace another with the expectation of maintaining or slightly modifying the biological activity of the first bioisostere. The bioisosteres in this case are thus atoms or groups of atoms having similar size, shape and electron density. Preferred bioisosteres of esters, amides or carboxylic acids are compounds containing two sites for hydrogen bond acceptance. In one embodiment, the ester, amide or carboxylic acid bioisostere is a 5-membered monocyclic heteroaryl ring, such as an optionally substituted 1H-imidazolyl, an optionally substituted oxazolyl, 1H-tetrazolyl, [1,2,4]triazolyl, or an optionally substituted [1,2,4]oxadiazolyl.

In various aspects, it is contemplated herein that the disclosed compounds further comprise their isotopically-labelled or isotopically-substituted variants, i.e., compounds identical to those described, but for the fact that one or more atoms are replaced by an atom having an atomic mass or mass number different from the atomic mass or mass number typically found in nature. Examples of isotopes that can be incorporated into compounds of the disclosure include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this disclosure. Certain isotopically-labelled compounds of the present disclosure, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present disclosure and prodrugs thereof can generally be prepared by carrying out the procedures below, by substituting a readily available isotopically labelled reagent for a non-isotopically labelled reagent.

In various aspects, the disclosed compounds can possess at least one center of asymmetry, they can be present in the form of their racemates, in the form of the pure enantiomers and/or diastereomers or in the form of mixtures of these enantiomers and/or diastereomers. The stereoisomers can be present in the mixtures in any arbitrary proportions. In some aspects, provided this is possible, the disclosed compounds can be present in the form of the tautomers.

Thus, methods which are known per se can be used, for example, to separate the disclosed compounds which possess one or more chiral centers and occur as racemates into their optical isomers, i.e., enantiomers or diastereomers. The separation can be effected by means of column separation on chiral phases or by means of recrystallization from an optically active solvent or using an optically active acid or base or by means of derivatizing with an optically active reagent, such as an optically active alcohol, and subsequently cleaving off the residue.

In various aspects, the disclosed compounds can be in the form of a co-crystal. The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Preferred co-crystals include p-toluenesulfonic acid and benzenesulfonic acid.

The term "pharmaceutically acceptable co-crystal" means one that is compatible with the other ingredients of the formulation and not deleterious to the recipient thereof.

In a further aspect, the disclosed compounds can be isolated as solvates and, in particular, as hydrates of a disclosed compound, which can be obtained, for example, by crystallization from a solvent or from aqueous solution. In this connection, one, two, three or any arbitrary number of solvate or water molecules can combine with the compounds according to the disclosure to form solvates and hydrates.

The disclosed compounds can be used in the form of salts derived from inorganic or organic acids. Pharmaceutically acceptable salts include salts of acidic or basic groups present in the disclosed compounds. Suitable pharmaceutically acceptable salts include base addition salts, including alkali metal salts, e.g., sodium or potassium salts; alkaline earth metal salts, e.g., calcium or magnesium salts; and salts formed with suitable organic ligands, e.g., quaternary ammonium salts, which may be similarly prepared by reacting the drug compound with a suitable pharmaceutically acceptable base. The salts can be prepared in situ during the final isolation and purification of the compounds of the present disclosure; or following final isolation by reacting a free base function, such as a secondary or tertiary amine, of a disclosed compound with a suitable inorganic or organic acid; or reacting a free acid function, such as a carboxylic acid, of a disclosed compound with a suitable inorganic or organic base.

Acidic addition salts can be prepared in situ during the final isolation and purification of a disclosed compound, or separately by reacting moieties comprising one or more nitrogen groups with a suitable acid. In various aspects, acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. In a further aspect, salts further include, but are not limited, to the following: hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, butyrate, camphorate, camphorsulfonate, digluconate, glycerophosphate, hemisulfate, heptanoate, hexanoate, fumarate, hydrochloride, 2-hydroxyethanesulfonate (isethionate), nicotinate, 2-naphthalenesulfonate, oxalate, pectinate, persulfate, 3-phenylpropionate, picrate, pivalate, propionate, succinate, tartrate, thiocyanate, phosphate, glutamate, bicarbonate, undecanoate, and pamoate (i.e., 1,1'-methylene-bis-(2-hydroxy-3-naphthoate)) salts. Also, basic nitrogen-containing groups can be quatemized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others.

Basic addition salts can be prepared in situ during the final isolation and purification of a disclosed compound, or separately by reacting carboxylic acid moieties with a suitable base such as the hydroxide, carbonate or bicarbonate of a pharmaceutical acceptable metal cation or with ammonia, or an organic primary, secondary or tertiary amine. Pharmaceutical acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like. In further aspects, bases which may be used in the preparation of pharmaceutically acceptable salts include the following: ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

D. Methods of Making the Compounds

In one aspect, the disclosure relates to methods of making compounds useful as antibacterial agents, which can be useful in the treatment of bacterial infections. In one aspect, the disclosure relates to the disclosed synthetic manipulations. In a further aspect, the disclosed compounds comprise the products of the synthetic methods described herein.

In a further aspect, the disclosed compounds comprise a compound produced by a synthetic method described herein. In a still further aspect, the disclosure comprises a pharmaceutical composition comprising a therapeutically effective amount of the product of the disclosed methods and a pharmaceutically acceptable carrier. In a still further aspect, the disclosure comprises a method for manufacturing a medicament comprising combining at least one product of the disclosed methods with a pharmaceutically acceptable carrier or diluent.

The compounds of this disclosure can be prepared by employing reactions as shown in the disclosed schemes, in addition to other standard manipulations that are known in the literature, exemplified in the experimental sections or clear to one skilled in the art. For clarity, examples having a fewer substituent can be shown where multiple substituents are allowed under the definitions disclosed herein. Thus, the following examples are provided so that the disclosure might be more fully understood, are illustrative only, and should not be construed as limiting.

It is contemplated that each disclosed method can further comprise additional steps, manipulations, and/or components. It is also contemplated that any one or more step, manipulation, and/or component can be optionally omitted from the disclosure. It is understood that a disclosed method can be used to provide the disclosed compounds. It is also understood that the products of the disclosed methods can be employed in the disclosed compositions, kits, and uses.

Synthesis Route 1

In one aspect, a useful intermediate for the preparation of aryl substituted aminomethyl spectinomycin analogues of the present disclosure can be prepared generically by the synthesis scheme as shown below. All positions are defined herein.

SCHEME 1A

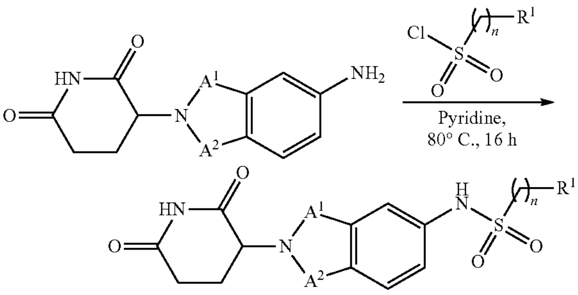

Compounds are represented in generic form, with substituents as noted in compound descriptions elsewhere herein. A more specific example is set forth below.

SCHEME 1B

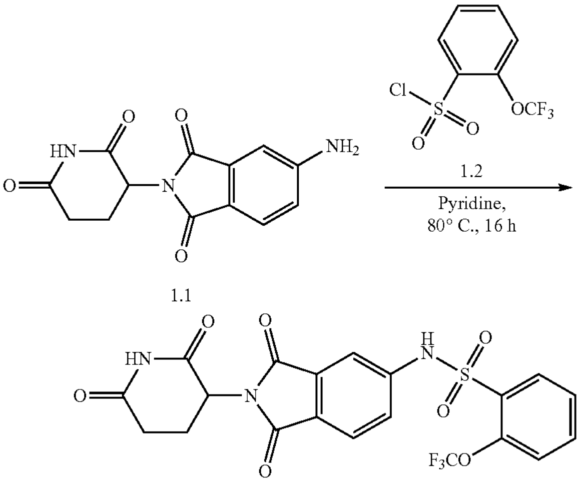

1.1

1.3

A substituted N-(2-(2,6-dioxopiperidinyl-3-yl)-1,3-dioxoisoindolin-5-yl)arylsulfonamide analog of the present disclosure, e.g. compound 1.3 in reaction Scheme 1B above, and related compounds, can be prepared beginning with a 5-amino-2-(2,6-dioxopiperidin-3-yl)isoindoline-1,3-dione, compound 1.1, and reacting with a suitable sulfonyl chloride, compound 1.2, in a suitable solvent, e.g., pyridine, and carried out for a suitable period of time, e.g., 8-24 hours, at a suitable temperature, e.g., about 70° C. to about 100° C., under an inert atmosphere, e.g., under nitrogen. Following reaction, the reaction mixture can be concentrated to dryness (or an oil) and the resulting solid (or oil) reconstituted (or diluted) in a suitable solvent, e.g., DMSO. Further purification can be carried out as described in detail in the Examples, i.e., using a Waters purification/analytical LC/UV/ELSD system and parallel evaporations were carried out using a Genevac HT-24. Other purification methods as known to the skilled artisan can be used in the alternative, e.g., recrystallization. As can be appreciated by one skilled in the art, alternative or modified conditions can be used for the above reaction.

It is contemplated that each disclosed method can further comprise additional steps, manipulations, and/or components. It is also contemplated that any one or more step, manipulation, and/or component can be optionally omitted from the disclosure. It is understood that a disclosed method can be used to provide the disclosed compounds. It is also understood that the products of the disclosed methods can be employed in the disclosed methods of using.

E. Pharmaceutical Compositions

In various aspects, the present disclosure relates to pharmaceutical compositions comprising a therapeutically effective amount of at least one disclosed compound, at least one product of a disclosed method, or a pharmaceutically acceptable salt thereof. As used herein, "pharmaceutically-acceptable carriers" means one or more of a pharmaceutically acceptable diluents, preservatives, antioxidants, solubilizers, emulsifiers, coloring agents, releasing agents, coating agents, sweetening, flavoring and perfuming agents, and adjuvants. The disclosed pharmaceutical compositions can be conveniently presented in unit dosage form and prepared by any of the methods well known in the art of pharmacy and pharmaceutical sciences.

In a further aspect, the disclosed pharmaceutical compositions comprise a therapeutically effective amount of at least one disclosed compound, at least one product of a disclosed method, or a pharmaceutically acceptable salt thereof as an active ingredient, a pharmaceutically acceptable carrier, optionally one or more other therapeutic agent, and optionally one or more adjuvant. The disclosed pharmaceutical compositions include those suitable for oral, rectal, topical, pulmonary, nasal, and parenteral administration, although the most suitable route in any given case will depend on the particular host, and nature and severity of the conditions for which the active ingredient is being administered. In a further aspect, the disclosed pharmaceutical composition can be formulated to allow administration orally, nasally, via inhalation, parenterally, paracancerally, transmucosally, transdermally, intramuscularly, intravenously, intradermally, subcutaneously, intraperitonealy, intraventricularly, intracranially and intratumorally.

As used herein, "parenteral administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

In various aspects, the present disclosure also relates to a pharmaceutical composition comprising a pharmaceutically acceptable carrier or diluent and, as active ingredient, a therapeutically effective amount of a disclosed compound, a product of a disclosed method of making, a pharmaceutically acceptable salt, a hydrate thereof, a solvate thereof, a polymorph thereof, or a stereochemically isomeric form thereof. In a further aspect, a disclosed compound, a product of a disclosed method of making, a pharmaceutically acceptable salt, a hydrate thereof, a solvate thereof, a polymorph thereof, or a stereochemically isomeric form thereof, or any subgroup or combination thereof may be formulated into various pharmaceutical forms for administration purposes.

Pharmaceutically acceptable salts can be prepared from pharmaceutically acceptable non-toxic bases or acids. For therapeutic use, salts of the disclosed compounds are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are contemplated by the present disclosure. Pharmaceutically acceptable acid and base addition salts are meant to comprise the therapeutically active non-toxic acid and base addition salt forms which the disclosed compounds are able to form.

In various aspects, a disclosed compound comprising an acidic group or moiety, e.g., a carboxylic acid group, can be used to prepare a pharmaceutically acceptable salt. For example, such a disclosed compound may comprise an isolation step comprising treatment with a suitable inorganic or organic base. In some cases, it may be desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before.

Bases which can be used to prepare the pharmaceutically acceptable base-addition salts of the base compounds are those which can form non-toxic base-addition salts, i.e., salts containing pharmacologically acceptable cations such as, alkali metal cations (e.g., lithium, potassium and sodium), alkaline earth metal cations (e.g., calcium and magnesium), ammonium or other water-soluble amine addition salts such as N-methylglucamine-(meglumine), lower alkanolammonium and other such bases of organic amines. In a further aspect, derived from pharmaceutically acceptable organic non-toxic bases include primary, secondary, and tertiary amines, as well as cyclic amines and substituted amines such as naturally occurring and synthesized substituted amines. In various aspects, such pharmaceutically acceptable organic non-toxic bases include, but are not limited to, ammonia, methylamine, ethylamine, propylamine, isopropylamine, any of the four butylamine isomers, betaine, caffeine, choline, dimethylamine, diethylamine, diethanolamine, dipropylamine, diisopropylamine, di-n-butylamine, N,N'-dibenzylethylenediamine, pyrrolidine, piperidine, morpholine, trimethylamine, triethylamine, tripropylamine, tromethamine, 2-diethylaminoethanol, 2-dimethylaminoethanol, ethanolamine, quinuclidine, pyridine, quinoline and isoquinoline; benzathine, N-methyl-D-glucamine, ethylenediamine, N-ethylmorpholine, N-ethylpiperidine, glucamine, glucosamine, methylglucamine, morpholine, piperazine, piperidine, polyamine resins, procaine, purines, theobromine, hydrabamine salts, and salts with amino acids such as, for example, histidine, arginine, lysine and the like. The foregoing salt forms can be converted by treatment with acid back into the free acid form.

In various aspects, a disclosed compound comprising a protonatable group or moiety, e.g., an amino group, can be used to prepare a pharmaceutically acceptable salt. For example, such a disclosed compound may comprise an isolation step comprising treatment with a suitable inorganic or organic acid. In some cases, it may be desirable in practice to initially isolate a compound from the reaction mixture as a pharmaceutically unacceptable salt and then simply convert the latter back to the free base compound by treatment with an basoc reagent, and subsequently convert the free base to a pharmaceutically acceptable acid addition salt. These acid addition salts can be readily prepared using conventional techniques, e.g., by treating the corresponding basic compounds with an aqueous solution containing the desired pharmacologically acceptable anions and then evaporating the resulting solution to dryness, preferably under reduced pressure. Alternatively, they also can be prepared by treating the free base form of the disclosed compound with a suitable pharmaceutically acceptable non-toxic inorganic or organic acid.

Acids which can be used to prepare the pharmaceutically acceptable acid-addition salts of the base compounds are those which can form non-toxic acid-addition salts, i.e., salts containing pharmacologically acceptable anions formed from their corresponding inorganic and organic acids. Exemplary, but non-limiting, inorganic acids include hydrochloric hydrobromic, sulfuric, nitric, phosphoric and the like. Exemplary, but non-limiting, organic acids include acetic, benzenesulfonic, benzoic, camphorsulfonic, citric, ethanesulfonic, fumaric, gluconic, glutamic, isethionic, lactic, maleic, malic, mandelicmethanesulfonic, mucic, pamoic, pantothenic, succinic, tartaric, p-toluenesulfonic acid and the like. In a further aspect, the acid-addition salt comprises an anion formed from hydrobromic, hydrochloric, maleic, phosphoric, sulfuric, and tartaric acids.

In practice, the compounds of the present disclosure, or pharmaceutically acceptable salts thereof, of the present disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the present disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. The term "unit dosage form," as used herein, refers to physically discrete units suitable as unitary dosages, each unit containing a predetermined quantity of active ingredient calculated to produce the desired therapeutic effect in association with the required pharmaceutical carrier. That is, a "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets (including scored or coated tablets), capsules or pills for oral administration; single dose vials for injectable solutions or suspension; suppositories for rectal administration; powder packets; wafers; and segregated multiples thereof. This list of unit dosage forms is not intended to be limiting in any way, but merely to represent typical examples of unit dosage forms.

The pharmaceutical compositions disclosed herein comprise a compound of the present disclosure (or pharmaceutically acceptable salts thereof) as an active ingredient, a pharmaceutically acceptable carrier, and optionally one or more additional therapeutic agents. In various aspects, the disclosed pharmaceutical compositions can include a pharmaceutically acceptable carrier and a disclosed compound, or a pharmaceutically acceptable salt thereof. In a further aspect, a disclosed compound, or pharmaceutically acceptable salt thereof, can also be included in a pharmaceutical composition in combination with one or more other therapeutically active compounds. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Techniques and compositions for making dosage forms useful for materials and methods described herein are described, for example, in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Because of the ease in administration, oral administration can be a preferred dosage form, and tablets and capsules represent the most advantageous oral dosage unit forms in which case solid pharmaceutical carriers are obviously employed. However, other dosage forms may be suitable depending upon clinical population (e.g., age and severity of clinical condition), solubility properties of the specific disclosed compound used, and the like. Accordingly, the disclosed compounds can be used in oral dosage forms such as pills, powders, granules, elixirs, tinctures, suspensions, syrups, and emulsions. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

The disclosed pharmaceutical compositions in an oral dosage form can comprise one or more pharmaceutical excipient and/or additive. Non-limiting examples of suitable excipients and additives include gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentacrythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with 01-012-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances useful in preparing an oral dosage form are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example EudragitR RS), copolymerizates of acrylic and methacrylic acid esters and trimethyl ammonium methacrylate (for example EudragitR RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances in the disclosed oral dosage forms are: citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. In a further aspect, a disintegrator can include, for example, starch, methyl cellulose, agar, bentonite, xanthan gum, and the like.

In various aspects, an oral dosage form, such as a solid dosage form, can comprise a disclosed compound that is attached to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a disclosed compound can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In various aspects, a solid oral dosage form, such as a tablet, can be coated with an enteric coating to prevent ready decomposition in the stomach. In various aspects, enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa "Application of solid dispersions of Nifedipine with enteric coating agent to prepare a sustained-release dosage form" Chem. Pharm. Bull. 33:1615-1619 (1985). Various enteric coating materials may be selected on the basis of testing to achieve an enteric coated dosage form designed ab initio to have a preferable combination of dissolution time, coating thicknesses and diametral crushing strength (e.g., see S. C. Porter et al. "The Properties of Enteric Tablet Coatings Made From Polyvinyl Acetate-phthalate and Cellulose acetate Phthalate", J. Pharm. Pharmacol. 22:42p (1970)). In a further aspect, the enteric coating may comprise hydroxypropylmethylcellulose phthalate, methacrylic acid-methacrylic acid ester copolymer, polyvinyl acetate-phthalate and cellulose acetate phthalate.

In various aspects, an oral dosage form can be a solid dispersion with a water soluble or a water insoluble carrier. Examples of water soluble or water insoluble carrier include, but are not limited to, polyethylene glycol, polyvinylpyrrolidone, hydroxypropylmethyl-cellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

In various aspects, an oral dosage form can be in a liquid dosage form, including those that are ingested, or alternatively, administered as a mouth wash or gargle. For example, a liquid dosage form can include aqueous suspensions, which contain the active materials in admixture with excipients suitable for the manufacture of aqueous suspensions. In addition, oily suspensions may be formulated by suspending the active ingredient in a vegetable oil, for example *arachis* oil, olive oil, sesame oil or coconut oil, or in a mineral oil such as liquid paraffin. Oily suspensions may also contain various excipients. The pharmaceutical compositions of the present disclosure may also be in the form of oil-in-water emulsions, which may also contain excipients such as sweetening and flavoring agents.

For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulphoxide, triglycerides and the like.

In the case of a liquid dosage form such as a drinkable solutions, the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic C1-C6-carboxylic acids with ammonia or primary, secondary or tertiary C1-C4-amines or C1-C4-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, tromethamine (for example as 0.1 to 20% aqueous solution), aliphatic amino acids.

In preparing the disclosed liquid dosage form can comprise solubilizers and emulsifiers such as the following non-limiting examples can be used: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20. Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride). Examples of oleotriglycerides are olive oil, peanut oil, castor oil, sesame oil, cottonseed oil, corn oil. See also Dr. H. P. Fiedler "Lexikon der Hillsstoffe für Pharmazie, Kostnetik and angrenzende Gebiete" 1971, pages 191-195.

In various aspects, a liquid dosage form can further comprise preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

It may optionally be necessary to stabilize a liquid dosage form with physiologically acceptable bases or buffers to a pH range of approximately 6 to 9. Preference may be given to as neutral or weakly basic a pH value as possible (up to pH 8).

In order to enhance the solubility and/or the stability of a disclosed compound in a disclosed liquid dosage form, a parenteral injection form, or an intravenous injectable form, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the present disclosure in pharmaceutical compositions.

In various aspects, a disclosed liquid dosage form, a parenteral injection form, or an intravenous injectable form can further comprise liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Pharmaceutical compositions of the present disclosure suitable injection, such as parenteral administration, such as intravenous, intramuscular, or subcutaneous administration. Pharmaceutical compositions for injection can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for parenteral administration can include sterile aqueous or oleaginous solutions, suspensions, or dispersions. Furthermore, the compositions can be in the form of sterile powders for the extemporaneous preparation of such sterile injectable solutions or dispersions. In some aspects, the final injectable form is sterile and must be effectively fluid for use in a syringe. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. In some aspects, a disclosed parenteral formulation can comprise about 0.01-0.1 M, e.g. about 0.05 M, phosphate buffer. In a further aspect, a disclosed parenteral formulation can comprise about 0.9% saline.

In various aspects, a disclosed parenteral pharmaceutical composition can comprise pharmaceutically acceptable carriers such as aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but not limited to water, alcoholic/aqueous solutions, emulsions or suspensions, including saline and buffered media. Parenteral vehicles can include mannitol, normal serum albumin, sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like. In a further aspect, a disclosed parenteral pharmaceutical composition can comprise may contain minor amounts of additives such as substances that enhance isotonicity and chemical stability, e.g., buffers and preservatives. Also contemplated for injectable pharmaceutical compositions are solid form preparations that are intended to be converted, shortly before use, to liquid form preparations. Furthermore, other adjuvants can be included to render the formulation isotonic with the blood of the subject or patient.

In addition to the pharmaceutical compositions described herein above, the disclosed compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, e.g., as a sparingly soluble salt.

Pharmaceutical compositions of the present disclosure can be in a form suitable for topical administration. As used herein, the phrase "topical application" means administration onto a biological surface, whereby the biological surface includes, for example, a skin area (e.g., hands, forearms, elbows, legs, face, nails, anus and genital areas) or a mucosal membrane. By selecting the appropriate carrier and optionally other ingredients that can be included in the composition, as is detailed herein below, the compositions of the present disclosure may be formulated into any form typically employed for topical application. A topical pharmaceutical composition can be in a form of a cream, an ointment, a paste, a gel, a lotion, milk, a suspension, an aerosol, a spray, foam, a dusting powder, a pad, and a patch. Further, the compositions can be in a form suitable for use in transdermal devices. These formulations can be prepared, utilizing a compound of the present disclosure, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emollience). As with other carriers or vehicles, an ointment base should be inert, stable, nonirritating and nonsensitizing. As explained in Remington: The Science and Practice of Pharmacy, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the active agent, are present in a water or alcohol base. Lotions are typically preferred for treating large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethylcellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to Remington: The Science and Practice of Pharmacy, supra, for further information.

Pastes are semisolid dosage forms in which the bioactive agent is suspended in a suitable base. Depending on the nature of the base, pastes are divided between fatty pastes or those made from a single-phase aqueous gel. The base in a fatty paste is generally petrolatum, hydrophilic petrolatum and the like. The pastes made from single-phase aqueous gels generally incorporate carboxymethylcellulose or the like as a base. Additional reference may be made to Remington: The Science and Practice of Pharmacy, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; modified cellulose, such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or aqueous alkanolic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. Patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Examples of patch configuration which can be utilized with the present disclosure include a single-layer or multi-layer drug-in-adhesive systems which are characterized by the inclusion of the drug directly within the skin-contacting adhesive. In such a transdermal patch design, the adhesive not only serves to affix the patch to the skin, but also serves as the formulation foundation, containing the drug and all the excipients under a single backing film. In the multi-layer drug-in-adhesive patch a membrane is disposed between two distinct drug-in-adhesive layers or multiple drug-in-adhesive layers are incorporated under a single backing film.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition. Representative examples of suitable carriers according to the present disclosure therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers according to the present disclosure include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

Topical compositions of the present disclosure can, if desired, be presented in a pack or dispenser device, such as an FDA-approved kit, which may contain one or more unit dosage forms containing the active ingredient. The dispenser device may, for example, comprise a tube. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising the topical composition of the disclosure formulated in a pharmaceutically acceptable carrier may also be prepared, placed in an appropriate container, and labeled for treatment of an indicated condition.

Another patch system configuration which can be used by the present disclosure is a reservoir transdermal system design which is characterized by the inclusion of a liquid compartment containing a drug solution or suspension separated from the release liner by a semi-permeable membrane and adhesive. The adhesive component of this patch system can either be incorporated as a continuous layer between the membrane and the release liner or in a concentric configuration around the membrane. Yet another patch system configuration which can be utilized by the present disclosure is a matrix system design which is characterized by the inclusion of a semisolid matrix containing a drug solution or suspension which is in direct contact with the release liner. The component responsible for skin adhesion is incorporated in an overlay and forms a concentric configuration around the semisolid matrix.

Pharmaceutical compositions of the present disclosure can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Pharmaceutical compositions containing a compound of the present disclosure, and/or pharmaceutically acceptable salts thereof, can also be prepared in powder or liquid concentrate form.

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The disclosed pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Pharmaceutical compositions comprising a disclosed compound formulated in a compatible pharmaceutical carrier may also be prepared, placed in an appropriate container, and labeled for treatment of an indicated condition.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the present disclosure.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In the treatment conditions which require of modulation of cereblon protein an appropriate dosage level will generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 mg of the active ingredient, particularly 1.0, 5.0, 10, 15, 20, 25, 50, 75, 100, 150, 200, 250, 300, 400, 500, 600, 750, 800, 900 and 1000 mg of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

In the treatment conditions which require of modulation of GSPT1 activity an appropriate dosage level will generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 mg of the active ingredient, particularly 1.0, 5.0, 10, 15, 20, 25, 50, 75, 100, 150, 200, 250, 300, 400, 500, 600, 750, 800, 900 and 1000 mg of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

In the treatment conditions which require of inhibition of cellular proliferation an appropriate dosage level will generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 mg of the active ingredient, particularly 1.0, 5.0, 10, 15, 20, 25, 50, 75, 100, 150, 200, 250, 300, 400, 500, 600, 750, 800, 900 and 1000 mg of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

Such unit doses as described hereinabove and hereinafter can be administered more than once a day, for example, 2, 3, 4, 5 or 6 times a day. In various aspects, such unit doses can be administered 1 or 2 times per day, so that the total dosage for a 70 kg adult is in the range of 0.001 to about 15 mg per kg weight of subject per administration. In a further aspect, dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The present disclosure is further directed to a method for the manufacture of a medicament for modulating cereblon protein (e.g., treatment of one or more disorders associated with a cereblon function or dysfunction, such as a cancer) in mammals (e.g., humans) comprising combining one or more disclosed compounds, products, or compositions with a pharmaceutically acceptable carrier or diluent. Thus, in one aspect, the present disclosure further relates to a method for manufacturing a medicament comprising combining at least one disclosed compound or at least one disclosed product with a pharmaceutically acceptable carrier or diluent, wherein the medicament is useful for modulation of cereblon protein.

The present disclosure is further directed to a method for the manufacture of a medicament for modulating GSPT1 (e.g., treatment of one or more disorders associated with a cereblon function or dysfunction, such as a cancer) in mammals (e.g., humans) comprising combining one or more disclosed compounds, products, or compositions with a pharmaceutically acceptable carrier or diluent. Thus, in one aspect, the present disclosure further relates to a method for manufacturing a medicament comprising combining at least one disclosed compound or at least one disclosed product with a pharmaceutically acceptable carrier or diluent, wherein the medicament is useful for modulation of GSPT1 protein.

The present disclosure is further directed to a method for the manufacture of a medicament for inhibitihng cellular proliferation (e.g., treatment of one or more disorders associated with a cereblon function or dysfunction, such as a cancer) in mammals (e.g., humans) comprising combining one or more disclosed compounds, products, or compositions with a pharmaceutically acceptable carrier or diluent. Thus, in one aspect, the present disclosure further relates to a method for manufacturing a medicament comprising combining at least one disclosed compound or at least one disclosed product with a pharmaceutically acceptable carrier or diluent, wherein the medicament is useful for inhibiting cellular proliferation.

The disclosed pharmaceutical compositions can further comprise other therapeutically active compounds, which are usually applied in the treatment of the above mentioned pathological or clinical conditions.

It is understood that the disclosed compositions can be prepared from the disclosed compounds. It is also understood that the disclosed compositions can be employed in the disclosed methods of using.

As already mentioned, the present disclosure relates to a pharmaceutical composition comprising a therapeutically effective amount of a disclosed compound, a product of a disclosed method of making, a pharmaceutically acceptable salt, a hydrate thereof, a solvate thereof, a polymorph thereof, and a pharmaceutically acceptable carrier. Additionally, the present disclosure relates to a process for preparing such a pharmaceutical composition, characterized in that a pharmaceutically acceptable carrier is intimately mixed with a therapeutically effective amount of a compound according to the present disclosure.

As already mentioned, the present disclosure also relates to a pharmaceutical composition comprising a disclosed compound, a product of a disclosed method of making, a pharmaceutically acceptable salt, a hydrate thereof, a solvate thereof, a polymorph thereof, and one or more other drugs in the treatment, prevention, control, amelioration, or reduction of risk of diseases or conditions for a disclosed compound or the other drugs may have utility as well as to the use of such a composition for the manufacture of a medicament. The present disclosure also relates to a combination of disclosed compound, a product of a disclosed method of making, a pharmaceutically acceptable salt, a hydrate thereof, a solvate thereof, a polymorph thereof, and an additional therapeutic agent, e.g., an inhibitor of cellular proliferation or anti-cancer therapeutic. The present disclosure also relates to such a combination for use as a medicine. The present disclosure also relates to a product comprising (a) disclosed compound, a product of a disclosed method of making, a pharmaceutically acceptable salt, a hydrate thereof, a solvate thereof, a polymorph thereof, and (b) an additional therapeutic agent, as a combined preparation for simultaneous, separate or sequential use in the treatment or prevention of a condition in a mammal, including a human, the treatment or prevention of which is affected or facilitated by the modulatory effect of the disclosed compound and the additional therapeutic agent. The different drugs of such a combination or product may be combined in a single preparation together with pharmaceutically acceptable carriers or diluents, or they may each be present in a separate preparation together with pharmaceutically acceptable carriers or diluents.

F. Methods of Using the Compounds

In various aspects, the present disclosure provides methods of treatment comprising administration of a therapeutically effective amount of a disclosed compound or pharmaceutical composition as disclosed herein above to a subject in need thereof.

In a further aspect, the present disclosure provides methods for the treatment of a disorder of uncontrolled cellular proliferation in a mammal comprising the step of administering to the mammal a therapeutically effective amount of at least one disclosed compound or pharmaceutically acceptable salt thereof, or at least one disclosed pharmaceutical composition.

In a further aspect, the present disclosure provides methods for modulating of cereblon activity in a mammal comprising the step of administering to the mammal a therapeutically effective amount of at least one disclosed compound or pharmaceutically acceptable salt thereof, or at least one disclosed pharmaceutical composition.

In a further aspect, the present disclosure provides methods for modulating of cereblon activity in at least one cell, comprising the step of contacting the at least one cell with an effective amount of at least one disclosed compound, or a pharmaceutically acceptable salt thereof; or at least one disclosed pharmaceutical composition.

In a further aspect, the disorder of uncontrolled cellular proliferation is a cancer, e.g., a cancer is selected from a brain cancer, lung cancer, hematological cancer, bladder cancer, colon cancer, cervical cancer, ovarian cancer, squamous cell cancer, kidney cancer, peritoneal cancer, breast cancer, gastric cancer, colorectal cancer, prostate cancer, pancreatic cancer, genitourinary tract cancer, lymphatic system cancer, stomach cancer, larynx cancer, malignant melanoma, colorectal cancer, endometrial carcinoma, thyroid cancer, rhabdosarcoma, and combinations thereof. In a still further aspect, the cancer is a hematological cancer is selected from chronic myeloid leukemia (CML), acute myeloid leukemia (AML), chronic lymphoid leukemia (CLL), acute lymphoid leukemia (ALL), hairy cell leukemia, chronic myelomonocytic leukemia (CMML), juvenile myelomonocyte leukemia (JMML), large granular lymphocytic leukemia (LGL), acute lymphocytic leukemia, acute lymphoblastic leukemia, B-cell lymphoma, T-cell-lymphoma, Hodgkin's lymphoma, non-Hodgkin's lymphoma, hairy cell lymphoma, Burkett's lymphoma, Hodgkin lymphoma, non-Hodgkin lymphoma, and combinations thereof.

In a further aspect, the disclosed methods for the treatment of a disorder of uncontrolled cellular proliferation in a mammal further comprise the step of administering a therapeutically effective amount of at least one agent known to treat a cancer, e.g., uracil mustard, chlormethine, cyclophosphamide, ifosfamide, melphalan, chlorambucil, pipobroman, triethylenemelamine, triethylenethiophosphoramine, busulfan, carmustine, lomustine, streptozocin, dacarbazine, temozolomide, thiotepa, altretamine, methotrexate, 5-fluorouracil, floxuridine, cytarabine, 6-mercaptopurine, 6-thioguanine, fludarabine phosphate, pentostatin, bortezomib, vinblastine, vincristine, vinorelbine, vindesine, bleomycin, dactinomycin, daunorubicin, doxorubicin, epirubicin, dexamethasone, clofarabine, cladribine, pemextresed, idarubicin, paclitaxel, docetaxel, ixabepilone, mithramycin, topotecan, irinotecan, deoxycoformycin, mitomycin-C, L-asparaginase, interferons, etoposide, teniposide 17α-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, cisplatin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, oxaliplatin, gefinitib, capecitabine, erlotinib, azacitidine, temozolomide, gemcitabine, vasostatin, and combinations thereof.

In a further aspect, the disclosed methods for modulating of cereblon activity in at least one cell further comprise the step of contacting the at least one cell with an effective amount of at least one agent known to treat a cancer, e.g., uracil mustard, chlormethine, cyclophosphamide, ifosfamide, melphalan, chlorambucil, pipobroman, triethylenemelamine, triethylenethiophosphoramine, busulfan, carmustine, lomustine, streptozocin, dacarbazine, temozolomide, thiotepa, altretamine, methotrexate, 5-fluorouracil, floxuridine, cytarabine, 6-mercaptopurine, 6-thioguanine, fludarabine phosphate, pentostatin, bortezomib, vinblastine, vincristine, vinorelbine, vindesine, bleomycin, dactinomycin, daunorubicin, doxorubicin, epirubicin, dexamethasone, clofarabine, cladribine, pemextresed, idarubicin, paclitaxel, docetaxel, ixabepilone, mithramycin, topotecan, irinotecan, deoxycoformycin, mitomycin-C, L-asparaginase, interferons, etoposide, teniposide 17α-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, cisplatin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, oxaliplatin, gefinitib, capecitabine, erlotinib, azacitidine, temozolomide, gemcitabine, vasostatin, and combinations thereof.

In a further aspect, the disclosed methods for modulating of cereblon activity in a mammal comprising the step of administering to the mammal further comprise the step of the step of administering a therapeutically effective amount of at least one agent known to treat a cancer, e.g., uracil mustard, chlormethine, cyclophosphamide, ifosfamide, melphalan, chlorambucil, pipobroman, triethylenemelamine, triethylenethiophosphoramine, busulfan, carmustine, lomustine, streptozocin, dacarbazine, temozolomide, thiotepa, altretamine, methotrexate, 5-fluorouracil, floxuridine, cytarabine, 6-mercaptopurine, 6-thioguanine, fludarabine phosphate, pentostatin, bortezomib, vinblastine, vincristine, vinorelbine, vindesine, bleomycin, dactinomycin, daunorubicin, doxorubicin, epirubicin, dexamethasone, clofarabine, cladribine, pemextresed, idarubicin, paclitaxel, docetaxel, ixabepilone, mithramycin, topotecan, irinotecan, deoxycoformycin, mitomycin-C, L-asparaginase, interferons, etoposide, teniposide 17α-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, cisplatin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, oxaliplatin, gefinitib, capecitabine, erlotinib, azacitidine, temozolomide, gemcitabine, vasostatin, and combinations thereof.

G. Kits

In a further aspect, the present disclosure relates to kits comprising at least one disclosed compound, or a pharmaceutically acceptable salt thereof; or at least one disclosed pharmaceutical composition; and one or more of: (a) at least one agent known to increase cereblon activity; (b) at least one agent known to decrease cereblon activity; (c) at least one agent known to increase GSPT1 activity; (d) at least one agent known to decrease GSPT1 activity; (e) at least one agent known to increase cellular proliferation; (f) at least one agent known to decrease cellular proliferation; (g) at least one agent known to treat a disorder associated with cereblon activity; (h) at least one agent known to treat a disorder associated with GSPT1 activity; (i) at least one agent known to treat a disorder of uncontrolled cellular proliferation; and/or (j) instructions for treating a disorder of uncontrolled cellular proliferation.

The disclosed compounds and/or pharmaceutical compositions comprising the disclosed compounds can conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient. In further aspects, a kit can include optional components that aid in the administration of the unit dose to patients, such as vials for reconstituting powder forms, syringes for injection, customized IV delivery systems, inhalers, etc. Additionally, a kit can contain instructions for preparation and administration of the compositions. The kit can be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

In a further aspect, the disclosed kits can be packaged in a daily dosing regimen (e.g., packaged on cards, packaged with dosing cards, packaged on blisters or blow-molded plastics, etc.). Such packaging promotes products and increases patient compliance with drug regimens. Such packaging can also reduce patient confusion. The present disclosure also features such kits further containing instructions for use.

In a further aspect, the present disclosure also provides a pharmaceutical pack or kit comprising one or more containers filled with one or more of the ingredients of the pharmaceutical compositions of the disclosure. Associated with such container(s) can be a notice in the form prescribed by a governmental agency regulating the manufacture, use or sale of pharmaceuticals or biological products, which notice reflects approval by the agency of manufacture, use or sale for human administration.

In various aspects, the disclosed kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using or treating, and/or the disclosed compositions.

H. Research Tools

The disclosed compounds and pharmaceutical compositions have activity as modulators of cereblon protein. In a further aspect, the disclosed compounds and pharmaceutical compositions have activity as modulators of GSPT1 expression and/or activity. In a still further aspect, the disclosed compounds and pharmaceutical compositions have activity as inhibitors of cellular proliferation. As such, the disclosed compounds are also useful as research tools. Accordingly, one aspect of the present disclosure relates to a method of using a compound of the disclosure as a research tool, the method comprising conducting a biological assay using a compound of the disclosure. Compounds of the disclosure can also be used to evaluate new chemical compounds. Thus another aspect of the disclosure relates to a method of evaluating a test compound in a biological assay, comprising: (a) conducting a biological assay with a test compound to provide a first assay value; (b) conducting the biological assay with a compound of the disclosure to provide a second assay value; wherein step (a) is conducted either before, after or concurrently with step (b); and (c) comparing the first assay value from step (a) with the second assay value from step (b). Exemplary biological assays include a cereblon assay or a GSPT1 assay that can be conducted in vitro or in a cell culture system as disclosed herein, or alternatively, an assay of cellular proliferation using a cell-line and cellular proliferation assay as disclosed herein. Still another aspect of the disclosure relates to a method of studying a biological system, e.g., a model animal for a clinical condition, or biological sample comprising a cereblon protein the method comprising: (a) contacting the biological system or sample with a compound of the disclosure; and (b) determining the effects caused by the compound on the biological system or sample. A further aspect of the disclosure relates to a method of studying a biological system, e.g., a model animal for a clinical condition, or biological sample comprising a GSPT1 protein the method comprising: (a) contacting the biological system or sample with a compound of the disclosure; and (b) determining the effects caused by the compound on the biological system or sample. In various aspects, the disclosed compounds are useful as chemical probes for the study of GSPT1/2 in vitro and in vivo.

I. References

References are cited herein throughout using the format of reference number(s) enclosed by parentheses corresponding to one or more of the following numbered references. For example, citation of references numbers 1 and 2 immediately herein below would be indicated in the disclosure as (Refs. 1 and 2).

1. Chamberlain, P. P. and Hamann, L. G. Development of Targeted Protein Degradation Therapeutics. Nat Chem Biol 2019, 15 (10), 937-944.
2. Hanzl, A. and Winter, G. E. Targeted Protein Degradation: Current and Future Challenges. Current Opinion in Chemical Biology 2020, 56, 35-41.
3. Toure, M. and Crews, C. M. Small-Molecule PROTACS: New Approaches to Protein Degradation. Angew. Chem. Int. Ed. 2016, 55 (6), 1966-1973.
4. Schapira, M., et al. Targeted Protein Degradation: Expanding the Toolbox. Nat Rev Drug Discov 2019, 18 (12), 949-963.
5. Baek, K. and Schulman, B. A. Molecular Glue Concept Solidifies. Nat Chem Biol 2020, 16 (1), 2-3.
6. Fink, E. C. and Ebert, B. L. The Novel Mechanism of Lenalidomide Activity. Blood 2015, 126 (21), 2366-2369.
7. Kronke, J., et al. Lenalidomide Causes Selective Degradation of IKZF1 and IKZF3 in Multiple Myeloma Cells. Science 2014, 343 (6168), 301-305.
8. Han, T., et al. Anticancer Sulfonamides Target Splicing by Inducing RBM39 Degradation via Recruitment to DCAF15. Science 2017, 356 (6336), eaal3755.
9. Knott, M. M. L., et al. Targeting the Undruggable: Exploiting Neomorphic Features of Fusion Oncoproteins in Childhood Sarcomas for Innovative Therapies. Cancer Metastasis Rev 2019, 38 (4), 625-642.
10. Bushweller, J. H. Targeting Transcription Factors in Cancer—from Undruggable to Reality. Nat Rev Cancer 2019, 19 (11), 611-624.
11. Sievers, Q. L., et al. Defining the Human C2H2 Zinc Finger Degrome Targeted by Thalidomide Analogs through CRBN. Science 2018, 362 (6414), eaat0572.
12. Krönke, J., et al. Lenalidomide Induces Ubiquitination and Degradation of CK1α in Del(5q) MDS. Nature 2015, 523 (7559), 183-188.
13. Matyskiela, M. E., et al. A Cereblon Modulator (CC-220) with Improved Degradation of Ikaros and Aiolos. J. Med. Chem. 2018, 61 (2), 535-542.
14. Matyskiela, M. E., et al. A Novel Cereblon Modulator Recruits GSPT1 to the CRL4CRBN Ubiquitin Ligase. Nature 2016, 535 (7611), 252-257.
15. Sperling, A. S., et al. Patterns of Substrate Affinity, Competition, and Degradation Kinetics Underlie Biological Activity of Thalidomide Analogs. Blood 2019, 134 (2), 160-170.
16. Matyskiela, M. E., et al. Crystal Structure of the SALL4-Pomalidomide-Cereblon-DDB1 Complex. Nat Struct Mol Biol 2020, 27 (4), 319-322.
17. Yang, J., et al. Simple Structural Modifications Converting a Bona Fide MDM2 PROTAC Degrader into a Molecular Glue Molecule: A Cautionary Tale in the Design of PROTAC Degraders. J. Med. Chem. 2019, 62 (21), 9471-9487.
18. Ishoey, M., et al. Translation Termination Factor GSPT1 Is a Phenotypically Relevant Off-Target of Heterobifunctional Phthalimide Degraders. ACS Chem. Biol. 2018, 13 (3), 553-560.
19. Alexander, T. B., et al. The Genetic Basis and Cell of Origin of Mixed Phenotype Acute Leukaemia. Nature 2018, 562 (7727), 373-379.
20. Li, J.-F., et al. Transcriptional Landscape of B Cell Precursor Acute Lymphoblastic Leukemia Based on an International Study of 1,223 Cases. Proc Natl Acad Sci USA 2018, 115 (50), E11711-E11720.
21. Schwartz, J. R., et al. Comprehensive Genomic Profiling of Pediatric Therapy-Related Myeloid Neoplasms Identifies Mecom Dysregulation to Be Associated with Poor Outcome. Blood 2019, 134 (Supplement_1), 1394-1394.
22. Hinai, A. A. and Valk, P. J. M. Review: Aberrant EVI1 Expression in Acute Myeloid Leukaemia. Br J Haematol 2016, 172 (6), 870-878.
23. Northcott, P. A., et al. The Whole-Genome Landscape of Medulloblastoma Subtypes. Nature 2017, 547 (7663), 311-317.
24. Northcott, P. A., et al. Enhancer Hijacking Activates GFI1 Family Oncogenes in Medulloblastoma. Nature 2014, 511 (7510), 428-434.
25. Nowak, R. P., et al. Plasticity in Binding Confers Selectivity in Ligand-Induced Protein Degradation. Nat Chem Biol 2018, 14 (7), 706-714.
26. Leeson, P. D. and Springthorpe, B. The Influence of Drug-like Concepts on Decision-Making in Medicinal Chemistry. Nat Rev Drug Discov 2007, 6 (11), 881-890.
27. Kronke, J., et al. Lenalidomide Causes Selective Degradation of IKZF1 and IKZF3 in Multiple Myeloma Cells. Science 2014, 343 (6168), 301-305.
28. Lu, G., et al. Elucidating the Mechanism of Action of CC-90009, a Novel Cereblon E3 Ligase Modulator, in AML Via Genome-Wide CRISPR Screen. Blood 2019, 134 (Supplement_1), 405-405. https://doi.org/10.1182/blood-2019-125492.
29. Lu, G.; Lopez-Girona, A.; and Filvaroff, E. Methods for Treating Cancer and the Use of Biomarkers as a Predictor of Clinical Sensitivity to Therapies. U.S. Pat. Publ. No. 2017/199193A1 (published Jul. 13, 2017).
30. Bunnage, M. E.; Chekler, E. L. P.; and Jones, L. H. Target Validation Using Chemical Probes. Nat Chem Biol 2013, 9 (4), 195-199.
31. Chauvin, C.; Salhi, S.; and Jean-Jean, O. Human Eukaryotic Release Factor 3a Depletion Causes Cell Cycle Arrest at G1 Phase through Inhibition of the MTOR Pathway. MCB 2007, 27 (16), 5619-5629.
32. Uy, G. L., et al. Clinical Activity of CC-90009, a Cereblon E3 Ligase Modulator and First-in-Class GSPT1 Degrader, As a Single Agent in Patients with Relapsed or Refractory Acute Myeloid Leukemia (R/R AML): First Results from a Phase I Dose-Finding Study. Blood 2019, 134 (Supplement_1), 232-232.
33. Hopkins, A. L.; Groom, C. R.; and Alex, A. Ligand Efficiency: A Useful Metric for Lead Selection. Drug Discovery Today 2004, 9 (10), 430-431.
34. Abadzapatero, C. and Metz, J. Ligand Efficiency Indices as Guideposts for Drug Discovery. Drug Discovery Today 2005, 10 (7), 464-469.
35. Bai, B., et al. Deep Multilayer Brain Proteomics Identifies Molecular Networks in Alzheimer's Disease Progression. Neuron 2020, 106 (4), 700. https://doi. org/10.1016/j. neuron.2020.04.031.

36. Connelly, J. P. and Pruett-Miller, S. M. CRIS.Py: A Versatile and High-Throughput Analysis Program for CRISPR-Based Genome Editing. Sci Rep 2019, 9 (1), 4194.

37. Bai, B., et al. Deep Profiling of Proteome and Phosphoproteome by Isobaric Labeling, Extensive Liquid Chromatography, and Mass Spectrometry. In Methods in Enzymology; Elsevier, 2017; Vol. 585, pp 377-395. https://doi.org/10.1016/bs.mie.2016.10.007.

38. Larson, B.; Banks, P.; and Sherman, H.; Rothenberg, M. Automation of Cell-Based Drug Absorption Assays in 96-Well Format Using Permeable Support Systems. J Lab Autom. 2012, 17 (3), 222-232.

39. Uchida, M., et al. A Modified Fast (4 Day) 96-Well Plate Caco-2 Permeability Assay. Journal of Pharmacological and Toxicological Methods 2009, 59 (1), 39-43.

40. Di, L., et al. High Throughput Microsomal Stability Assay for Insoluble Compounds. International Journal of Pharmaceutics 2006, 317 (1), 54-60.

41. Di, L., et al. Applications of High Throughput Microsomal Stability Assay in Drug Discovery. CCHTS 2008, 11 (6), 469-476. https://doi.org/10.2174/138620708784911429.

@@@

J. Aspects

The following listing of exemplary aspects supports and is supported by the disclosure provided herein.

Aspect 1. A compound having a structure represented by a formula:

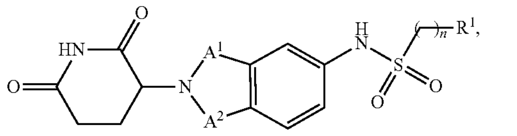

wherein n is an integer selected from 0, 1, and 2; wherein each of $A^1$ and $A^2$ is independently selected from —(C═O)— and —$CH_2$—, provided that at least one of $A^1$ and $A^2$ is —(C═O)—; wherein $R^1$ is selected from: (a) a 5- to 10-membered aryl or heteroaryl optionally substituted with a group selected from halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl; and (b) a 5- to 10-membered cycloalkyl optionally substituted with a group selected from halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl; or a pharmaceutically acceptable salt thereof.

Aspect 2. The compound of 2, wherein the compound excludes compounds having a structure:

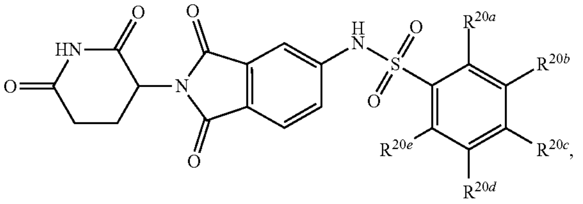

wherein $R^{20a}$ is selected from bromo, methyl, —$CF_3$, and —$OCF_3$; and wherein each of $R^{20b}$, $R^{20c}$, $R^{20d}$, and $R^{20e}$ is independently selected from hydrogen, halogen, and methyl; or a pharmaceutically acceptable salt thereof; and a compound having a structure represented by a formula:

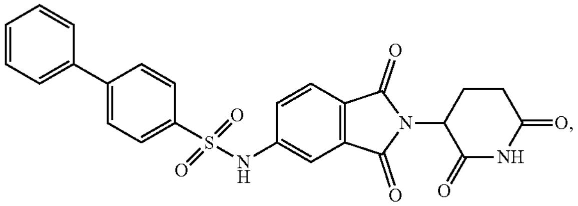 [SMILES: O=C1CCC(N2C(=O)c3ccc(NS(=O)(=O)c4ccc(-c5ccccc5)cc4)cc3C2=O)C(=O)N1]

or a pharmaceutically acceptable salt thereof.

Aspect 3. The compound of Aspect 2, wherein the excluded compound

Aspect 4. The compound of 2, wherein $R^{20a}$ is bromo.

Aspect 5. The compound of 4, wherein $R^{20a}$ is methyl.

Aspect 6. The compound of 2, wherein $R^{20a}$ is selected from —$CF_3$ and —$OCF_3$.

Aspect 7. The compound of any one of Aspect 2-Aspect 6, wherein each of $R^{20b}$, $R^{20c}$, $R^{20d}$, and $R^{20e}$ is hydrogen.

Aspect 8. The compound of any one of Aspect 2-Aspect 6, wherein at least one of $R^{20b}$, $R^{20c}$, $R^{20d}$ and $R^{20e}$ is halogen.

Aspect 9. The compound of any one of Aspect 2-Aspect 6, wherein at least one of $R^{20b}$, $R^{20c}$, $R^{20d}$, and $R^{20e}$ is methyl.

Aspect 10. The compound of any one of Aspect 2-Aspect 9, having a structure represented by a formula:

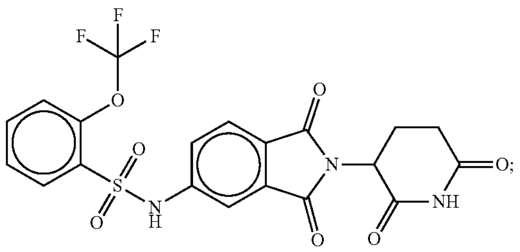

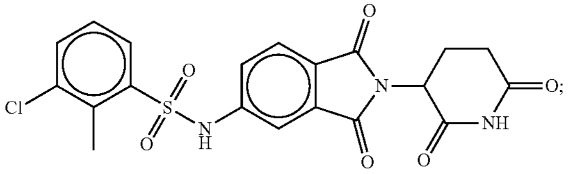

-continued

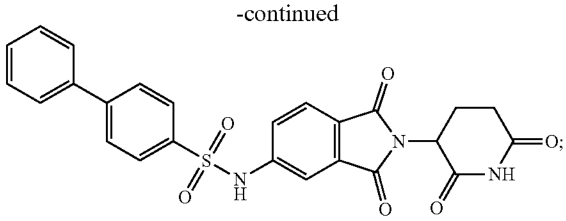

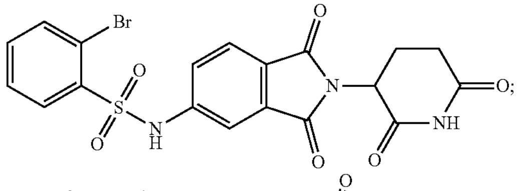

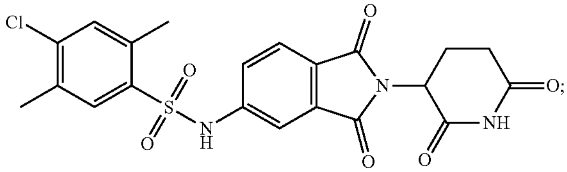

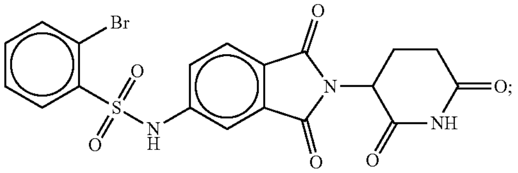

or

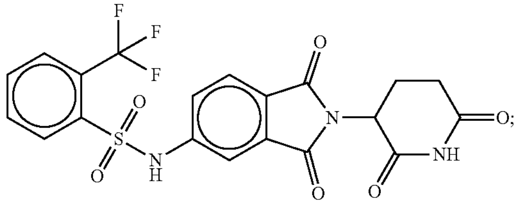

or a subgroup thereof.

Aspect 11. The compound of any one of 1-Aspect 10, n is selected from 0 and 1.

Aspect 12. The compound of any one of 1-Aspect 10, n is 0.

Aspect 13. The compound of any one of 1-Aspect 10, n is 1.

Aspect 14. The compound of any one of 1-Aspect 13, wherein $A^1$ is —(C═O)—; and wherein and $A^2$ is —$CH_2$—.

Aspect 15. The compound of any one of 1-Aspect 13, wherein $A^1$ is —$CH_2$—; and wherein and $A^2$ is —(C═O)—.

Aspect 16. The compound of any one of 1-Aspect 13, wherein each of $A^1$ and $A^2$ is —(C═O)—.

Aspect 17. The compound of any one of 1-Aspect 16, wherein R1 is $Ar^1$; and wherein $Ar^1$ is a 5- to 10-membered aryl or heteroaryl optionally substituted with a group selected from halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl.

Aspect 18. The compound of Aspect 17, wherein $Ar^1$ is a pyridinyl having substituent groups $R^{11}$, $R^{12}$, $R^{13}$, and $R^{14}$; and wherein each of $R^{11}$, $R^{12}$, $R^{13}$, and $R^{14}$ is independently selected from hydrogen, halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl.

Aspect 19. The compound of Aspect 18, wherein each of $R^{11}$, $R^{12}$, $R^{13}$, and $R^{14}$ is independently selected from hydrogen, —Cl, —Br, —$SF_5$, —CN, —$N_3$, —CN, —$CH_2F$, —$CHF_2$, —$CF_3$, —$CH_2Cl$, —$CHCl_2$, —$Cl_3$, —$CH_2Br$, —$CHBr_2$, —$CBr_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2CH_2Br$, —$CH_2CHBr_2$, —$CH_2CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_2CH_2F$, —$OCH_2CHF_2$, —$OCH_2CF_3$, —$OCH_2CH_2Cl$, —$OCH_2CHCl_2$, —$OCH_2CCl_3$, —$OCH_2CH_2Br$, —$OCH_2CHBr_2$, —$OCH_2CBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl.

Aspect 20. The compound of Aspect 19, wherein each of $R^{11}$, $R^{12}$, $R^{13}$, and $R^{14}$ is independently selected from hydrogen, —Cl, —Br, —$CH_2F$, —$CHF_2$, —$CF_3$, —$CH_2Cl$, —$CHCl_2$, —$CCl_3$, —$CH_2Br$, —$CHBr_2$, —$CBr_3$, —$OCH_2F$, —$OCHF_2$, —$OCHF_3$, —$OCHH_2Cl$, —$OCHCl_2$, —$OCCl_3$, —$OCH_2Br$, —$OCHBr_2$, —$OCBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl.

Aspect 21. The compound of Aspect 19, wherein each of $R^{11}$, $R^{12}$, $R^{13}$, and $R^{14}$ is independently selected from hydrogen, —Cl, —$CCl_3$, —$OCF_3$, —$OCCl_3$, —$OCH_3$, methyl, ethyl, propyl, isopropyl, butyl, isobutyl, and tert-butyl.

Aspect 22. The compound of Aspect 19, wherein each of $R^{11}$, $R^{12}$, $R^{13}$, and $R^{14}$ is independently selected from hydrogen, —Cl, —$OCF_3$, methyl, ethyl, and tert-butyl.

Aspect 23. The compound of Aspect 18, wherein each of $R^{11}$, $R^{12}$, $R^{13}$, and $R^{14}$ is independently selected from hydrogen, halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl, provided that at least one $R^{11}$, $R^{12}$, $R^{13}$, and $R^{14}$ is not hydrogen.

Aspect 24. The compound of Aspect 23, wherein each of $R^{11}$, $R^{12}$, $R^{13}$, and $R^{14}$ is independently selected from hydrogen, —Cl, —Br, —$SF_5$, —CN, —$N_3$, —CN, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2CH_2Br$, —$CH_2CHBr_2$, —$CH_2CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_2CH_2F$, —$OCH_2CHF_2$, —$OCH_2CF_3$, —$OCH_2CH_2Cl$, —$OCH_2CHCl_2$, —$OCH_2CCl_3$, —$OCH_2CH_2Br$, —$OCH_2CHBr_2$, —$OCH_2CBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl, provided that at least one $R^{11}$, $R^{12}$, $R^{13}$, and $R^{14}$ is not hydrogen.

Aspect 25. The compound of Aspect 23, wherein each of $R^{11}$, $R^{12}$, $R^{13}$, and $R^{14}$ is independently selected from hydrogen, —Cl, —Br, —$CH_2F$, —$CHF_2$, —$CF_3$, —$CH_2Cl$, —$CHCl_2$, —$CCl_3$, —$CH_2Br$, —$CHBr_2$, —$CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl, provided that at least one $R^{11}$, $R^{12}$, $R^{13}$, and $R^{14}$ is not hydrogen.

Aspect 26. The compound of Aspect 23, wherein each of $R^{11}$, $R^{12}$, $R^{13}$, and $R^{14}$ is independently selected from hydrogen, —Cl, —$CCl_3$, —$OCF_3$, —$OCCl_3$, —$OCH_3$, methyl, ethyl, propyl, isopropyl, butyl, isobutyl, and tert-butyl, provided that at least one $R^{11}$, $R^{12}$, $R^{13}$, and $R^{14}$ is not hydrogen.

Aspect 27. The compound of Aspect 23, wherein each of $R^{11}$, $R^{12}$, $R^{13}$, and $R^{14}$ is independently selected from hydrogen, —Cl, —$OCF_3$, methyl, ethyl, and tert-butyl, provided that at least one $R^{11}$, $R^{12}$, $R^{13}$, and $R^{14}$ is not hydrogen.

Aspect 28. The compound of Aspect 18, wherein each of $R^{11}$, $R^{12}$, $R^{13}$, and $R^{14}$ is independently selected from hydrogen, halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl, provided that only one of $R^{11}$, $R^{12}$, $R^{13}$, and $R^{14}$ is not hydrogen.

Aspect 29. The compound of Aspect 28, wherein each of $R^{11}$, $R^{12}$, $R^{13}$, and $R^{14}$ is independently selected from hydrogen, —Cl, —Br, —$SF_5$, —CN, —$N_3$, —CN, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2CH_2Br$, —$CH_2CHBr_2$, —$CH_2CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_2CH_2F$, —$OCH_2CHF_2$, —$OCH_2CF_3$, —$OCH_2CH_2Cl$, —$OCH_2CHCl_2$, —$OCH_2CCl_3$, —$OCH_2CH_2Br$, —$OCH_2CHBr_2$, —$OCH_2CBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl, provided that only one of $R^{11}$, $R^{12}$, $R^{13}$, and $R^{14}$ is not hydrogen.

Aspect 30. The compound of Aspect 28, wherein each of $R^{11}$, $R^{12}$, $R^{13}$, and $R^{14}$ is independently selected from hydrogen, —Cl, —Br, —$CH_2F$, —$CHF_2$, —$CF_3$, —$CH_2Cl$, —$CHCl_2$, —$CCl_3$, —$CH_2Br$, —$CHBr_2$, —$CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl, provided that only one of $R^{11}$, $R^{12}$, $R^{13}$, and $R^{14}$ is not hydrogen.

Aspect 31. The compound of Aspect 28, wherein each of $R^{11}$, $R^{12}$, $R^{13}$, and $R^{14}$ is independently selected from hydrogen, —Cl, —$CCL_3$, —$OCF_3$, —$OCCl_3$, —$OCH_3$, methyl, ethyl, propyl, isopropyl, butyl, isobutyl, and tert-butyl, provided that only one of $R^{11}$, $R^{12}$, $R^{13}$, and $R^{14}$ is not hydrogen.

Aspect 32. The compound of Aspect 28, wherein each of $R^{11}$, $R^{12}$, $R^{13}$, and $R^{14}$ is independently selected from hydrogen, —Cl, —$OCF_3$, methyl, ethyl, and tert-butyl, provided that only one of $R^{11}$, $R^{12}$, $R^{13}$, and $R^{14}$ is not hydrogen.

Aspect 33. The compound of Aspect 18, wherein each of $R^{11}$, $R^{12}$, $R^{13}$, and $R^{14}$ is independently selected from hydrogen, halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl, provided that only two of $R^{11}$, $R^{12}$, $R^{13}$, and $R^{14}$ are not hydrogen.

Aspect 34. The compound of Aspect 33, wherein each of $R^{11}$, $R^{12}$, $R^{13}$, and $R^{14}$ is independently selected from hydrogen, —Cl, —Br, —$SF_5$, —CN, —$N_3$, —CN, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2CH_2Br$, —$CH_2CHBr_2$, —$CH_2CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_2CH_2F$, —$OCH_2CHF_2$, —$OCH_2CF_3$, —$OCH_2CH_2Cl$, —$OCH_2CHCl_2$, —$OCH_2CCl_3$, —$OCH_2CH_2Br$, —$OCH_2CHBr_2$, —$OCH_2CBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl, provided that only two of $R^{11}$, $R^{12}$, $R^{13}$, and $R^{14}$ are not hydrogen.

Aspect 35. The compound of Aspect 33, wherein each of $R^{11}$, $R^{12}$, $R^{13}$, and $R^{14}$ is independently selected from hydrogen, —Cl, —Br, —$CH_2F$, —$CHF_2$, —$CF_3$, —$CH_2Cl$, —$CHCl_2$, —$CCl_3$, —$CH_2Br$, —$CHBr_2$, —$CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl, provided that only two of $R^{11}$, $R^{12}$, $R^{13}$, and $R^{14}$ are not hydrogen.

Aspect 36. The compound of Aspect 33, wherein each of $R^{11}$, $R^{12}$, $R^{13}$, and $R^{14}$ is independently selected from hydrogen, —Cl, —$CCl_3$, —$OCF_3$, —$OCCl_3$, —$OCH_3$, methyl, ethyl, propyl, isopropyl, butyl, isobutyl, and tert-butyl, provided that only two of $R^{11}$, $R^{12}$, $R^{13}$, and $R^{14}$ are not hydrogen.

Aspect 37. The compound of Aspect 33, wherein each of $R^{11}$, $R^{12}$, $R^{13}$, and $R^{14}$ is independently selected from hydrogen, —Cl, —$OCF_3$, methyl, ethyl, and tert-butyl, provided that only two of $R^{11}$, $R^{12}$, $R^{13}$, and $R^{14}$ are not hydrogen.

Aspect 38. The compound of Aspect 18, wherein each of $R^{11}$, $R^{12}$, $R^{13}$, and $R^{14}$ is hydrogen.

Aspect 39. The compound of Aspect 17, wherein $Ar^1$ is a pyrimidinyl having substituent groups $R^{11}$, $R^{12}$, and $R^{13}$; and wherein each of $R^{11}$, $R^{12}$, and $R^{13}$ is independently selected from hydrogen, halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl.

Aspect 40. The compound of Aspect 39, wherein each of $R^{11}$, $R^{12}$, and $R^{13}$ is independently selected from hydrogen, —Cl, —Br, —$SF_5$, —CN, —$N_3$, —CN, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2CH_2Br$, —$CH_2CHBr_2$, —$CH_2CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_2CH_2F$, —$OCH_2CHF_2$, —$OCH_2CF_3$, —$OCH_2CH_2Cl$, —$OCH_2CHCl_2$, —$OCH_2CCl_3$, —$OCH_2CH_2Br$, —$OCH_2CHBr_2$, —$OCH_2CBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl.

Aspect 41. The compound of Aspect 40, wherein each of $R^{11}$, $R^{12}$, and $R^{13}$ is independently selected from hydrogen, —Cl, —Br, —$CH_2F$, —$CHF_2$, —$CF_3$, —$CH_2Cl$, —$CHCl_2$, —$CCl_3$, —$CH_2Br$, —$CHBr_2$, —$CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl.

Aspect 42. The compound of Aspect 40, wherein each of $R^{11}$, $R^{12}$, and $R^{13}$ is independently selected from hydrogen, —Cl, —$CCl_3$, —$OCF_3$, —$OCCl_3$, —$OCH_3$, methyl, ethyl, propyl, isopropyl, butyl, isobutyl, and tert-butyl.

Aspect 43. The compound of Aspect 40, wherein each of $R^{11}$, $R^{12}$, and $R^{13}$ is independently selected from hydrogen, —Cl, —$OCF_3$, methyl, ethyl, and tert-butyl.

Aspect 44. The compound of Aspect 39, wherein each of $R^{11}$, $R^{12}$, and $R^{13}$ is independently selected from hydrogen, halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl, provided that at least one $R^{11}$, $R^{12}$, and $R^{13}$ is not hydrogen.

Aspect 45. The compound of Aspect 44, wherein each of $R^{11}$, $R^{12}$, and $R^{13}$ is independently selected from hydrogen, —Cl, —Br, —$SF_5$, —CN, —$N_3$, —CN, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2CH_2Br$, —$CH_2CHBr_2$, —$CH_2CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_2CH_2F$, —$OCH_2CHF_2$, —$OCH_2CF_3$, —$OCH_2CH_2Cl$, —$OCH_2CHCl_2$, —$OCH_2CCl_3$, —$OCH_2CH_2Br$, —$OCH_2CHBr_2$, —$OCH_2CBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl, provided that at least one $R^{11}$, $R^{12}$, and $R^{13}$ is not hydrogen.

Aspect 46. The compound of Aspect 44, wherein each of $R^{11}$, $R^{12}$, and $R^{13}$ is independently selected from hydrogen, —Cl, —Br, —$CH_2F$, —$CHF_2$, —$CF_3$, —$CH_2Cl$, —$CHCl_2$, —$CCl_3$, —$CH_2Br$, —$CHBr_2$, —$CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl, provided that at least one $R^{11}$, $R^{12}$, and $R^{13}$ is not hydrogen.

Aspect 47. The compound of Aspect 44, wherein each of $R^{11}$, $R^{12}$, and $R^{13}$ is independently selected from hydrogen, —Cl, —$CCl_3$, —$OCF_3$, —$OCCl_3$, —$OCH_3$, methyl, ethyl, propyl, isopropyl, butyl, isobutyl, and tert-butyl, provided that at least one $R^{11}$, $R^{12}$, and $R^{13}$ is not hydrogen.

Aspect 48. The compound of Aspect 44, wherein each of $R^{11}$, $R^{12}$, and $R^{13}$ is independently selected from hydrogen, —Cl, —$OCF_3$, methyl, ethyl, and tert-butyl, provided that at least one $R^{11}$, $R^{12}$, and $R^{13}$ is not hydrogen.

Aspect 49. The compound of Aspect 39, wherein each of $R^{11}$, $R^{12}$, and $R^{13}$ is independently selected from hydrogen, halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl, provided that only one of $R^{11}$, $R^{12}$, and $R^{13}$ is not hydrogen.

Aspect 50. The compound of Aspect 49, wherein each of $R^{11}$, $R^{12}$, and $R^{13}$ is independently selected from hydrogen, —Cl, —Br, —$SF_5$, —CN, —$N_3$, —CN, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2CH_2Br$, —$CH_2CHBr_2$, —$CH_2CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_2CH_2F$, —$OCH_2CHF_2$, —$OCH_2CF_3$, —$OCH_2CH_2Cl$, —$OCH_2CHCl_2$, —$OCH_2CCl_3$, —$OCH_2CH_2Br$, —$OCH_2CHBr_2$, —$OCH_2CBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl, provided that only one of $R^{11}$, $R^{12}$, and $R^{13}$ is not hydrogen.

Aspect 51. The compound of Aspect 49, wherein each of $R^{11}$, $R^{12}$, and $R^{13}$ is independently selected from hydrogen, —Cl, —Br, —$CH_2F$, —$CHF_2$, —$CF_3$, —$CH_2Cl$, —$CHCl_2$, —$CCl_3$, —$CH_2Br$, —$CHBr_2$, —$CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl, provided that only one of $R^{11}$, $R^{12}$, $R^{13}$, $R^{14}$, and $R^{15}$ is not hydrogen.

Aspect 52. The compound of Aspect 49, wherein each of $R^{11}$, $R^{12}$, and $R^{13}$ is independently selected from hydrogen, —Cl, —$CCl_3$, —$OCF_3$, —$OCCl_3$, —$OCH_3$, methyl, ethyl, propyl, isopropyl, butyl, isobutyl, and tert-butyl, provided that only one of $R^{11}$, $R^{12}$, and $R^{13}$ is not hydrogen.

Aspect 53. The compound of Aspect 49, wherein each of $R^{11}$, $R^{12}$, and $R^{13}$ is independently selected from hydrogen, —Cl, —$OCF_3$, methyl, ethyl, and tert-butyl, provided that only one of $R^{11}$, $R^{12}$, and $R^{13}$ is not hydrogen.

Aspect 54. The compound of Aspect 39, wherein each of $R^{11}$, $R^{12}$, and $R^{13}$ is independently selected from hydrogen, halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl, provided that only one of $R^{11}$, $R^{12}$, and $R^{13}$ is not hydrogen.

Aspect 55. The compound of Aspect 54, wherein each of $R^{11}$, $R^{12}$, and $R^{13}$ is independently selected from hydrogen, —Cl, —Br, —$SF_5$, —CN, —$N_3$, —CN, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2CH_2Br$, —$CH_2CHBr_2$, —$CH_2CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_2CH_2F$, —$OCH_2CHF_2$, —$OCH_2CF_3$, —$OCH_2CH_2Cl$, —$OCH_2CHCl_2$, —$OCH_2CCl_3$, —$OCH_2CH_2Br$, —$OCH_2CHBr_2$, —$OCH_2CBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl, provided that two of $R^{11}$, $R^{12}$, and $R^{13}$ are not hydrogen.

Aspect 56. The compound of Aspect 54, wherein each of $R^{11}$, $R^{12}$, and $R^{13}$ is independently selected from hydrogen, —Cl, —Br, —$CH_2F$, —$CHF_2$, —$CF_3$, —$CH_2Cl$, —$CHCl_2$, —$CCl_3$, —$CH_2Br$, —$CHBr_2$, —$CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl, provided that two of $R^{11}$, $R^{12}$, and $R^{13}$ are not hydrogen.

Aspect 57. The compound of Aspect 54, wherein each of $R^{11}$, $R^{12}$, and $R^{13}$ is independently selected from hydrogen, —Cl, —$CCl_3$, —$OCF_3$, —$OCCl_3$, —$OCH_3$, methyl, ethyl, propyl, isopropyl, butyl, isobutyl, and tert-butyl, provided that two of $R^{11}$, $R^{12}$, and $R^{13}$ are not hydrogen.

Aspect 58. The compound of Aspect 54, wherein each of $R^{11}$, $R^{12}$, and $R^{13}$ is independently selected from hydrogen, —Cl, —$OCF_3$, methyl, ethyl, and tert-butyl, provided that two of $R^{11}$, $R^{12}$, and $R^{13}$ are not hydrogen.

Aspect 59. The compound of Aspect 39, wherein each of $R^{11}$, $R^{12}$, and $R^{13}$ is hydrogen.

Aspect 60. The compound of Aspect 17, wherein $Ar^1$ is a 5-membered heteroaryl optionally substituted with a group selected from halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl.

Aspect 61. The compound of Aspect 60, wherein $Ar^1$ is selected from: (a) a 5-membered heteroaryl having one heteroatom and substituent groups $R^{11}$, $R^{12}$, and $R^{13}$; and wherein each of $R^{11}$, $R^{12}$, and $R^{13}$ is independently selected from hydrogen, halogen, $—SF_5$, —CN, $—N_3$, $—NH_2$, —OH, —CN, $—SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl; and (b) a 5-membered heteroaryl having two heteroatoms and substituent groups $R^{11}$, $R^{12}$, and $R^{13}$; and wherein each of $R^{11}$, $R^{12}$, and $R^{13}$ is independently selected from hydrogen, halogen, $—SF_5$, —CN, $—N_3$, $—NH_2$, —OH, —CN, $—SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl.

Aspect 62. The compound of Aspect 61, wherein $Ar^1$ is the 5-membered heteroaryl having one heteroatom; and wherein the heteroatom is selected from —O— and —S—.

Aspect 63. The compound of Aspect 61, wherein $Ar^1$ is the 5-membered heteroaryl having two heteroatoms; and wherein the two heteroatoms comprise a first heteroatom and a second heteroatom.

Aspect 64. The compound of Aspect 63, wherein the first heteroatom is —N=; and wherein the second heteroatom is selected from $—NR^{12}—$, —O—, and —S—.

Aspect 65. The compound of Aspect 63, wherein the first heteroatom is —N=; and wherein the second heteroatom is $—NR^{12}—$.

Aspect 66. The compound of any one of Aspect 61-Aspect 65, wherein each of $R^{11}$, $R^{12}$, and $R^{13}$ is independently selected from hydrogen, —Cl, —Br, $—SF_5$, —CN, $—N_3$, —CN, $—CH_2F$, $—CHF_2$, $—CF_3$, $—CH_2Cl$, $—CHCl_2$, $—CCl_3$, $—CH_2Br$, $—CHBr_2$, $—CBr_3$, $—CH_2CH_2F$, $—CH_2CHF_2$, $—CH_2CF_3$, $—CH_2CH_2Cl$, $—CH_2CHCl_2$, $—CH_2CCl_3$, $—CH_2CH_2Br$, $—CH_2CHBr_2$, $—CH_2CBr_3$, $—OCH_2F$, $—OCHF_2$, $—OCF_3$, $—OCH_2Cl$, $—OCHCl_2$, $—OCCl_3$, $—OCH_2Br$, $—OCHBr_2$, $—OCBr_3$, $—OCH_2CH_2F$, $—OCH_2CHF_2$, $—OCH_2CF_3$, $—OCH_2CH_2Cl$, $—OCH_2CHCl_2$, $—OCH_2CCl_3$, $—OCH_2CH_2Br$, $—OCH_2CHBr_2$, $—OCH_2CBr_3$, $—OCH_3$, $—OCH_2CH_3$, $—CH_2OH$, $—(CH_2)_2OH$, $—NHCH_3$, $—NHCH_2CH_3$, $—N(CH_3)2$, methyl, ethyl, propyl, isopropyl, butyl, isobutyl, and tert-butyl.

Aspect 67. The compound of Aspect 66, wherein each of $R^{11}$, $R^{12}$, and $R^{13}$ is independently selected from hydrogen, —Cl, —Br, $—CH_2F$, $—CHF_2$, $—CF_3$, $—CH_2Cl$, $—CHCl_2$, $—CCl_3$, $—CH_2Br$, $—CHBr_2$, $—CBr_3$, $—OCH_2F$, $—OCHF_2$, $—OCF_3$, $—OCH_2Cl$, $—OCHCl_2$, $—OCCl_3$, $—OCH_2Br$, $—OCHBr_2$, $—OCBr_3$, $—OCH_3$, $—OCH_2CH_3$, $—CH_2OH$, $—(CH_2)_2OH$, $—NHCH_3$, $—NHCH_2CH_3$, $—N(CH_3)2$, methyl, ethyl, propyl, isopropyl, butyl, isobutyl, and tert-butyl.

Aspect 68. The compound of Aspect 66, wherein each of $R^{11}$, $R^{12}$, and $R^{13}$ is independently selected from hydrogen, —Cl, $—CCl_3$, $—OCF_3$, $—OCCl_3$, $—OCH_3$, methyl, ethyl, propyl, isopropyl, butyl, isobutyl, and tert-butyl.

Aspect 69. The compound of Aspect 66, wherein each of $R^{11}$, $R^{12}$, and $R^{13}$ is independently selected from hydrogen, —Cl, $—OCF_3$, methyl, ethyl, and tert-butyl.

Aspect 70. The compound of any one of Aspect 61-Aspect 65, wherein each of $R^{11}$, $R^{12}$, and $R^{13}$ is independently selected from hydrogen, halogen, $—SF_5$, —CN, $—N_3$, $—NH_2$, —OH, —CN, $—SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl, provided that at least one $R^{11}$, $R^{12}$, and $R^{13}$ is not hydrogen.

Aspect 71. The compound of Aspect 70, wherein each of $R^{11}$, $R^{12}$, and $R^{13}$ is independently selected from hydrogen, —Cl, —Br, $—SF_5$, —CN, $—N_3$, —CN, $—CH_2F$, $—CHF_2$, $—CF_3$, $—CH_2Cl$, $—CHCl_2$, $—CCl_3$, —CH 2Br, $—CHBr_2$, $—CBr_3$, $—CH_2CH_2F$, $—CH_2CHF_2$, $—CH_2CF_3$, $—CH_2CH_2Cl$, $—CH_2CHCl_2$, $—CH_2CCl_3$, $—CH_2CH_2Br$, $—CH_2CHBr_2$, $—CH_2CBr_3$, $—OCH_2F$, $—OCHF_2$, $—OCF_3$, $—OCH_2Cl$, $—OCHCl_2$, $—OCCl_3$, $—OCH_2Br$, $—OCHBr_2$, $—OCBr_3$, $—OCH_2CH_2F$, $—OCH_2CHF_2$, $—OCH_2CF_3$, $—OCH_2CH_2Cl$, $—OCH_2CHCl_2$, $—OCH_2CCl_3$, $—OCH_2CH_2Br$, $—OCH_2CHBr_2$, $—OCH_2CBr_3$, $—OCH_3$, $—OCH_2CH_3$, $—CH_2OH$, $—(CH_2)_2OH$, $—NHCH_3$, $—NHCH_2CH_3$, $—N(CH_3)2$, methyl, ethyl, propyl, isopropyl, butyl, isobutyl, and tert-butyl, provided that at least one $R^{11}$, $R^{12}$, and $R^{13}$ is not hydrogen.

Aspect 72. The compound of Aspect 70, wherein each of $R^{11}$, $R^{12}$, and $R^{13}$ is independently selected from hydrogen, —Cl, —Br, $—CH_2F$, $—CHF_2$, $—CF_3$, $—CH_2Cl$, $—CHCl_2$, $—CCl_3$, $—CH_2Br$, $—CHBr_2$, $—CBr_3$, $—OCH_2F$, $—OCHF_2$, $—OCF_3$, $—OCH_2Cl$, $—OCHCl_2$, $—OCCl_3$, $—OCH_2Br$, $—OCHBr_2$, $—OCBr_3$, $—OCH_3$, $—OCH_2CH_3$, $—CH_2OH$, $—(CH_2)_2OH$, $—NHCH_3$, $—NHCH_2CH_3$, $—N(CH_3)2$, methyl, ethyl, propyl, isopropyl, butyl, isobutyl, and tert-butyl, provided that at least one $R^{11}$, $R^{12}$, and $R^{13}$ is not hydrogen.

Aspect 73. The compound of Aspect 70, wherein each of $R^{11}$, $R^{12}$, and $R^{13}$ is independently selected from hydrogen, —Cl, $—CCl_3$, $—OCF_3$, $—OCCl_3$, $—OCH_3$, methyl, ethyl, propyl, isopropyl, butyl, isobutyl, and tert-butyl, provided that at least one $R^{11}$, $R^{12}$, and $R^{13}$ is not hydrogen.

Aspect 74. The compound of Aspect 70, wherein each of $R^{11}$, $R^{12}$, and $R^{13}$ is independently selected from hydrogen, —Cl, $—OCF_3$, methyl, ethyl, and tert-butyl, provided that at least one $R^{11}$, $R^{12}$, and $R^{13}$ is not hydrogen.

Aspect 75. The compound of any one of Aspect 61-Aspect 65, wherein each of $R^{11}$, $R^{12}$, and $R^{13}$ is independently selected from hydrogen, halogen, $—SF_5$, —CN, $—N_3$, $—NH_2$, —OH, —CN, $—SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl, provided that only one of $R^{11}$, $R^{12}$, and $R^{13}$ is not hydrogen.

Aspect 76. The compound of Aspect 75, wherein each of $R^{11}$, $R^{12}$, and $R^{13}$ is independently selected from hydrogen, —Cl, —Br, $—SF_5$, —CN, $—N_3$, —CN, $—CH_2F$, $—CHF_2$, $—CF_3$, $—CH_2Cl$, $—CHCl_2$, $—CCl_3$, $—CH_2Br$, $—CHBr_2$, $—CBr_3$, $—CH_2CH_2F$, $—CH_2CHF_2$, $—CH_2CF_3$, $—CH_2CH_2Cl$, $—CH_2CHCl_2$, $—CH_2CCl_3$, $—CH_2CH_2Br$, $—CH_2CHBr_2$, $—CH_2CBr_3$, $—OCH_2F$, $—OCHF_2$, $—OCF_3$, $—OCH_2Cl$, $—OCHCl_2$, $—OCCl_3$, $—OCH_2Br$, $—OCHBr_2$, $—OCBr_3$, $—OCH_2CH_2F$, $—OCH_2CHF_2$, $—OCH_2CF_3$, $—OCH_2CH_2Cl$, $—OCH_2CHCl_2$, $—OCH_2CCl_3$, $—OCH_2CH_2Br$, $—OCH_2CHBr_2$, $—OCH_2CBr_3$, $—OCH_3$, $—OCH_2CH_3$, $—CH_2OH$, $—(CH_2)_2OH$, $—NHCH_3$, $—NHCH_2CH_3$, $—N(CH_3)2$, methyl, ethyl, propyl, isopropyl, butyl, isobutyl, and tert-butyl, provided that only one of $R^{11}$, $R^{12}$, and $R^{13}$ is not hydrogen.

Aspect 77. The compound of Aspect 75, wherein each of $R^{11}$, $R^{12}$, and $R^{13}$ is independently selected from hydrogen, —Cl, —Br, $—CH_2F$, $—CHF_2$, $—CF_3$, $—CH_2Cl$, $—CHCl_2$, $—CCl_3$, $—CH_2Br$, $—CHBr_2$, $—CBr_3$, $—OCH_2F$, $—OCHF_2$, $—OCF_3$, $—OCH_2Cl$, $—OCHCl_2$, $—OCCl_3$, $—OCH_2Br$, $—OCHBr_2$, $—OCBr_3$, $—OCH_3$, $—OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl, provided that only one of $R^{11}$, $R^{12}$, $R^{13}$, $R^{14}$, and $R^{15}$ is not hydrogen.

Aspect 78. The compound of Aspect 75, wherein each of $R^{11}$, $R^{12}$, and $R^{13}$ is independently selected from hydrogen, —Cl, —$CCl_3$, —$OCF_3$, —$OCCl_3$, —$OCH_3$, methyl, ethyl, propyl, isopropyl, butyl, isobutyl, and tert-butyl, provided that only one of $R^{11}$, $R^{12}$, and $R^{13}$ is not hydrogen.

Aspect 79. The compound of Aspect 75, wherein each of $R^{11}$, $R^{12}$, and $R^{13}$ is independently selected from hydrogen, —Cl, —$OCF_3$, methyl, ethyl, and tert-butyl, provided that only one of $R^{11}$, $R^{12}$, and $R^{13}$ is not hydrogen.

Aspect 80. The compound of any one of Aspect 61-Aspect 65, wherein each of $R^{11}$, $R^{12}$, and $R^{13}$ is independently selected from hydrogen, halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl, provided that only one of $R^{11}$, $R^{12}$, and $R^{13}$ is not hydrogen.

Aspect 81. The compound of Aspect 78, wherein each of $R^{11}$, $R^{12}$, and $R^{13}$ is independently selected from hydrogen, —Cl, —Br, —$SF_5$, —CN, —$N_3$, —CN, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2CH_2Br$, —$CH_2CHBr_2$, —$CH_2CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_2CH_2F$, —$OCH_2CHF_2$, —$OCH_2CF_3$, —$OCH_2CH_2Cl$, —$OCH_2CHCl_2$, —$OCH_2CCl_3$, —$OCH_2CH_2Br$, —$OCH_2CHBr_2$, —$OCH_2CBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl, provided that two of $R^{11}$, $R^{12}$, and $R^{13}$ are not hydrogen.

Aspect 82. The compound of Aspect 78, wherein each of $R^{11}$, $R^{12}$, and $R^{13}$ is independently selected from hydrogen, —Cl, —Br, —$CH_2F$, —$CHF_2$, —$CF_3$, —$CH_2Cl$, —$CHCl_2$, —$CCl_3$, —$CH_2Br$, —$CHBr_2$, —$CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl, provided that two of $R^{11}$, $R^{12}$, and $R^{13}$ are not hydrogen.

Aspect 83. The compound of Aspect 78, wherein each of $R^{11}$, $R^{12}$, and $R^{13}$ is independently selected from hydrogen, —Cl, —$CCl_3$, —$OCF_3$, —$OCCl_3$, —$OCH_3$, methyl, ethyl, propyl, isopropyl, butyl, isobutyl, and tert-butyl, provided that two of $R^{11}$, $R^{12}$, and $R^{13}$ are not hydrogen.

Aspect 84. The compound of Aspect 78, wherein each of $R^{11}$, $R^{12}$, and $R^{13}$ is independently selected from hydrogen, —Cl, —$OCF_3$, methyl, ethyl, and tert-butyl, provided that two of $R^{11}$, $R^{12}$, and $R^{13}$ are not hydrogen.

Aspect 85. The compound of any one of Aspect 61-Aspect 65, wherein each of $R^{11}$, $R^{12}$, and $R^{13}$ is hydrogen.

Aspect 86. The compound of any one of Aspect 61-Aspect 85, wherein $Ar^1$ has a structure represented by a formula:

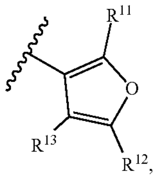,

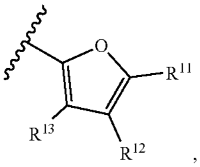,

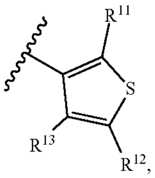, or

-continued

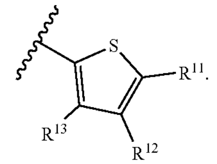.

Aspect 87. The compound of any one of Aspect 61-Aspect 85, wherein $Ar^1$ has a structure represented by a formula:

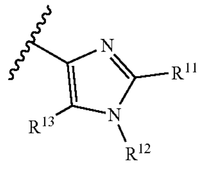 or 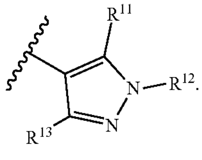.

Aspect 88. The compound of Aspect 60, wherein $Ar^1$ is a 5-membered heteroaryl having two heteroatoms comprising a first heteroatom and a second heteroatom; wherein the first heteroatom is —N═; and wherein the second heteroatom is selected from —O— and —S—; wherein $Ar^1$ is substited with $R^{11}$ and $R^{12}$; and wherein each of $R^{11}$ and $R^{12}$ is independently selected from hydrogen, halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl;

Aspect 89. The compound of Aspect 88, wherein each of $R^{11}$ and $R^{12}$ is independently selected from hydrogen, —Cl, —Br, —$SF_5$, —CN, —$N_3$, —CN, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2CH_2Br$, —$CH_2CHBr_2$, —$CH_2CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_2CH_2F$, —$OCH_2CHF_2$, —$OCH_2CF_3$, —$OCH_2CH_2Cl$, —$OCH_2CHCl_2$, —$OCH_2CCl_3$, —$OCH_2CH_2Br$, —$OCH_2CHBr_2$, —$OCH_2CBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl.

Aspect 90. The compound of Aspect 88, wherein each of $R^{11}$ and $R^{12}$ is independently selected from hydrogen, —Cl, —Br, —$CH_2F$, —$CHF_2$, —$CF_3$, —$CH_2Cl$, —$CHCl_2$, —$CCl_3$, —$CH_2Br$, —$CHBr_2$, —$CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl.

Aspect 91. The compound of Aspect 88, wherein each of $R^{11}$ and $R^{12}$ is independently selected from hydrogen, —Cl, —$CCl_3$, —$OCF_3$, —$OCCl_3$, —$OCH_3$, methyl, ethyl, propyl, isopropyl, butyl, isobutyl, and tert-butyl.

Aspect 92. The compound of Aspect 88, wherein each of $R^{11}$ and $R^{12}$ is independently selected from hydrogen, —Cl, —$OCF_3$, methyl, ethyl, and tert-butyl.

Aspect 93. The compound of any one of Aspect 88-Aspect 92, wherein at least one of $R^{11}$ and $R^{12}$ is hydrogen.

Aspect 94. The compound of any one of Aspect 88-Aspect 92, wherein each of $R^{11}$ and $R^{12}$ is hydrogen.

Aspect 95. The compound of any one of Aspect 88-Aspect 94, wherein $Ar^1$ has a structure represented by a formula:

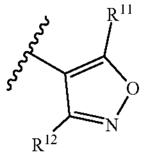

or

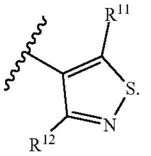

Aspect 96. The compound of any one of 1-Aspect 13, wherein R1 is Cy1; and wherein Cy1 is a 5- to 10-membered cycloalkyl optionally substituted with a 1, 2, 3, 4, or 5 groups independently selected from halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl.

Aspect 97. The compound of Aspect 96, wherein Cy1 is selected from cyclobutyl, cyclopentyl, cyclohexyl, and cycloheptyl.

Aspect 98. The compound of Aspect 97, wherein Cy1 is selected from cyclopentyl, cyclohexyl, and cycloheptyl.

Aspect 99. The compound of Aspect 97, wherein Cy1 is cyclohexyl.

Aspect 100. The compound of any one of Aspect 96-Aspect 99, wherein Cy1 is monosubstituted with a group selected from halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl.

Aspect 101. The compound of Aspect 100, wherein Cy1 is monosubstituted with a group selected from —Cl, —Br, —$SF_5$, —CN, —$N_3$, —CN, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2CH_2Br$, —$CH_2CHBr_2$, —$CH_2CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_2CH_2F$, —$OCH_2CHF_2$, —$OCH_2CF_3$, —$OCH_2CH_2Cl$, —$OCH_2CHCl_2$, —$OCH_2CCl_3$, —$OCH_2CH_2Br$, —$OCH_2CHBr_2$, —$OCH_2CBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl.

Aspect 102. The compound of Aspect 100, wherein Cy1 is monosubstituted with a group selected from —Cl, —Br, —$CH_2F$, —$CHF_2$, —$CF_3$, —$CH_2Cl$, —$CHCl_2$, —$CCl_3$, —$CH_2Br$, —$CHBr_2$, —$CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl.

Aspect 103. The compound of Aspect 100, wherein Cy1 is monosubstituted with a group selected from —Cl, —$CCl_3$, —$OCF_3$, —$OCCl_3$, —$OCH_3$, methyl, ethyl, propyl, isopropyl, butyl, isobutyl, and tert-butyl.

Aspect 104. The compound of Aspect 100, wherein Cy1 is monosubstituted with a group selected from —Cl, —$OCF_3$, methyl, ethyl, and tert-butyl.

Aspect 105. The compound of any one of Aspect 96-Aspect 99, wherein Cy1 is disubstituted with two groups independently selected from halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl.

Aspect 106. The compound of Aspect 105, wherein Cy1 is disubstituted with two groups independently selected from —Cl, —Br, —$SF_5$, —CN, —$N_3$, —CN, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2CH_2Br$, —$CH_2CHBr_2$, —$CH_2CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_2CH_2F$, —$OCH_2CHF_2$, —$OCH_2CF_3$, —$OCH_2CH_2Cl$, —$OCH_2CHCl_2$, —$OCH_2CCl_3$, —$OCH_2CH_2Br$, —$OCH_2CHBr_2$, —$OCH_2CBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl.

Aspect 107. The compound of Aspect 105, wherein Cy1 is disubstituted with two groups independently selected from —Cl, —Br, —$CH_2F$, —$CHF_2$, —$CF_3$, —$CH_2Cl$, —$CHCl_2$, —$CCl_3$, —$CH_2Br$, —$CHBr_2$, —$CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl.

Aspect 108. The compound of Aspect 105, wherein Cy1 is disubstituted with two groups independently selected from —Cl, —$CCl_3$, —$OCF_3$, —$OCCl_3$, —$OCH_3$, methyl, ethyl, propyl, isopropyl, butyl, isobutyl, and tert-butyl.

Aspect 109. The compound of Aspect 105, wherein Cy1 is disubstituted with two groups independently selected from —Cl, —$OCF_3$, methyl, ethyl, and tert-butyl.

Aspect 110. The compound of any one of Aspect 96-Aspect 99, wherein Cy1 is unsubstituted.

Aspect 111. The compound of any one of 1-Aspect 16, wherein the compound has a structure represented by a formula:

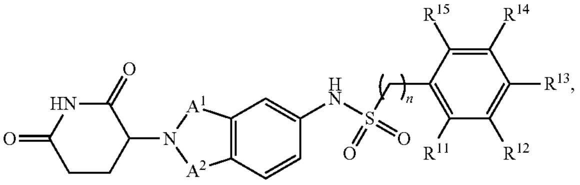

wherein n is an integer selected from 0, 1, and 2; wherein each of $A^1$ and $A^2$ is independently selected from —(C═O)— and —$CH_2$—, provided that at least one of $A^1$ and $A^2$ is —(C═O)—; wherein each of $R^{11}$, $R^{12}$, $R^{13}$, $R^{14}$, and $R^{15}$ is independently selected from hydrogen, halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl; or a pharmaceutically acceptable salt thereof.

Aspect 112. The compound of Aspect 111, wherein each of $R^{11}$, $R^{12}$, $R^{13}$, $R^{14}$, and $R^{15}$ is independently selected from hydrogen, halogen, —$SF_5$, —CN, —$N_3$, —$NH_2$, —OH, —CN, —$SCF_3$, C1-C3 alkoxy, C1-C3 haloalkyl, C1-C3 aminoalkyl, C1-C3 alkylamino, C1-C3 hydroxyalkyl, —O—(C1-C3 haloalkyl), C3-C8 cycloalkyl, C1-C6 alkyl, and phenyl, provided that at least one of $R^{11}$, $R^{12}$, $R^{13}$, $R^{14}$, and $R^{15}$ is not hydrogen.

Aspect 113. The compound of Aspect 111, wherein each of $R^{11}$, $R^{12}$, and $R^{13}$ is independently selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl, provided that at least one $R^{11}$, $R^{12}$, and $R^{13}$ is not hydrogen; and wherein each of $R^{14}$ and $R^{15}$ is hydrogen.

Aspect 114. The compound of Aspect 111, wherein each of $R^{11}$ and $R^{12}$ is independently selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl; and wherein each of $R^{13}$, $R^{14}$, and $R^{15}$ is hydrogen.

Aspect 115. The compound of Aspect 111, wherein each of $R^{11}$ and $R^{13}$ is independently selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl; and wherein each of $R^{12}$, $R^{14}$, and $R^{15}$ is hydrogen.

Aspect 116. The compound of Aspect 111, wherein each of $R^{11}$ and $R^{14}$ is independently selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl; and wherein each of $R^{12}$, $R^{13}$, and $R^{15}$ is hydrogen.

Aspect 117. The compound of Aspect 111, wherein $R^{11}$ is selected from halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl; and wherein each of $R^{12}$, $R^{13}$, $R^{14}$, and $R^{15}$ is hydrogen.

Aspect 118. The compound of Aspect 117, wherein $R^{11}$ is selected from —Cl, —Br, —$SF_5$, —CN, —$N_3$, —CN, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2CH_2Br$, —$CH_2CHBr_2$, —$CH_2CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_2CH_2F$, —$OCH_2CHF_2$, —$OCH_2CF_3$, —$OCH_2CH_2Cl$, —$OCH_2CHCl_2$, —$OCH_2CCl_3$, —$OCH_2CH_2Br$, —$OCH_2CHBr_2$, —$OCH_2CBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl.

Aspect 119. The compound of Aspect 117, wherein $R^{11}$ is selected from —Cl, —Br, —$CH_2F$, —$CHF_2$, —$CF_3$, —$CH_2Cl$, —$CHCl_2$, —$CCl_3$, —$CH_2Br$, —$CHBr_2$, —$CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl.

Aspect 120. The compound of Aspect 117, wherein $R^{11}$ is selected from —Cl, —$CCl_3$, —$OCF_3$, —$OCCl_3$, —$OCH_3$, methyl, ethyl, propyl, isopropyl, butyl, isobutyl, and tert-butyl.

Aspect 121. The compound of Aspect 117, wherein $R^{11}$ is selected from —Cl, —$OCF_3$, methyl, ethyl, and tert-butyl.

Aspect 122. The compound of Aspect 111, wherein $R^{12}$ is selected from halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, C1-C3 alkyl, and phenyl; and wherein each of $R^{12}$, $R^{13}$, $R^{14}$, and $R^{15}$ is hydrogen.

Aspect 123. The compound of Aspect 122, wherein $R^{11}$ is selected from —Cl, —Br, —$SF_5$, —CN, —$N_3$, —CN, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2CH_2Br$, —$CH_2CHBr_2$, —$CH_2CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_2CH_2F$, —$OCH_2CHF_2$, —$OCH_2CF_3$, —$OCH_2CH_2Cl$, —$OCH_2CHCl_2$, —$OCH_2CCl_3$, —$OCH_2CH_2Br$, —$OCH_2CHBr_2$, —$OCH_2CBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl.

Aspect 124. The compound of Aspect 122, wherein $R^{12}$ is selected from —Cl, —Br, —$CH_2F$, —$CHF_2$, —$CF_3$, —$CH_2Cl$, —$CHCl_2$, —$CCl_3$, —$CH_2Br$, —$CHBr_2$, —$CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl.

Aspect 125. The compound of Aspect 122, wherein $R^{12}$ is selected from —Cl, —$CCl_3$, —$OCF_3$, —$OCCl_3$, —$OCH_3$, methyl, ethyl, propyl, isopropyl, butyl, isobutyl, and tert-butyl.

Aspect 126. The compound of Aspect 122, wherein $R^{12}$ is selected from —Cl, —$OCF_3$, methyl, ethyl, and tert-butyl.

Aspect 127. The compound of Aspect 111, wherein $R^{13}$ is selected from halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, C1-C3 alkyl, and phenyl; and wherein each of $R^{12}$, $R^{13}$, $R^{14}$, and $R^{15}$ is hydrogen.

Aspect 128. The compound of Aspect 127, wherein $R^{13}$ is selected from —Cl, —Br, —$SF_5$, —CN, —$N_3$, —CN, —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2CH_2F$, —$CH_2CHF_2$, —$CH_2CF_3$, —$CH_2CH_2Cl$, —$CH_2CHCl_2$, —$CH_2CCl_3$, —$CH_2CH_2Br$, —$CH_2CHBr_2$, —$CH_2CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_2CH_2F$, —$OCH_2CHF_2$, —$OCH_2CF_3$, —$OCH_2CH_2Cl$, —$OCH_2CHCl_2$, —$OCH_2CCl_3$, —$OCH_2CH_2Br$, —$OCH_2CHBr_2$, —$OCH_2CBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl.

Aspect 129. The compound of Aspect 127, wherein $R^{13}$ is selected from —Cl, —Br, —$CH_2F$, —$CHF_2$, —$CF_3$, —$CH_2Cl$, —$CHCl_2$, —$CCl_3$, —$CH_2Br$, —$CHBr_2$, —$CBr_3$, —$OCH_2F$, —$OCHF_2$, —$OCF_3$, —$OCH_2Cl$, —$OCHCl_2$, —$OCCl_3$, —$OCH_2Br$, —$OCHBr_2$, —$OCBr_3$, —$OCH_3$, —$OCH_2CH_3$, —$CH_2OH$, —$(CH_2)_2OH$, —$NHCH_3$, —$NHCH_2CH_3$, —$N(CH_3)2$, methyl, ethyl, propyl, isopropyl, butyl, isobutyl, and tert-butyl.

Aspect 130. The compound of Aspect 127, wherein $R^{13}$ is selected from —Cl, —$CCl_3$, —$OCF_3$, —$OCCl_3$, —$OCH_3$, methyl, ethyl, propyl, isopropyl, butyl, isobutyl, and tert-butyl.

Aspect 131. The compound of Aspect 127, wherein $R^{13}$ is selected from —Cl, —$OCF_3$, methyl, ethyl, and tert-butyl.

Aspect 132. The compound of Aspect 111, having a structure represented by a formula:

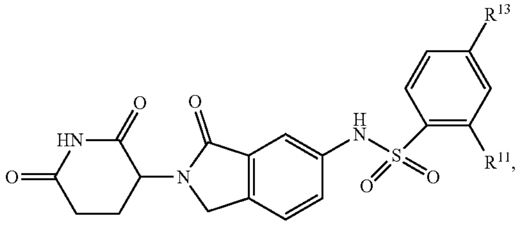

wherein each of $R^{11}$ and $R^{12}$ is independently selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl.

Aspect 133. The compound of Aspect 111, having a structure represented by a formula:

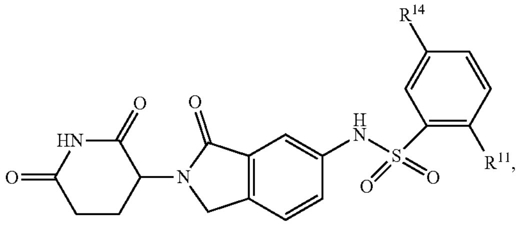

wherein each of $R^{11}$ and $R^{13}$ is independently selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl.

Aspect 134. The compound of Aspect 111, having a structure represented by a formula:

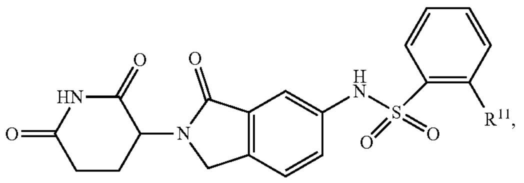

wherein each of $R^{11}$ and $R^{14}$ is independently selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl.

Aspect 135. The compound of Aspect 111, having a structure represented by a formula:

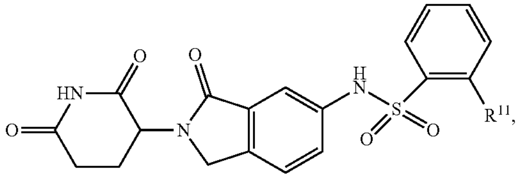

wherein $R^{11}$ is selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl.

Aspect 136. The compound of Aspect 111, having a structure represented by a formula:

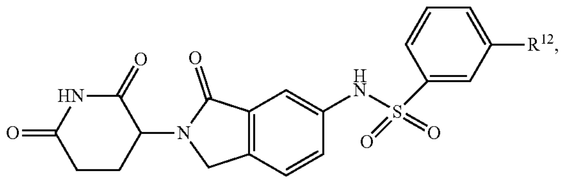

wherein $R^{12}$ is selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl.

Aspect 137. The compound of Aspect 111, having a structure represented by a formula:

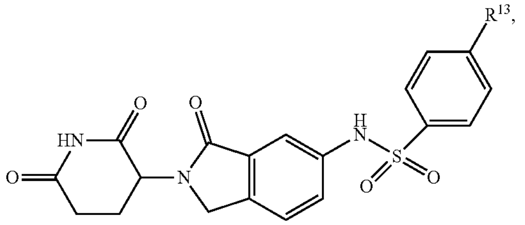

wherein $R^{13}$ is selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl.

Aspect 138. The compound of Aspect 111, having a structure represented by a formula:

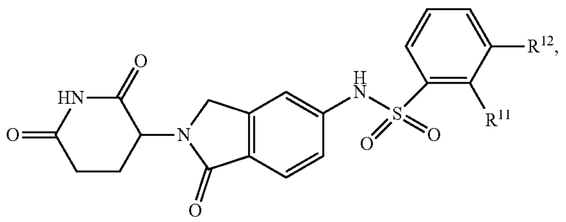

wherein each of $R^{11}$ and $R^{12}$ is independently selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl.

Aspect 139. The compound of Aspect 111, having a structure represented by a formula:

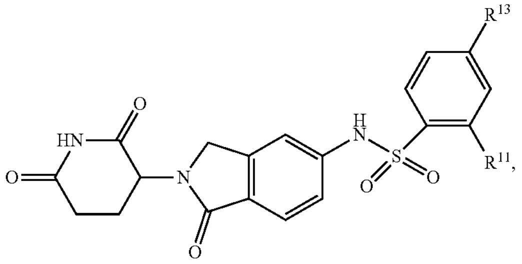

wherein each of $R^{11}$ and $R^{13}$ is independently selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl.

Aspect 140. The compound of Aspect 111, having a structure represented by a formula:

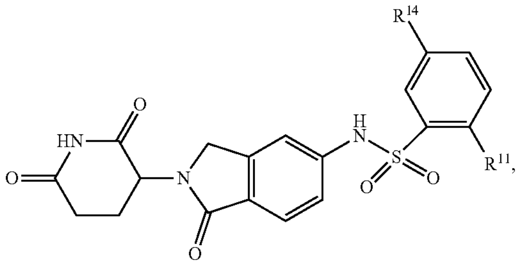

wherein each of $R^{11}$ and $R^{14}$ is independently selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl.

Aspect 141. The compound of Aspect 111, having a structure represented by a formula:

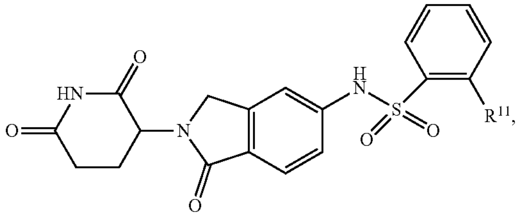

wherein $R^{11}$ is selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl.

Aspect 142. The compound of Aspect 111, having a structure represented by a formula:

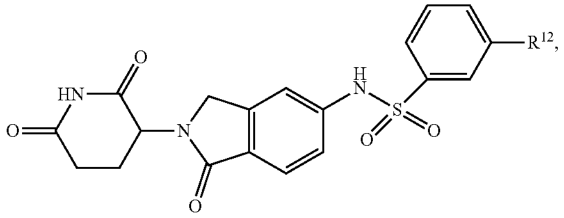

wherein $R^{12}$ is selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl.

Aspect 143. The compound of Aspect 111, having a structure represented by a formula:

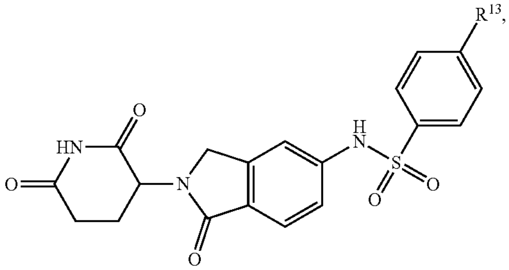

wherein $R^{13}$ is selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl.

Aspect 144. The compound of Aspect 111, having a structure represented by a formula:

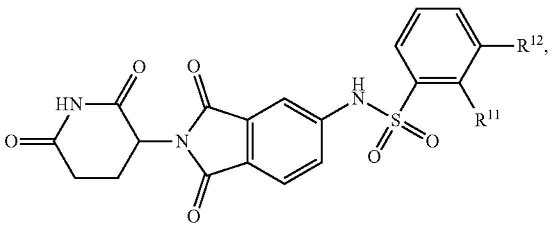

wherein each of $R^{11}$ and $R^{12}$ is independently selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl.

Aspect 145. The compound of Aspect 111, having a structure represented by a formula:

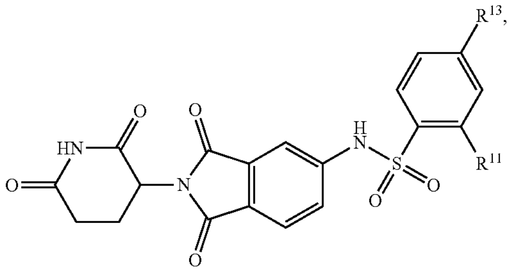

wherein each of $R^{11}$ and $R^{13}$ is independently selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl.

Aspect 146. The compound of Aspect 111, having a structure represented by a formula:

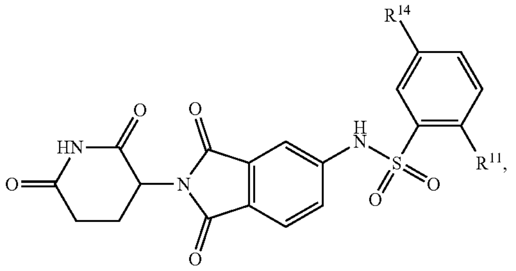

wherein each of $R^{11}$ and $R^{14}$ is independently selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl.

Aspect 147. The compound of Aspect 111, having a structure represented by a formula:

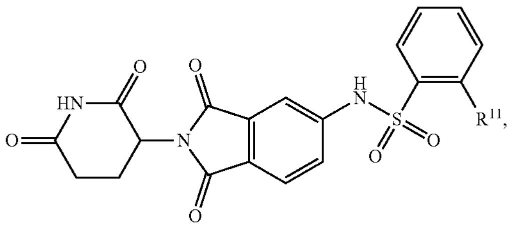

wherein $R^{11}$ is selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl.

Aspect 148. The compound of Aspect 111, having a structure represented by a formula:

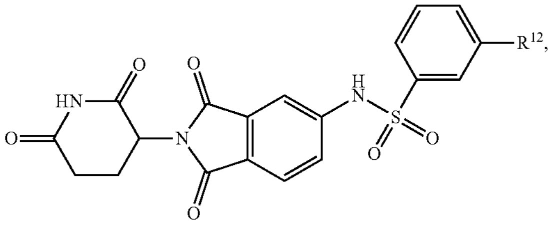

wherein $R^{12}$ is selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl.

Aspect 149. The compound of Aspect 111, having a structure represented by a formula:

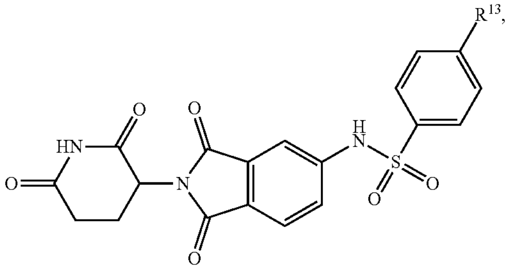

wherein $R^{13}$ is selected from hydrogen, halogen, —$SF_5$, —CN, —$N_3$, —$NH_2$, —OH, —CN, C1-C3 alkoxy, C1-C3 haloalkyl, C1-C3 aminoalkyl, C1-C3 alkylamino, C1-C3 hydroxyalkyl, —O—(C1-C3 haloalkyl), C1-C3 alkyl, and phenyl.

Aspect 150. The compound of 1, wherein the compound is present as:

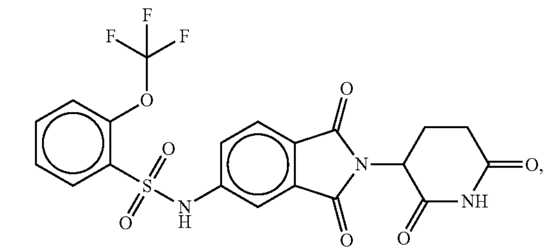

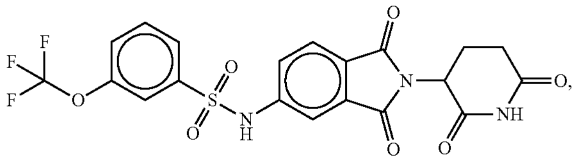

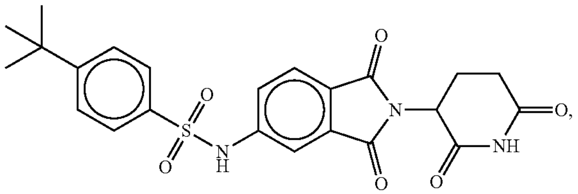

-continued
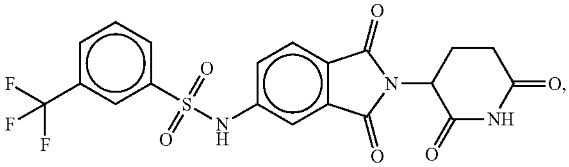,
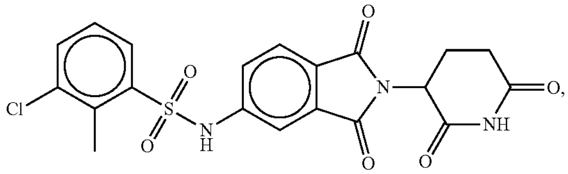,
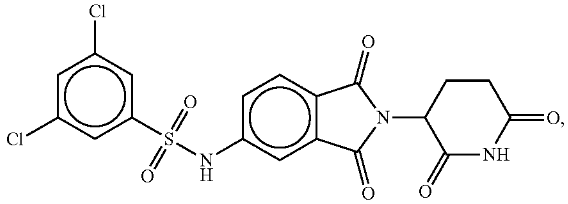,
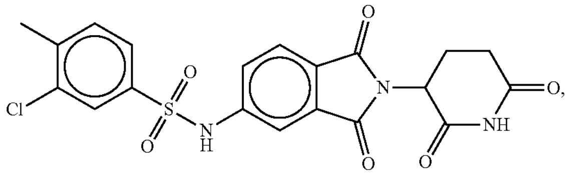,
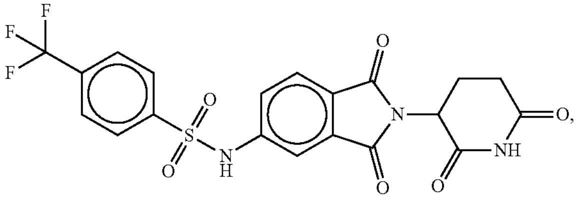,
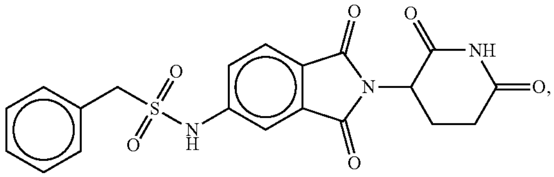,
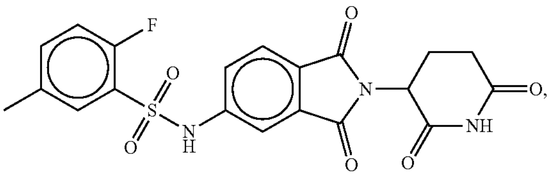,
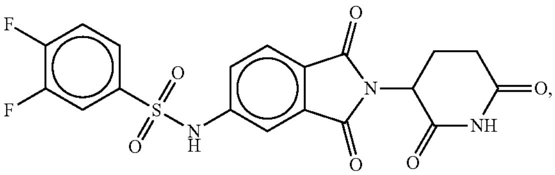,
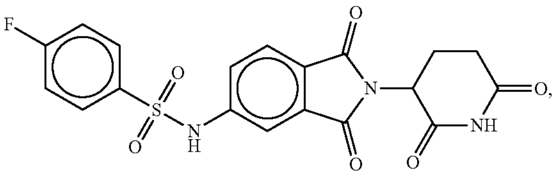,
-continued
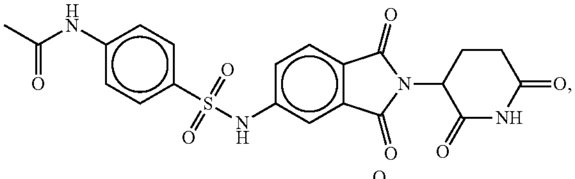,
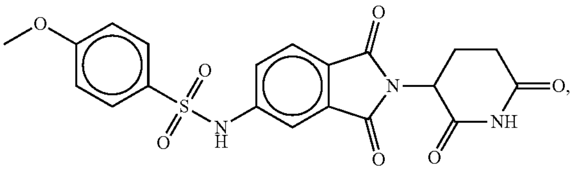,
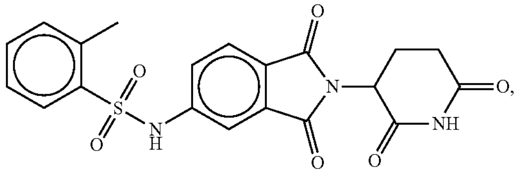,
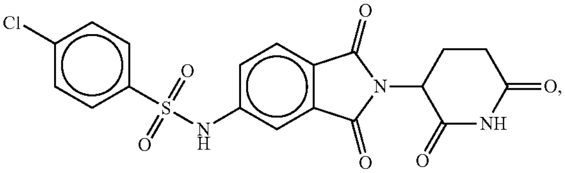,
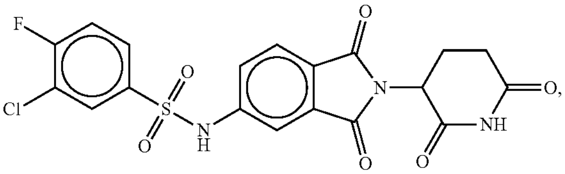,
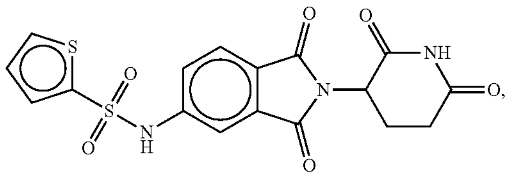,
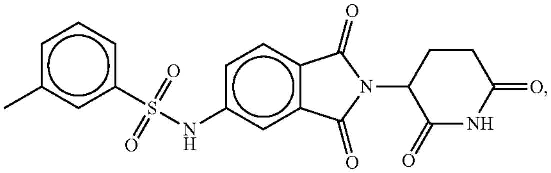,
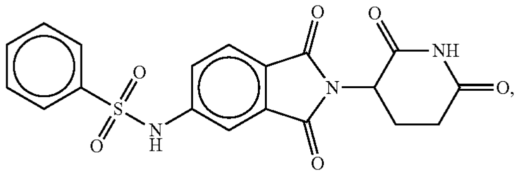,
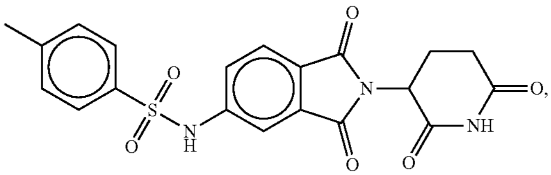,
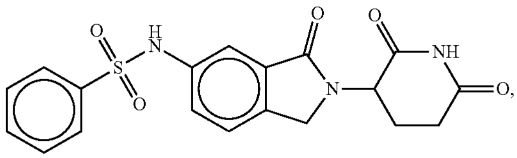,

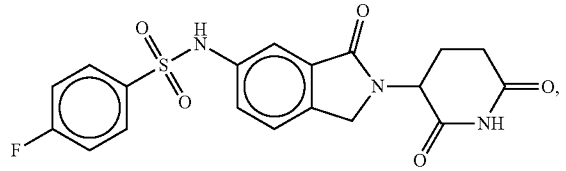
,
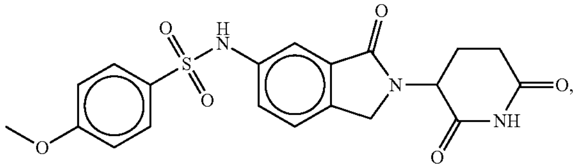
,
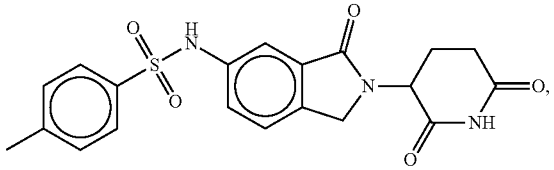
,
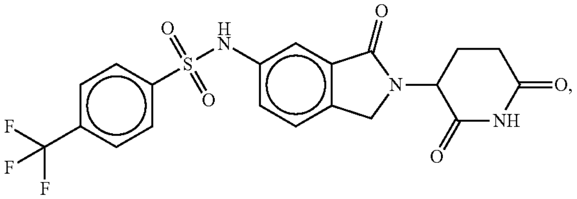
,
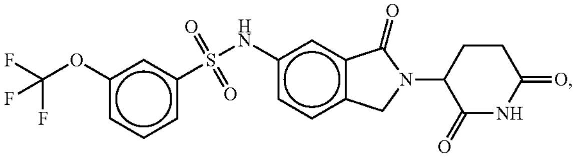
,
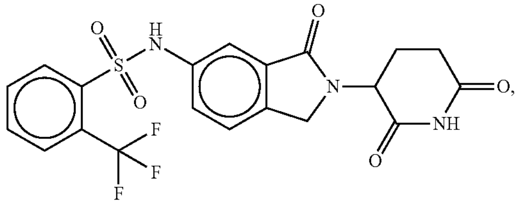
,
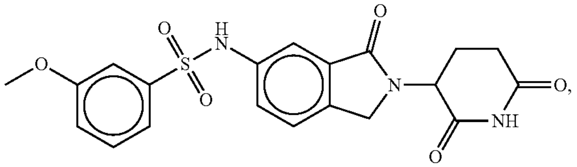
,
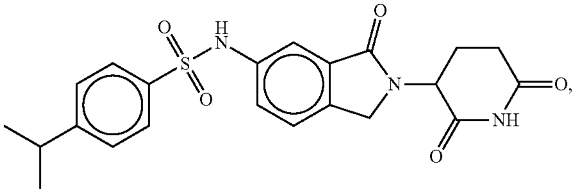
,
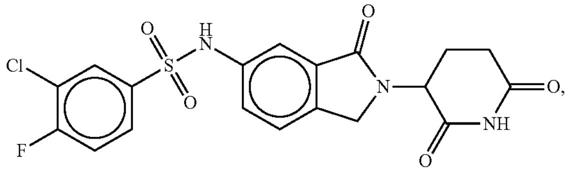
,
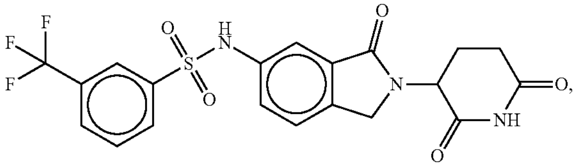
,
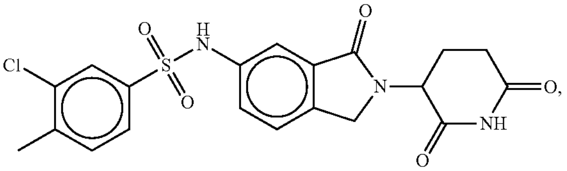
,
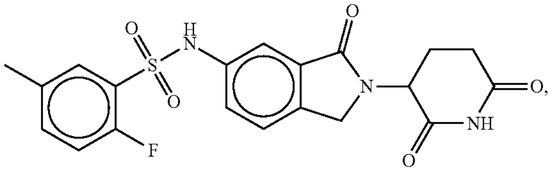
,
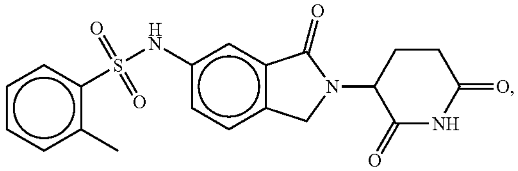
,
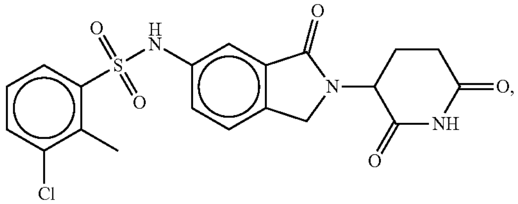
,
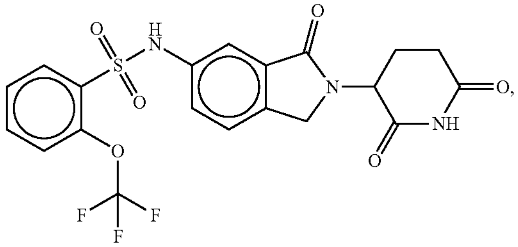
,
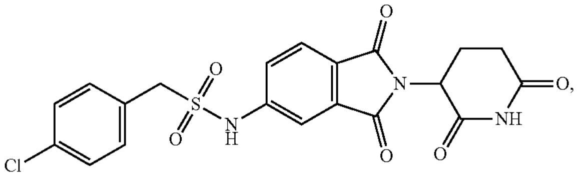
,
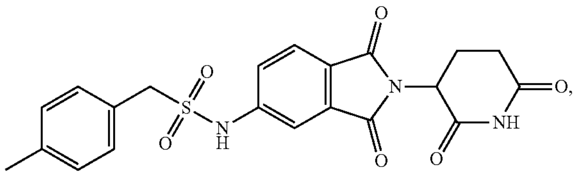
,
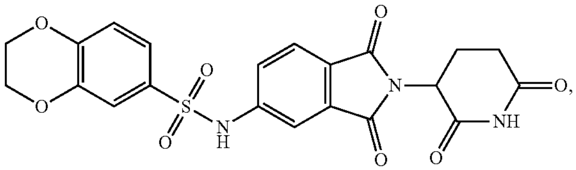
, -continued
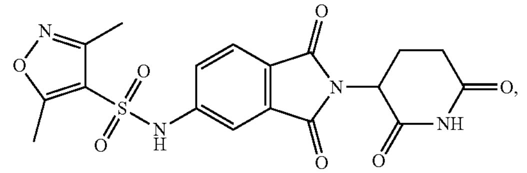
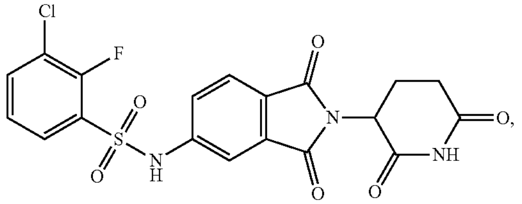
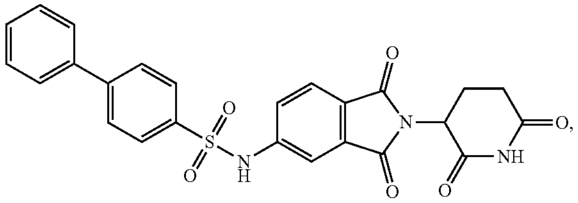
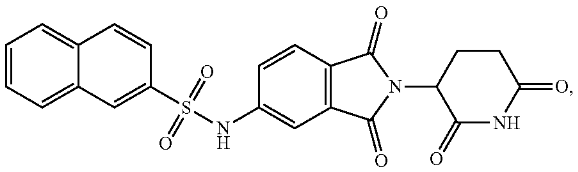
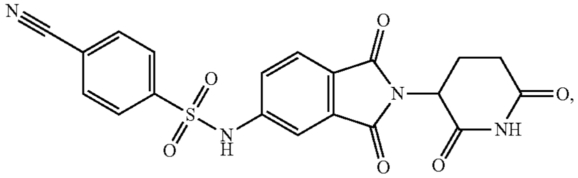
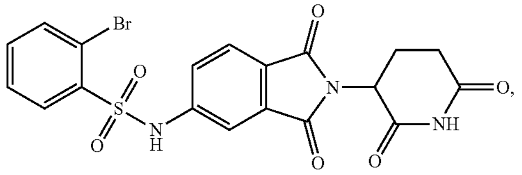
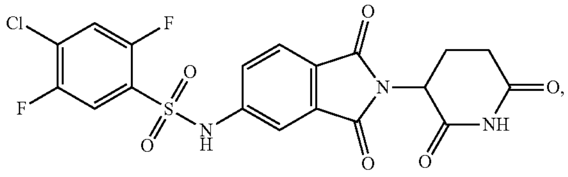
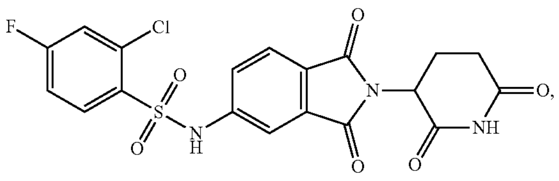
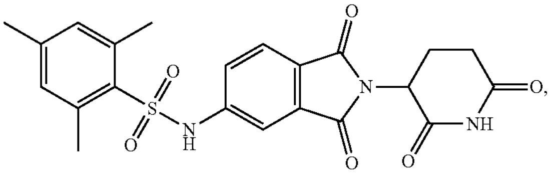
-continued
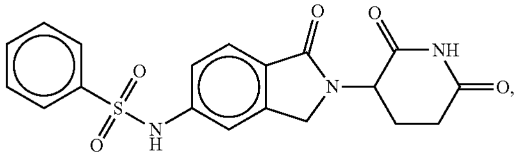
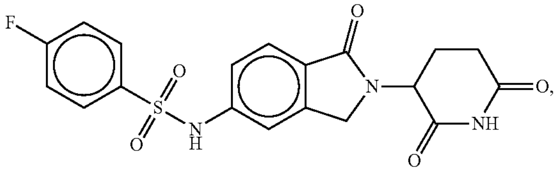
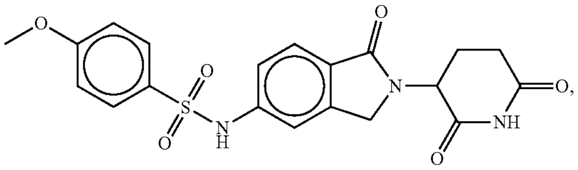
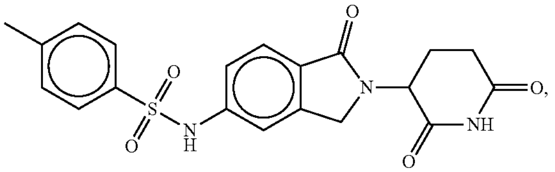
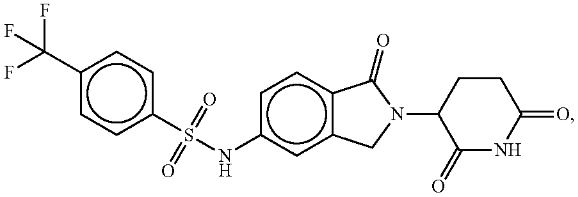
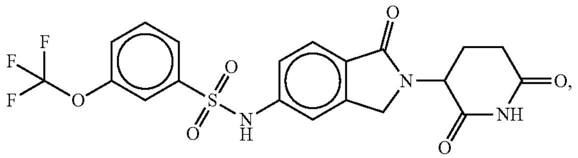
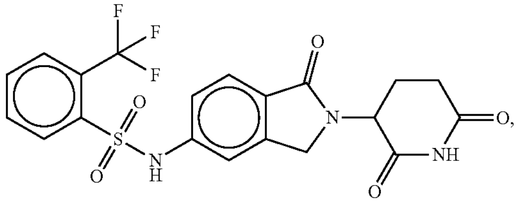
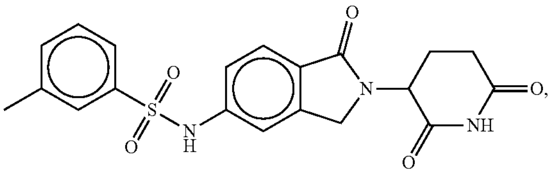
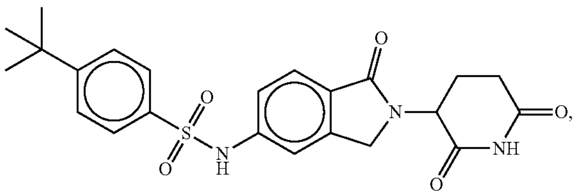

-continued
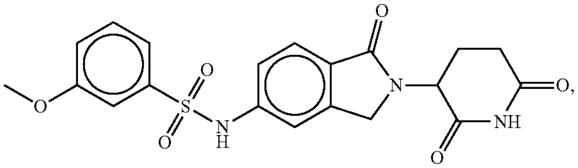,
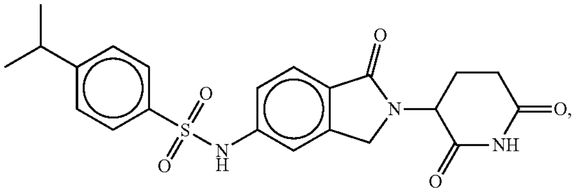,
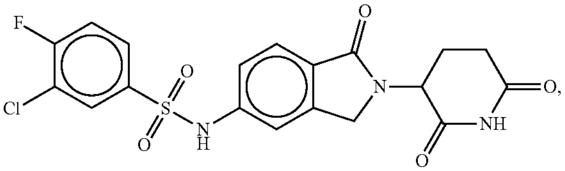,
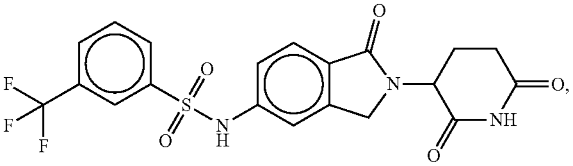,
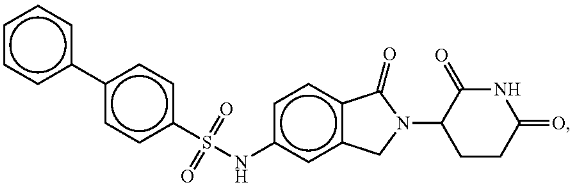,
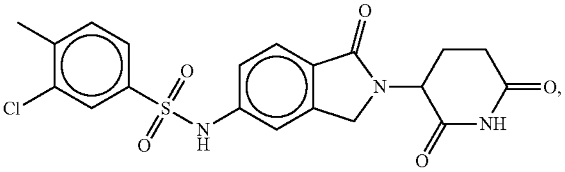,
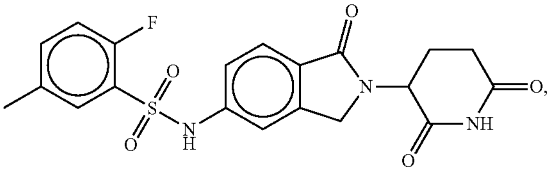,
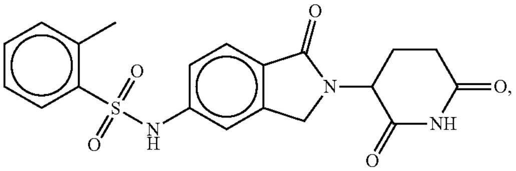,
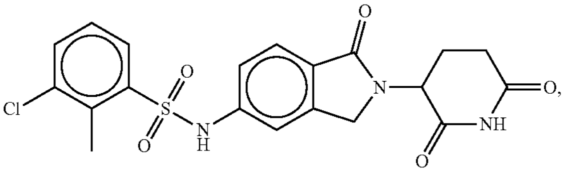,
-continued
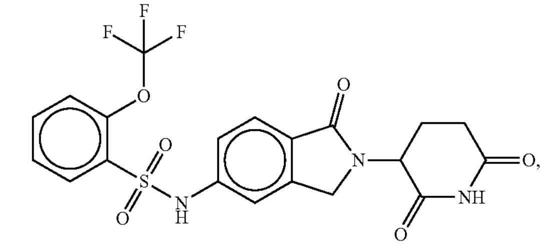,
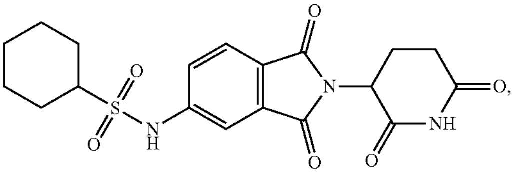,
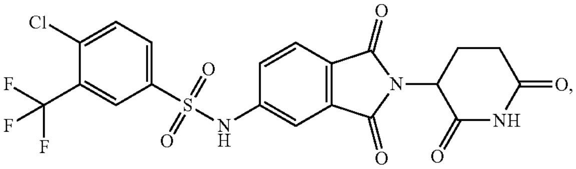,
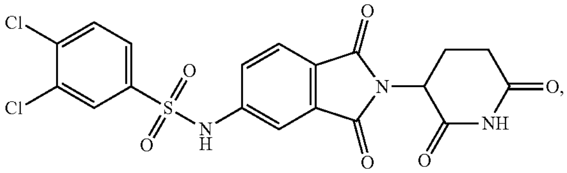,
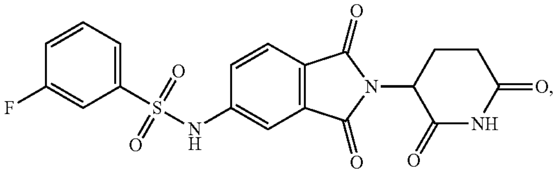,
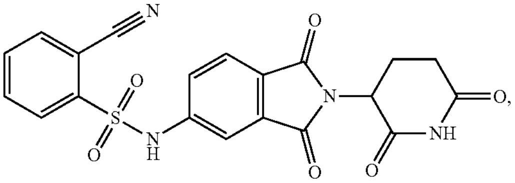,
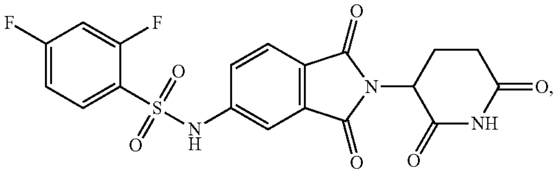,
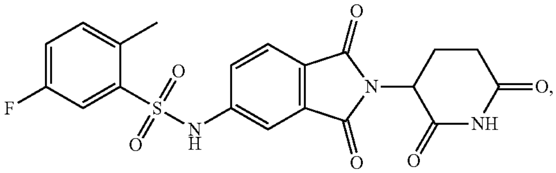,
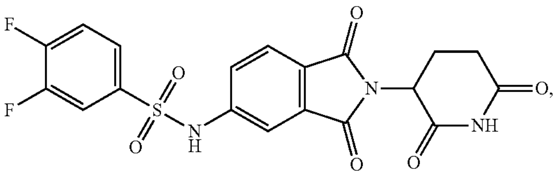, -continued
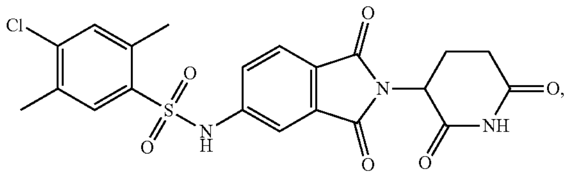
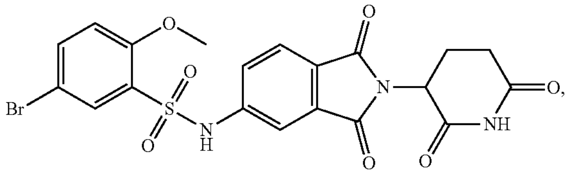
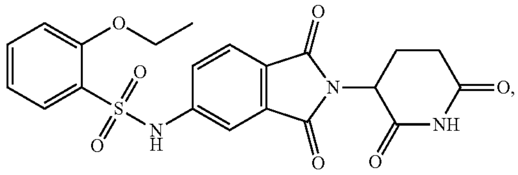
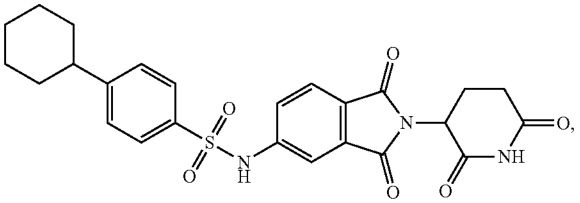
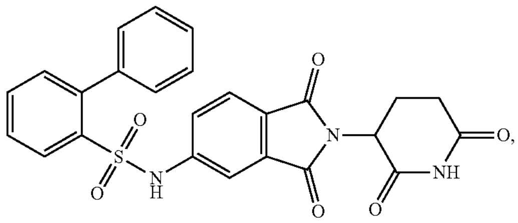
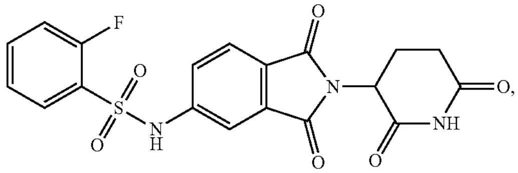
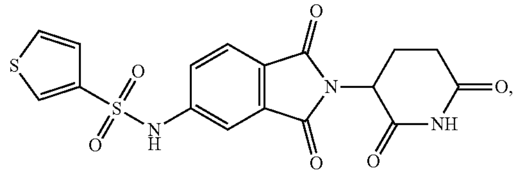
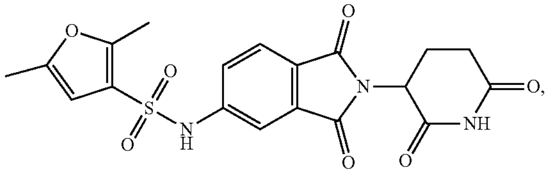
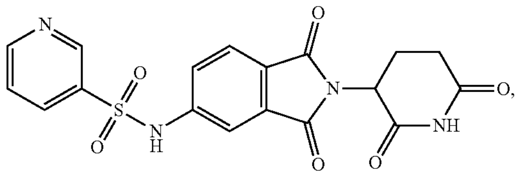
-continued
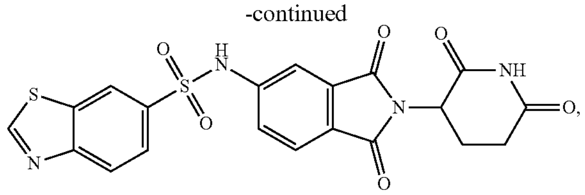
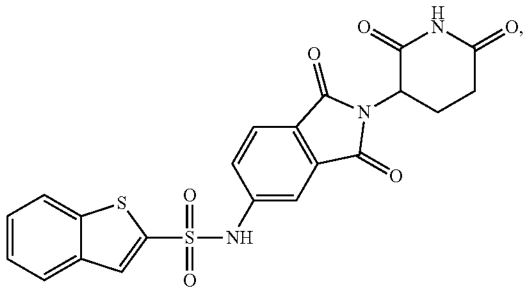
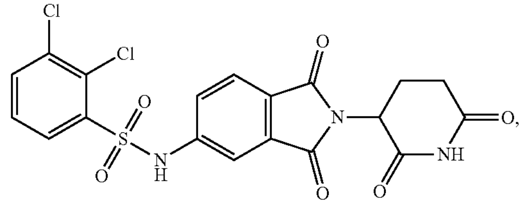
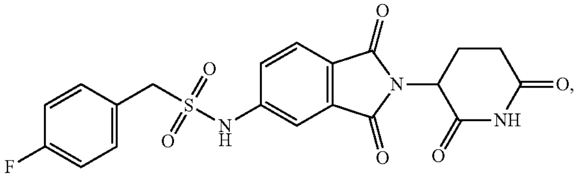
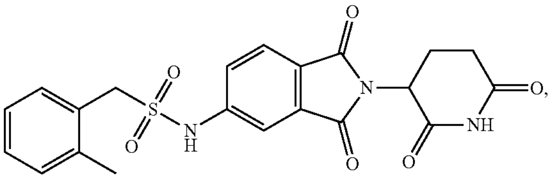
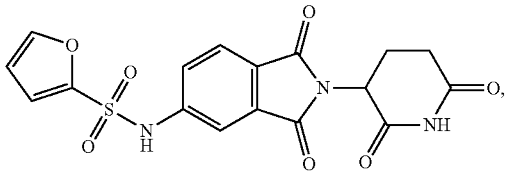
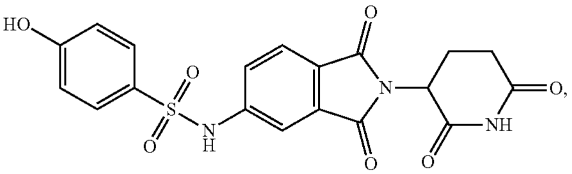
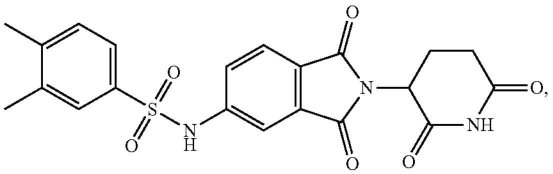
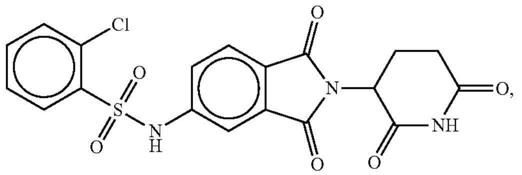

-continued
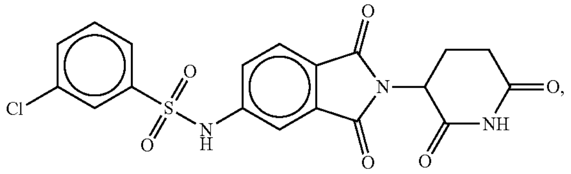
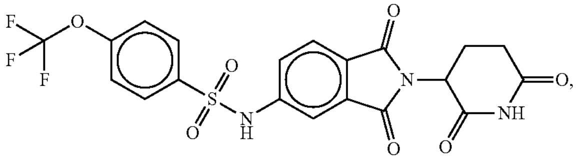
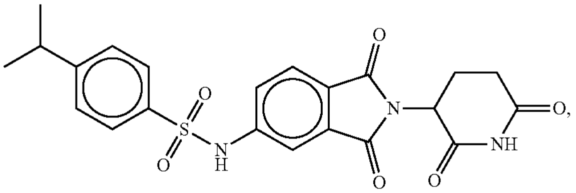
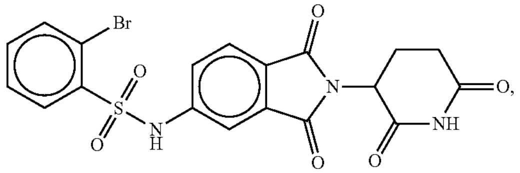
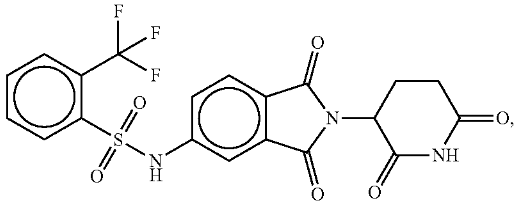
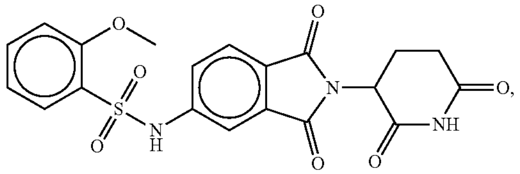
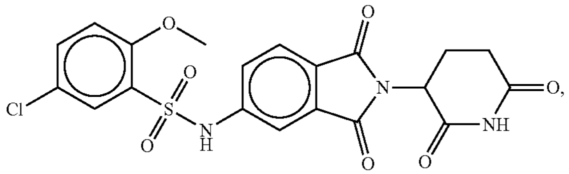
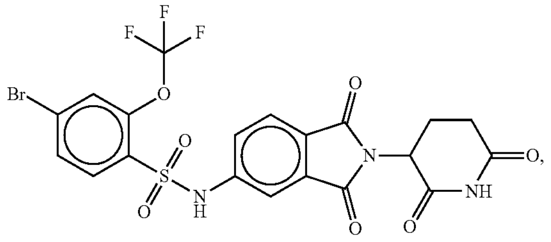
or
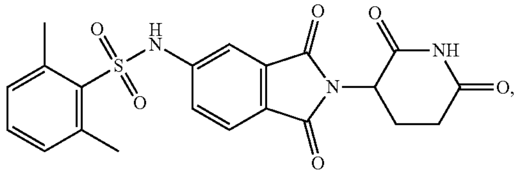
or a subgroup thereof.
Aspect 151. The compound of 1, wherein the compound is present as:
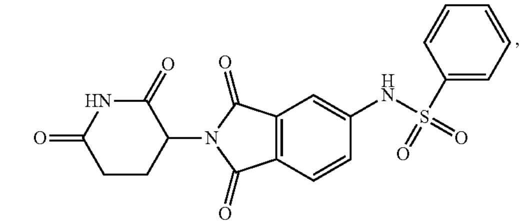
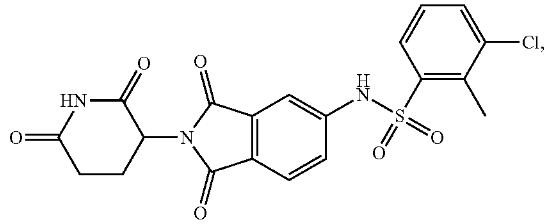
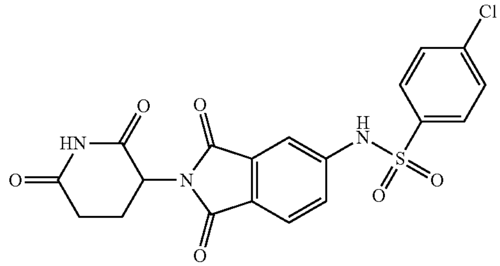
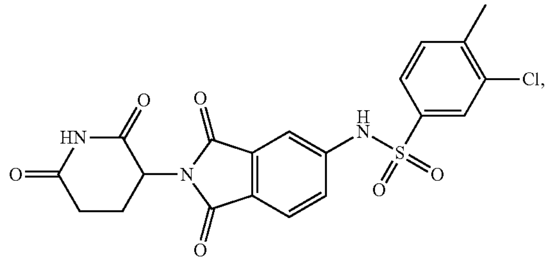
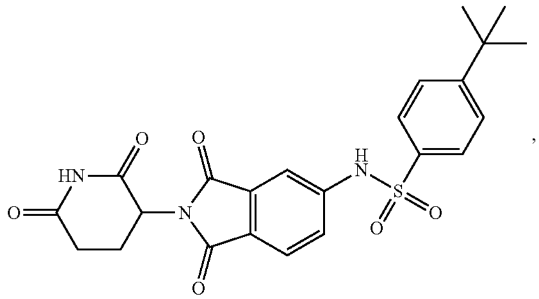
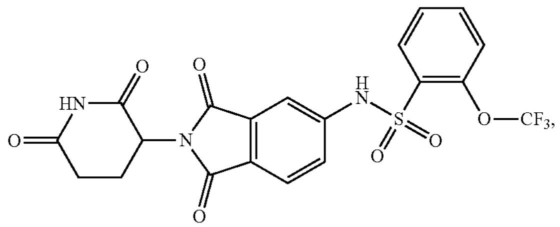

-continued
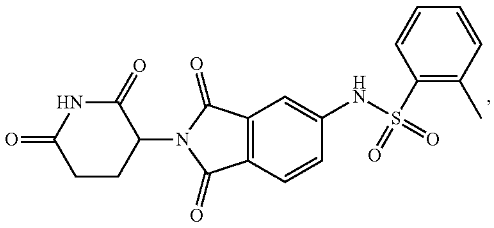
, or
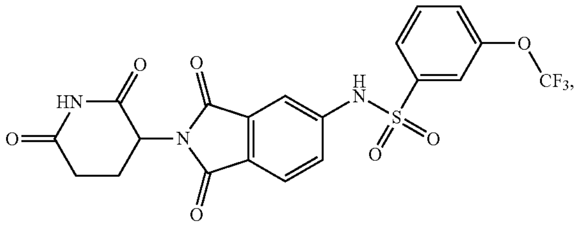
or a subgroup thereof.
Aspect 152. The compound of 1, wherein the compound is present as:
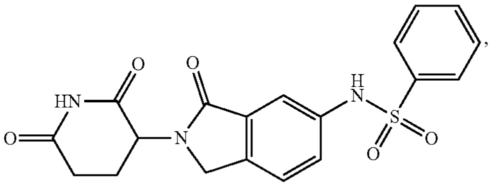
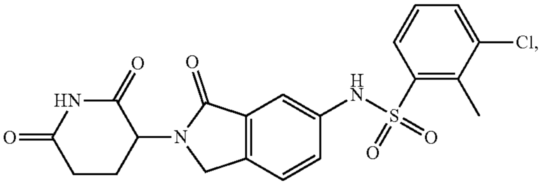
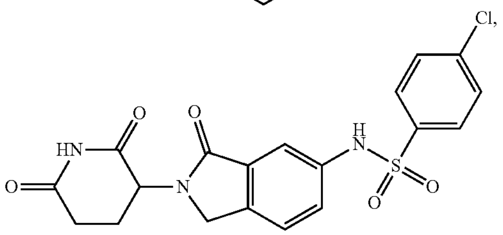
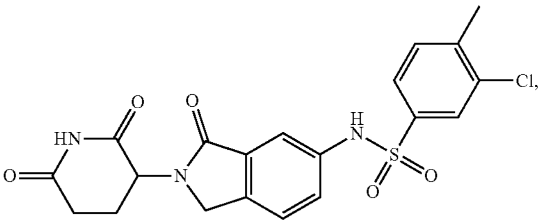
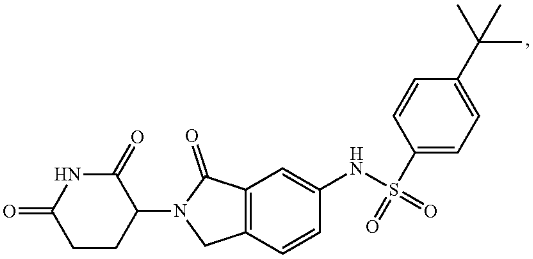
-continued
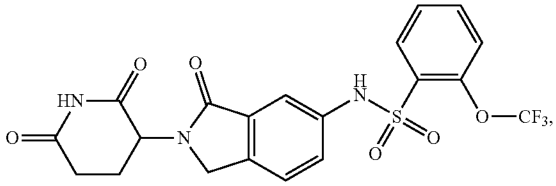
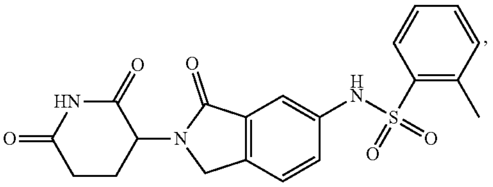
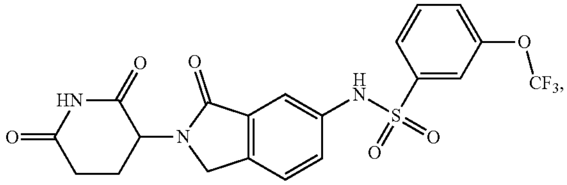 [SMILES: O=C1CCC(N2Cc3ccc(NS(=O)(=O)c4cccc(OC(F)(F)F)c4)cc3C2=O)C(=O)N1]
or a subgroup thereof.
Aspect 153. The compound of 1, wherein the compound is present as:
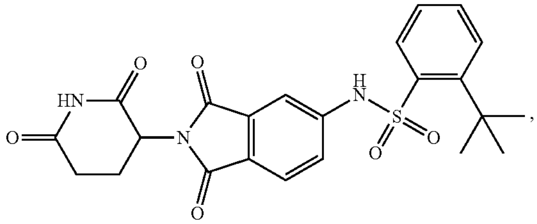
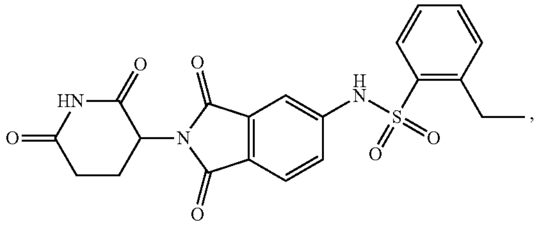
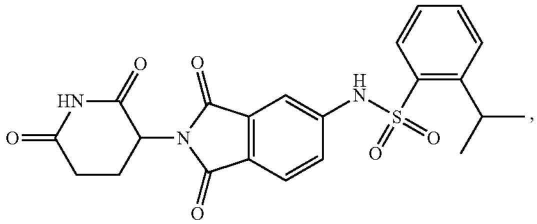
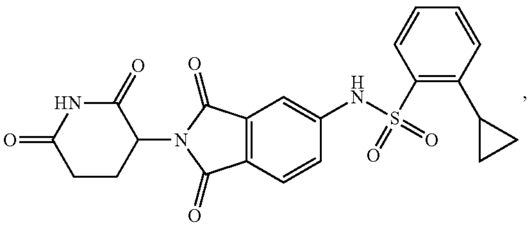

-continued
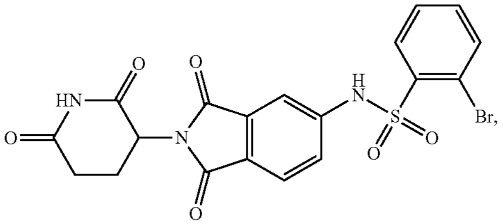
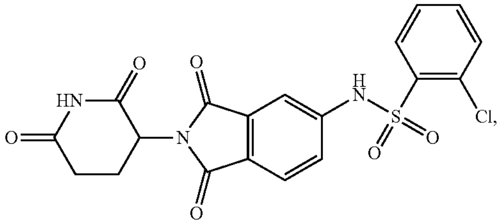
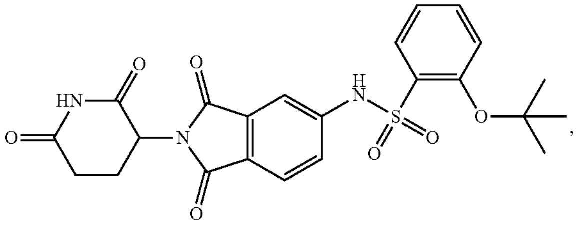
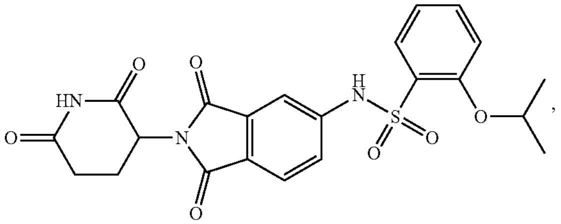
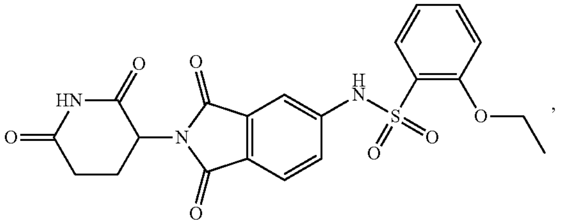
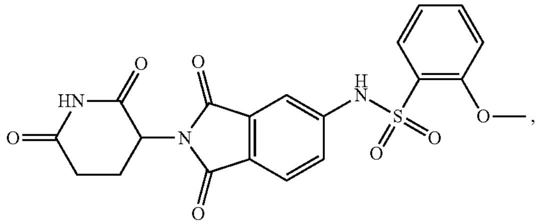
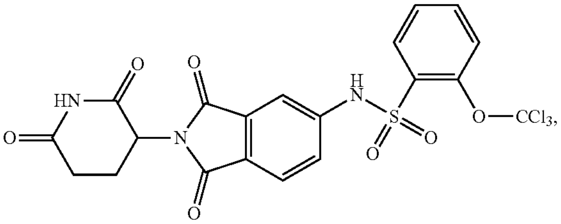
-continued
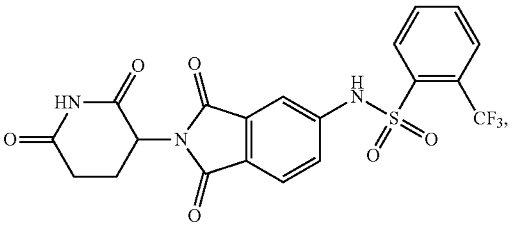
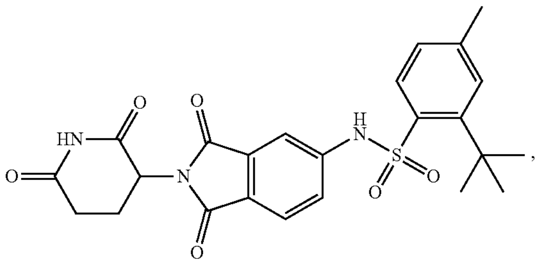
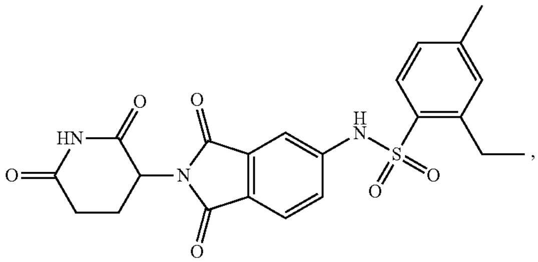
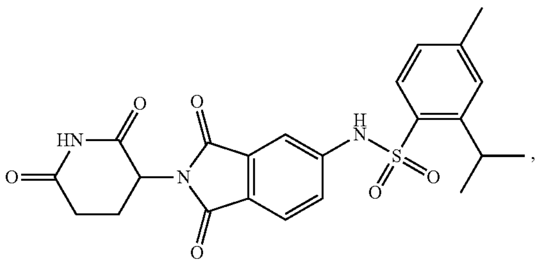
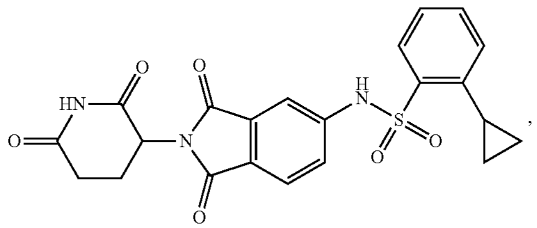
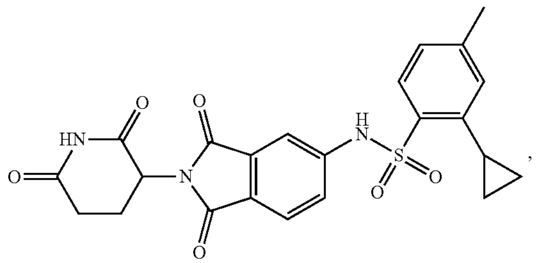

-continued

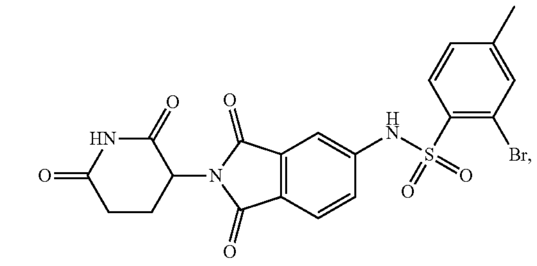

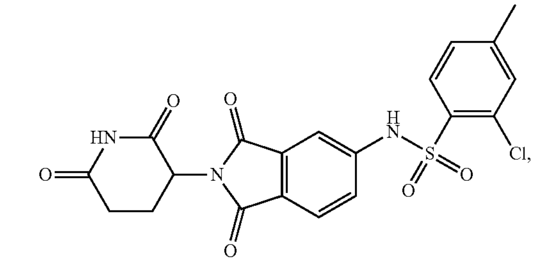

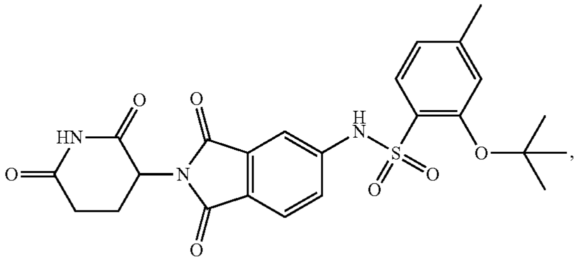

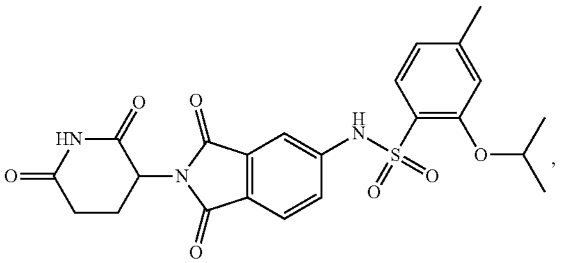

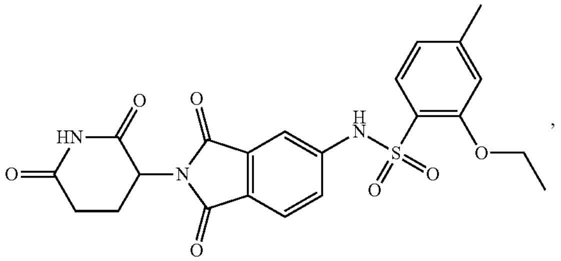

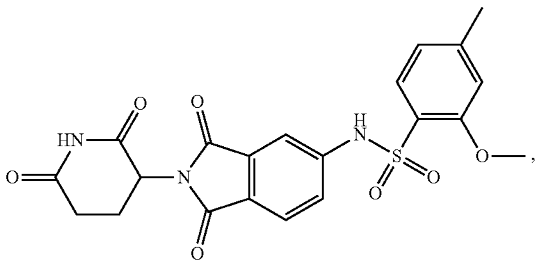

-continued

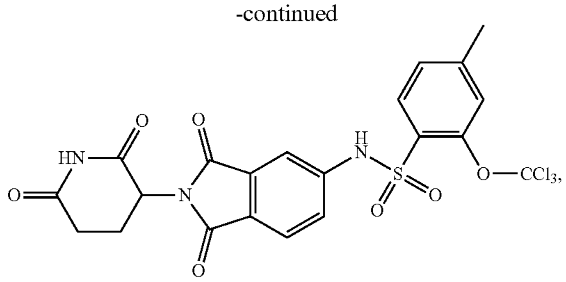

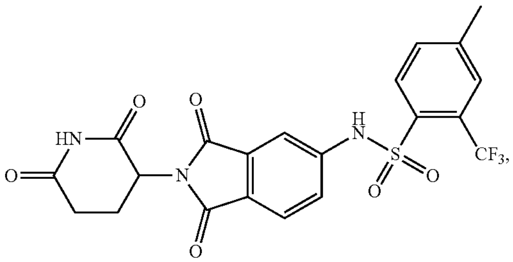

or

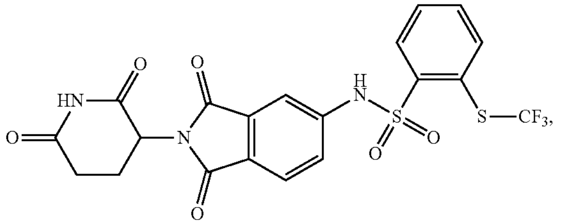

or a subgroup thereof.

Aspect 154. A pharmaceutical composition comprising a therapeutically effective amount of a compound of any of 1-Aspect 153, or a pharmaceutically acceptable salt, solvate, or polymorph thereof, and a pharmaceutically acceptable carrier.

Aspect 155. The pharmaceutical composition of Aspect 154, further comprising at least one agent known to treat a cancer.

Aspect 156. The pharmaceutical composition of Aspect 155, wherein the at least one agent known to treat a cancer is a hormone therapy agent; an alkylating agent, an antimetabolite agent, an antineoplastic antibiotic agent, a mitotic inhibitor agent, a mTor inhibitor agent, other chemotherapeutic agent, or combinations thereof.

Aspect 157. The pharmaceutical composition of Aspect 156, wherein the at least one agent known to treat a cancer is a hormone therapy agent is selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone, or a pharmaceutically acceptable salt thereof.

Aspect 158. The pharmaceutical composition of Aspect 156, wherein the at least one agent known to treat a cancer is a antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

Aspect 159. The pharmaceutical composition of Aspect 156, wherein the at least one agent known to treat a cancer is an antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof.

Aspect 160. The pharmaceutical composition of Aspect 156, wherein the at least one agent known to treat a cancer is an alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt.

Aspect 161. The pharmaceutical composition of Aspect 156, wherein the at least one agent known to treat a cancer is a mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt.

Aspect 162. The pharmaceutical composition of Aspect 156, wherein the at least one agent known to treat a cancer is a mTor inhibitor agent is selected from one or more of the group consisting of everolimus, siroliumus, and temsirolimus, or a pharmaceutically acceptable salt thereof.

Aspect 163. The pharmaceutical composition of Aspect 156, wherein the at least one agent known to treat a cancer is selected from uracil mustard, chlormethine, cyclophosphamide, ifosfamide, melphalan, chlorambucil, pipobroman, triethylenemelamine, triethylenethiophosphoramine, busulfan, carmustine, lomustine, streptozocin, dacarbazine, temozolomide, thiotepa, altretamine, methotrexate, 5-fluorouracil, floxuridine, cytarabine, 6-mercaptopurine, 6-thioguanine, fludarabine phosphate, pentostatin, bortezomib, vinblastine, vincristine, vinorelbine, vindesine, bleomycin, dactinomycin, daunorubicin, doxorubicin, epirubicin, dexamethasone, clofarabine, cladribine, pemextresed, idarubicin, paclitaxel, docetaxel, ixabepilone, mithramycin, topotecan, irinotecan, deoxycoformycin, mitomycin-C, L-asparaginase, interferons, etoposide, teniposide 17?-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, cisplatin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, oxaliplatin, gefinitib, capecitabine, erlotinib, azacitidine, temozolomide, gemcitabine, vasostatin, and combinations thereof.

Aspect 164. A method for the treatment of a disorder of uncontrolled cellular proliferation in a mammal comprising the step of administering to the mammal a therapeutically effective amount of at least one compound of any of 1-Aspect 153, or a pharmaceutically acceptable salt thereof; or at least one pharmaceutical composition of any one of Aspect 154-Aspect 163.

Aspect 165. The method of Aspect 164, wherein the mammal is a human.

Aspect 166. The method of Aspect 164, wherein the mammal has been diagnosed with a need for treatment of the disorder of uncontrolled cellular proliferation prior to the administering step.

Aspect 167. The method of Aspect 164, further comprising the step of identifying a mammal in need of treatment of the disorder of uncontrolled cellular proliferation.

Aspect 168. The method of Aspect 164, wherein the disorder of uncontrolled cellular proliferation is associated with cereblon (CRBN) dysfunction.

Aspect 169. The method of Aspect 168, wherein the disorder of uncontrolled cellular proliferation is a cancer.

Aspect 170. The method of Aspect 169, wherein the cancer is a pediatric cancer.

Aspect 171. The method of Aspect 169, wherein the cancer is a childhood acute leukemia (AL) or a medulloblastoma (MB) cancer.

Aspect 172. The method of Aspect 169, wherein the cancer is selected from a brain cancer, lung cancer, hematological cancer, bladder cancer, colon cancer, cervical cancer, ovarian cancer, squamous cell cancer, kidney cancer, peritoneal cancer, breast cancer, gastric cancer, colorectal cancer, prostate cancer, pancreatic cancer, genitourinary tract cancer, lymphatic system cancer, stomach cancer, larynx cancer, malignant melanoma, colorectal cancer, endometrial carcinoma, thyroid cancer, rhabdosarcoma, and combinations thereof.

Aspect 173. The method of Aspect 172, wherein the cancer is selected from lung cancer, ovarian cancer, and brain cancer.

Aspect 174. The method of Aspect 173, wherein the lung cancer is selected from small-cell lung cancer, non-small cell lung cancer, and combinations thereof.

Aspect 175. The method of Aspect 173, wherein the kidney cancer is a kidney clear cell carcinoma.

Aspect 176. The method of Aspect 173, wherein the brain cancer is selected from a glioblastoma, medullablastoma, glioma, and combinations thereof.

Aspect 177. The method of Aspect 173, wherein the bladder cancer is a bladder urothelial carcinoma.

Aspect 178. The method of Aspect 173, wherein the liver cancer is a hepatic carcinoma.

Aspect 179. The method of Aspect 173, wherein the hematological cancer is selected from chronic myeloid leukemia (CML), acute myeloid leukemia (AML), chronic lymphoid leukemia (CLL), acute lymphoid leukemia (ALL), hairy cell leukemia, chronic myelomonocytic leukemia (CMML), juvenile myelomonocyte leukemia (JMML), large granular lymphocytic leukemia (LGL), acute lymphocytic leukemia, acute lymphoblastic leukemia, B-cell lymphoma, T-cell-lymphoma, Hodgkin's lymphoma, non-Hodgkin's lymphoma, hairy cell lymphoma, Burkett's lymphoma, Hodgkin lymphoma, non-Hodgkin lymphoma, and combinations thereof.

Aspect 180. The method of any one of Aspect 164-Aspect 179, further comprising the step of administering a therapeutically effective amount of at least one agent known to treat a cancer.

Aspect 181. The method of Aspect 180, wherein the at least one agent is selected from uracil mustard, chlormethine, cyclophosphamide, ifosfamide, melphalan, chlorambucil, pipobroman, triethylenemelamine, triethylenethiophosphoramine, busulfan, carmustine, lomustine, streptozocin, dacarbazine, temozolomide, thiotepa, altretamine, methotrexate, 5-fluorouracil, floxuridine, cytarabine, 6-mercaptopurine, 6-thioguanine, fludarabine phosphate, pentostatin, bortezomib, vinblastine, vincristine, vinorelbine, vindesine, bleomycin, dactinomycin, daunorubicin, doxorubicin, epirubicin, dexamethasone, clofarabine, cladribine, pemextresed, idarubicin, paclitaxel, docetaxel, ixabepilone, mithramycin, topotecan, irinotecan, deoxycoformycin, mitomycin-C, L-asparaginase, interferons, etoposide, teniposide 17α-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, cisplatin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, oxaliplatin, gefinitib, capecitabine, erlotinib, azacitidine, temozolomide, gemcitabine, vasostatin, and combinations thereof.

Aspect 182. The method of Aspect 180, wherein the at least one agent is a DNA methyltransferase inhibitor, an HDAC-inhibitor, a glucocorticoid, an mTOR inhibitor, a cytotoxic agent, or combinations thereof.

Aspect 183. The method of Aspect 182, wherein the DNA methyltransferase inhibitor is 5-aza-2'-deoxycytidine, 5-azacytidine, zebularin, epigallocatechin-3-gallate, procaine, or combinations thereof.

Aspect 184. The method of Aspect 182, wherein the HDAC-inhibitor is vorinostat, entinostat, panbinostat, trichostatin A, mocetinostat, belinostat, dacinostat, givinostat, tubastatin A, pracinostat, droxinostat, quisinostat, romidepsin, valproic acid, AR-42 (OSU-HDAC42), tacedinaline, rocilinostat, apicidin, or combinations thereof.

Aspect 185. The method of Aspect 182, wherein the glucocorticoid is dexamethasone, prednisolone, methylprednisolone, betamethasone, triamicinolone, fludrocortisone, beclomethasone, or combinations thereof.

Aspect 186. The method of Aspect 182, wherein the mTor inhibitor is BEZ235, everolimus, temsirolimus, rapamycin, AZD8055, or cobminations thereof.

Aspect 187. The method of Aspect 182, wherein the cytotoxic agent is an alkylating agent, an antimetabolite agent, an antineoplastic antibiotic agent, a mitotic inhibitor agent, a mTor inhibitor agent or other chemotherapeutic agent.

Aspect 188. The method of Aspect 187, wherein the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt, hydrate, solvate, or polymorph thereof.

Aspect 189. The method of Aspect 187, wherein the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt, hydrate, solvate, or polymorph thereof.

Aspect 190. The method of Aspect 187, wherein the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof.

Aspect 191. The method of Aspect 187, wherein the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt, hydrate, solvate, or polymorph thereof.

Aspect 192. The method of Aspect 187, wherein the mTor inhibitor is everolimus, sirolimus, temsirolimus, or combinations thereof.

Aspect 193. The method of Aspect 187, wherein the other chemotherapeutic agent is an anthracycline, cytarabine, a purine analog, sorafenib, gemtuzumab ozogamicin, rituximab, or combinations thereof.

Aspect 194. The method of Aspect 193, wherein the anthracycline is daunorubicin, idarubicin, or combinations thereof.

Aspect 195. The method of Aspect 193, wherein the purine analog is cladribine, fludarabine, clofarabine, or combinations thereof.

Aspect 196. The method of any one of Aspect 180-Aspect 195, wherein the at least one compound, the at least one pharmaceutical composition, and the at least one agent are administered sequentially.

Aspect 197. The method of any one of Aspect 180-Aspect 195, wherein the at least one compound, the at least one pharmaceutical composition, and the at least one agent are administered simultaneously.

Aspect 198. The method of any one of Aspect 180-Aspect 195, wherein the at least one compound, the at least one pharmaceutical composition, and the at least one agent are co-formulated.

Aspect 199. The method of any one of Aspect 180-Aspect 195, wherein the at least one compound, the at least one pharmaceutical composition, and the at least one agent are co-packaged.

Aspect 200. A method for modulating of cereblon activity in a mammal comprising the step of administering to the mammal a therapeutically effective amount of at least one compound of any of Aspect 1-Aspect 153, or a pharmaceutically acceptable salt thereof; or at least one pharmaceutical composition of any one of Aspect 154-Aspect 163.

Aspect 201. The method of Aspect 200, wherein the mammal is a human.

Aspect 202. The method of Aspect 200, wherein the mammal has been diagnosed with a need for modulating of cereblon activity prior to the administering step.

Aspect 203. The method of Aspect 200, further comprising the step of identifying a mammal in need for modulating of cereblon activity Aspect 204. A method for modulating of cereblon activity in at least one cell, comprising the step of contacting the at least one cell with an effective amount of at least one compound of any of 1-Aspect 153, or a pharmaceutically acceptable salt thereof; or at least one pharmaceutical composition of any one of Aspect 154-Aspect 163.

Aspect 205. The method of Aspect 204, wherein the cell is mammalian.

Aspect 206. The method of Aspect 204, wherein the cell is human.

Aspect 207. The method of Aspect 204, wherein the cell has been isolated from a mammal prior to the contacting step.

Aspect 208. The method of Aspect 204, wherein contacting is via administration to a mammal.

Aspect 209. The method of Aspect 208, wherein the mammal has been diagnosed with a need for modulating of cereblon activity prior to the administering step.

Aspect 210. The method of Aspect 208, wherein the mammal has been diagnosed with a need for treatment of a disorder related to cereblon activity prior to the administering step.

Aspect 211. The method of Aspect 164, Aspect 200, or Aspect 204, wherein the compound inhibits cell proliferation with an IC50 of less than about 20 μM when determined in a cell viability assay using MV4-11 cells as described herein; and/or wherein the compound exhibits cereblon binding with an IC50 of less than about 10 μM using a fluorescence polarization assay as described herein.

Aspect 212. The method of Aspect 211, wherein the compound inhibits cell proliferation with an IC50 of less than about 15 μM; and/or wherein the compound exhibits cereblon binding with an IC50 of less than about 7.5 μM.

Aspect 213. The method of Aspect 211, wherein the compound inhibits cell proliferation with an IC50 of less than about 10 μM; and/or wherein the compound exhibits cereblon binding with an IC50 of less than about 5 μM.

Aspect 214. The method of Aspect 211, wherein the compound inhibits cell proliferation with an IC50 of less than about 10 μM; and/or wherein the compound exhibits cereblon binding with an IC50 of less than about 1 μM.

Aspect 215. The method of Aspect 211, wherein the compound inhibits cell proliferation with an IC50 of less than about 5 μM; and/or wherein the compound exhibits cereblon binding with an IC50 of less than about 500 nM.

Aspect 216. The method of Aspect 211, wherein the compound inhibits cell proliferation with an IC50 of less than about 1 μM; and/or wherein the compound exhibits cereblon binding with an IC50 of less than about 100 nM.

Aspect 217. The method of Aspect 211, wherein the compound inhibits cell proliferation with an IC50 of less than about 100 nM; and/or wherein the compound exhibits cereblon binding with an IC50 of less than about 100 nM.

Aspect 218. The method of Aspect 211, wherein the compound inhibits cell proliferation with an IC50 of less than about 10 nM; and/or wherein the compound exhibits cereblon binding with an IC50 of less than about 50 nM.

Aspect 219. The method of Aspect 211, wherein the compound inhibits cell proliferation with an IC50 of less than about 1 nM; and/or wherein the compound exhibits cereblon binding with an IC50 of less than about 50 nM.

Aspect 220. The method of Aspect 211, wherein the compound inhibits cell proliferation with an IC50 of less than about 0.1 nM; and/or wherein the compound exhibits cereblon binding with an IC50 of less than about 50 nM.

Aspect 221. The method of Aspect 211, wherein the compound inhibits cell proliferation with an IC50 of less than about 0.01 nM; and/or wherein the compound exhibits cereblon binding with an IC50 of less than about 50 nM.

Aspect 222. The method of Aspect 211, wherein the compound inhibits cell proliferation with an IC50 of less than about 0.01 nM; and/or wherein the compound exhibits cereblon binding with an IC50 of less than about 25 nM.

Aspect 223. A kit comprising at least one compound of any of 1-Aspect 153, or a pharmaceutically acceptable salt thereof; or at least one pharmaceutical composition of any one of Aspect 154-Aspect 163; and one or more of: (a) at least one agent known to increase cereblon activity; (b) at least one agent known to decrease cereblon activity; (c) at least one agent known to increase GSPT1 activity; (d) at least one agent known to decrease GSPT1 activity; (e) at least one agent known to increase cellular proliferation; (f) at least one agent known to decrease cellular proliferation; (g) at least one agent known to treat a disorder associated with cereblon activity; (h) at least one agent known to treat a disorder associated with GSPT1 activity; (i) at least one agent known to treat a disorder of uncontrolled cellular proliferation; and/or (j) instructions for treating a disorder of uncontrolled cellular proliferation.

Aspect 224. The kit of Aspect 223, wherein the at least one compound or the at least one product and the at least one agent are co-formulated.

Aspect 225. The kit of Aspect 223, wherein the at least one compound or the at least one product and the at least one agent are co-packaged.

Aspect 226. The kit of any one of Aspect 223-Aspect 225, further comprising instructions to provide the compound in connection with surgery.

Aspect 227. The kit of Aspect 226, wherein the instructions provide that surgery is performed prior to the administering of at least one compound.

Aspect 228. The kit of Aspect 226, wherein the instructions provide that surgery is performed after the administering of at least one compound.

Aspect 229. The kit of Aspect 226, wherein the instructions provide that the administering of at least one compound is to effect presurgical debulking of a tumor.

Aspect 230. The kit of Aspect 226, wherein the instructions provide that surgery is performed at about the same time as the administering of at least one compound.

Aspect 231. The kit of any one of Aspect 223-Aspect 230, further comprising instructions to provide the at least one compound or the pharmaceutical composition in connection with radiotherapy.

Aspect 232. The kit of Aspect 231, wherein the instructions provide that radiotherapy is performed prior to the administering of at least one compound.

Aspect 233. The kit of Aspect 231, wherein the instructions provide that radiotherapy is performed after the step of the administering of at least one compound.

Aspect 234. The kit of Aspect 231, wherein the instructions provide that radiotherapy is performed at about the same time as the step of the administering of at least one compound.

Aspect 235. The kit of any one of Aspect 223-Aspect 234, further comprising a plurality of dosage forms, the plurality comprising one or more doses; wherein each dose comprises a therapeutically effective amount of the at least one compound or the pharmaceutical composition and the at least one agent.

Aspect 236. The kit of Aspect 235, wherein each dose of the at least one compound or the pharmaceutical composition and the at least one agent are co-formulated.

Aspect 237. The kit of Aspect 235, wherein each dose of the at least one compound or the pharmaceutical composition and the at least one agent are co-packaged.

Aspect 238. The kit of Aspect 235, wherein the dosage forms are formulated for oral administration and/or intravenous administration.

Aspect 239. The kit of Aspect 235, wherein the dosage formas are formulated for oral administration.

Aspect 240. The kit of Aspect 235, wherein the dosage forms are formulated for intravenous administration.

Aspect 241. The kit of Aspect 235, wherein the dosage form for the at least one compound or the pharmaceutical composition is formulated for oral administration and the dosage form for the at least one agent is formulated for intravenous administration.

Aspect 242. The kit of Aspect 235, wherein the dosage form for the at least one compound or the pharmaceutical composition is formulated for intravenous administration and the dosage form for the at least one agent is formulated for oral administration.

Aspect 243. A kit comprising at least one compound of any of 1-Aspect 153, or a pharmaceutically acceptable salt thereof; or at least one pharmaceutical composition of any one of Aspect 154-Aspect 163; and one or more of: (a) at least one agent known to increase cereblon activity; (b) at least one agent known to decrease cereblon activity; (c) at least one agent known to increase cellular proliferation; (d) at least one agent known to decrease cellular proliferation; (e) at least one agent known to treat a disorder associated with cereblon activity; (f) at least one agent known to treat a disorder of uncontrolled cellular proliferation; and/or (g) instructions for treating a disorder of uncontrolled cellular proliferation.

Aspect 244. The kit of Aspect 243, wherein the at least one compound or the at least one product and the at least one agent are co-formulated.

Aspect 245. The kit of Aspect 243, wherein the at least one compound or the at least one product and the at least one agent are co-packaged.

Aspect 246. The kit of any one of Aspect 243-Aspect 245, further comprising instructions to provide the compound in connection with surgery.

Aspect 247. The kit of Aspect 246, wherein the instructions provide that surgery is performed prior to the administering of at least one compound.

Aspect 248. The kit of Aspect 246, wherein the instructions provide that surgery is performed after the administering of at least one compound.

Aspect 249. The kit of Aspect 246, wherein the instructions provide that the administering of at least one compound is to effect presurgical debulking of a tumor.

Aspect 250. The kit of Aspect 246, wherein the instructions provide that surgery is performed at about the same time as the administering of at least one compound.

Aspect 251. The kit of any one of Aspect 243-Aspect 250, further comprising instructions to provide the at least one compound or the pharmaceutical composition in connection with radiotherapy.

Aspect 252. The kit of Aspect 251, wherein the instructions provide that radiotherapy is performed prior to the administering of at least one compound.

Aspect 253. The kit of Aspect 251, wherein the instructions provide that radiotherapy is performed after the step of the administering of at least one compound.

Aspect 254. The kit of Aspect 251, wherein the instructions provide that radiotherapy is performed at about the same time as the step of the administering of at least one compound.

Aspect 255. The kit of any one of Aspect 243-Aspect 254, further comprising a plurality of dosage forms, the plurality comprising one or more doses; wherein each dose comprises a therapeutically effective amount of the at least one compound or the pharmaceutical composition and the at least one agent.

Aspect 256. The kit of Aspect 255, wherein each dose of the at least one compound or the pharmaceutical composition and the at least one agent are co-formulated.

Aspect 257. The kit of Aspect 255, wherein each dose of the at least one compound or the pharmaceutical composition and the at least one agent are co-packaged.

Aspect 258. The kit of Aspect 255, wherein the dosage forms are formulated for oral administration and/or intravenous administration.

Aspect 259. The kit of Aspect 255, wherein the dosage formas are formulated for oral administration.

Aspect 260. The kit of Aspect 255, wherein the dosage forms are formulated for intravenous administration.

Aspect 261. The kit of Aspect 255, wherein the dosage form for the at least one compound or the pharmaceutical composition is formulated for oral administration and the dosage form for the at least one agent is formulated for intravenous administration.

Aspect 262. The kit of Aspect 255, wherein the dosage form for the at least one compound or the pharmaceutical composition is formulated for intravenous administration and the dosage form for the at least one agent is formulated for oral administration.

Aspect 263. A kit comprising at least one compound of any of 1-Aspect 153, or a pharmaceutically acceptable salt thereof; or at least one pharmaceutical composition of any one of Aspect 154-Aspect 163; and one or more of: (a) at least one agent known to increase GSPT1 activity; (b) at least one agent known to decrease GSPT activity; (c) at least one agent known to increase cellular proliferation; (d) at least one agent known to decrease cellular proliferation; (e) at least one agent known to treat a disorder associated with GSPT1 activity; (f) at least one agent known to treat a disorder of uncontrolled cellular proliferation; and/or (g) instructions for treating a disorder of uncontrolled cellular proliferation.

Aspect 264. The kit of Aspect 263, wherein the at least one compound or the at least one product and the at least one agent are co-formulated.

Aspect 265. The kit of Aspect 263, wherein the at least one compound or the at least one product and the at least one agent are co-packaged.

Aspect 266. The kit of any one of Aspect 263-Aspect 265, further comprising instructions to provide the compound in connection with surgery.

Aspect 267. The kit of Aspect 266, wherein the instructions provide that surgery is performed prior to the administering of at least one compound.

Aspect 268. The kit of Aspect 266, wherein the instructions provide that surgery is performed after the administering of at least one compound.

Aspect 269. The kit of Aspect 266, wherein the instructions provide that the administering of at least one compound is to effect presurgical debulking of a tumor.

Aspect 270. The kit of Aspect 266, wherein the instructions provide that surgery is performed at about the same time as the administering of at least one compound.

Aspect 271. The kit of any one of Aspect 263-Aspect 270, further comprising instructions to provide the at least one compound or the pharmaceutical composition in connection with radiotherapy.

Aspect 272. The kit of Aspect 271, wherein the instructions provide that radiotherapy is performed prior to the administering of at least one compound.

Aspect 273. The kit of Aspect 271, wherein the instructions provide that radiotherapy is performed after the step of the administering of at least one compound.

Aspect 274. The kit of Aspect 271, wherein the instructions provide that radiotherapy is performed at about the same time as the step of the administering of at least one compound.

Aspect 275. The kit of any one of Aspect 263-Aspect 274, further comprising a plurality of dosage forms, the plurality comprising one or more doses; wherein each dose comprises a therapeutically effective amount of the at least one compound or the pharmaceutical composition and the at least one agent.

Aspect 276. The kit of Aspect 275, wherein each dose of the at least one compound or the pharmaceutical composition and the at least one agent are co-formulated.

Aspect 277. The kit of Aspect 275, wherein each dose of the at least one compound or the pharmaceutical composition and the at least one agent are co-packaged.

Aspect 278. The kit of Aspect 275, wherein the dosage forms are formulated for oral administration and/or intravenous administration.

Aspect 279. The kit of Aspect 275, wherein the dosage formas are formulated for oral administration.

Aspect 280. The kit of Aspect 275, wherein the dosage forms are formulated for intravenous administration.

Aspect 281. The kit of Aspect 275, wherein the dosage form for the at least one compound or the pharmaceutical composition is formulated for oral administration and the dosage form for the at least one agent is formulated for intravenous administration.

Aspect 282. The kit of Aspect 275, wherein the dosage form for the at least one compound or the pharmaceutical composition is formulated for intravenous administration and the dosage form for the at least one agent is formulated for oral administration.

Aspect 283. Use of a compound at least one compound of any of 1-Aspect 153, or a pharmaceutically acceptable salt thereof; or at least one pharmaceutical composition of any one of Aspect 154-Aspect 163; or combinations thereof in the manufacture of a medicament for the treatment of a disorder associated with a cereblon dysfunction in a mammal.

Aspect 284. Use of a compound at least one compound of any of 1-Aspect 153, or a pharmaceutically acceptable salt thereof; or at least one pharmaceutical composition of any one of Aspect 154-Aspect 163; or combinations thereof in the manufacture of a medicament for the treatment of a disorder of uncontrolled cellular proliferation in a mammal.

Aspect 285. A compound having a structure represented by a formula:

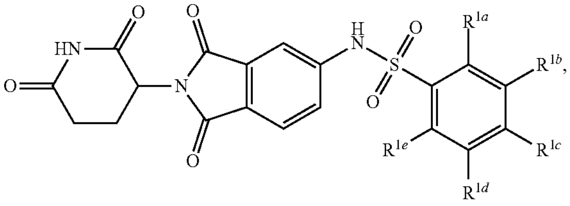

wherein $R^{1a}$ is selected from bromo, methyl, —$CF_3$, and —$OCF_3$; and wherein each of $R^{1b}$, $R^{1c}$, $R^{1d}$, and $R^{1e}$ is independently selected from hydrogen, halogen, and methyl; or a pharmaceutically acceptable salt thereof.

Aspect 286. The compound of Aspect 286, wherein $R^{1a}$ is bromo.

Aspect 287. The compound of Aspect 286, wherein $R^{1a}$ is methyl.

Aspect 288. The compound of Aspect 286, wherein $R^{1a}$ is selected from —$CF_3$ and —$OCF_3$.

Aspect 289. The compound of Aspect 286, wherein each of $R^{1b}$, $R^{1c}$, $R^{1d}$, and $R^{1e}$ is hydrogen.

Aspect 290. The compound of Aspect 286, wherein at least one of Rib, $R^{1c}$, $R^{1d}$, and $R^{1e}$ is halogen.

Aspect 291. The compound of Aspect 286, wherein at least one of Rib, $R^{1c}$, $R^{1d}$, and $R^{1e}$ is methyl.

Aspect 292. The compound of Aspect 286, having a structure represented by a formula:

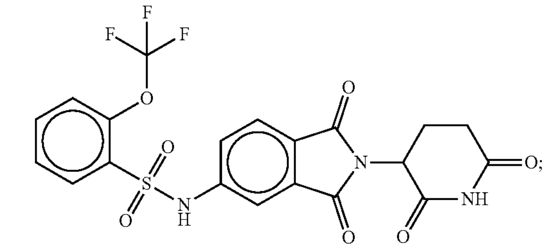

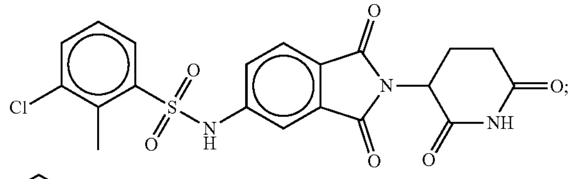

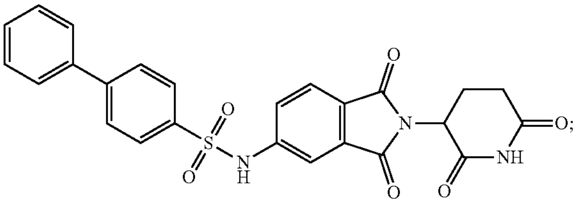 [SMILES: O=C1CCC(N2C(=O)c3ccc(NS(=O)(=O)c4ccc(-c5ccccc5)cc4)cc3C2=O)C(=O)N1]

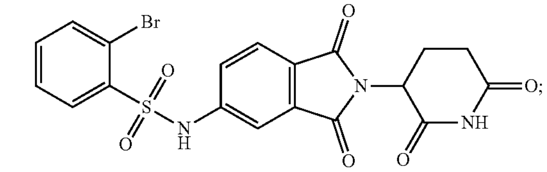

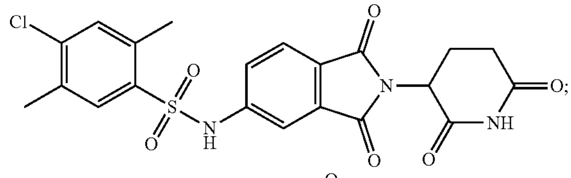

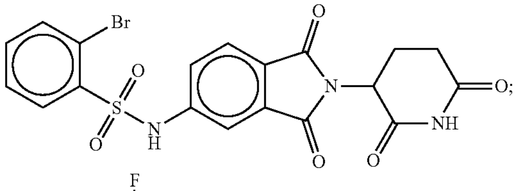

or

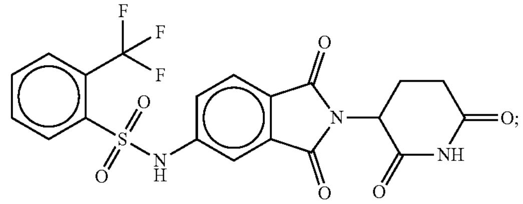

or a subgroup thereof.

Aspect 293. A compound having a structure represented by a formula:

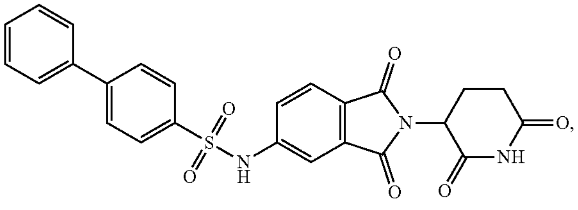

or a pharmaceutically acceptable salt thereof.

Aspect 294. A pharmaceutical composition comprising a therapeutically effective amount of a compound of any of Aspect 286-Aspect 293, or a pharmaceutically acceptable salt, solvate, or polymorph thereof, and a pharmaceutically acceptable carrier.

Aspect 295. The pharmaceutical composition of Aspect 294, further comprising at least one agent known to treat a cancer.

Aspect 296. The pharmaceutical composition of Aspect 295, wherein the at least one agent known to treat a cancer is a hormone therapy agent; an alkylating agent, an antimetabolite agent, an antineoplastic antibiotic agent, a mitotic inhibitor agent, a mTor inhibitor agent, other chemotherapeutic agent, or combinations thereof.

Aspect 297. The pharmaceutical composition of Aspect 296, wherein the at least one agent known to treat a cancer is a hormone therapy agent is selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone, or a pharmaceutically acceptable salt thereof.

Aspect 298. The pharmaceutical composition of Aspect 296, wherein the at least one agent known to treat a cancer is a antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof.

Aspect 299. The pharmaceutical composition of Aspect 296, wherein the at least one agent known to treat a cancer is an antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof.

Aspect 300. The pharmaceutical composition of Aspect 296, wherein the at least one agent known to treat a cancer is an alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt.

Aspect 301. The pharmaceutical composition of Aspect 296, wherein the at least one agent known to treat a cancer is a mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt.

Aspect 302. The pharmaceutical composition of Aspect 296, wherein the at least one agent known to treat a cancer is a mTor inhibitor agent is selected from one or more of the group consisting of everolimus, siroliumus, and temsirolimus, or a pharmaceutically acceptable salt thereof.

Aspect 303. The pharmaceutical composition of Aspect 296, wherein the at least one agent known to treat a cancer is selected from uracil mustard, chlormethine, cyclophosphamide, ifosfamide, melphalan, chlorambucil, pipobroman, triethylenemelamine, triethylenethiophosphoramine, busulfan, carmustine, lomustine, streptozocin, dacarbazine, temozolomide, thiotepa, altretamine, methotrexate, 5-fluorouracil, floxuridine, cytarabine, 6-mercaptopurine, 6-thioguanine, fludarabine phosphate, pentostatin, bortezomib, vinblastine, vincristine, vinorelbine, vindesine, bleomycin, dactinomycin, daunorubicin, doxorubicin, epirubicin, dexamethasone, clofarabine, cladribine, pemextresed, idarubicin, paclitaxel, docetaxel, ixabepilone, mithramycin, topotecan, irinotecan, deoxycoformycin, mitomycin-C, L-asparaginase, interferons, etoposide, teniposide 17?-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, cisplatin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, oxaliplatin, gefinitib, capecitabine, erlotinib, azacitidine, temozolomide, gemcitabine, vasostatin, and combinations thereof.

Aspect 304. A method for the treatment of a disorder of uncontrolled cellular proliferation in a mammal comprising the step of administering to the mammal a therapeutically effective amount of at least one compound of any of Aspect 285-Aspect 293, or a pharmaceutically acceptable salt thereof; or at least one pharmaceutical composition of any one of Aspect 294-Aspect 303.

Aspect 305. The method of Aspect 304, wherein the mammal is a human.

Aspect 306. The method of Aspect 304, wherein the mammal has been diagnosed with a need for treatment of the disorder of uncontrolled cellular proliferation prior to the administering step.

Aspect 307. The method of Aspect 304, further comprising the step of identifying a mammal in need of treatment of the disorder of uncontrolled cellular proliferation.

Aspect 308. The method of Aspect 304, wherein the disorder of uncontrolled cellular proliferation is associated with a GSTP1 dysfunction.

Aspect 309. The method of Aspect 308, wherein the disorder of uncontrolled cellular proliferation is a cancer.

Aspect 310. The method of Aspect 309, wherein the cancer is a pediatric cancer.

Aspect 311. The method of Aspect 309, wherein the cancer is a childhood acute leukemia (AL) or a medulloblastoma (MB) cancer.

Aspect 312. The method of Aspect 309, wherein the cancer is selected from a brain cancer, lung cancer, hematological cancer, bladder cancer, colon cancer, cervical cancer, ovarian cancer, squamous cell cancer, kidney cancer, peritoneal cancer, breast cancer, gastric cancer, colorectal cancer, prostate cancer, pancreatic cancer, genitourinary tract cancer, lymphatic system cancer, stomach cancer, larynx cancer, malignant melanoma, colorectal cancer, endometrial carcinoma, thyroid cancer, rhabdosarcoma, and combinations thereof.

Aspect 313. The method of Aspect 312, wherein the cancer is selected from lung cancer, ovarian cancer, and brain cancer.

Aspect 314. The method of Aspect 313, wherein the lung cancer is selected from small-cell lung cancer, non-small cell lung cancer, and combinations thereof.

Aspect 315. The method of Aspect 313, wherein the kidney cancer is a kidney clear cell carcinoma.

Aspect 316. The method of Aspect 313, wherein the brain cancer is selected from a glioblastoma, medullablastoma, glioma, and combinations thereof.

Aspect 317. The method of Aspect 173, wherein the bladder cancer is a bladder urothelial carcinoma.

Aspect 318. The method of Aspect 313, wherein the liver cancer is a hepatic carcinoma.

Aspect 319. The method of Aspect 313, wherein the hematological cancer is selected from chronic myeloid leukemia (CML), acute myeloid leukemia (AML), chronic lymphoid leukemia (CLL), acute lymphoid leukemia (ALL), hairy cell leukemia, chronic myelomonocytic leukemia (CMML), juvenile myelomonocyte leukemia (JMML), large granular lymphocytic leukemia (LGL), acute lymphocytic leukemia, acute lymphoblastic leukemia, B-cell lymphoma, T-cell-lymphoma, Hodgkin's lymphoma, non-Hodgkin's lymphoma, hairy cell lymphoma, Burkett's lymphoma, Hodgkin lymphoma, non-Hodgkin lymphoma, and combinations thereof.

Aspect 320. The method of any one of Aspect 304-Aspect 319, further comprising the step of administering a therapeutically effective amount of at least one agent known to treat a cancer.

Aspect 321. The method of Aspect 320, wherein the at least one agent is selected from uracil mustard, chlormethine, cyclophosphamide, ifosfamide, melphalan, chlorambucil, pipobroman, triethylenemelamine, triethylenethiophosphoramine, busulfan, carmustine, lomustine, streptozocin, dacarbazine, temozolomide, thiotepa, altretamine, methotrexate, 5-fluorouracil, floxuridine, cytarabine, 6-mercaptopurine, 6-thioguanine, fludarabine phosphate, pentostatin, bortezomib, vinblastine, vincristine, vinorelbine, vindesine, bleomycin, dactinomycin, daunorubicin, doxorubicin, epirubicin, dexamethasone, clofarabine, cladribine, pemextresed, idarubicin, paclitaxel, docetaxel, ixabepilone, mithramycin, topotecan, irinotecan, deoxycoformycin, mitomycin-C, L-asparaginase, interferons, etoposide, teniposide 17α-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, cisplatin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, oxaliplatin, gefinitib, capecitabine, erlotinib, azacitidine, temozolomide, gemcitabine, vasostatin, and combinations thereof.

Aspect 322. The method of Aspect 320, wherein the at least one agent is a DNA methyltransferase inhibitor, an HDAC-inhibitor, a glucocorticoid, an mTOR inhibitor, a cytotoxic agent, or combinations thereof.

Aspect 323. The method of Aspect 322, wherein the DNA methyltransferase inhibitor is 5-aza-2'-deoxycytidine, 5-azacytidine, zebularin, epigallocatechin-3-gallate, procaine, or combinations thereof.

Aspect 324. The method of Aspect 322, wherein the HDAC-inhibitor is vorinostat, entinostat, panbinostat, trichostatin A, mocetinostat, belinostat, dacinostat, givinostat, tubastatin A, pracinostat, droxinostat, quisinostat, romidepsin, valproic acid, AR-42 (OSU-HDAC42), tacedinaline, rocilinostat, apicidin, or combinations thereof.

Aspect 325. The method of Aspect 322, wherein the glucocorticoid is dexamethasone, prednisolone, methylprednisolone, betamethasone, triamicinolone, fludrocortisone, beclomethasone, or combinations thereof.

Aspect 326. The method of Aspect 322, wherein the mTor inhibitor is BEZ235, everolimus, temsirolimus, rapamycin, AZD8055, or cobminations thereof.

Aspect 327. The method of Aspect 322, wherein the cytotoxic agent is an alkylating agent, an antimetabolite agent, an antineoplastic antibiotic agent, a mitotic inhibitor agent, a mTor inhibitor agent or other chemotherapeutic agent.

Aspect 328. The method of Aspect 327, wherein the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt, hydrate, solvate, or polymorph thereof.

Aspect 329. The method of Aspect 327, wherein the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt, hydrate, solvate, or polymorph thereof.

Aspect 330. The method of Aspect 327, wherein the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof.

Aspect 331. The method of Aspect 327, wherein the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt, hydrate, solvate, or polymorph thereof.

Aspect 332. The method of Aspect 327, wherein the mTor inhibitor is everolimus, sirolimus, temsirolimus, or combinations thereof.

Aspect 333. The method of Aspect 327, wherein the other chemotherapeutic agent is an anthracycline, cytarabine, a purine analog, sorafenib, gemtuzumab ozogamicin, rituximab, or combinations thereof.

Aspect 334. The method of Aspect 333, wherein the anthracycline is daunorubicin, idarubicin, or combinations thereof.

Aspect 335. The method of Aspect 333, wherein the purine analog is cladribine, fludarabine, clofarabine, or combinations thereof.

Aspect 336. The method of any one of Aspect 180-Aspect 335, wherein the at least one compound, the at least one pharmaceutical composition, and the at least one agent are administered sequentially.

Aspect 337. The method of any one of Aspect 180-Aspect 335, wherein the at least one compound, the at least one pharmaceutical composition, and the at least one agent are administered simultaneously.

Aspect 338. The method of any one of Aspect 180-Aspect 335, wherein the at least one compound, the at least one pharmaceutical composition, and the at least one agent are co-formulated.

Aspect 339. The method of any one of Aspect 180-Aspect 335, wherein the at least one compound, the at least one pharmaceutical composition, and the at least one agent are co-packaged.

Aspect 340. A method for modulating of GSPT1 activity in a mammal comprising the step of administering to the mammal a therapeutically effective amount of at least one compound of any of Aspect 285-Aspect 293, or a pharmaceutically acceptable salt thereof; or at least one pharmaceutical composition of any one of Aspect 294-Aspect 303.

Aspect 341. The method of Aspect 340, wherein the mammal is a human.

Aspect 342. The method of Aspect 340, wherein the mammal has been diagnosed with a need for modulating of GSPT1 activity prior to the administering step.

Aspect 343. The method of Aspect 340, further comprising the step of identifying a mammal in need for modulating of GSPT1 activity Aspect 344. A method for modulating of GSPT1 activity in at least one cell, comprising the step of contacting the at least one cell with an effective amount of at least one compound of any of Aspect 285-Aspect 293, or a pharmaceutically acceptable salt thereof; or at least one pharmaceutical composition of any one of Aspect 294-Aspect 303.

Aspect 345. The method of Aspect 344, wherein the cell is mammalian.

Aspect 346. The method of Aspect 344, wherein the cell is human.

Aspect 347. The method of Aspect 344, wherein the cell has been isolated from a mammal prior to the contacting step.

Aspect 348. The method of Aspect 344, wherein contacting is via administration to a mammal.

Aspect 349. The method of Aspect 208, wherein the mammal has been diagnosed with a need for modulating of GSPT1 activity prior to the administering step.

Aspect 350. The method of Aspect 208, wherein the mammal has been diagnosed with a need for treatment of a disorder related to GSPT1 activity prior to the administering step.

Aspect 351. The method of Aspect 304, Aspect 340, or Aspect 344, wherein the compound inhibits cell proliferation with an IC50 of less than about 20 μM when determined in a cell viability assay using MV4-11 cells as described herein; and/or wherein the compound exhibits GSPT1 binding with an IC50 of less than about 10 μM using a cell viability assay comprising a HEK293 HiBit tagged cell-line.

Aspect 352. The method of Aspect 351, wherein the compound inhibits cell proliferation with an IC50 of less than about 15 μM; and/or wherein the compound exhibits GSPT1 binding with an 1050 of less than about 7.5 μM.

Aspect 353. The method of Aspect 351, wherein the compound inhibits cell proliferation with an IC50 of less than about 10 μM; and/or wherein the compound exhibits GSPT1 binding with an 1050 of less than about 5 μM.

Aspect 354. The method of Aspect 351, wherein the compound inhibits cell proliferation with an IC50 of less than about 10 μM; and/or wherein the compound exhibits GSPT1 binding with an 1050 of less than about 1 μM.

Aspect 355. The method of Aspect 351, wherein the compound inhibits cell proliferation with an IC50 of less than about 5 μM; and/or wherein the compound exhibits GSPT1 binding with an 1050 of less than about 500 nM.

Aspect 356. The method of Aspect 351, wherein the compound inhibits cell proliferation with an IC50 of less than about 1 μM; and/or wherein the compound exhibits GSPT1 binding with an 1050 of less than about 100 nM.

Aspect 357. The method of Aspect 351, wherein the compound inhibits cell proliferation with an IC50 of less than about 100 nM; and/or wherein the compound exhibits GSPT1 binding with an 1050 of less than about 100 nM.

Aspect 358. The method of Aspect 351, wherein the compound inhibits cell proliferation with an IC50 of less than about 10 nM; and/or wherein the compound exhibits GSPT1 binding with an 1050 of less than about 50 nM.

Aspect 359. The method of Aspect 351, wherein the compound inhibits cell proliferation with an IC50 of less than about 1 nM; and/or wherein the compound exhibits GSPT1 binding with an 1050 of less than about 50 nM.

Aspect 360. The method of Aspect 351, wherein the compound inhibits cell proliferation with an IC50 of less than about 0.1 nM; and/or wherein the compound exhibits GSPT1 binding with an 1050 of less than about 50 nM.

Aspect 361. The method of Aspect 351, wherein the compound inhibits cell proliferation with an IC50 of less than about 0.01 nM; and/or wherein the compound exhibits GSPT1 binding with an 1050 of less than about 50 nM.

Aspect 362. The method of Aspect 351, wherein the compound inhibits cell proliferation with an IC50 of less than about 0.01 nM; and/or wherein the compound exhibits GSPT1 binding with an 1050 of less than about 25 nM.

Aspect 363. A kit comprising at least one compound of any of Aspect 285-Aspect 293, or a pharmaceutically acceptable salt thereof; or at least one pharmaceutical composition of any one of Aspect 294-Aspect 303; and one or more of: (a) at least one agent known to increase GSPT1 activity; (b) at least one agent known to decrease GSPT1 activity; (c) at least one agent known to increase cellular proliferation; (d) at least one agent known to decrease cellular proliferation; (e) at least one agent known to treat a disorder associated with GSPT1 activity; (f) at least one agent known to treat a disorder associated with GSPT1 activity; (g) at least one agent known to treat a disorder of uncontrolled cellular proliferation; and/or (h) instructions for treating a disorder of uncontrolled cellular proliferation.

Aspect 364. The kit of Aspect 363, wherein the at least one compound or the at least one product and the at least one agent are co-formulated.

Aspect 365. The kit of Aspect 363, wherein the at least one compound or the at least one product and the at least one agent are co-packaged.

Aspect 366. The kit of any one of Aspect 363-Aspect 225, further comprising instructions to provide the compound in connection with surgery.

Aspect 367. The kit of Aspect 226, wherein the instructions provide that surgery is performed prior to the administering of at least one compound.

Aspect 368. The kit of Aspect 226, wherein the instructions provide that surgery is performed after the administering of at least one compound.

Aspect 369. The kit of Aspect 226, wherein the instructions provide that the administering of at least one compound is to effect presurgical debulking of a tumor.

Aspect 370. The kit of Aspect 226, wherein the instructions provide that surgery is performed at about the same time as the administering of at least one compound.

Aspect 371. The kit of any one of Aspect 363-Aspect 230, further comprising instructions to provide the at least one compound or the pharmaceutical composition in connection with radiotherapy.

Aspect 372. The kit of Aspect 231, wherein the instructions provide that radiotherapy is performed prior to the administering of at least one compound.

Aspect 373. The kit of Aspect 231, wherein the instructions provide that radiotherapy is performed after the step of the administering of at least one compound.

Aspect 374. The kit of Aspect 231, wherein the instructions provide that radiotherapy is performed at about the same time as the step of the administering of at least one compound.

Aspect 375. The kit of any one of Aspect 363-Aspect 234, further comprising a plurality of dosage forms, the plurality comprising one or more doses; wherein each dose comprises a therapeutically effective amount of the at least one compound or the pharmaceutical composition and the at least one agent.

Aspect 376. The kit of Aspect 235, wherein each dose of the at least one compound or the pharmaceutical composition and the at least one agent are co-formulated.

Aspect 377. The kit of Aspect 235, wherein each dose of the at least one compound or the pharmaceutical composition and the at least one agent are co-packaged.

Aspect 378. The kit of Aspect 235, wherein the dosage forms are formulated for oral administration and/or intravenous administration.

Aspect 379. The kit of Aspect 235, wherein the dosage formas are formulated for oral administration.

Aspect 380. The kit of Aspect 235, wherein the dosage forms are formulated for intravenous administration.

Aspect 381. The kit of Aspect 235, wherein the dosage form for the at least one compound or the pharmaceutical composition is formulated for oral administration and the dosage form for the at least one agent is formulated for intravenous administration.

Aspect 382. The kit of Aspect 235, wherein the dosage form for the at least one compound or the pharmaceutical composition is formulated for intravenous administration and the dosage form for the at least one agent is formulated for oral administration.

Aspect 383. Use of a compound at least one compound of any of Aspect 285-Aspect 293, or a pharmaceutically acceptable salt thereof; or at least one pharmaceutical composition of any one of Aspect 294-Aspect 303; or combinations thereof in the manufacture of a medicament for the treatment of a disorder associated with a cereblon dysfunction in a mammal.

Aspect 384. Use of a compound at least one compound of any of Aspect 285-Aspect 293, or a pharmaceutically acceptable salt thereof; or at least one pharmaceutical composition of any one of Aspect 294-Aspect 303; or combinations thereof in the manufacture of a medicament for the treatment of a disorder of uncontrolled cellular proliferation in a mammal.

From the foregoing, it will be seen that aspects herein are well adapted to attain all the ends and objects hereinabove set forth together with other advantages which are obvious and which are inherent to the structure.

While specific elements and steps are discussed in connection to one another, it is understood that any element and/or steps provided herein is contemplated as being combinable with any other elements and/or steps regardless of explicit provision of the same while still being within the scope provided herein.

It will be understood that certain features and subcombinations are of utility and may be employed without reference to other features and subcombinations. This is contemplated by and is within the scope of the claims.

Since many possible aspects may be made without departing from the scope thereof, it is to be understood that all matter herein set forth or shown in the accompanying drawings and detailed description is to be interpreted as illustrative and not in a limiting sense.

It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure and to be encompassed by the claims herein.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

K. Examples

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Cell Culture and Materials

MV-4-11 cell line was purchased from the American Type Culture Collection (ATCC, Manassas, VA) and maintained in Iscove's Modified Dulbecco's medium (IMDM; (ATCC) supplemented with 10% FBS. HD-MB03 cell line was obtained from Drs. Milde, Witt and Deubzer (see Milde, T., et al. *J Neurooncol* 2012, 110, 335-348). HD-MB03 and M B004 cells were grown in neurobasal medium supplemented with glutamine, streptomycin, penicillin, B27, EGF, bFGF and heparin as previously described (see Shadrick, W. R., et al. *Bioorg Med Chem.* 2018 Jan. 1; 26(1):25-36). MB002 and MB004 cells were obtained from Dr Yoon-Jae Cho (see Bandopadhayay, P., et al., *Clin Cancer Res.* 2014 Feb. 15; 20(4):912-25). MB002 cells were cultured in 80% neurobasal medium supplemented with glutamine, streptomycin, penicillin, B27 and 20% conditioned media from previous passages; EGF, bFGF and heparin were also added to the medium. MHH-CALL4 cells were obtained from German Collection of Microorganisms and Cell Cultures GmbH (DSMZ, Germany) and were cultured in RPM11640 medium supplemented with 10% FBS (Hyclone), Penicillin/Streptomycin (100 units/mL) and Glutamine (100 μM). Cell identity was confirmed by STR profiling using PowerPlex® Fusion System (Promega).

2. Chemistry: General Methods and Synthesis

All reagents and solvents were obtained from commercially available sources and were used without further purification. Reactions were set up in air and carried out under nitrogen atmosphere. Parallel synthesis was accomplished using MiniBlock XT synthesizers purchased from Mettler-Toledo AutoChem placed on a stirring hot plate. Library compounds were filtered using a 96 well Thomson 2 mL filter plate (25 μm) containing Celite 545 into a Waters 96 well 2 ml receiving plate prior to purification. Automated weighing was done using a Bohdan Balance Automator (Mettler-Toldeo AutoChem) and parallel evaporations were carried out using a Genevac HT-24. HPLC analyses were accomplished using an UPLC/UV/ELSD/SQD (Single Quadrupole Detector) with stationary phase: BEH C18, 1.7 μm, solvents: A: 0.1% formic acid in water, B: 0.1% formic acid in acetonitrile, detector types: PDA (210 to 400 nm) and ELSD. Library purification was performed on the Waters purification/analytical LC/UV/ELSD system. Column: Gemini Aixia Packed C18 50 mm×30 mm, 5 μm. Collection: UV at 214 nm and/or ELSD. Gradients: water/acetonitrile/0.1% formic acid, beginning acetonitrile percentage varied based on retention times determined in pre-purification analysis on the UPLC. Nuclear magnetic resonance (NMR) spectra were obtained on a Bruker NMR spectrometer at 500 MHz for 1H-NMR spectra and 125 MHz for 13C-NMR spectra. Chemical shifts (ppm) are reported relative to the solvent peak. Signals are designated as follows: s, singlet; d, doublet; dd, doublet of doublet; t, triplet; q, quadruplet; m, multiplet. Coupling constants (J) are expressed in Hertz. High resolution mass spectral data were obtained on a Waters Xevo G2 QTof mass spectrometer. The purity of final compounds was performed on an Acquity UPLC BEH C18 1.7 μm, 2.1×50 mm column (Waters Corporation, Milford, MA) using an Acquity ultra performance liquid chromatography system. The flow rate was 0.7 mL/min. The sample injection volume was 3 μL. The UPLC column was maintained at 50° C. and the gradient program started at 90% A (0.1% formic acid in MilliQ H2O), changed to 95% B (0.1% formic acid in Acetonitrile) over 2.5 min, held for 0.35 minutes, then to 90% A over 0.05 minutes.

3. General Procedure for the Synthesis of Sulfonamides

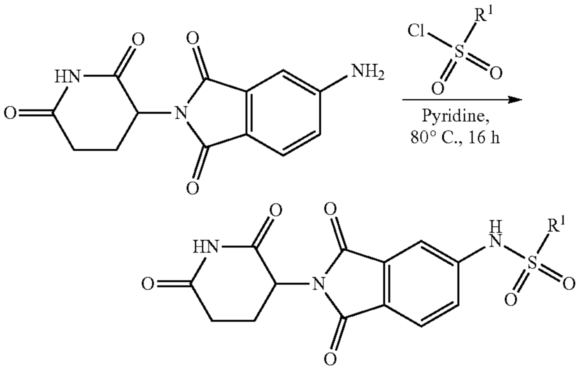

In a 48 position Mettler Toledo XT reaction block containing 11.5×110 mm test tubes equipped with a stir bar was added 0.1 mmol of 5-amino-2-(2,6-dioxopiperidin-3-yl) isoindoline-1,3-dione and the corresponding sulfonyl chloride (2.0 equiv, 0.2 mmol) for compounds 1-37 and 94-103, whereas 0.075 mmol of 5-amino-2-(2,6-dioxopiperidin-3-yl)isoindoline-1,3-dione and the corresponding sulfonyl chloride (2.0 equiv, 0.15 mmol) for compounds 38-93 (see Table 2 immediately following the Examples below). Anhydrous pyridine (500 uL) was added and the reactions were heated in a reaction block to 80° C. and stirred overnight under nitrogen. The reactions were checked by UPLC the next morning, concentrated to dryness and diluted with 1 mL of DMSO. Pre-purification analysis in the UPLC was done with water/acetonitrile/0.1% formic acid. Library purification was performed on the Waters purification/analytical LC/UV/ELSD system and parallel evaporations were carried out using a Genevac HT-24. Exemplary compounds 1-2, 5, 7, and 20 were obtained using methods described below, and shown in the general synthesis scheme above. The specific reaction sequence for each of the compounds 1-2, 5, 7, and 20 is shown preceding the characterization data for the compound immediately below. Additional characterization data for compounds 1-103 is shown in Table 2 immediately following the Examples below.

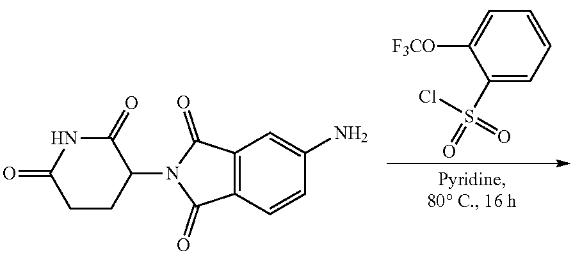

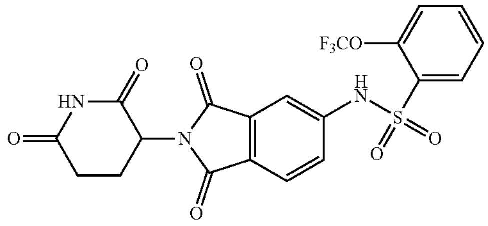

1

N-(2-(2,6-dioxopiperidin-3-yl)-1,3-dioxoisoindolin-5-yl)-2-(trifluoromethoxy)benzenesulfonamide (1). Yield: 34 mg, 68%. $^1$H NMR (500 MHz, DMSO-$d_6$) δ 11.60 (s, 1H), 11.11 (s, 1H), 8.10 (dd, J=8.1, 1.7 Hz, 1H), 7.86-7.78 (m, 2H), 7.64-7.57 (m, 2H), 7.54-7.47 (m, 2H), 5.09 (dd, J=12.9, 5.4 Hz, 1H), 2.86 (ddd, J=17.1, 13.9, 5.5 Hz, 1H), 2.58 (dt, J=17.1, 3.4 Hz, 1H), 2.46 (m, 1H), 2.02 (m, 1H). LCMS (m/z) M+H=498.2. HRMS: calcd for $C_{20}H_{14}F_3N_3O_7S$+H: 498.0583; found: 498.0582 [M+H].

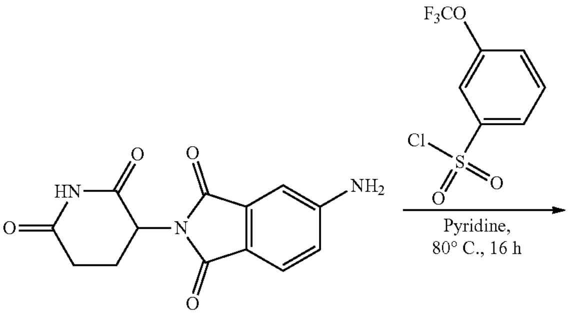

-continued

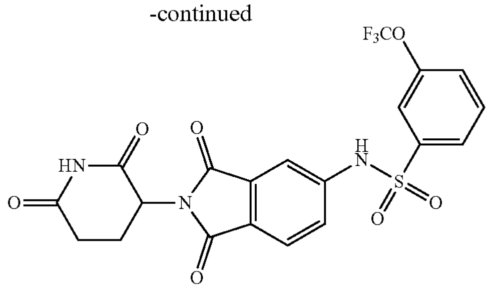

2

N-(2-(2,6-dioxopiperidin-3-yl)-1,3-dioxoisoindolin-5-yl)-3-(trifluoromethoxy)benzenesulfonamide (2). Yield: 16 mg, 32%. Purity >95%. $^{1}$H NMR (500 MHz, DMSO-$d_6$) δ 11.42 (s, 1H), 11.11 (s, 1H), 7.88 (d, J=7.8 Hz, 1H), 7.84 (d, J=8.8 Hz, 1H), 7.80-7.73 (m, 2H), 7.71 (dd, J=8.1, 2.3 Hz, 1H), 7.58-7.51 (m, 2H), 5.10 (dd, J=12.9, 5.4 Hz, 1H), 2.87 (ddd, J=17.2, 13.9, 5.5 Hz, 1H), 2.58 (dt, J=17.2, 3.4 Hz, 1H), 2.51-2.42 (m, 1H), 2.01 (dtd, J=13.1, 5.4, 2.3 Hz, 1H). LCMS (m/z) M+H=498.2. HRMS: calcd for $C_{20}H_{14}F_3N_3O_7S$+H: 498.0583; found: 498.0578 [M+H].

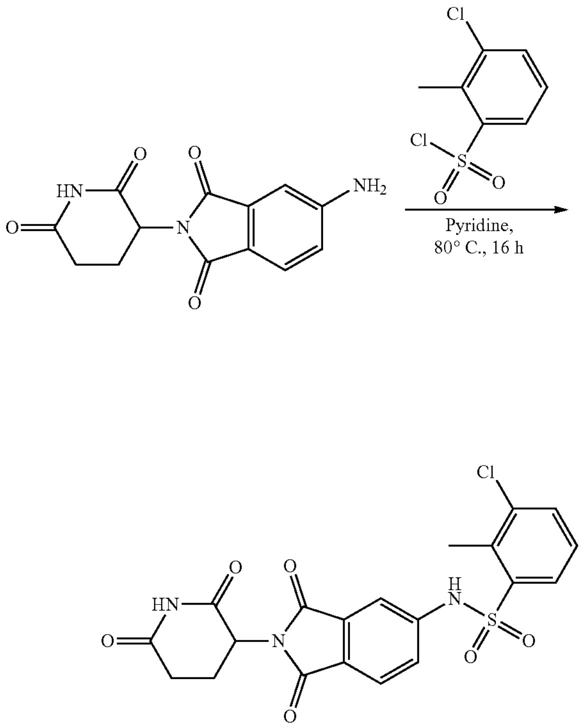

5

3-chloro-N-(2-(2,6-dioxopiperidin-3-yl)-1,3-dioxoisoindolin-5-yl)-2-methylbenzenesulfonamide (5). Yield: 26 mg, 56%. Purity >95%. $^{1}$H NMR (500 MHz, DMSO-$d_6$) δ 11.64 (s, 1H), 11.10 (s, 1H), 8.00 (d, J=8.0 Hz, 1H), 7.81 (d, J=8.7 Hz, 1H), 7.77 (d, J=8.0 Hz, 1H), 7.47 (dt, J=8.1, 4.5 Hz, 2H), 5.08 (dd, J=12.9, 5.4 Hz, 1H), 2.86 (ddd, J=17.2, 13.9, 5.4 Hz, 1H), 2.67 (s, 3H), 2.58 (dt, J=17.1, 3.4 Hz, 1H), 2.46 (m, 1H), 2.01 (dtd, J=13.0, 5.4, 2.3 Hz, 1H). LCMS (m/z) M+H=462.5. HRMS: calcd for $C_{20}H_{16}ClN_3O_6S$+H: 462.0527; found: 462.0515 [M+H].

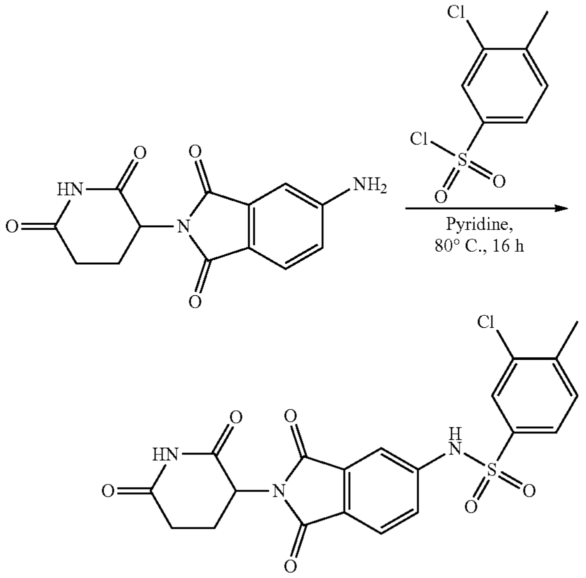

7

3-chloro-N-(2-(2,6-dioxopiperidin-3-yl)-1,3-dioxoisoindolin-5-yl)-4-methylbenzenesulfonamide (7). Yield: 29 mg, 62%. Purity >95%. $^{1}$H NMR (500 MHz, DMSO-$d_6$) δ 11.33 (s, 1H), 11.11 (s, 1H), 7.88-7.81 (m, 2H), 7.71 (d, J=8.1 Hz, 1H), 7.59 (d, J=8.2 Hz, 1H), 7.53-7.52 (m, 2H), 5.10 (dd, J=12.8, 5.4 Hz, 1H), 2.87 (ddd, J=18.0, 14.0, 5.4 Hz, 2H), 2.62-2.55 (m, 1H), 2.49-2.45 (m, 1H), 2.37 (s, 3H), 2.10-1.99 (m, 1H). LCMS (m/z) M+H=462.4. HRMS: calcd for $C_{20}H_{16}ClN_3O_6S$+H: 462.0527; found: 462.0519 [M+H].

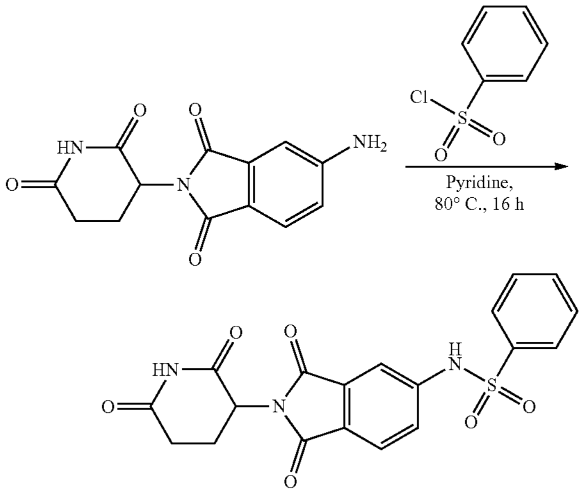

20

N-(2-(2,6-dioxopiperidin-3-yl)-1,3-dioxoisoindolin-5-yl)benzenesulfonamide (20). Yield: 25 mg, 61%. Purity >95%. $^{1}$H NMR (500 MHz, DMSO-$d_6$) δ 11.31 (s, 1H), 11.10 (s, 1H), 7.87 (dd, J=7.4, 1.7 Hz, 2H), 7.82 (d, J=8.1 Hz, 1H), 7.66 (t, J=7.3 Hz, 1H), 7.62-7.59 (m, 2H), 7.56-7.48 (m, 2H), 5.09 (dd, J=12.9, 5.4 Hz, 1H), 2.86 (ddd, J=17.2, 13.9, 5.4 Hz, 1H), 2.60-2.56 (m, 1H), 2.51-2.43 (m, 1H), 2.04-1.99 (m, 1H). LCMS (m/z) M+H=414.4. HRMS: calcd for $C_{19}H_{15}N_3O_6S$+H: 414.0760; found: 414.0750 [M+H].

4. CRBN Fluorescence Polarization Assay

In this competitive fluorescent polarization assay Cy5 conjugated lenalidomide analog (Cy5-O-Len)[13] was used as a fluorescent probe. 6XHis-CRBN-DDB1 protein (200 nM) and Cy5-O-Len probe (30 nM) were combined in 20 mM HEPES pH 7, 150 mM NaCl, 0.005% Tween-20 assay buffer. 20 μL of this assay cocktail was dispensed into wells of Corning 3821 black 384-well plates. Compounds were transferred to the assay plate from a dose-response plate using a Pintool on a Biomek FXP Laboratory Automation Workstation (Beckman Coulter). The plates were incubated in the dark for 1 hour at room temperature and then read on an Envision plate reader (PerkinElmer, Massachusetts, USA). $IC_{50}$ values were determined using a proprietary software RISE (Robust Investigation of Screening Experiments), developed in house on the Pipeline Pilot platform (Biovia, v. 17.2.0). Data represent the mean of three independent determinations.

5. MV-4-11 Cell Viability Assay

MV-4-11 cell line was purchased from the American Type Culture Collection (ATCC, Manassas, VA). The cells were cultured according to recommendations in IMDM cell culture media (ATCC). Exponentially growing MV-4-11 cells were plated at 1,000 cells per well in Corning 8804BC white 384-well assay plates and incubated overnight at 37° C. in a humidified 5% $CO_2$ incubator. Compounds were transferred to the assay plate from a dose-response plate using a Pintool on a Biomek FXP Laboratory Automation Workstation (Beckman Coulter). Cytotoxicity was determined following 72 hours of incubation using Promega Cell Titer Glo reagent according to the manufacturer's recommendation. Luminescence was measured on an Envision plate reader (Perkin-Elmer).

6. Cell Proliferation and Lenalidomide Competition Assay

Compounds were screened in human cancer cell lines and each cell line was cultured in the complete medium recommended by the vendor and seeded in Corning 8804BC white 384-well assay plates at density of 1,000, 1,000, 1,000, 1,500 and 7,500 cells per well, for MV4-11, HD-MB03, MB004, MB002 and MHH-CALL4 cells respectively. After overnight incubation at 37° C. in a humidified 5% $CO_2$ incubator, cells were treated with compounds in dose-response format using a Pintool on a Biomek $FX^P$ Laboratory Automation Workstation (Beckman Coulter). For lenalidomide competition assay, MV4-11 cell line was co-treated with 10 μM of Lenalidomide and DMSO or the respective compounds. After 72 h incubation, cell proliferation was assessed using Cell Titer-Glo (CTG) luminescent cell viability assay (Promega) according to the manufacturer's instruction. Luminescence signal was measured using an Envision plate reader (Perkin-Elmer).

7. MV4-11 CRBN KO Cell Line

Figure 7:
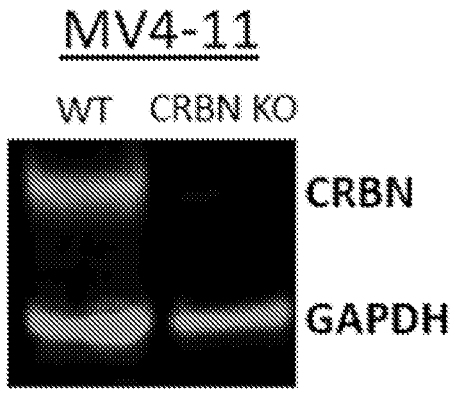
FIG. 7 shows representative Western blot data obtained using for wild-type and Cereblon deficient MV4-11 cell lines (clone 4B12) showing detected of CRBN protein versus a GAPDH control.

CRBN-deficient MV4:11 cells were generated using CRISPR-Cas9 technology. Briefly, 400,000 MV4:11 cells were transiently co-transfecting with precomplexed ribonuclear proteins (RNPs) consisting of 100 pmol of chemically modified sgRNA (5'-UGUAUGUGAUGUCGGCAGAC-3', Synthego) (SEQID: 8) and 35 pmol of Cas9 protein (St. Jude Protein Production Core) via nucleofection (Lonza, 4D-Nucleofector™ X-unit) using solution SF and program DJ-100 in small (20 μl) cuvettes according to the manufacturer's recommended protocol. Five days post nucleofection, cells were single-cell sorted by FACs to enrich for GFP+(transfected) cells, clonally selected, and verified for the desired targeted modification via targeted deep sequencing using gene specific primers with partial Illumina adapter overhangs (hCRBN.F—5'-GCAGAGAGTGAGGAAGAA-GATGA-3' (SEQID: 6) and hCRBN.R—5'-GCC-CATGTCCTCATCCACAA-3', (SEQID: 7); overhangs not shown) and analyzed using CRIS.py (Ref. 36). Two hCRBN knockout clones were identified. Protein knockout was confirmed by Western blot (FIG. 7). The genotype of each clone is indicated below. Upper case base pairs are insertions and (−) are deletions.

```
WT
                                         (SEQ ID: 1)
5'ttttgacaccagtctgccgacatcacatacagtatgtaattta 3'

Clones
1B6
-1 bp
                                         (SEQ ID: 2)
5'ttttgacaccagtctg-cgacatcacatacagtatgtaattta 3'

+1 bp
                                         (SEQ ID: 3)
5'ttttgacaccagtctTgccgacatcacatacagtatgtaattta 3'

4B12
-1 bp
                                         (SEQ ID: 4)
5'ttttgacaccagtc-gccgacatcacatacagtatgtaattta 3'

-1 bp
                                         (SEQ ID: 5)
5'ttttgacaccag-ctgccgacatcacatacagtatgtaattta 3'
```

8. Immunoblot Analysis

MV4-11 cells were seeded in 6-well plates ($1\times10^6$ cells per well). After overnight incubation, the cells were treated with indicated concentrations for specific timepoints. The harvested cells were spin down, washed with PBS and lysed with 1× LDS loading buffer followed by sonication and heated at 70° C. Prepared samples were loaded on NuPAGE 4-12% Bis-Tris protein gels and transferred to nitrocellulose membrane. After blocking the membrane with LI-COR TBS blocking buffer and incubation in primary antibody overnight, the corresponding protein signals were detected using IRDye secondary antibodies and Odyssey Imaging System. Image Studio Lite Ver 5.2 was used for blot quantification. Antibodies: Rabbit anti-human eRF3/GSPT1 pAb (ab126090, abcam), mouse art-human Ikaros mAb (sc-398265, Santa cruz), mouse anti-GAPDH mAb (so-47724, Santa cruz) were used as primary antibodies. IRDye®, 800CW Goat anti-Mouse IgG Secondary Antibody and IRDye® 680RD Goat anti-Rabbit IgG Secondary Antibody were used as secondary antibodies.

9. Caspase 3/7 Activity Assay

Mv4:11 cells were seeded in white 384-well assay plates at density of 1000 cells per well in triplicates for 3 separate timepoint experiments (4,8, 24 hrs). After overnight incubation, cells were treated with compounds in dose-response format using a Pintool on a Biomek FXP Laboratory Automation Workstation (Beckman Coulter). After 4, 8 and 24 hrs incubation, the caspase 3/7 activity was assessed using Caspase-Glo® 3/7 Assay (Promega) according to the manufacturer's instruction. Luminescence signal was measured using an Envision plate reader (Perkin-Elmer).

10. Protein Digestion and Peptide Isobaric Labeling by Tmt Reagents

The experiment was performed with a previously optimized protocol (Ref. 37) with slight modification. Cell pellets were lysed in lysis buffer (50 mM HEPES, pH 8.5, 8 M urea and 0.5% sodium deoxycholate). To profile whole proteome, the protein lysates (approximately 100 μg of protein per sample were proteolyzed with LysC (Wako) at an enzyme-to-substrate ratio of 1:100 (w/w) for 2 h at 21° C. Following this the samples were diluted to a final 2 M Urea concentration, and further digested with trypsin (Promega) at an enzyme-to-substrate ratio of 1:50 (w/w) for at least 3 h. The peptides were reduced by adding 1 mM DTT for 30 min at 21° C. followed by alkylation with 10 mM iodoacetamide for 30 min in the dark. The unreacted IAA was quenched with 30 mM DTT for 30 min. Finally, the digestion was stopped by adding trifluoroacetic acid (TFA) to 1%, desalted using C18 cartridges (Harvard Apparatus) and dried by speedvac. The purified peptides were resuspended in 50 mM HEPES (pH 8.5), labeled with TMT reagents (Thermo Scientific). The differentially labeled samples were pooled equally, desalted and dried for the subsequent peptide fractionation. Peptide Analysis by two-dimensional liquid chromatography-Tandem Mass Spectrometry (LC/LC-MS/MS) and MS Data analysis are described in the Supplementary Material.

11. Aqueous Solubility Assay

Solubility assays were carried out on a Biomek FX lab automation workstation (Beckman Coulter, Inc., Fullerton, CA) using μSOL Evolution software (pION Inc., Woburn, MA). 10 μL of 10 mM compound stock (in DMSO) was added to 190 μL 1-propanol to make a reference stock plate. 5 μL from this reference stock plate were mixed with 70 μL 1-propanol and 75 μL citrate phosphate-buffered saline (PBS;isotonic) to make the reference plate, and the UV spectrum (250-500 nm) of the reference plate was read. 6 μL of 10 mM test compound stock was added to 594 μL buffer in a 96-well storage plate and mixed. The storage plate was sealed and incubated at RT for 18 h. The suspension was then filtered through a 96-well filter plate (pION Inc., Woburn, MA). 75 μL of filtrate was mixed with 75 μL 1-propanol to make the sample plate, and the UV spectrum of the sample plate was read. Calculations were carried out with μSOL Evolution software based on the area under the curve (AUC) of the UV spectrum of the sample and reference plates. All compounds were tested in triplicate.

12. Mdckii-Mdr1 Permeability Assay

High throughput MDCKIIMDR1 permeability was performed in the Transwell® 0.4 μm polycarbonate membrane 96-well system with modified methods (Refs. 38-39). MDCKIIMDR1 cells were maintained at 37° C. in a humidified incubator with an atmosphere of 5% $CO_2$. The cells were cultured in 75 $cm^2$ flasks with Dulbecco's Modified Eagle's Medium (DMEM) containing 10% fetal bovine serum (FBS), 1% non-essential amino acids (NEAA), 100 units/ml of penicillin, and 100 μg/ml of streptomycin. The MDCKIIMDR1 cells were seeded onto inserts at a density of $2\times10^4$ and $1\times10^4$ cells/insert separately. The medium in the wells was exchanged each other day, and the trans epithelial electrical resistance (TEER) value was measured using an epithelial volt-ohm meter (Millipore, Billerica, Massachusetts). MDCKII-MDR1 cells were grown for 4 days to reach consistent TEER values (typically 2000 ohms greater than initial value when cells are first seeded into transwells), indicating that the cells had formed a confluent polarized monolayer. For transport experiments, each cultured monolayer on the 96-well plate was washed twice with a transport buffer (HBSS/25 mM HEPES, pH 7.4). The permeability assay was initiated by the addition of each compound solution (10 μmol/L) into inserts (apical side, A) or receivers (basolateral side, B). The MDCKII-MDR1 cell monolayers were incubated for 1 hour at 37° C. Fractions were collected from receivers (if apical to basal permeability) or inserts (if basal to apical permeability), and concentrations were assessed by UPLC/MS (Waters; Milford, MA). All compounds were tested in triplicates. The A→B (or B→A) apparent permeability coefficients (Papp) of each compound were calculated using the equation, $Papp=dQ/dt\times1/AC_0$, where dQ/dt equals the flux of a drug across the monolayer, A equals the total insert well surface area, and $C_0$ is the initial concentration of substrate in the donor compartment. The efflux ratio was determined by dividing the $P_{app}$ in the B-A direction by the $P_{app}$ in the A-B direction. An efflux ratio >2 suggested that a given substrate was actively transported across the membrane.

13. Liver Microsomes Stability Assay

The liver microsome stability assay was carried as previously described (Refs. 40-41). NADPH regenerating agent solutions A and B and mouse liver microsomes (CD-1) were obtained from BD Gentest (Woburn, MA). Pooled human liver microsomes were purchased from XenoTech (Lenexa, KS). Ninety-six deep well plates were obtained from Midsci (St. Louis, MO). Ninety-six analytical plates were obtained from Corning Incorporated (Acton, MA). Sample preparation for microsomal stability was modified from Di's publications. A set of incubation times of 0, 15, 30, 60, 120, and 240 min were used. DMSO stock solutions of test compounds and verapamil (system control) were prepared at 10 mM concentration. Concentrated human or mouse liver microsomes (20 mg/mL protein concentration) and 0.5 M EDTA were diluted into 0.1 M potassium phosphate buffer (pH 7.4) and mixed well, followed by compounds solutions being spiked. This solution was mixed and 90 μL was transferred to 6 time points plates (each in triplicate wells). For the time 0 h plate, 3 fold (v:v) cold acetonitrile with internal standard (40 ng/ml warfarin) was added to each well, followed by addition of NADPH regenerating agent (mixing NADPH solutions A and B in PBS, pH7.4) and no incubation. For the other five time points' plate, NADPH regenerating agent was added to each well to initiate the reaction, the plate was incubated at 37° C. for the required time, followed by quenching of the reaction by adding 3-fold volume of cold acetonitrile with internal standard (40 ng/mLwarfarin) to each well. The final concentration of each component applied in this reaction was liver microsome protein at 0.5 mg/mL, EDTA at 1 mM, compound at 10 μM, NADPH A at 1.3 mM, and NADPH B at 0.4 U/mL. All plates were sealed and mixed well at 600 rpm for 10 min after quenching and were centrifuged at 4000 rpm for 20 min. The supernatants were transferred to analytical plates and diluted by millipore water for analysis by LC-MS/MS. Conditions for SCIEX Qtrap UHPLC-MS/MS system are described separately. The metabolic stability was evaluated via the half-life from least-squares fit of the multiple time points based on first-order kinetics.

14. Plasma Protein Binding Assay

Stock solutions were prepared at 10 mM in DMSO. Dulbecco's phosphate buffered saline (DPBS; pH 7.4) was obtained from Invitrogen (Carlsbad, CA). Single-Use RED (rapid equilibrium dialysis) device was obtained from Thermo scientific (Rockford, IL). Human and mouse plasma were obtained from GeneTex (Irvine, CA). Sample preparation for plasma protein binding was modified from Waters' method (see Waters, N.J., et al., *J Pharm Sci.* 2008 October; 97(10):4586-95). The Teflon base plate with the RED inserts was used without any pre-conditioning the membrane inserts. Plasma was thawed and centrifuged at 1000 rpm for 10 min to remove any particulates. Each compound was prepared at 10 μM in human or mouse plasma. Spiked plasma solutions (300 μL) were placed into the sample chamber (indicated by the red ring) and 500 μL of DPBS into the adjacent chamber. The plate was sealed and incubated at 37° C. on an orbital shaker (100 rpm) for 4 hours. After incubation, the seal was removed from the RED plate and the volume of the insert confirmed—little to no volume change occurred. Aliquots (50 μL) were removed from each side of the insert and dispensed into a 96-well deep plate. An equal volume of blank plasma or DPBS was added to the required wells to create analytically identical sample matrices (matrix matching) followed by quenching 3 fold (v:v) cold acetonitrile containing 40 ng/ml warfarin IS. All of the plates were sealed and mixed well at 600 rpm for 10 min and were centrifuged at 4000 rpm for 20 min. The supernatants were transferred to analytical plates and diluted by Millipore water appropriately for analysis by LC-MS/MS. Conditions for SCIEX Qtrap UHPLC-MS/MS system are described separately. The test compound concentrations were quantified in both buffer and plasma chambers via peak areas relative to the internal standard. The percentage of the test compound bound to plasma was calculated on following equations: % Free=(Concentration buffer chamber/concentration plasma chamber)×100% and % Bound=100%-% Free.

15. UPLC/MS/UV System

Chromatographic separation was performed on an Acquity UPLC BEH C18 1.7 μm, 2.1×50 mm column (Waters Corporation, Milford, MA) using an Acquity ultra performance liquid chromatography system. Data were acquired using MassLynx v. 4.1 and analyzed using the QuanLynx software suite. This was coupled to an SQ mass spectrometer. The total flow rate was 1.0 mL/min for generic method and 0.9 mL/min for medium polar method. The sample injection volume was 10 μL. The column temperature was maintained at 55° C. Samples were analyzed in acidic condition: solvent A was 0.1% formic acid in MilliQ H2O and solvent B was 0.1% formic acid in ACN. Samples were eluted under generic or medium polar gradients. For a generic gradient: 0-0.2 min, 10-30% of solvent B; 0.2-1.6 min, 30-95% of solvent B; 1.6-1.95 min, 95% of solvent B; 1.95-2 min, 95-10% of solvent B. For a medium polar gradient: 0-0.2 min, 10% of solvent B; 0.2-1.6 min, 10-95% of solvent B; 1.6-1.95 min, 95% of solvent B; 1.95-2 min, 95-10% of solvent B. The mass spectrometer was operated with electrospray ionization in positive ionization mode. The conditions were as follows: capillary voltage 3.4 kV, cone voltage 30 V, source temperature 130° C., desolvation temperature 400° C., desolvation gas 800 L/hr, cone gas 100 L/hr. A full range scan from m/z=100-1000 in 0.2 s was used to monitor compounds. A single ion recording mass spectrometry for each compound was used to determine the quantification of the samples.

16. UHPLC-MS/MS System

LC-MS chromasolv grade acetonitrile (ACN) was purchased from Fisher Scientific (Loughborough, UK). LC-MS chromasolv grade and formic acid were obtained from Sigma-Aldrich (St. Louis, MO). Milli-Q water as an ultrapure laboratory grade water was used in aqueous mobile phase. Chromatographic separation was performed on an Acquity UPLC BEH C18 1.7 μm, 2.1×50 mm column (Waters Corporation, Milford, MA) using a Sciex ExionLC™ with 6500+ Qtrap system. Data were acquired using Analyst v 1.7 and analyzed using the OS software suite. The UPLC column was maintained at 55° C. Mobile phase A was 0.1% formic acid in MilliQ H2O and solvent B was 0.1% formic acid in ACN. The flow rate was 0.9 mL/min with a gradient of 0-0.2 min, B % 1-1%; 0.2-0.5 min, B % 1-50%; 0.5-1.6 min, B % 50-95%; 1.6-1.95 min, B % 95-95%; 1.95-1.96 min, B % 95-1%; and 1.96-2.2 min, B % 1-1%. The sample injection volume was 2 μL. The mass spectrometer was operated in positive-ion mode with electrospray ionization. The conditions were as follow: ion spray voltage 5 kV, temperature 500° C., curtain gas with a low collision gas, gas 1 and gas 2 were 60. MRM transition of 498.0>425.0 for compound 5 was automatically optimized using DiscoveryQuant™ Software. The delustering potential, collision energy and collision cell exit potential were 80, 41 and 13 volts respectively.

17. Pharmacokinetics (PK) Study

Healthy female CD1 mice (8-12 weeks old) weighing between 20 to 30 g were procured from Global, India. Three mice were housed in each cage. Temperature and humidity were maintained at 22±3° C. and 30-70%, respectively and illumination was controlled to give a sequence of 12 hr light and 12 hr dark cycle. Temperature and humidity were recorded by auto-controlled data logger system. All the animals were provided laboratory rodent diet (Envigo Research private Ltd, Hyderabad). Reverse osmosis water treated with ultraviolet light was provided ad libitum. Formulation vehicle: 5% v/v NMP: 5% v/v Solute HS-15 and 90% v/v normal saline. Animals in Group 1 were administered intravenously as slow bolus injection through tail vein, with solution formulation of compound 5 at 3 mg/kg dose. Animals in Group 2 were administered through oral route with solution formulation of compound 5 at 10 mg/kg dose. The dosing volume for intravenous was 5 mL/kg and for oral administration 10 mL/kg. Blood samples (approximately 60 μL) were collected under light isoflurane anesthesia (Surgivet®) from retro orbital plexus from a set of three mice at 0.08 (for IV only), 0.25, 0.5, 1, 2, 4, 6 (for PO only), 8, 12 and 24 hr. Immediately after blood collection, plasma was harvested by centrifugation at 4000 rpm, 10 min at 40° C. and samples were stored at −70±10° C. until bioanalysis. Concentrations of compound 5 in mouse plasma samples were determined by fit for purpose LC-MS/MS method. Non-Compartmental-Analysis tool of Phoenix WinNonlin® (Version 8.0) was used to assess the pharmacokinetic parameters. Peak plasma concentration (Cmax) and time for the peak plasma concentration (Tmax) were the observed values. The areas under the concentration time curve (AUClast and AUCinf) were calculated by linear trapezoidal rule. The terminal elimination rate constant, ke was determined by regression analysis of the linear terminal portion of the log plasma concentration-time curve. Clearance was estimated as Dose/AUCinf and Vss as CL*MRT. The oral bioavailability was calculated as ratio of dose normalized AUC of oral and intravenous group multiplied by 100.

18. Results—Activity of Disclosed Compounds

Two representative disclosed compounds were assessed on five cell lines to understand and annotate compounds that could be functioning through general cytotoxic mechanisms. The two hits, sulfonamides 1 and 2 shared a common scaffold represented in Table 1 and demonstrated potent antiproliferative activity in MV4-11 ($EC_{50}$=1.5 and 52 nM). The subsequent hit characterization and mechanistic studies described here were carried out in MV4-11 cells.

TABLE 1

Activity and physiochemical property data for representative compounds.

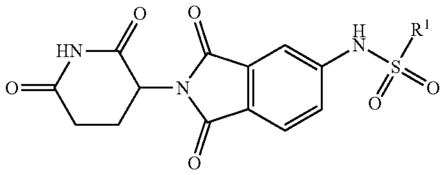

| Cmpd No.* | $R^1$** | CRBN $IC_{50}$ (μM)[a] | MV4-11 $EC_{50}$ (μM)[a] | Sol.[a,b] (μM) | $P_{app}$[a,c] (nm/s) | GSPT1 $DC_{50}$[a,c] (nM) | IKZF1 $DC_{50}$[a,c] (nM) | DE[e] (GSPT1) |
|---|---|---|---|---|---|---|---|---|
| 1 | 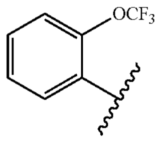 [SMILES: *c1ccccc1OC(F)(F)F] | 0.002 | 0.0015 | 67 | 23 | 2.1 | 30 | 0.25 |
| 2 | 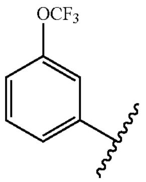 [SMILES: *c1cccc(OC(F)(F)F)c1] | 0.054 | >10 | 64 | 40 | — | — | — |
| 5 | 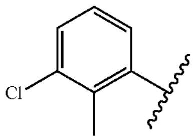 [SMILES: *c1cccc(Cl)c1C] | 0.038 | 0.052 | 64 | 36 | 9.7 | 275 | 0.25 |
| 7 | 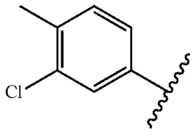 [SMILES: *c1ccc(C)c(Cl)c1] | 0.013 | >10 | ND | 46 | — | — | — |
| 20 | 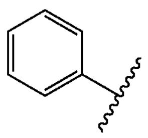 [SMILES: *c1ccccc1] | 0.072 | >10 | 71 | 36 | — | — | — |
| CC90009 | — | ND | 0.062 | 77 | 49 | 1.6 | 9.9 | 0.27 |

*"Cmpd No." is the compound number and corresponds to the same compound numbering system used herein througout.

**$R^1$ in the compound structure shown above.

[a]All values are the mean of 2≥ independent experiments.

[b]Aqueous solubility measured at pH = 7.4 in triplicate.

[c]Permeability in MDCK-MDR1 cells.

[d]$DC_{50}$ values calculated from concentration-dependent protein degradation curves in MV4-11 cells after 24 h treatment ($DC_{50}$ is compound concentration at which 50% of target protein is degraded).

[e]Degradation Efficiency (DE) = $pD_{50}$/NHA. ND = Not Determined.

Figure 2B:
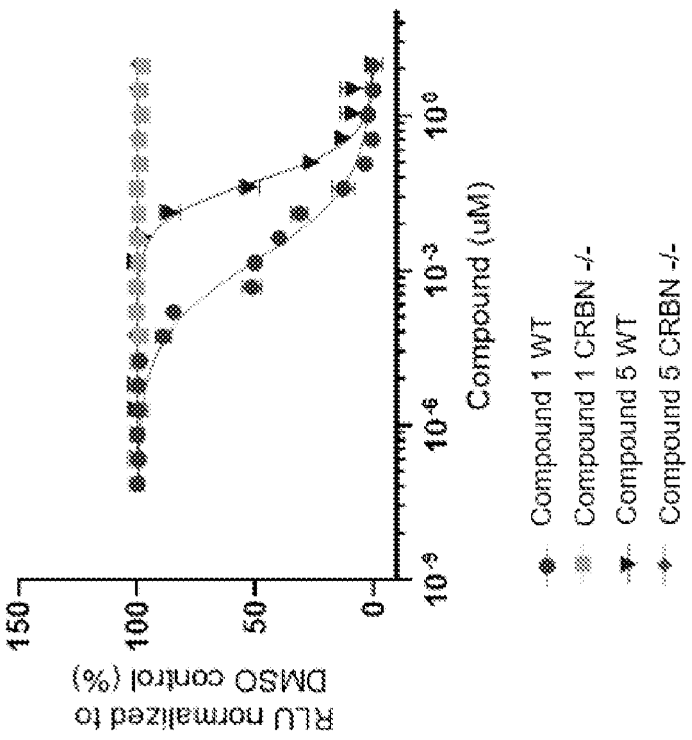
FIGS. 2A-2B show representative data for the effect of the treatment with increasing concentrations of compounds 1 and 5 over 3 days on viability of MV4-11 cells under the conditions described.
Figure 2A:
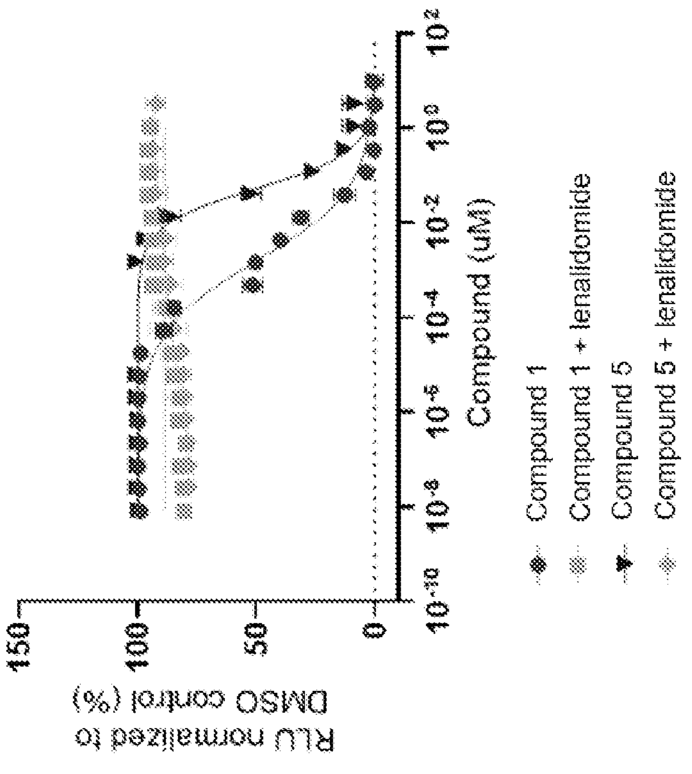

In view of the foregoing potent antiproliferative effects in cells, studies were carried out to assess whether the effect was CRBN-dependent. Ligand competition experiments were carried out. Briefly, MV4-11 cells were treated with 1 or 5 in dose-response in the presence of high concentrations of lenalidomide (10 μM). Excess lenalidomide results in saturation of the CRBN binding site, thus making it inaccessible for other CRBN modulators to bind and thereby abrogating the antiproliferative effects of 1 and 5 as shown in FIG. 2A. In an orthogonal approach, compounds 1 and 5 were tested in wild-type and CRBN knockout MV4-11 cells in a cell viability assay (FIGS. 2B and 7). The results show that in the absence of CRBN the antiproliferative activity of the compounds was abolished, further confirming a CRBN-dependent mechanism.

Figure 3B:
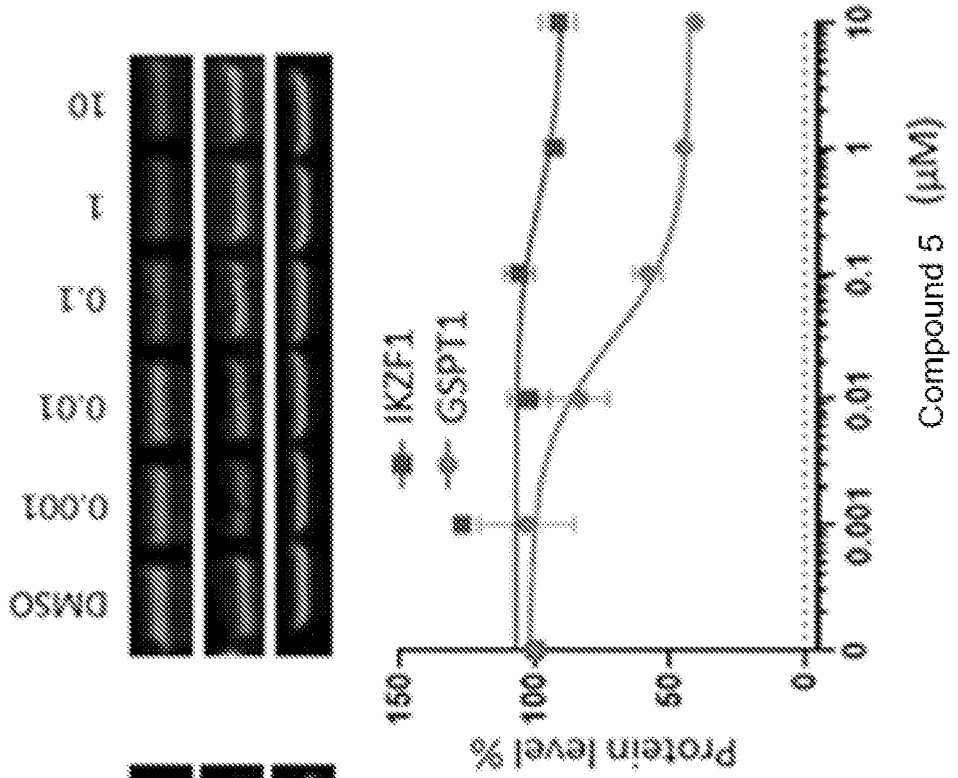
FIGS. 3A-3D show representative data for the effect of the treatment with increasing concentrations of compounds 1 and 5 on levels of GSPT1 and IKZF1 in MV4-11 cells. Immunoblot images are shown above the graphs, and the quantified band intensities from these immunoblots are plotted in each graph. The immunoblots are labeled to indicate the protein detected, i.e., GSPT1 and IKZF1 proteins versus GAPDH control. Each lane of the immunoblot is labelled to show the concentration of the given compound used to treat MV4-11 cells.
Figure 3A:
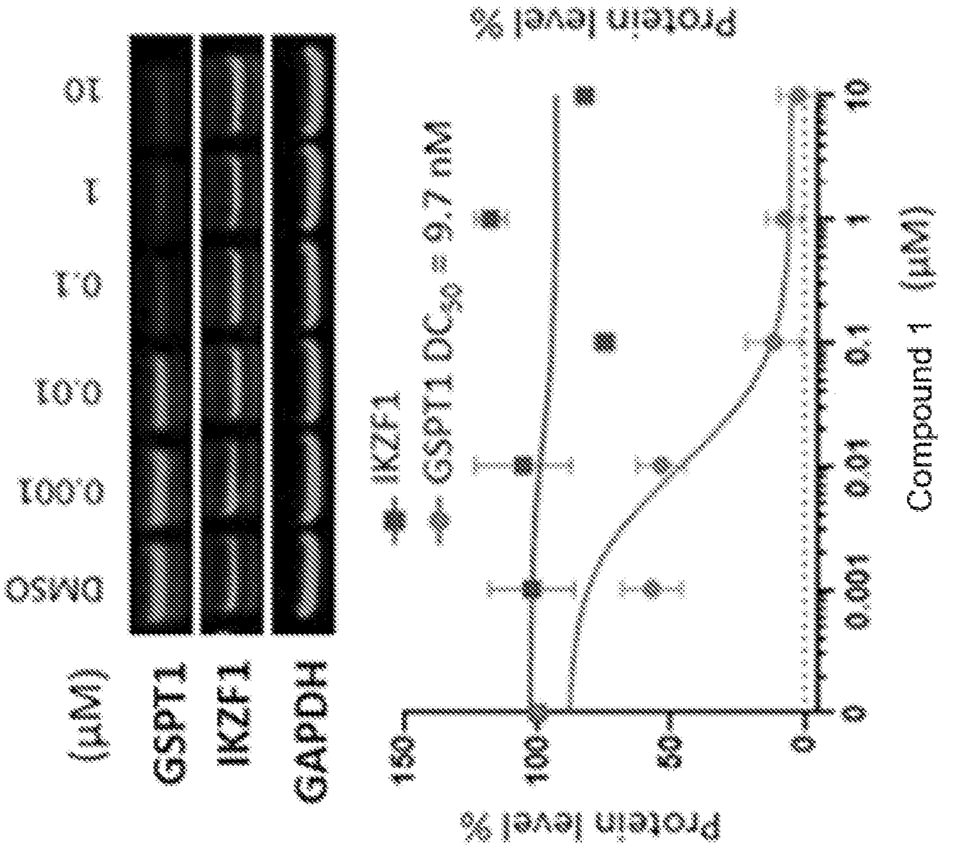

Immunoblot experiments were carried out to determine if the cytotoxicity was associated with degradation of known neosubstrates. In other experiments (data not shown), among various prior art compounds examined, it was determined that CC-885 displayed antiproliferative effects in all four cell lines listed in Table 1 above, and studies were carried out to determine whether the disclosed compounds similarly degraded GSPT1 and IKZF1. Immunoblotting experiments were performed after 4 hours drug exposure based on literature evidence that neosubstrate degradation occurs rapidly, typically by 4 to 8 hours of IMiD treatment (Refs. 9 and 27). As illustrated in FIG. 2A, compound 1 displayed dose dependent decrease in GSPT1 protein abundance with a half-maximal degradation concentration ($DC_{50}$) of 9.7 nM and nearly complete protein degradation (90%) at 100 nM. Compound 5 showed partial depletion of GSPT1 at 4 h and residual levels of GSPT1 protein remained even at the highest concentration (10 μM, maximum degradation efficacy, $D_{max}$=60%). Notably, compounds 1 and 5 did not significantly degrade IKZF1 at 4 hours at any of the concentrations tested, providing a wide window of selectivity for GSPT1, as shown in FIGS. 3A and 3B.

Figure 3D:
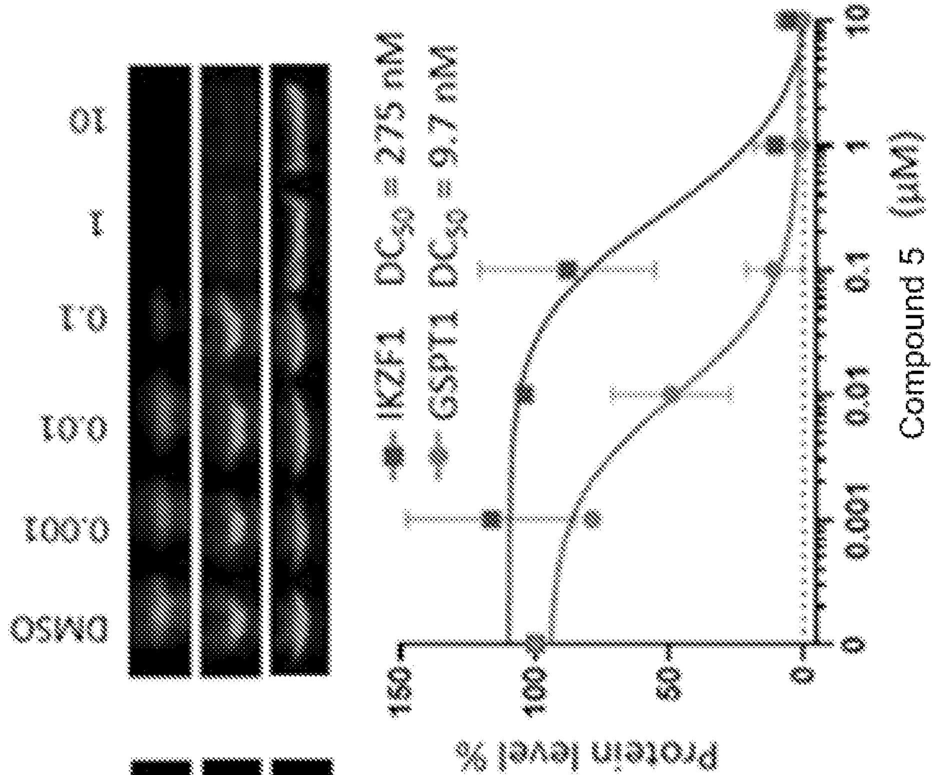
Figure 3C:
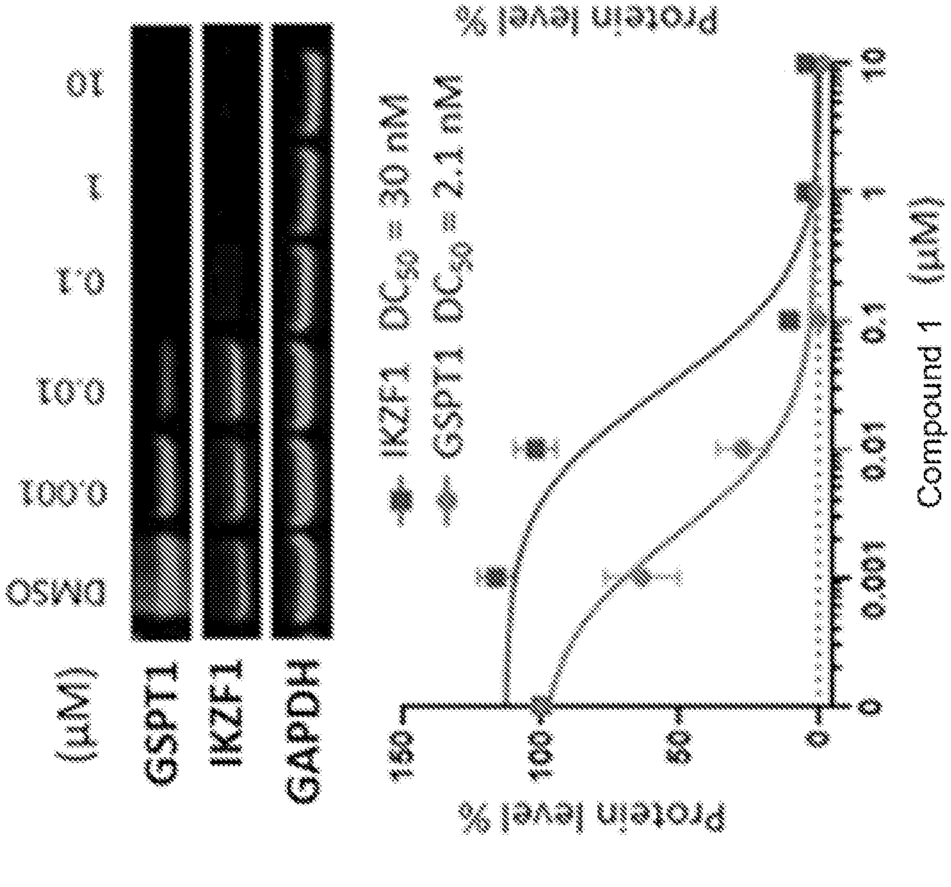
Figure 8:
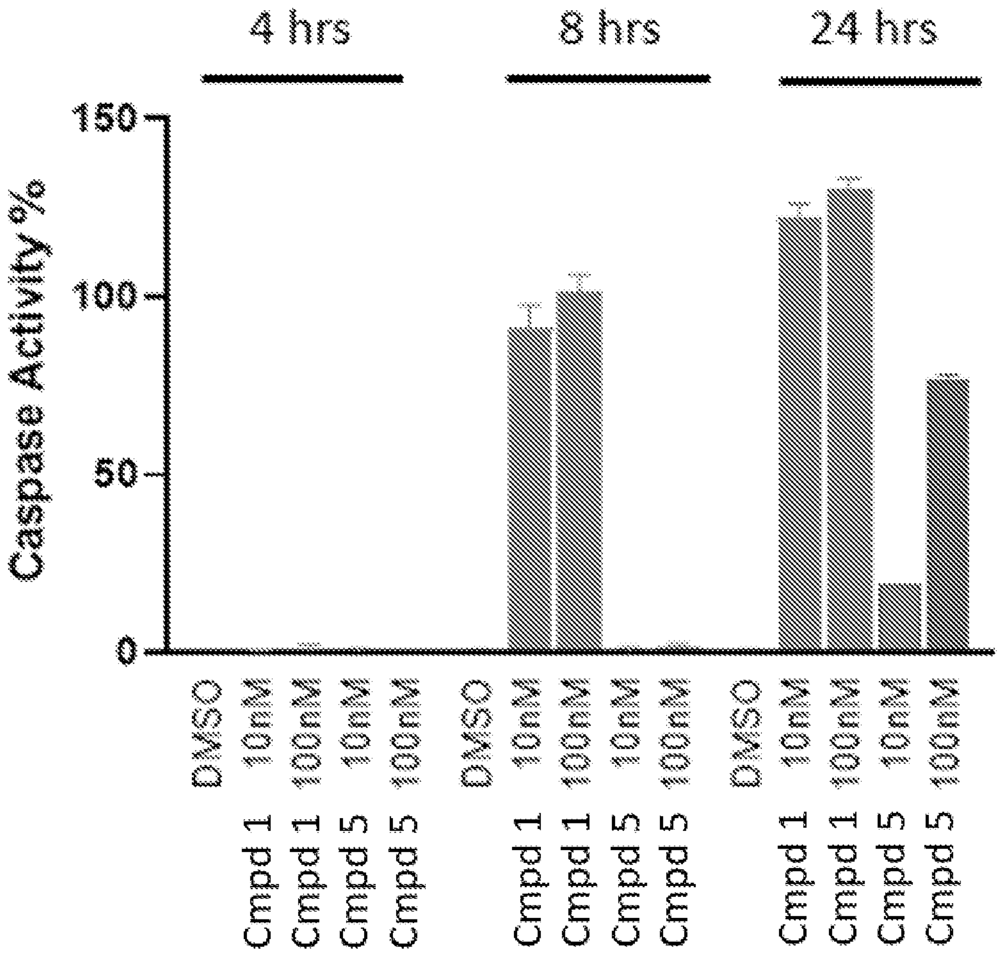
FIG. 8 shows representative data for caspase activation for compounds 1 and 5 at 4, 8, and 24 hours of treatment for the indicated concentrations versus DMSO control treatment.

To determine if GSPT1 and IKZF1 degradation profiles were sustained over time, the protein levels at 24 hours were examined (FIGS. 3C and 3D). Interestingly, whereas the GSPT1 degradation profile for 1 was mostly unchanged, compound 5 reached 90% protein degradation at 100 nM with a $DC_{50}$ of 10 nM. These data suggest that both compounds reached similar extent of GSPT1 degradation, but at different rates. It has been reported that depletion of GSPT1 leads to induction of apoptosis (see Refs. 28 and 29) and to correlate the degradation profiles of compounds 1 and 5 to their antiproliferative activities, they were tested in a luminescent Caspase-Glo assay in dose response at 3 time points (4, 8 and 24 hours; see Ref. 14). In the case of compound 1, caspase activation was measurable at 8 hours at both concentrations tested (10 and 100 nM), whereas caspase activity for compound 5 was delayed and only observed at the 24 hour time point (FIG. 8). Collectively, these experiments demonstrate that the faster and more efficient depletion of GSPT1 by compound 1 relative to compound 2 results in earlier induction of apoptosis and correlates with higher antiproliferative potency.

It is also interesting to note that the treatment of MV4-11 cells over 24 hours with both compounds 1 and 2 resulted in a dose-dependent decrease of the IKZF1 protein abundance. The $DC_{50}$ values for GSPT1 and IKZF1 calculated at 24 hours showed a modest selectivity window for compound 1 (14-fold), whereas from a chemical probe perspective a more optima[30] 30-fold selectivity profile was obtained for compound 2 (FIG. 3B). The delay of IKZF1 protein reduction was notable, considering that all IMiDs are known to degrade IKZF1 shortly after drug treatment (as early as 3 hours; see Ref. 7) A potential interpretation of these results is that upon rapid degradation of GSPT1 (which has an essential role in global protein synthesis), production of other proteins was inhibited, resulting in their decreased abundance at later time points.[31] It remains to be determined whether IKZF1 protein levels were indirectly affected by the rapid degradation of GSPT1 leading to alternative mechanisms affecting transcription and translation, or if the compounds indeed directly degraded IKZF1 with slower kinetics.

Figures 9A, 9B:
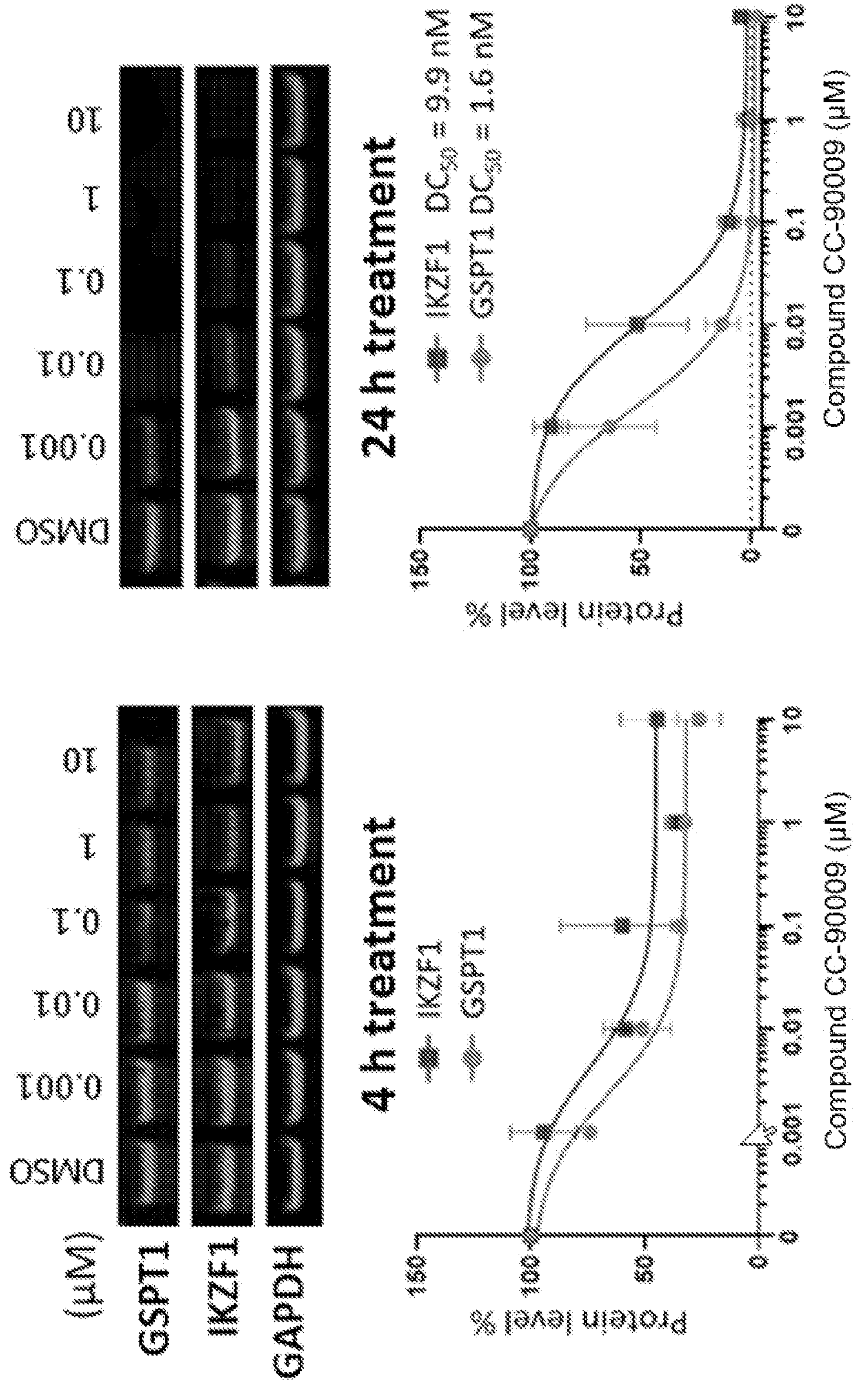
FIGS. 9A-9B show representative data for the effect of the treatment with increasing concentrations of control compound, prior art compound CC-90009, on levels of GSPT1 and IKZF1 in MV4-11 cells. Immunoblot images are shown above the graphs, and the quantified band intensities from these immunoblots are plotted in each graph. The immunoblots are labeled to indicate the protein detected, i.e., GSPT1 and IKZF1 proteins versus GAPDH control. Each lane of the immunoblot is labelled to show the concentration of the given compound used to treat MV4-11 cells.

The degradation profiles of disclosed compounds was compared to prior art compound CC-90009, currently the only GSPT1 degrader that has entered the clinic and had recently successfully completed phase 1 clinical trials for AML indication (NCT02848001; see Ref. 32). The data herein shows after treatment for 4 hours in MV4-11 cells with CC-90009, only partial degradation of GSPT1 ($D_{max}$=74% at 10 μM). However, unlike either compound 1 or 5, after 4 hours treatment it also degraded IKZF1 protein with $D_{max}$ of 55% at 10 μM (Supp. FIG. 6A). Interestingly, at the 24 h time point the degradation profile of CC-90009 was somewhat similar to compound 1, achieving $D_{max}$>90% for both GSPT1 and IKZF1 proteins with $DC_{50}$ values of 1.6 and 10 nM, respectively (Table 1 and FIG. 9B).

To numerically express and compare degraders' performance, a metric was devised that was inspired by the commonly used ligand efficiency (LE) index (see Refs. 33-34), which is referred to herein as "degradation efficiency" (DE). DE is defined as a degrader's $pDC_{50}$ value normalized by its number of heavy atoms (DE=$pDC_{50}$/NHA). Owing to their similar molecular size and $DC_{50}$ values, after 24 hours incubation compounds 1 and 5 displayed in MV4-11 cells the GSPT1 protein degradation efficiency similar to compound CC-90009 (Table 1). Overall, these data illustrate similar GSPT1 degradation potency but distinct neosubstrate specificity profile of compounds 1 and 5 relative to the GSPT1 degrader currently in clinical development.

The library design allowed us a rapid access to several direct analogues of the screening hits and generation of a preliminary structure-activity relationship (SAR) information. The analogues were generally found to display high aqueous solubility with modest cell permeability, and potent CRBN affinity with no apparent correlation between CRBN binding and cellular potency (Table 1). For example, compounds 5 and 2 shared similar CRBN binding affinities ($IC_{50}$=0.038 μM and 0.072 μM, respectively), but significantly different MV4-11 potency ($EC_{50}$=0.052 μM and >10 μM, respectively) despite of similar physicochemical properties such as aqueous solubility and permeability. However, what transpired from these preliminary SAR data was the critical importance of the ortho-substitution for the cell potency. For example, the regioisomer of hit compound 5 lacking the ortho-substituent, compound 7, was a potent CRBN binder ($IC_{50}$=0.013 μM) but showed no effect on cell viability (MV4-11 $EC_{50}$>10 μM). In a similar fashion, whereas unsubstituted phenylsulfonamide 20 was inactive, 2-$OCF_3$ derivative 1 was among the most potent compound among the compounds examined herein, while 3-$OCF_3$ analogue showed no activity in MV4-11 cells (Table 1). It was confirmed that compound 2 had no effects on the protein levels of GSPT1 and IKZF1 by immunoblotting (FIG. 6), supporting the observation that small chemical alterations have substantial impact in the protein homeostasis machinery posing significant challenges for medicinal chemistry optimization. Without wishing to be bound by a particular theory, it is believed that these observations cannot be explained by differences in physicochemical properties, CRBN binding or cellular permeability.

Figure 4:
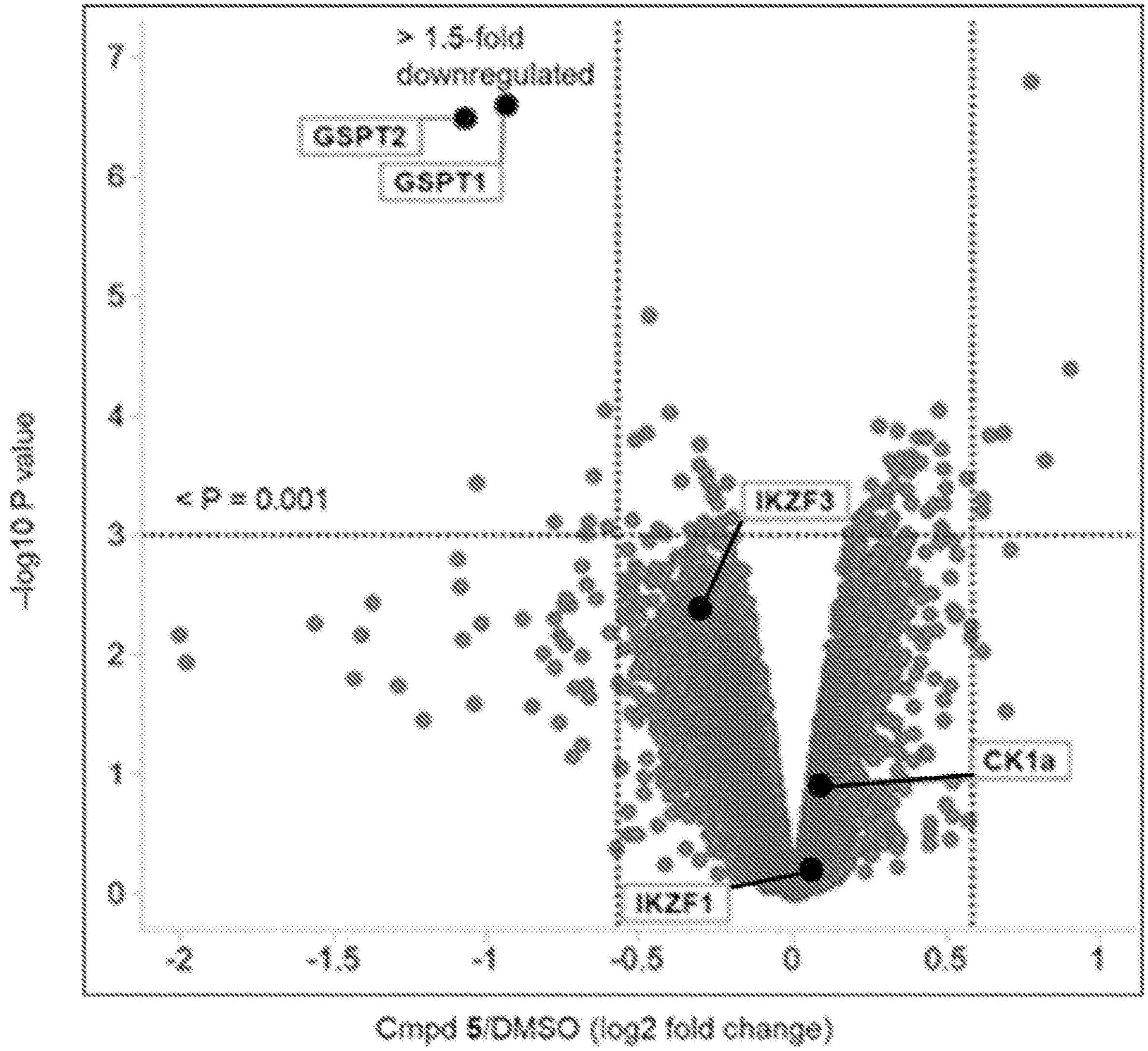
FIG. 4 shows representative data obtained in a TMT-proteomics experiment with compound 1 at 24 hours (10 nM). The dataset shown represents an average of n=4 replicates. Proteins downregulated more than 1.5-fold (dotted line on Log 2=−0.58 on X-axis) with p-value less than 0.001 (dotted line on $-\mathrm{Log}_{10}$ P value=3 on Y-axis) are shown in the upper left region of the plot. Highlighted, as indicated, in the dataset are the results for GSPT1, GSPT2, IKZF3, CK1a, and IKZF1.
Figure 5:
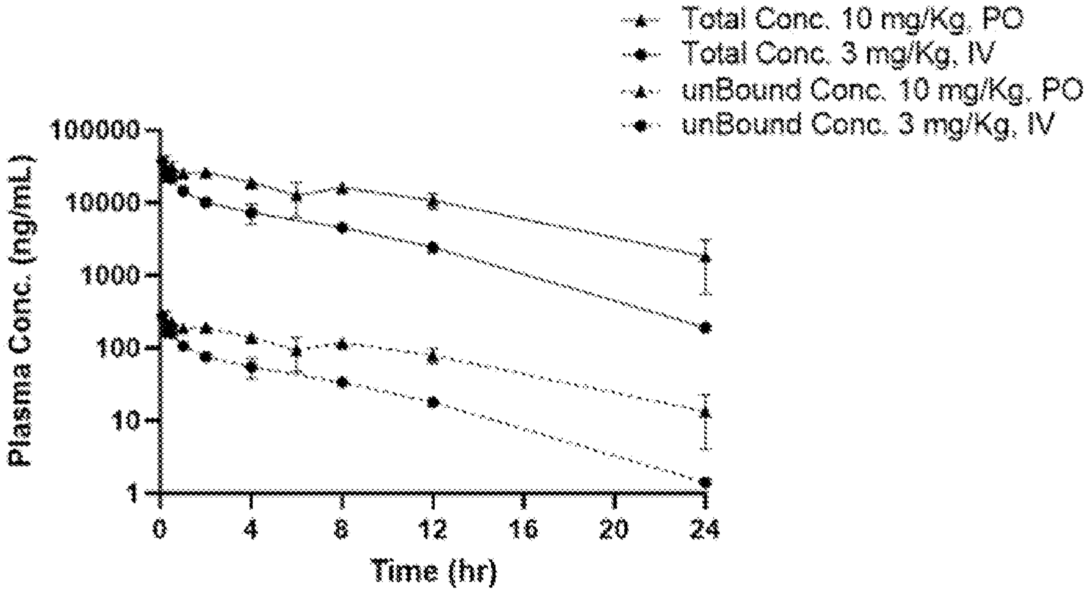
FIG. 5 shows representative pharmacokinetics data obtained using compound 1 in CD1 mice following a single intravenous (IV) and oral administration (PO) as indicated. Dose levels, as indicated, are: 3 mg/Kg IV, and 10 mg/Kg, PO. Formulation vehicle: 5% v/v NMP: 5% v/v Solute HS-15 and 90% v/v normal saline. The pharmacokinetic parameters obtained from this study are shown below the graph.

To explore the effects of compound 1 on cellular protein levels more broadly and evaluate its overall proteome-wide selectivity, multiplexed mass spectrometry-based proteomic analysis was performed in MV4-11 cells. Upon 24 hours of drug or DMSO treatment, proteins were extracted and digested into peptides. The resulting peptides were differentially labeled with tandem mass tags (TMT) isobaric reagents, equally pooled and analyzed by liquid chromatography and mass spectrometry (see Ref. 35), leading to the quantification of 8,427 unique proteins (FIG. 4). Compound 1 reduced abundance of only GSPT1 and GSPT2, confirming neosubstrate specificity in addition to establishing a broader selectivity profile for 1.

19. Results—Pharmacokinetics of a Representative Disclosed Compound

Figure 6:
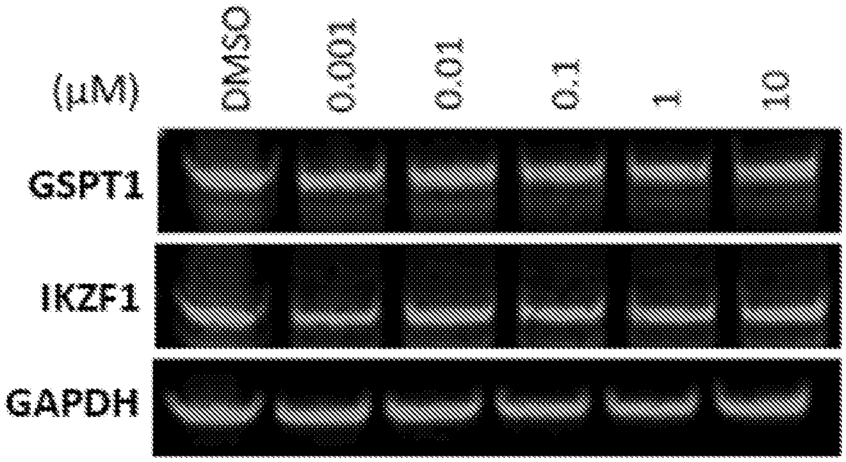
FIG. 6 shows representative Western blot data obtained using compound 2 on the levels of GSPT1 and IKZF1 in MV4-11 cells. The immunoblots are labeled to indicate the protein detected, i.e., GSPT1 and IKZF1 proteins versus GAPDH control. Each lane of the immunoblot is labelled to show the concentration of the given compound used to treat MV4-11 cells.

ADME data were obtained in-vitro for compound 1 to evaluate its suitability for in-vivo studies. Compound 1 was found stable in mouse and human liver microsomes (t112=4.7 and 5.7 hrs, respectively) with low intrinsic clearance ($Cl_{int}$=12 and 4 mL/min/kg). Plasma protein binding was high and measured to be 99.3% and 99.1% for mouse and human respectively. With its ADME profile established, we evaluated the pharmacokinetics of compound 1 in mice (FIG. 6). Upon dosing at 3 mg/kg IV, we observed low clearance (0.46 mL/min/kg), in agreement with the liver microsomes stability data. The terminal elimination half-life ($t_{1/2}$) was calculated to be 3.4 hrs and the volume of distribution was low at 0.15 L/kg, indicating minimal extravascular distribution with compound restriction mainly in the blood compartment. A single oral dose of compound 1 at 10 mg/kg gave peak plasma concentrations at 0.25 h, suggesting rapid absorption and the oral bioavailability was calculated to be 84% (FIG. 7). This PK profile warrants further exploration of compound 1 in animal disease models and supports the prospect of this novel chemical series of molecular glues.

20. Results—Cereblon Binding Activity of Disclosed Compounds

Cereblon binding activity was determined as described herein above, and the results are provided below in Table 3 for representative disclosed compounds. In Table 3 below, cereblon binding IC50 values are categorized as follows: "A" represents $IC_{50}$ value <1 uM; and "B" represents $IC_{50}$ value between 1 and 10 uM.

TABLE 3

Cereblon binding activity for representative compounds.

| Cmpd No.* | CRBN FP $IC_{50}$ |
|---|---|
| 1 | A |
| 2 | A |
| 3 | A |
| 4 | A |
| 5 | A |
| 6 | A |
| 7 | A |
| 8 | — |
| 9 | B |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | B |
| 22 | A |
| 23 | A |
| 24 | B |
| 25 | A |
| 26 | A |
| 27 | A |
| 28 | A |
| 29 | A |
| 30 | A |
| 31 | B |
| 32 | A |
| 33 | A |
| 34 | A |
| 35 | A |
| 36 | A |
| 37 | A |
| 38 | B |
| 39 | — |
| 40 | A |
| 41 | — |
| 42 | — |
| 43 | A |
| 44 | A |
| 45 | A |
| 46 | A |
| 47 | A |
| 48 | — |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | — |
| 70 | — |
| 71 | A |
| 72 | A |
| 73 | — |
| 74 | B |
| 75 | A |
| 76 | B |
| 77 | A |
| 78 | B |
| 79 | B |
| 80 | B |
| 81 | A |
| 82 | A |
| 83 | A |
| 84 | A |
| 85 | B |

TABLE 3-continued

Cereblon binding activity for representative compounds.

| Cmpd No.* | CRBN FP $IC_{50}$ |
|---|---|
| 86 | A |
| 87 | A |
| 88 | A |
| 89 | A |
| 90 | B |
| 91 | A |
| 92 | B |
| 93 | A |
| 94 | — |
| 95 | A |
| 96 | A |
| 97 | — |
| 98 | A |
| 99 | A |
| 100 | A |
| 101 | — |
| 102 | — |
| 103 | — |

21. Results—GSPT1 Activity of Disclosed Compounds

GSPT1 activity was determined using the assay described herein below and the results are provided below in Table 4 for representative disclosed compounds. In Table 4 below, cereblon binding $EC_{50}$ values are categorized as follows: "A" represents $EC_{50}$ value <1 μM; "B" represents $EC_{50}$ value between 1 and 10 μM; and "C" represents $EC_{50}$ value of >10 μM.

TABLE 4

GSPT1 activity for representative compounds.

| Cmpd No.* | GSPT1 HiBit $EC_{50}$ |
|---|---|
| 1 | A |
| 2 | C |
| 4 | C |
| 5 | A |
| 7 | C |
| 8 | C |
| 9 | C |
| 10 | C |
| 12 | C |
| 15 | B |
| 16 | C |
| 17 | C |
| 18 | C |
| 20 | C |
| 21 | C |
| 38 | C |
| 43 | A |
| 44 | C |
| 46 | A |
| 63 | C |
| 67 | C |
| 70 | C |

TABLE 4-continued

GSPT1 activity for representative compounds.

| Cmpd No.* | GSPT1 HiBit $EC_{50}$ |
|---|---|
| 71 | C |
| 72 | C |
| 75 | C |
| 76 | C |
| 77 | A |
| 78 | C |
| 81 | C |
| 82 | C |
| 83 | C |
| 87 | C |
| 89 | C |
| 90 | C |
| 92 | C |
| 95 | C |
| 96 | C |
| 98 | A |
| 99 | A |
| 100 | C |

hGSPT1 HiBiT cell line. HEK293_hGSPT1_HiBiT tagged cells were generated using CRISPR-Cas12a technology. Briefly, ~400,000 HEK293 cells were transiently co-transfecting with precomplexed ribonuclear proteins (RNPs) consisting of 80 pmol of crRNA (IDT), 62 pmol of Cas12a protein (IDT), 3 ug of ssODN donor (IDT; AltR™ modifications), 78 pmol of electroporation enhancer (IDT), and 200 ng of pMaxGFP(Lonza). The transfection was performed via nucleofection (Lonza, 4D-Nucleofector™ X-unit) using solution P3 and program CM-130 in a small (20 ul) cuvette according to the manufacturer's recommended protocol. Five days post-nucleofection, cells were single cell sorted for GFP+(transfected) cells by FACs in 96-well plates and clonally selected. Clones were screened and verified for the desired modification via targeted deep sequencing using gene specific primers with partial Illumina adapter overhangs as previously described.[58] In brief, clonal cell pellets were harvested, lysed and used to generate gene specific amplicons with partial Illumina adapters in PCR #1. Amplicons were indexed in PCR #2 and pooled with other targeted amplicons for other loci to create sequence diversity. Additionally, 10% PhiX Sequencing Control V3 (Illumina) was added to the pooled amplicon library prior to running the sample on an Miseq Sequencer System (Illumina) to generate paired 2×250 bp reads. Samples were demultiplexed using the index sequences, fastq files were generated, and NGS analysis was performed using CRIS.py.[59] Final clones were authenticated using the PowerPlex® Fusion System (Promega) performed at the Hartwell Center (St. Jude) and tested negative for mycoplasma by the MycoAlert™Plus Mycoplasma Detection Kit (Lonza). Editing construct sequences and screening primers are listed below in Table 4.

TABLE 4

| Name | Sequence (5' to 3') |
|---|---|
| hGSPT Cas12a crRNA (CAGE635.GSPT1.g1) | TTTCTCTGGAACCAGTTTCAGAACT |
| CAGE635.g1.anti.ssODN HiBiT tag and silent blocking modifications to prevent Cas12a recutting after integration are in upper case. *Alt-R modifications (IDT) | *ttcctcacagtattgtgcagggtcatcaagaaaatgcttaGCTAATCTTCTT GAACAGCCGCCAGCCGCTCACgtcCttctctggaaccagtttcaga acttttccaattgcaatggtcttacctagaaatgaaattttaa |
| CAGE635.hGSPT1.DS.F (NGS overhangs not shown) | GGTTTGGCAGTAAAGCTAGTTAAT |
| CAGE635.hGSPT1.DS.R (NGS overhangs not shown) | GTGAAGTAGGCTTCTGCAGTC |

hGSPT1 HiBiT assay. HEK293 hGSPT1 HiBiT tag cells were seeded in white 384-well assay plates at density of 800 cells per well in triplicates. After overnight incubation, cells were treated with compounds in dose-response format using a Pintool on a Biomek FXP Laboratory Automation Work-station (Beckman Coulter). After 4 hrs incubation, the level of GSPT1 HiBiT tag protein was evaluated using Nano-Glo® HiBiT Lytic Detection System (Promega) according to the manufacturer's instruction. Luminescence signal was measured using an Envision plate reader (Perkin-Elmer).

Table 2 follows herein below in landscape format.

It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

TABLE 2

Yield, Purity, and MS Data for Exemplary Disclosed Compounds.

| Cmpd No.* | Structure | Yield** (mgs) | Yield (%) | Purity (%) | M + 1 | Ret. Time | Mol. Wt. |
|---|---|---|---|---|---|---|---|
| 1 | 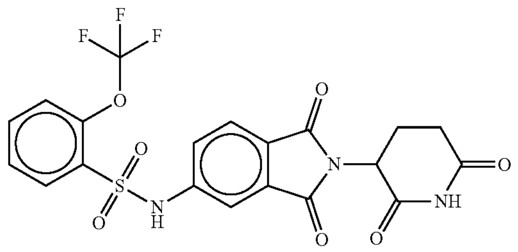 | 34 | 68.4 | >95 | 498.1 | 0.71 | 497.4 |
| 2 | 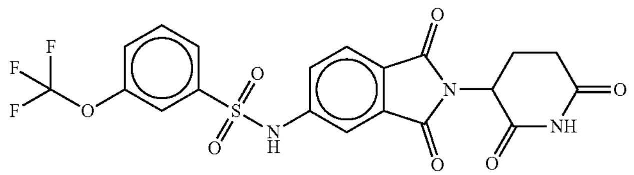 | 15.7 | 31.6 | >95 | 498.1 | 0.77 | 497.4 |
| 3 | 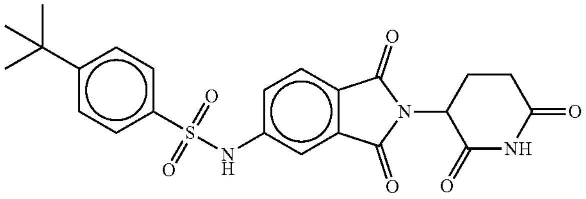 | 30.4 | 64.7 | >95 | 470.1 | 0.85 | 469.5 |

TABLE 2-continued
| Yield, Purity, and MS Data for Exemplary Disclosed Compounds. | | | | | | | |
|---|---|---|---|---|---|---|---|
| 4 | 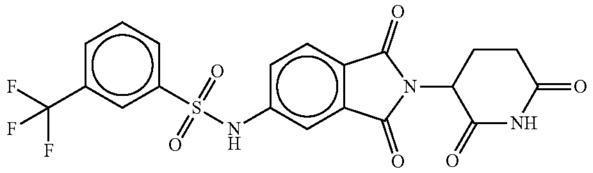 | 28.4 | 59 | >95 | 482.1 | 0.73 | 481.4 |
| 5 | 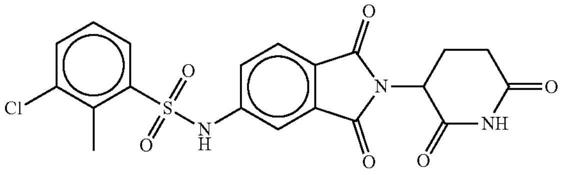 | 25.7 | 55.6 | >95 | 462.0 | 0.74 | 461.9 |
| 6 | 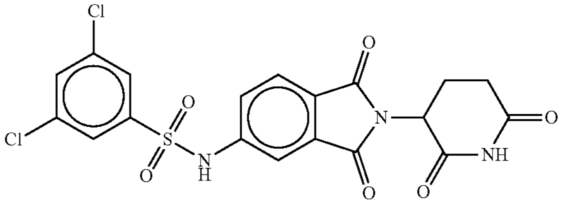 | 24.9 | 51.6 | >95 | 482.0 | 0.8 | 482.3 |
| 7 | 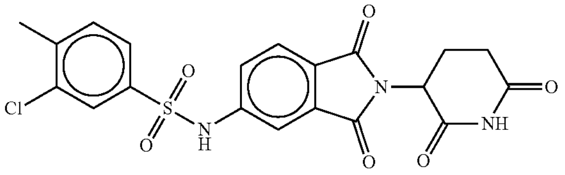 | 28.5 | 61.7 | >95 | 462.0 | 0.75 | 461.9 |
| 8 | 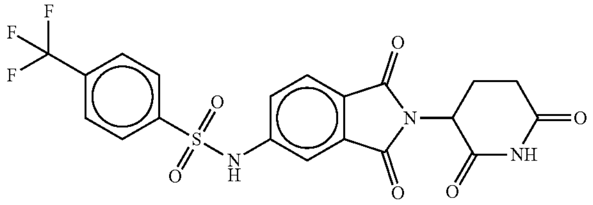 | 29.8 | 61.9 | >95 | 482.1 | 1.82 | 481.4 |
| 9 | 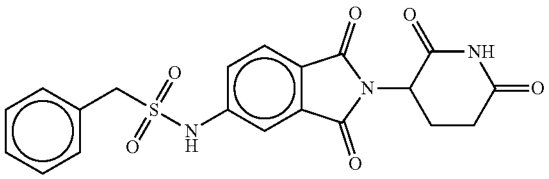 | 4.4 | 10.3 | >95 | 428.1 | 0.57 | 427.4 |
| 10 | 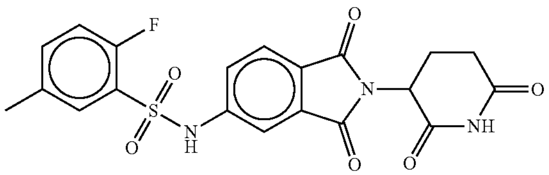 | 21 | 47.1 | >95 | 446.1 | 0.64 | 445.4 |
| 11 | 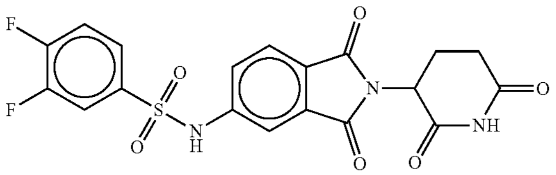 | 24 | 53.4 | >95 | 450.0 | 0.65 | 449.4 |

TABLE 2-continued
Yield, Purity, and MS Data for Exemplary Disclosed Compounds.
| | | | | | | | |
|---|---|---|---|---|---|---|---|
| 12 | 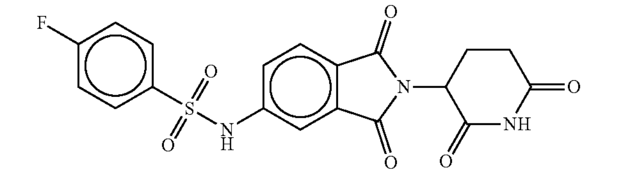 | 21.1 | 48.9 | >95 | 432.1 | 0.6 | 431.4 |
| 13 | 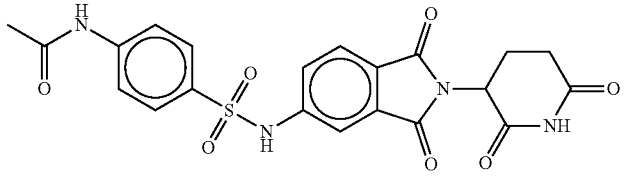 | 22 | 46.8 | >95 | 471.1 | 0.48 | 470.5 |
| 14 | 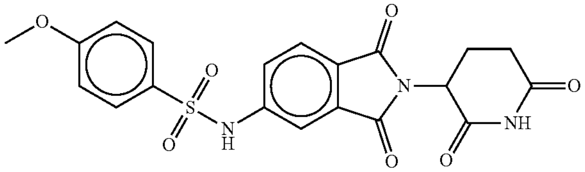 | 12.4 | 28 | >95 | 444.1 | 0.6 | 443.4 |
| 15 | 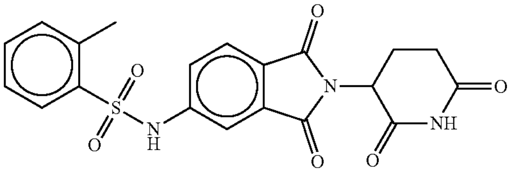 | 9.9 | 23.2 | >95 | 428.1 | 0.62 | 427.4 |
| 16 | 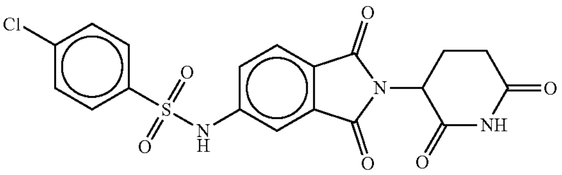 | 7.6 | 16.9 | >95 | 448.0 | 0.68 | 447.8 |
| 17 | 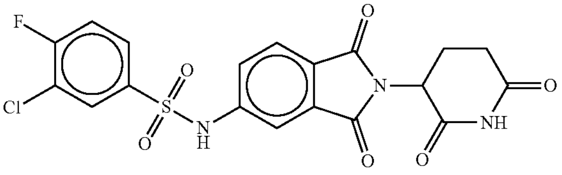 | 22.4 | 48.1 | >95 | 466.0 | 0.69 | 465.8 |
| 18 | 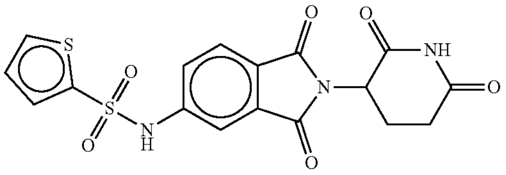 | 8.1 | 19.3 | >95 | 420.0 | 0.55 | 419.4 |
| 19 | 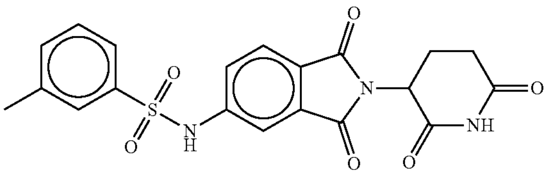 | 24.4 | 57.1 | >95 | 428.1 | 0.64 | 427.4 |

TABLE 2-continued
Yield, Purity, and MS Data for Exemplary Disclosed Compounds.
| | | | | | | | |
|---|---|---|---|---|---|---|---|
| 20 | 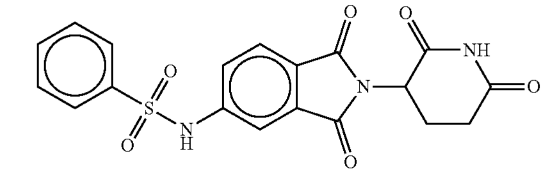 | 25.4 | 61.4 | >95 | 414.1 | 0.57 | 413.4 |
| 21 | 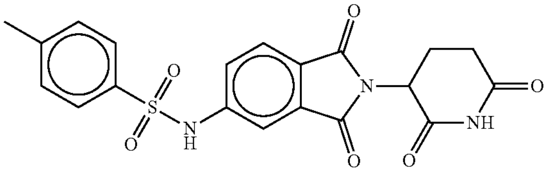 | 8.3 | 19.4 | >95 | 428.1 | 0.64 | 427.4 |
| 22 | 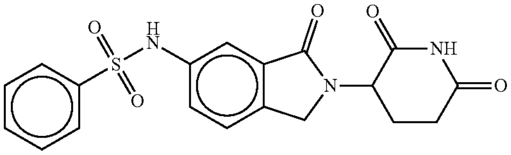 | 6.9 | 23 | >95 | 400.1 | 0.53 | 399.4 |
| 23 | 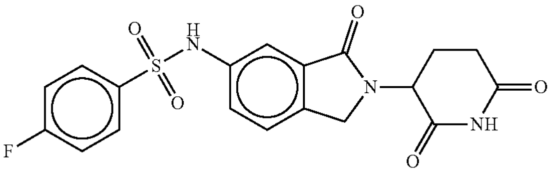 | 7.3 | 23.3 | >95 | 418.1 | 0.55 | 417.4 |
| 24 | 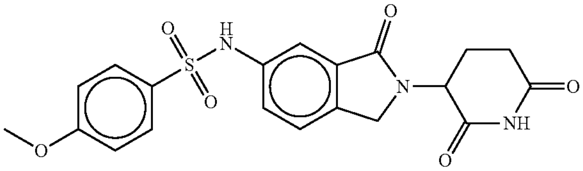 | 11.1 | 34.5 | >95 | 430.1 | 0.55 | 429.4 |
| 25 | 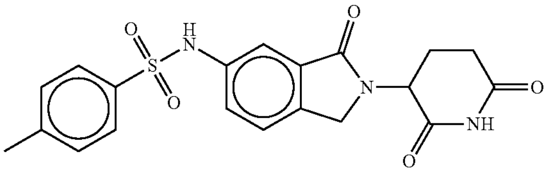 | 6.2 | 19.9 | >95 | 414.1 | 0.59 | 413.4 |
| 26 | 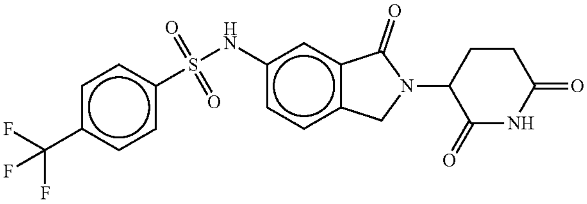 | 10.9 | 31.1 | >95 | 468.1 | 0.69 | 467.4 |
| 27 | 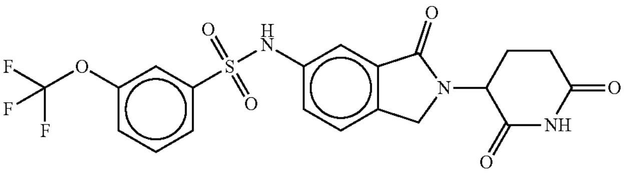 | 10.8 | 29.8 | >95 | 484.1 | 0.69 | 483.4 |

TABLE 2-continued
| Yield, Purity, and MS Data for Exemplary Disclosed Compounds. | | | | | | | |
|---|---|---|---|---|---|---|---|
| 28 | 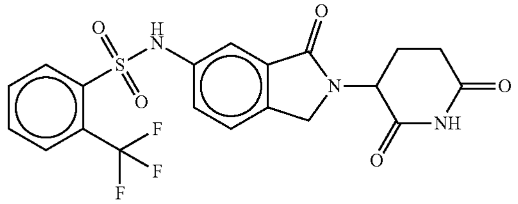 | 15.8 | 45.1 | >95 | 468.1 | 0.63 | 467.4 |
| 29 | 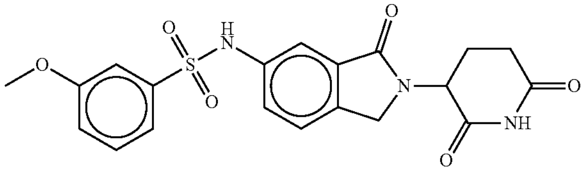 | 17.4 | 54 | >95 | 430.1 | 0.56 | 429.4 |
| 30 | 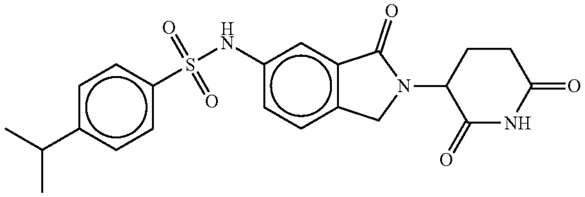 | 6.8 | 20.5 | >95 | 442.1 | 0.71 | 441.5 |
| 31 | 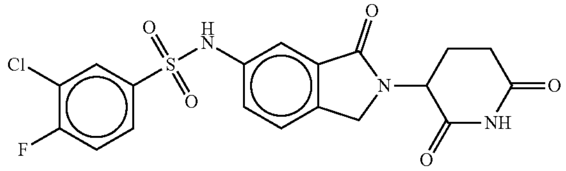 | 16.2 | 47.8 | >95 | 452.0 | 0.65 | 451.9 |
| 32 | 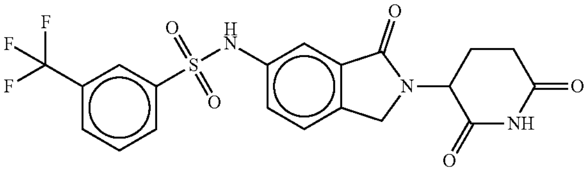 | 8.3 | 23.7 | >95 | 468.1 | 0.67 | 467.4 |
| 33 | 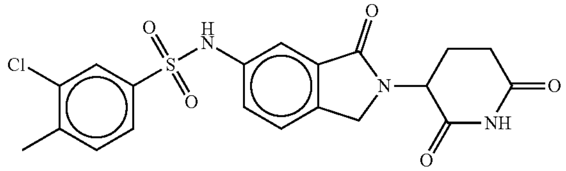 | 9.7 | 28.9 | >95 | 448.1 | 0.69 | 447.9 |
| 34 | 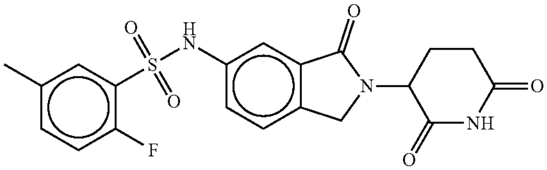 | 20.4 | 63 | >95 | 432.1 | 0.59 | 431.4 |
| 35 | 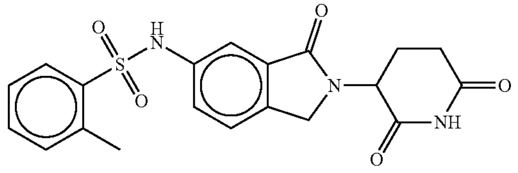 | 13.2 | 42.6 | >95 | 414.1 | 0.57 | 413.4 |

TABLE 2-continued
Yield, Purity, and MS Data for Exemplary Disclosed Compounds.
| | | | | | | | |
|---|---|---|---|---|---|---|---|
| 36 | 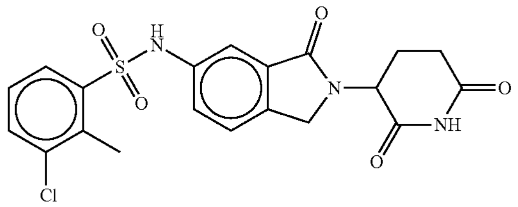 | 8.5 | 25.3 | >95 | 448.1 | 0.69 | 447.9 |
| 37 | 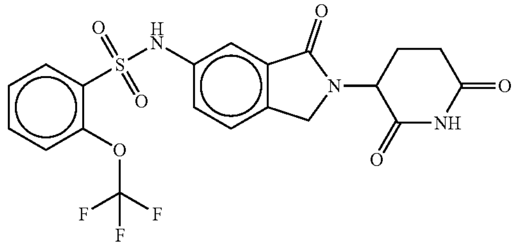 | 5.2 | 14.3 | >95 | 484.1 | 0.65 | 483.4 |
| 38 | 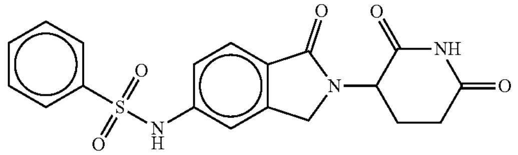 | 7.4 | 24.7 | >95 | 400.1 | 0.52 | 399.4 |
| 39 | 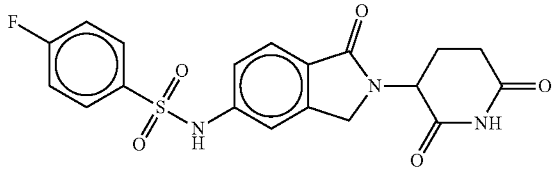 | 9.2 | 29.4 | >95 | 418.1 | 0.55 | 417.4 |
| 40 | 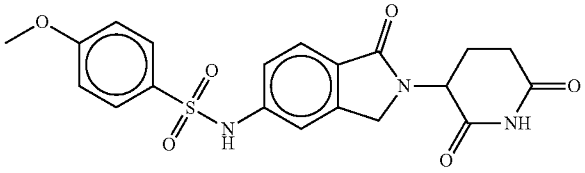 | 9.6 | 29.8 | >95 | 430.1 | 0.54 | 429.4 |
| 41 | 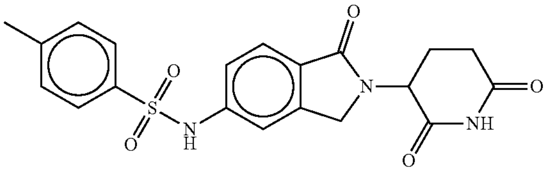 | 4.9 | 15.8 | >95 | 414.1 | 0.58 | 413.4 |
| 42 | 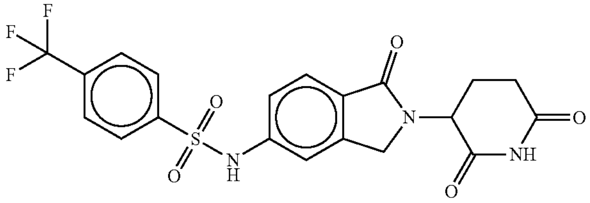 | 14.6 | 41.6 | >95 | 468.1 | 0.68 | 467.4 |
| 43 | 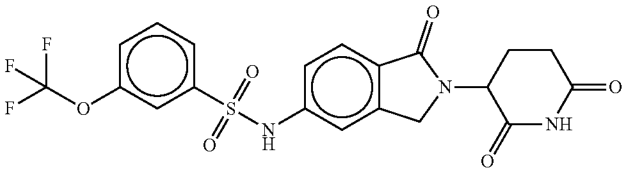 | 19.1 | 52.7 | >95 | 484.1 | 0.7 | 483.4 |

TABLE 2-continued
| Yield, Purity, and MS Data for Exemplary Disclosed Compounds. | | | | | | | |
|---|---|---|---|---|---|---|---|
| 44 | 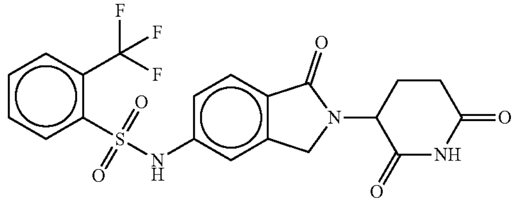 | 10.8 | 30.8 | >95 | 468.1 | 0.61 | 467.4 |
| 45 | 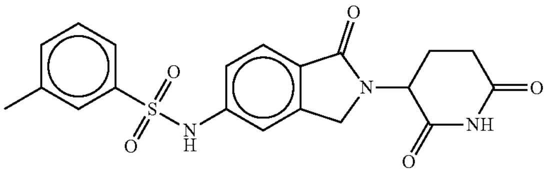 | 11.2 | 36.1 | >95 | 414.1 | 0.58 | 413.4 |
| 46 | 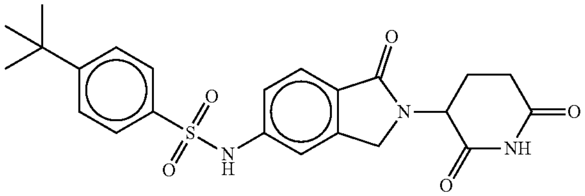 | 9.1 | 26.6 | >95 | 456.2 | 0.77 | 455.5 |
| 47 | 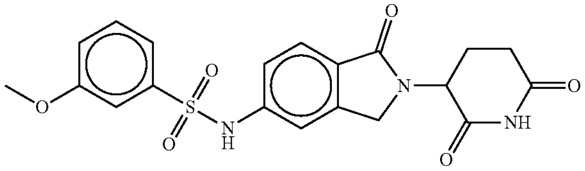 | 12.9 | 40.1 | >95 | 430.1 | 0.55 | 429.4 |
| 48 | 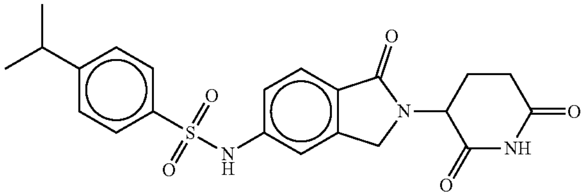 | 7.3 | 22.1 | >95 | 442.1 | 0.7 | 441.5 |
| 49 | 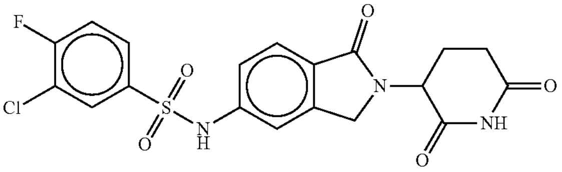 | 12.7 | 37.5 | >95 | 452.0 | 0.65 | 451.9 |
| 50 | 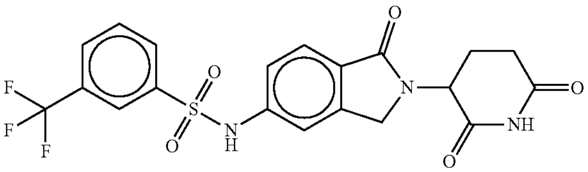 | 7.9 | 22.5 | >95 | 468.1 | 0.67 | 467.4 |
| 51 | 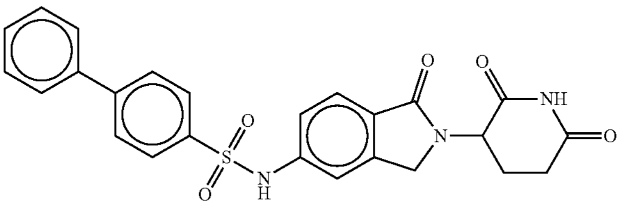 | 10.3 | 28.9 | >95 | 476.1 | 0.76 | 475.5 |

TABLE 2-continued
Yield, Purity, and MS Data for Exemplary Disclosed Compounds.
| | | | | | | | |
|---|---|---|---|---|---|---|---|
| 52 | 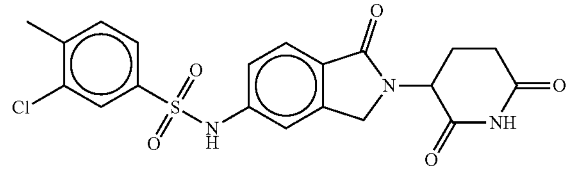 | 4.8 | 14.3 | >95 | 448.1 | 0.68 | 447.9 |
| 53 | 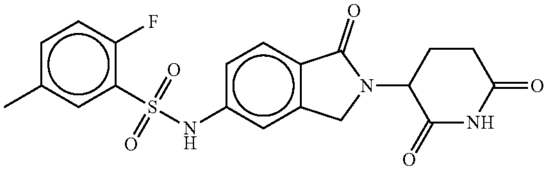 | 7.7 | 23.8 | >95 | 432.1 | 0.59 | 431.4 |
| 54 | 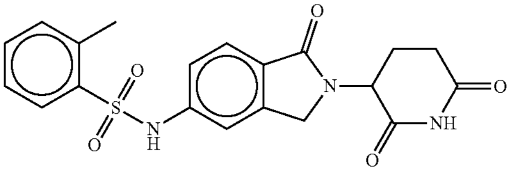 | 8.9 | 28.7 | >95 | 414.1 | 0.56 | 413.4 |
| 55 | 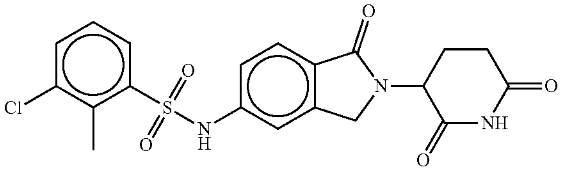 | 11.6 | 34.5 | >95 | 448.1 | 0.68 | 447.9 |
| 56 | 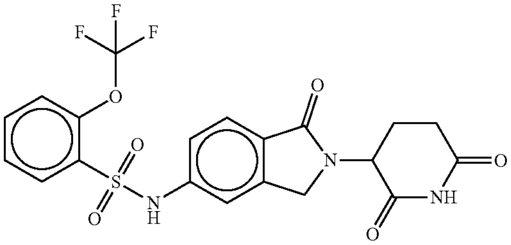 | 14.9 | 41.1 | >95 | 484.1 | 0.65 | 483.4 |
| 57 | 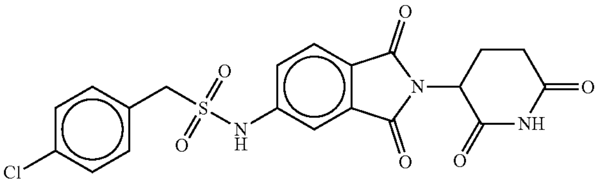 | 4.2 | 12.1 | >95 | 462.0 | 0.65 | 461.9 |
| 58 | 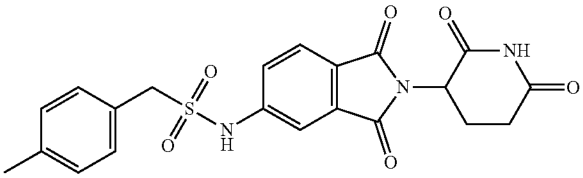 [SMILES: Cc1ccc(CS(=O)(=O)Nc2ccc3c(c2)C(=O)N(C2CCC(=O)NC2=O)C3=O)cc1] | 3.9 | 11.8 | 80-85 | 442.1 | 0.63 | 441.5 |
| 59 | 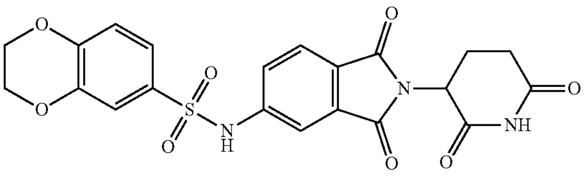 [SMILES: O=C1CCC(N2C(=O)c3ccc(NS(=O)(=O)c4ccc5c(c4)OCCO5)cc3C2=O)C(=O)N1] | 2.4 | 6.8 | >95 | 472.1 | 0.56 | 471.4 |

TABLE 2-continued
Yield, Purity, and MS Data for Exemplary Disclosed Compounds.
| | | | | | | | |
|---|---|---|---|---|---|---|---|
| 60 | 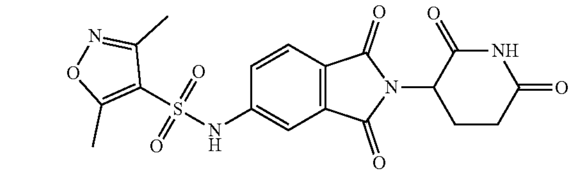 [SMILES: Cc1noc(C)c1S(=O)(=O)Nc1ccc2c(c1)C(=O)N(C1CCC(=O)NC1=O)C2=O] | 3.1 | 9.6 | 80-85 | 433.1 | 0.53 | 432.4 |
| 61 | 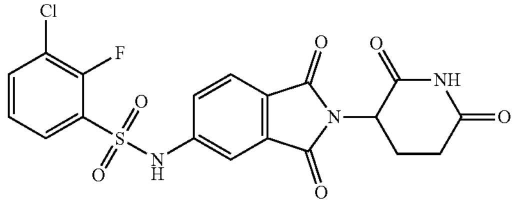 [SMILES: O=C1CCC(N2C(=O)c3ccc(NS(=O)(=O)c4cccc(Cl)c4F)cc3C2=O)C(=O)N1] | 4.2 | 12 | >95 | 466.0 | 0.65 | 465.8 |
| 62 | 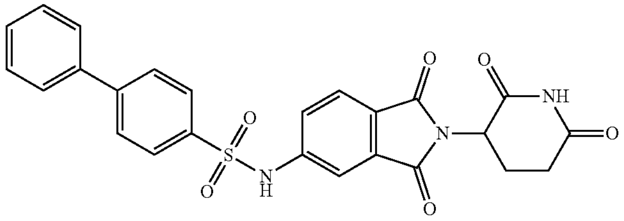 [SMILES: O=C1CCC(N2C(=O)c3ccc(NS(=O)(=O)c4ccc(-c5ccccc5)cc4)cc3C2=O)C(=O)N1] | 3.8 | 10.4 | >95 | 490.1 | 0.81 | 489.5 |
| 63 | 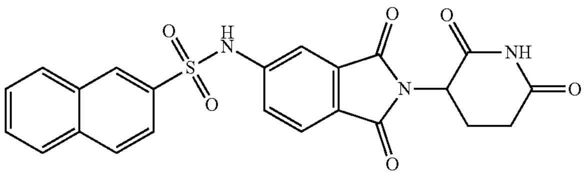 [SMILES: O=C1CCC(N2C(=O)c3ccc(NS(=O)(=O)c4ccc5ccccc5c4)cc3C2=O)C(=O)N1] | 3.6 | 10.4 | >95 | 464.1 | 0.71 | 463.5 |
| 64 | 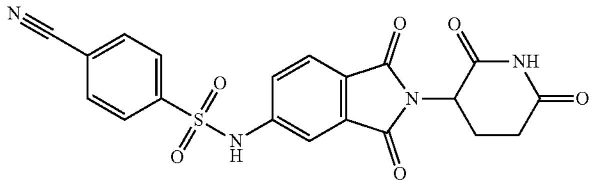 [SMILES: N#Cc1ccc(S(=O)(=O)Nc2ccc3c(c2)C(=O)N(C2CCC(=O)NC2=O)C3=O)cc1] | 3.4 | 10.3 | 90-95 | 439.1 | 0.54 | 438.4 |
| 65 | 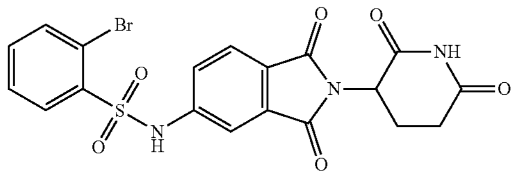 [SMILES: O=C1CCC(N2C(=O)c3ccc(NS(=O)(=O)c4ccccc4Br)cc3C2=O)C(=O)N1] | 6.1 | 16.5 | 85-90 | 492.0 | 0.6 | 492.3 |
| 66 | 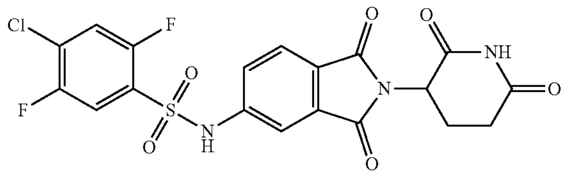 [SMILES: O=C1CCC(N2C(=O)c3ccc(NS(=O)(=O)c4cc(F)c(Cl)cc4F)cc3C2=O)C(=O)N1] | 4.5 | 12.4 | 90-95 | 484.0 | 0.71 | 483.8 |
| 67 | 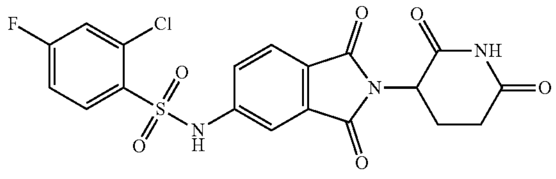 [SMILES: O=C1CCC(N2C(=O)c3ccc(NS(=O)(=O)c4ccc(F)cc4Cl)cc3C2=O)C(=O)N1] | 3.8 | 10.9 | 90-95 | 466.0 | 0.63 | 465.8 |

TABLE 2-continued
Yield, Purity, and MS Data for Exemplary Disclosed Compounds.
| | | | | | | | |
|---|---|---|---|---|---|---|---|
| 68 | 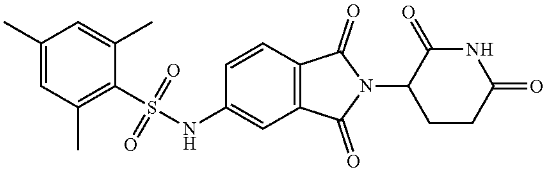 [SMILES: Cc1cc(C)c(S(=O)(=O)Nc2ccc3c(c2)C(=O)N(C2CCC(=O)NC2=O)C3=O)c(C)c1] | 5 | 14.6 | >95 | 456.1 | 0.76 | 455.5 |
| 69 | 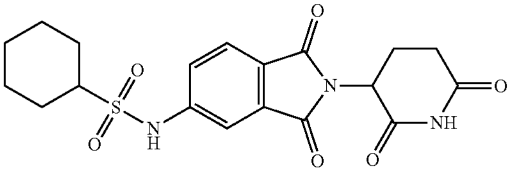 [SMILES: O=C1CCC(N2C(=O)c3ccc(NS(=O)(=O)C4CCCCC4)cc3C2=O)C(=O)N1] | 0.6 | 1.9 | 90-95 | 420.1 | 0.62 | 419.5 |
| 70 | 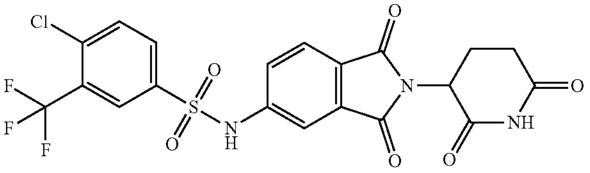 [SMILES: O=C1CCC(N2C(=O)c3ccc(NS(=O)(=O)c4ccc(Cl)c(C(F)(F)F)c4)cc3C2=O)C(=O)N1] | 17.6 | 45.5 | >95 | 516.0 | 0.82 | 515.8 |
| 71 | 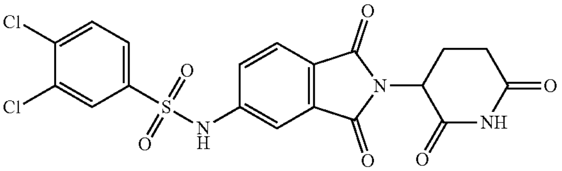 [SMILES: O=C1CCC(N2C(=O)c3ccc(NS(=O)(=O)c4ccc(Cl)c(Cl)c4)cc3C2=O)C(=O)N1] | 18.9 | 52.3 | >95 | 482.0 | 0.77 | 482.3 |
| 72 | 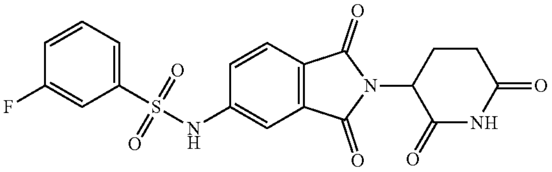 [SMILES: O=C1CCC(N2C(=O)c3ccc(NS(=O)(=O)c4cccc(F)c4)cc3C2=O)C(=O)N1] | 7.3 | 22.6 | >95 | 432.1 | 0.59 | 431.4 |
| 73 | 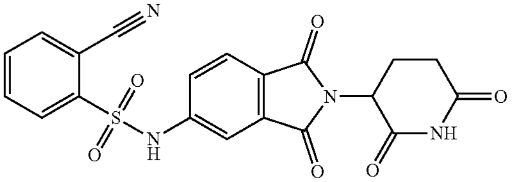 [SMILES: N#Cc1ccccc1S(=O)(=O)Nc1ccc2c(c1)C(=O)N(C1CCC(=O)NC1=O)C2=O] | 5.4 | 16.4 | 80-85 | 439.1 | 0.49 | 438.4 |
| 74 | 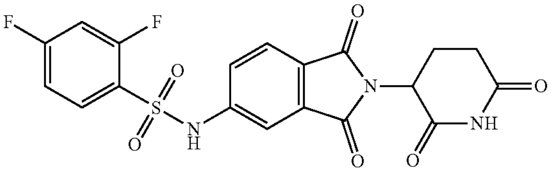 [SMILES: O=C1CCC(N2C(=O)c3ccc(NS(=O)(=O)c4ccc(F)cc4F)cc3C2=O)C(=O)N1] | 12.3 | 36.5 | >95 | 450.0 | 0.59 | 449.4 |
| 75 | 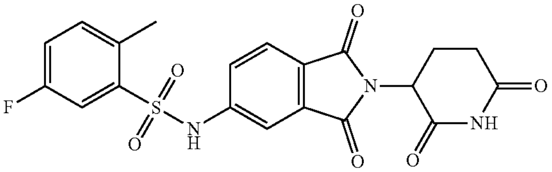 [SMILES: Cc1ccc(F)cc1S(=O)(=O)Nc1ccc2c(c1)C(=O)N(C1CCC(=O)NC1=O)C2=O] | 24.3 | 72.7 | >95 | 446.1 | 0.65 | 445.4 |

TABLE 2-continued
Yield, Purity, and MS Data for Exemplary Disclosed Compounds.
| | | | | | | | |
|---|---|---|---|---|---|---|---|
| 76 | 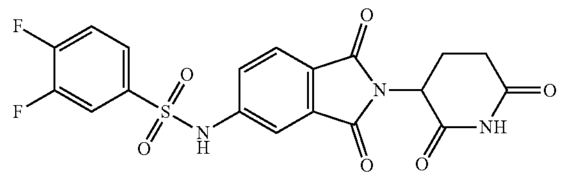 [SMILES: O=C1CCC(N2C(=O)c3ccc(NS(=O)(=O)c4ccc(F)c(F)c4)cc3C2=O)C(=O)N1] | 15.4 | 45.7 | >95 | 450.0 | 0.63 | 449.4 |
| 77 | 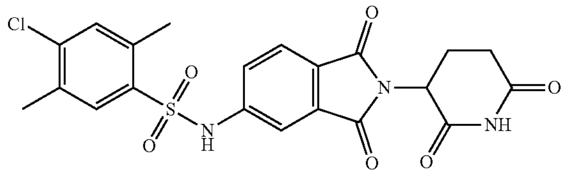 [SMILES: Cc1cc(S(=O)(=O)Nc2ccc3c(c2)C(=O)N(C2CCC(=O)NC2=O)C3=O)c(C)cc1Cl] | 24.7 | 69.2 | >95 | 476.1 | 0.83 | 475.9 |
| 78 | 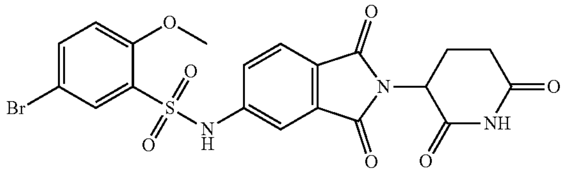 [SMILES: COc1ccc(Br)cc1S(=O)(=O)Nc1ccc2c(c1)C(=O)N(C1CCC(=O)NC1=O)C2=O] | 2.7 | 6.9 | >95 | 522.0 | 0.69 | 522.3 |
| 79 | 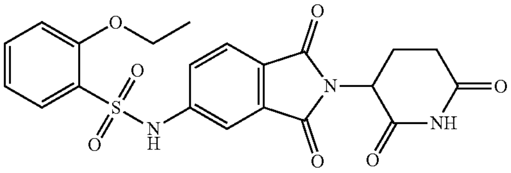 [SMILES: CCOc1ccccc1S(=O)(=O)Nc1ccc2c(c1)C(=O)N(C1CCC(=O)NC1=O)C2=O] | 4.6 | 13.4 | >95 | 458.1 | 0.61 | 457.5 |
| 80 | 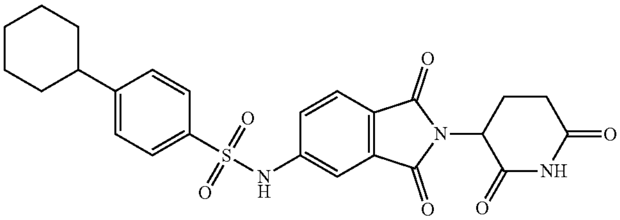 [SMILES: O=C1CCC(N2C(=O)c3ccc(NS(=O)(=O)c4ccc(C5CCCCC5)cc4)cc3C2=O)C(=O)N1] | 20.3 | 54.6 | >95 | 496.1 | 0.99 | 495.6 |
| 81 | 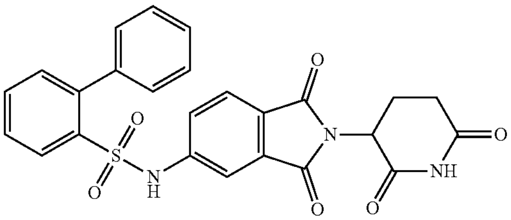 [SMILES: O=C1CCC(N2C(=O)c3ccc(NS(=O)(=O)c4ccccc4-c4ccccc4)cc3C2=O)C(=O)N1] | 8 | 21.8 | 90-95 | 490.1 | 0.77 | 489.5 |
| 82 | 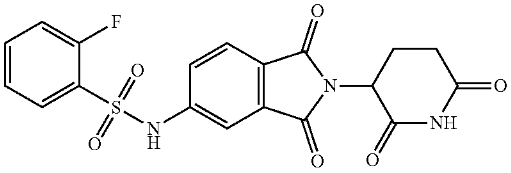 [SMILES: O=C1CCC(N2C(=O)c3ccc(NS(=O)(=O)c4ccccc4F)cc3C2=O)C(=O)N1] | 16.6 | 51.3 | >95 | 432.1 | 0.55 | 431.4 |
| 83 | 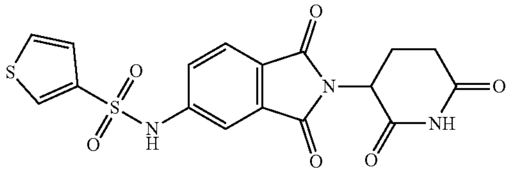 [SMILES: O=C1CCC(N2C(=O)c3ccc(NS(=O)(=O)c4ccsc4)cc3C2=O)C(=O)N1] | 6.4 | 20.4 | >95 | 420.0 | 0.51 | 419.4 |

TABLE 2-continued
Yield, Purity, and MS Data for Exemplary Disclosed Compounds.
| | | | | | | | |
|---|---|---|---|---|---|---|---|
| 84 | 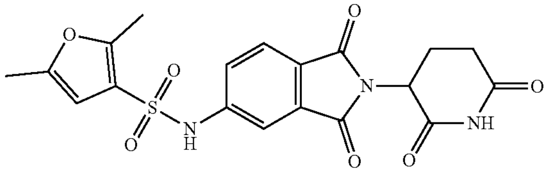 [SMILES: Cc1cc(S(=O)(=O)Nc2ccc3c(c2)C(=O)N(C2CCC(=O)NC2=O)C3=O)c(C)o1] | 18.1 | 55.9 | >95 | 432.1 | 0.61 | 431.4 |
| 85 | 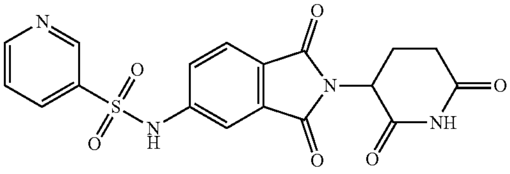 [SMILES: O=C1CCC(N2C(=O)c3ccc(NS(=O)(=O)c4cccnc4)cc3C2=O)C(=O)N1] | 9 | 29 | >95 | 415.1 | 0.43 | 414.4 |
| 86 | 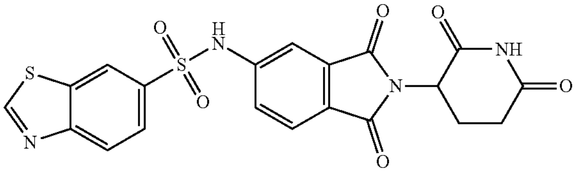 [SMILES: O=C1CCC(N2C(=O)c3ccc(NS(=O)(=O)c4ccc5ncsc5c4)cc3C2=O)C(=O)N1] | 9 | 25.5 | >95 | 471.0 | 0.51 | 470.5 |
| 87 | 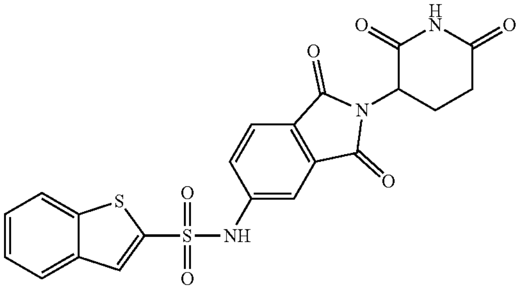 [SMILES: O=C1CCC(N2C(=O)c3ccc(NS(=O)(=O)c4cc5ccccc5s4)cc3C2=O)C(=O)N1] | 14.8 | 42 | >95 | 470.0 | 0.72 | 469.5 |
| 88 | 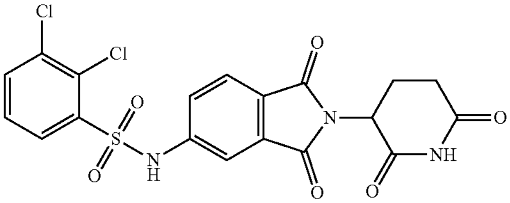 [SMILES: O=C1CCC(N2C(=O)c3ccc(NS(=O)(=O)c4cccc(Cl)c4Cl)cc3C2=O)C(=O)N1] | 16.6 | 45.9 | >95 | 482.0 | 0.69 | 482.3 |
| 89 | 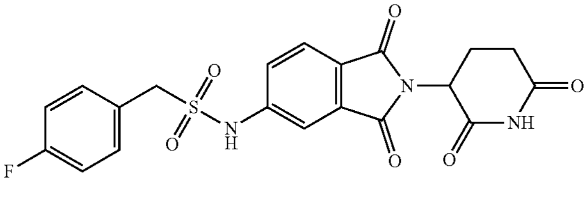 [SMILES: O=C1CCC(N2C(=O)c3ccc(NS(=O)(=O)Cc4ccc(F)cc4)cc3C2=O)C(=O)N1] | 5 | 14.9 | 90-95 | 446.1 | 0.58 | 445.4 |
| 90 | 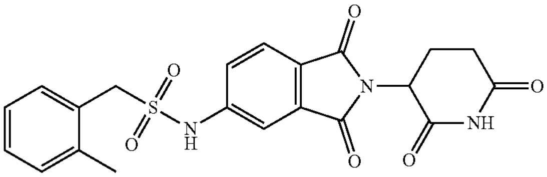 [SMILES: Cc1ccccc1CS(=O)(=O)Nc1ccc2c(c1)C(=O)N(C1CCC(=O)NC1=O)C2=O] | 11.5 | 34.7 | >95 | 442.1 | 0.62 | 441.5 |

TABLE 2-continued
Yield, Purity, and MS Data for Exemplary Disclosed Compounds.
| | | | | | | | |
|---|---|---|---|---|---|---|---|
| 91 | 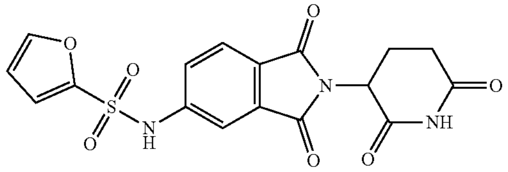 [SMILES: O=C1CCC(N2C(=O)c3ccc(NS(=O)(=O)c4ccco4)cc3C2=O)C(=O)N1] | 15.4 | 50.9 | >95 | 404.0 | 0.48 | 403.4 |
| 92 | 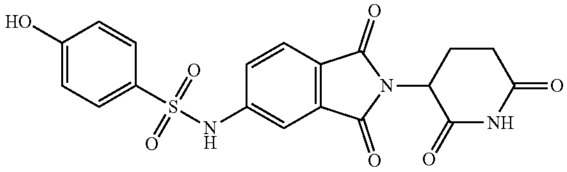 [SMILES: O=C1CCC(N2C(=O)c3ccc(NS(=O)(=O)c4ccc(O)cc4)cc3C2=O)C(=O)N1] | 9.5 | 29.5 | 90-95 | 430.1 | 0.45 | 429.4 |
| 93 | 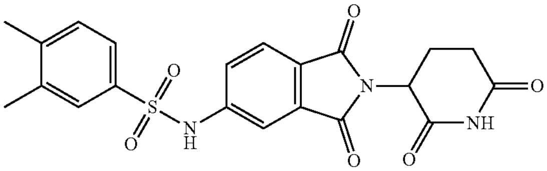 [SMILES: Cc1ccc(S(=O)(=O)Nc2ccc3c(c2)C(=O)N(C2CCC(=O)NC2=O)C3=O)cc1C] | 19.8 | 59.8 | >95 | 442.1 | 0.68 | 441.5 |
| 94 | 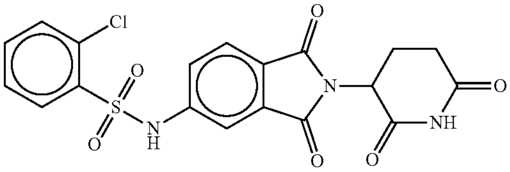 | 13.2 | 40.3 | >95 | 448.5 | 0.62 | 447.8 |
| 95 | 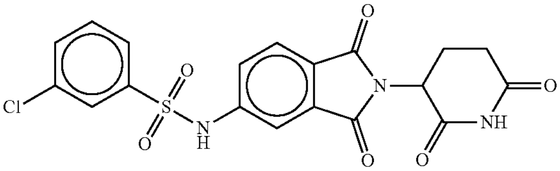 | 9.0 | 27.5 | >95 | 448.4 | 0.69 | 447.8 |
| 96 | 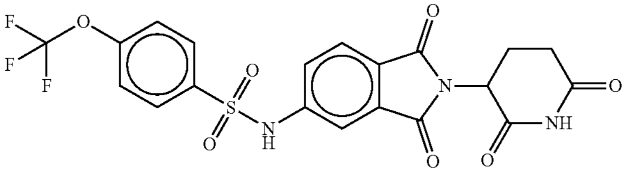 | 4.5 | 12.4 | >95 | 498.6 | 0.78 | 497.4 |
| 97 | 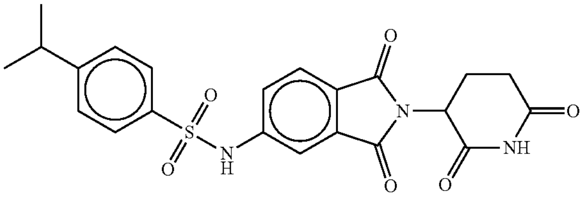 | 7 | 16.8 | >95 | 456.7 | 0.8 | 455.5 |
| 98 | 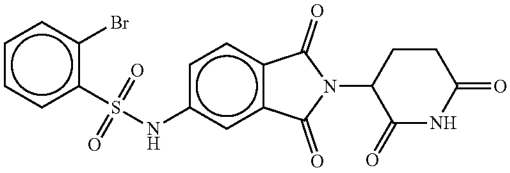 | 4 | 8.9 | >95 | 494.5 | 0.63 | 492.3 |

TABLE 2-continued

Yield, Purity, and MS Data for Exemplary Disclosed Compounds.

| | | | | | | | |
|---|---|---|---|---|---|---|---|
| 99 | 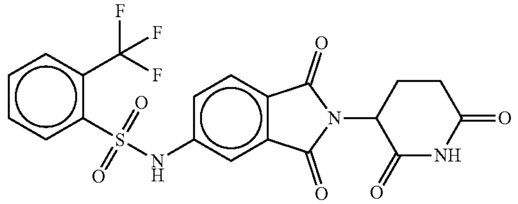 | 13 | 29.5 | >95 | 482.5 | 0.68 | 481.4 |
| 100 | 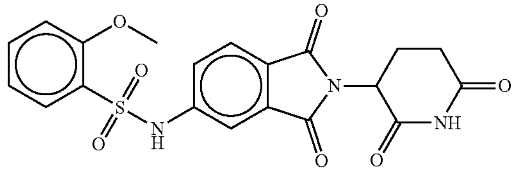 | 17 | 41.9 | >95 | 444.4 | 0.57 | 443.4 |
| 101 | 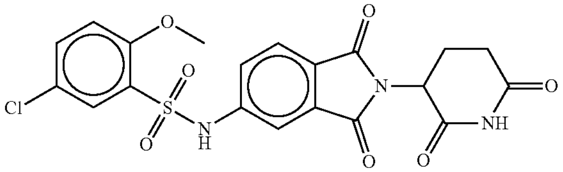 | 0.7 | 1.6 | >95 | 479.5 | 0.69 | 477.9 |
| 102 | 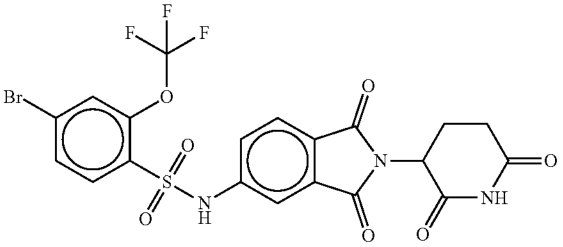 | 6.4 | 12.1 | >95 | 577.2 | 0.85 | 576.3 |
| 103 | 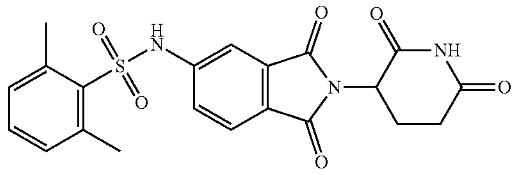 [SMILES: Cc1cccc(C)c1S(=O)(=O)Nc1ccc2c(c1)C(=O)N(C1CCC(=O)NC1=O)C2=O] | 19.8 | 61.3 | >95 | 442.3 | 0.70 | 441.5 |

| Cmpd No.* | Structure | IUPAC Name‡ | SMILES‡ |
|---|---|---|---|
| 1 | 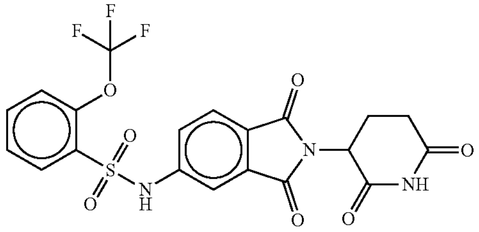 | N-(2-(2,6-dioxo-piperidin-3-yl)-1,3-dioxoiso-indolin-5-yl)-2-(trifluoro-methoxy) benzene-sulfonamide | FC(F)(F)Oc1ccccc1S(=O)(=O)Nc2ccc3C(=O)N(C4CCC(=O)NC4=O)C(=O)c3c2 |
| 2 | 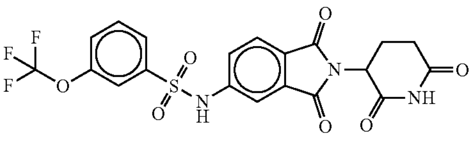 | N-(2-(2,6-dioxopiperidin-3-yl)-1,3-dioxoisoindolin-5-yl)-3-(trifluoro-methoxy)benzene-sulfonamide | FC(F)(F)Oc1cccc(c1)S(=O)(=O)Nc2ccc3C(=O)N(C4CCC(=O)NC4=O)C(=O)c3c2 |

TABLE 2-continued

| Yield, Purity, and MS Data for Exemplary Disclosed Compounds. | | | |
|---|---|---|---|
| 3 | 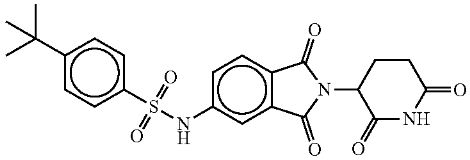 | 4-(tert-butyl)-N-(2-(2,6-dioxo-piperidin-3-yl)-1,3-dioxoisoindolin-5-yl) benzenesulfonamide | CC(C)(C)c1ccc(cc1)S(=O)(=O)Nc2ccc3C(=O)N(C4CCC(=O)NC4=O)C(=O)c3c2 |
| 4 | 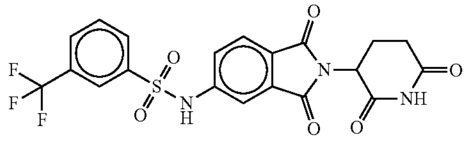 | N-(2-(2,6-dioxopiperidin-3-yl)-1,3-dioxoisoindolin-5-yl)-3-(trifluoro-methyl)benzene-sulfonamide | FC(F)(F)c1cccc(c1)S(=O)(=O)Nc2ccc3C(=O)N(C4CCC(=O)NC4=O)C(=O)c3c2 |
| 5 | 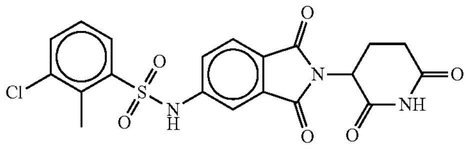 | 3-chloro-N-(2-(2,6-dioxopiperidin-3-yl)-1,3-dioxoisoindolin-5-yl)-2-methylbenzene-sulfonamide | Cc1c(Cl)cccc1S(=O)(=O)Nc2ccc3C(=O)N(C4CCC(=O)NC4=O)C(=O)c3c2 |
| 6 | 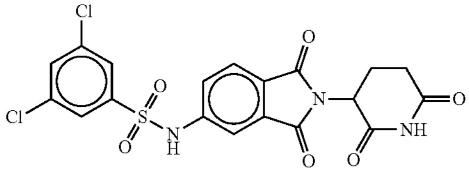 | 3,5-dichloro-N-(2-(2,6-dioxopiperidin-3-yl)-1,3-dioxoisoindolin-5-yl)benzene-sulfonamide | Clc1cc(Cl)cc(c1)S(=O)(=O)Nc2ccc3C(=O)C4CCC(=O)NC4=O)C(=O)c3c2 |
| 7 | 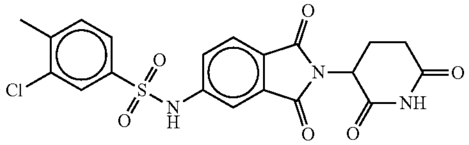 | 3-chloro-N-(2-(2,6-dioxopiperidin-3-yl)-1,3-dioxoisoindolin-5-yl)benzene-sulfonamide | Cc1ccc(cc1Cl)S(=O)(=O)Nc2ccc3C(=O)N(C4CCC(=O)NC4=O)C(=O)c3c2 |
| 8 | 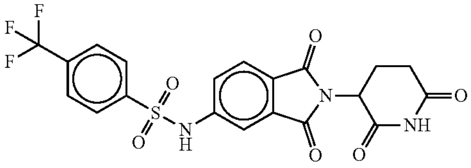 | N-(2-(2,6-dioxopiperidin-3-yl)-1,3-dioxoiso-indolin-5-yl)-4-(trifluoromethyl) benzenesulfonamide | FC(F)(F)c1ccc(cc1)S(=O)(=O)Nc2ccc3C(=O)N(C4CCC(=O)NC4=O)C(=O)c3c2 |
| 9 | 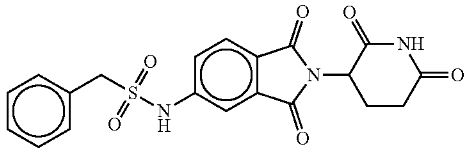 | N-(2-(2,6-dioxopiperidin-3-yl)-1,3-dioxoiso-indolin-5-yl)-1-phenylmethane-sulfonamide | O=C1CCC(N2C(=O)c3ccc(NS(=O)(=O)Cc4ccccc4)cc3C2=O)C(=O)N1 |
| 10 | 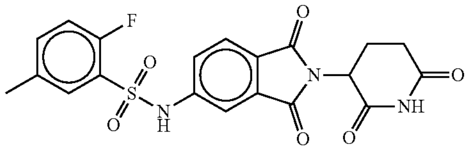 | N-(2-(2,6-dioxopiperidin-3-yl)-1,3-dioxo-isoindolin-5-yl)-2-fluoro-5-methyl-benzenesulfonamide | Cc1ccc(F)c(c1)S(=O)(=O)Nc2ccc3C(=O)N(C4CCC(=O)NC4=O)C(=O)c3c2 |
| 11 | 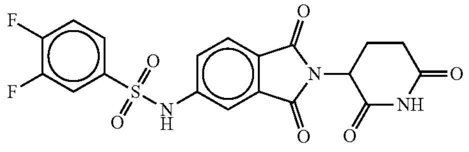 | N-(2-(2,6-dioxo-piperidin-3-yl)-1,3-dioxoiso-indolin-5-yl)-3,4-difluorobenzene-sulfonamide | Fc1ccc(cc1F)S(=O)(=O)Nc2ccc3C(=O)N(C4CCC(=O)NC4=O)C(=O)c3c2 |

TABLE 2-continued

Yield, Purity, and MS Data for Exemplary Disclosed Compounds.

| | | | |
|---|---|---|---|
| 12 | 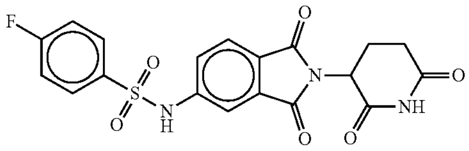 | N-(2-(2,6-dioxopiperidin-3-yl)-1,3-dioxoisoindolin-5-yl)-4-fluorobenzenesulfonamide | Fc1ccc(cc1)S(=O)(=O)Nc2ccc3C(=O)N(C4CCC(=O)NC4=O)C(=O)c3c2 |
| 13 | 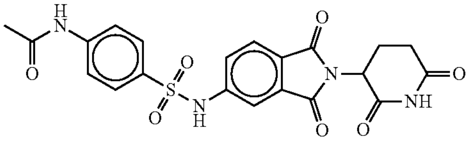 | N-(4-(N-(2-(2,6-dioxopiperidin-3-yl)-1,3-dioxoisoindolin-5-yl)sulfamoyl)phenyl)acetamide | CC(=O)Nc1ccc(cc1)S(=O)(=O)Nc2ccc3C(=O)N(C4CCC(=O)NC4=O)C(=O)c3c2 |
| 14 | 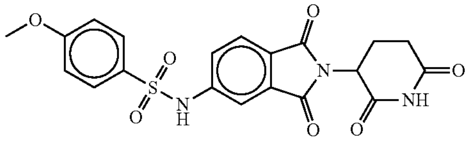 | N-(2-(2,6-dioxopiperidin-3-yl)-1,3-dioxoisoindolin-5-yl)-4-methoxybenzenesulfonamide | COc1ccc(cc1)S(=O)(=O)Nc2ccc3C(=O)N(C4CCC(=O)NC4=O)C(=O)c3c2 |
| 15 | 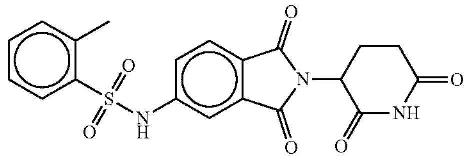 | N-(2-(2,6-dioxopiperidin-3-yl)-1,3-dioxoisoindolin-5-yl)-2-methylbenzenesulfonamide | Cc1ccccc1S(=O)(=O)Nc2ccc3C(=O)N(C4CCC(=O)NC4=O)C(=O)c3c2 |
| 16 | 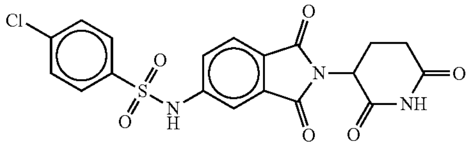 | 4-chloro-N-(2-(2,6-dioxopiperidin-3-yl)-1,3-dioxoisoindolin-5-yl)-benzenesulfonamide | Clc1ccc(cc1)S(=O)(=O)Nc2ccc3C(=O)N(C4CCC(=O)NC4=O)C(=O)c3c2 |
| 17 | 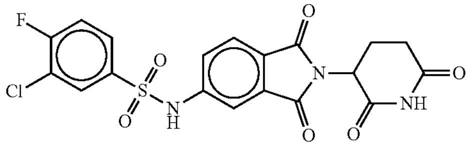 | 3-chloro-N-(2-(2,6-dioxopiperidin-3-yl)-1,3-dioxoisoindolin-5-yl)-4-fluorobenzesulfonamide | Fc1ccc(cc1Cl)S(=O)(=O)Nc2ccc3C(=O)N(C4CCC(=O)NC4=O)C(=O)c3c2 |
| 18 | 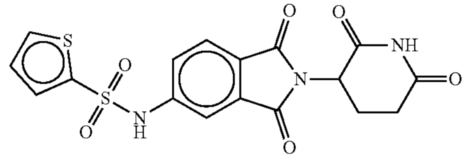 | N-(2-(2,6-dioxopiperidin-3-yl)-1,3-dioxoisoindolin-5-yl)thiophene-2-sulfonamide | O=C1CCC(N2C(=O)c3ccc(NS(=O)(=O)c4cccs4)cc3C2=O)C(=O)N1 |
| 19 | 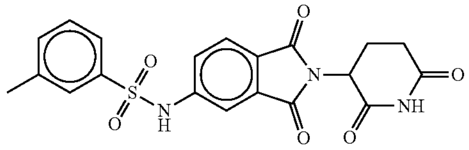 | N-(2-(2,6-dioxopiperidin-3-yl)-1,3-dioxoisoindolin-5-yl)-3-methylbenzenesulfonamide | Cc1cccc(c1)S(=O)(=O)Nc2ccc3C(=O)N(C4CCC(=O)NC4=O)C(=O)c3c2 |
| 20 | 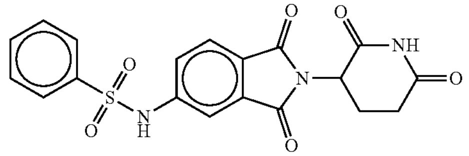 | N-(2-(2,6-dioxopiperidin-3-yl)-1,3-dioxoisoindolin-5-yl)benzenesulfonamide | O=C1CCC(N2C(=O)c3ccc(NS(=O)(=O)c4ccccc4)cc3C2=O)C(=O)N1 |

TABLE 2-continued

Yield, Purity, and MS Data for Exemplary Disclosed Compounds.

| | | | |
|---|---|---|---|
| 21 | 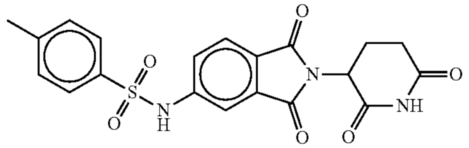 | N-(2-(2,6-dioxo-piperidin-3-yl)-1,3-dioxoisoindolin-5-yl)-4-methyl-benzenesulfonamide | Cc1ccc(cc1)S(=O)(=O)Nc2ccc3C(=O)N(C4CCC(=O)NC4=O)C(=O)c3c2 |
| 22 | 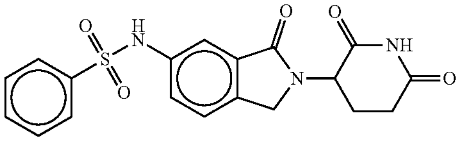 | N-(2-(2,6-dioxo-piperidin-3-yl)-3-oxoisoindolin-5-yl) benzenesulfonamide | O=C1CCC(N2Cc3ccc(NS(=O)(=O)c4ccccc4)cc3C2=O)C(=O)N1 |
| 23 | 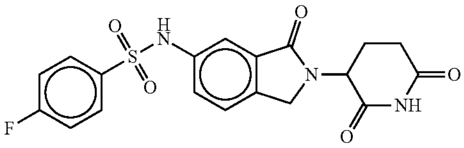 | N-(2-(2,6-dioxo-piperidin-3-yl)-3-oxoisoindolin-5-yl)-4-fluorobenzene-sulfonamide | Fc1ccc(cc1)S(=O)(=O)Nc2ccc3CN(C4CC(=O)NC4=O)C(=O)c3c2 |
| 24 | 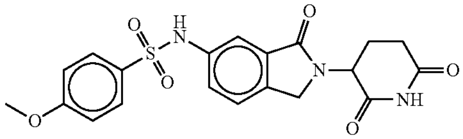 | N-(2-(2,6-dioxo-piperidin-3yl)-3-oxoisoindolin-5-yl)-4-methoxy-benzenesulfonamide | COc1ccc(cc1)S(=O)(=O)Nc2ccc3CN(C4CCC(=O)NC4=O)C(=O)c3c2 |
| 25 | 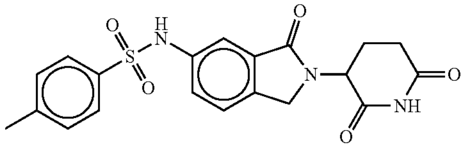 | N-(2-(2,6-dioxo-piperidin-3-yl)-3-oxoisoindolin-5-yl)-4-methyl-benzenesulfonamide | Cc1ccc(cc1)S(=O)(=O)Nc2ccc3CN(C4CC(=O)NC4=O)C(=O)c3c2 |
| 26 | 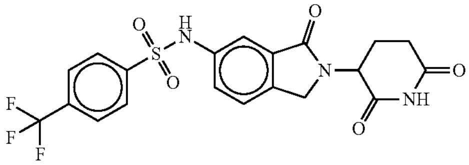 | N-(2-(2,6-dioxo-piperidin-3-yl)-3-oxoisoindolin-5-yl)-4-(trifluoro-methyl)benzene-sulfonamide | FC(F)(F)c1ccc(cc1)S(=O)(=O)Nc2ccc3CN(C4CCC(=O)NC4=O)C(=O)c3c2 |
| 27 | 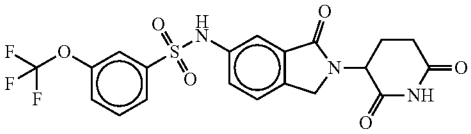 | N-(2-(2,6-dioxo-piperidin-3-yl)-3-oxoisoindolin-5-yl)-3-(trifluoro-methoxy)benzene-sulfonamide | FC(F)(F)Oc1cccc(c1)S(=O)(=O)Nc2ccc3CN(C4CCC(=O)NC4=O)C(=O)c3c2 |
| 28 | 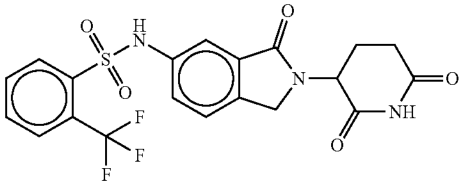 | N-(2-(2,6-dioxo-piperidin-3-yl)-3-oxoisoindolin-5-yl)-2-(trifluoro-methyl)benzene-sulfonamide | FC(F)(F)c1ccccc1S(=O)(=O)Nc2ccc3CN(C4CCC(=O)NC4=O)C(=O)c3c2 |
| 29 | 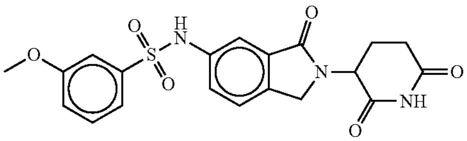 | N-(2-(2,6-dioxo-piperidin-3-yl)-3-oxoisoindolin-5-yl)-3-methoxy-benzenesulfonamide | COc1cccc(c1)S(=O)(=O)Nc2ccc3CN(C4CCC(=O)NC4=O)C(=O)c3c2 |

TABLE 2-continued

Yield, Purity, and MS Data for Exemplary Disclosed Compounds.

| | | | |
|---|---|---|---|
| 30 | 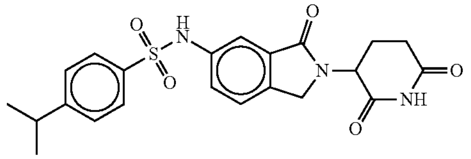 | N-(2-(2,6-dioxo-piperidin-3-yl)-3-oxoisoindolin-5-yl)-4-isopropyl-benzenesulfonamide | CC(C)c1ccc(cc1)S(=O)(=O)Nc2ccc3CN(C4CCC(=O)NC4=O)C(=O)c3c2 |
| 31 | 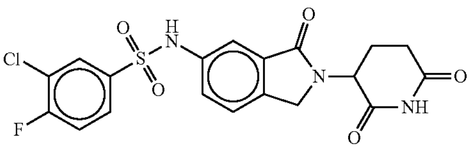 | 3-chloro-N-(2-(2,6-dioxopiperidin-3-yl)-3-oxoisoindolin-5-yl)-4-fluoro-benzenesulfonamide | Fc1ccc(cc1Cl)S(=O)(=O)Nc2ccc3CN(C4CCC(=O)NC4=O)C(=O)c3c2 |
| 32 | 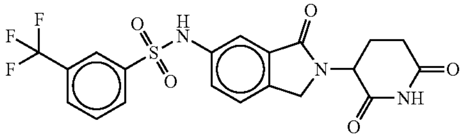 | N-(2-(2,6-dioxo-piperidin-3-yl)-3-oxoisoindolin-5-yl)-3-(trifluoro-methyl)benzene-sulfonamide | FC(F)(F)c1cccc(c1)S(=O)(=O)Nc2ccc3CN(C4CCC(=O)NC4=O)C(=O)c3c2 |
| 33 | 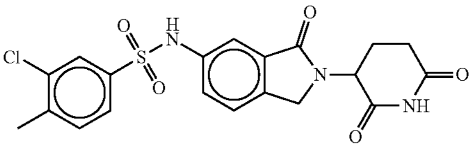 | 3-chloro-N-(2-(2,6-dioxopiperidin-3-yl)-3-oxoisoindolin-5-yl)-4-methyl-benzenesulfonamide | Cc1ccc(cc1Cl)S(=O)(=O)Nc2ccc3CN(C4CCC(=O)NC4=O)C(=O)c3c2 |
| 34 | 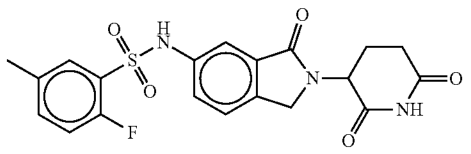 | N-(2-(2,6-dioxo-piperidin-3-yl)-3-oxoisoindolin-5-yl)-2-fluoro-5-methylbenzene-sulfonamide | Cc1ccc(F)c(c1)S(=O)(=O)Nc2ccc3CN(C4CCC(=O)NC4=O)C(=O)c3c2 |
| 35 | 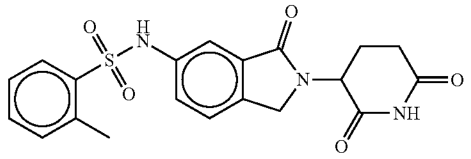 | N-(2-(2,6-dioxo-piperidin-3-yl)-3-oxoisoindolin-5-yl)-2-methyl-benzenesulfonamide | Cc1ccccc1S(=O)(=O)Nc2ccc3CN(C4CCC(=O)NC4=O)C(=O)c3c2 |
| 36 | 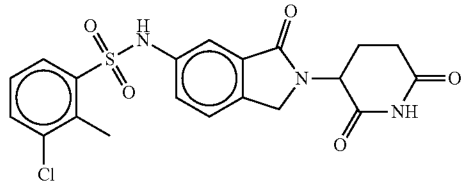 | 3-chloro-N-(2-(2,6-dioxopiperidin-3-yl)-3-oxoisoindolin-5-yl)-2-methyl-benzenesulfonamide | Cc1c(Cl)cccc1S(=O)(=O)Nc2ccc3CN(C4CCC(=O)NC4=O)C(=O)c3c2 |
| 37 | 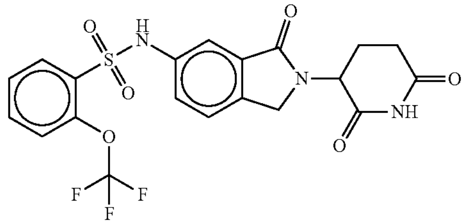 | N-(2-(2,6-dioxo-piperidin-3-yl)-3-oxoisoindolin-5-yl)-2-(trifluoro-methoxy)benzene-sulfonamide | FC(F)(F)Oc1ccccc1S(=O)(=O)Nc2ccc3CN(C4CCC(=O)NC4=O)C(=O)c3c2 |
| 38 | 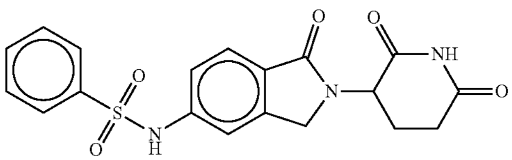 | N-(2-(2,6-dioxo-piperidin-3-yl)-1-oxoisoindolin-5-yl)benzene-sulfonamide | O=C1CCC(N2Cc3cc(NS(=O)(=O)c4ccccc4)ccc3C2=O)C(=O)N1 |

TABLE 2-continued

| Yield, Purity, and MS Data for Exemplary Disclosed Compounds. | | | |
|---|---|---|---|
| 39 | 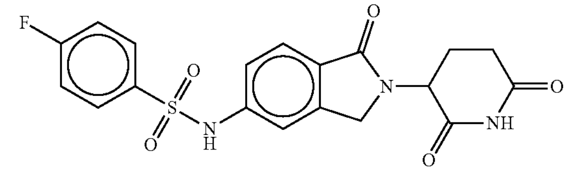 | N-(2-(2,6-dioxo-piperidin-3-yl)-1-oxoisoindolin-5-yl)-4-fluoro-benzenesulfonamide | Fc1ccc(cc1)S(=O)(=O)Nc2ccc3C(=O)N(Cc3c2)C4CCC(=O)NC4=O |
| 40 | 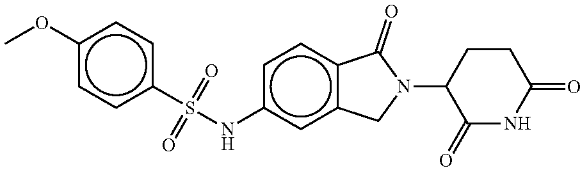 | N-(2-(2,6-dioxo-piperidin-3-yl)-1-oxoisoindolin-5-yl)-4-methoxy-benzenesulfonamide | COc1ccc(cc1)S(=O)(=O)Nc2ccc3C(=O)N(Cc3c2)C4CCC(=O)NC4=O |
| 41 | 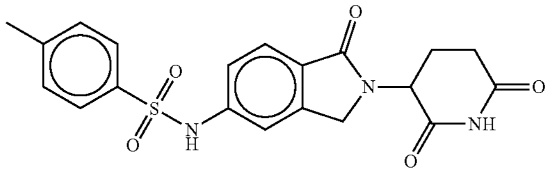 | N-(2-(2,6-dioxo-piperidin-3-yl)-1-oxoisoindolin-5-yl)-4-methyl-benzenesulfonamide | Cc1ccc(cc1)S(=O)(=O)Nc2ccc3C(=O)N(Cc3c2)C4CCC(=O)NC4=O |
| 42 | 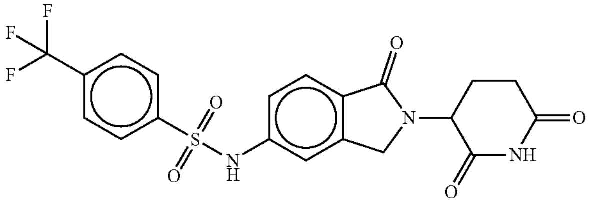 | N-(2-(2,6-dioxo-piperidin-3-yl)-1-oxoisoindolin-5-yl)-4-(trifluoro-methyl)benzene-sulfonamide | FC(F)(F)c1ccc(cc1)S(=O)(=O)Nc2ccc3C(=O)N(Cc3c2)C4CCC(=O)NC4=O |
| 43 | 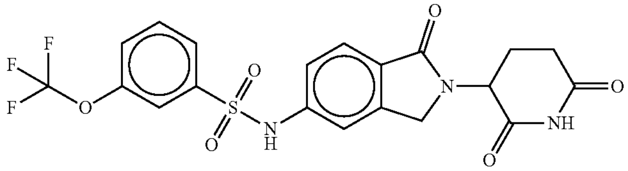 | N-(2-(2,6-dioxo-piperidin-3-yl)-1-oxoisoindolin-5-yl)-3-(trifluoro-methoxy)benzene-sulfonamide | FC(F)(F)Oc1cccc(c1)S(=O)(=O)Nc2ccc3C(=O)N(Cc3c2)C4CCC(=O)NC4=O |
| 44 | 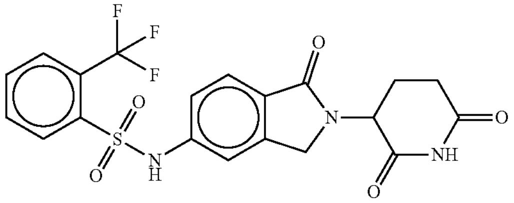 | N-(2-(2,6-dioxopiperidin-3-yl)-1-oxoisoindolin-5-yl)-2-(trifluoro-methyl)benzene-sulfonamide | FC(F)(F)c1ccccc1S(=O)(=O)Nc2ccc3C(=O)N(Cc3c2)C4CCC(=O)NC4=O |
| 45 | 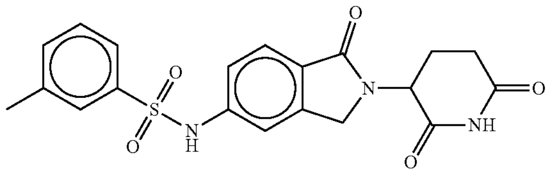 | N-(2-(2,6-dioxo-piperidin-3-yl)-1-oxoisoindolin-5-yl)-3-methyl-benzenesulfonamide | Cc1cccc(c1)S(=O)(=O)Nc2ccc3C(=O)N(Cc3c2)C4CCC(=O)NC4=O |
| 46 | 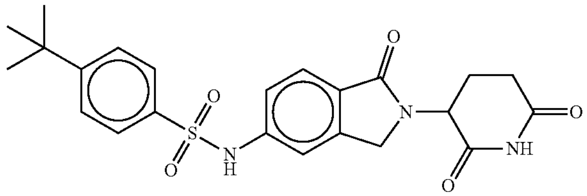 | 4-(tert-butyl)-N-(2,6-dioxopiperidin-3-yl)-1-oxoisoindolin-5-yl)benzene-sulfonamide | CC(C)(C)c1ccc(cc1)S(=O)(=O)Nc2ccc3C(=O)N(Cc3c2)C4CCC(=O)NC4=O |

TABLE 2-continued

| Yield, Purity, and MS Data for Exemplary Disclosed Compounds. | | | |
|---|---|---|---|
| 47 | 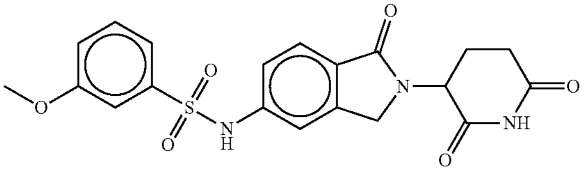 | N-(2-(2,6-dioxo-piperidin-3-yl)-1-oxoisoindolin-5-yl)-3-methoxy-benzenesulfonamide | COc1cccc(c1)S(=O)(=O)Nc2ccc3C(=O)N(Cc3c2)C4CCC(=O)NC4=O |
| 48 | 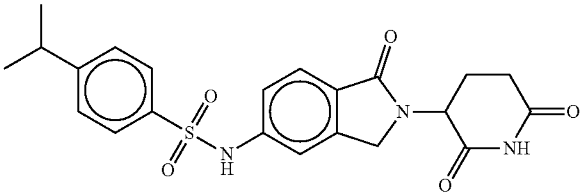 | N-(2-(2,6-dioxo-piperidin-3-yl)-1-oxoisoindolin-5-yl)-4-isopropyl-benzenesulfonamide | CC(C)c1ccc(cc1)S(=O)(=O)Nc2ccc3C(=O)N(Cc3c2)C4CCC(=O)NC4=O |
| 49 | 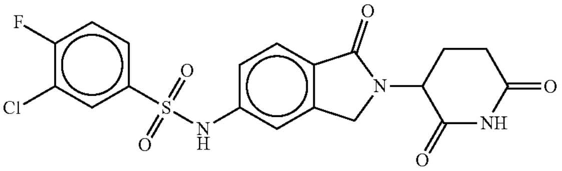 | 3-chloro-N-(2-(2,6-dioxopiperidin-3-yl)-1-oxoisoindolin-5-yl)-4-fluorobenzene-sulfonamide | Fc1ccc(cc1Cl)S(=O)(=O)Nc2ccc3C(=O)N(Cc3c2)C4CCC(=O)NC4=O |
| 50 | 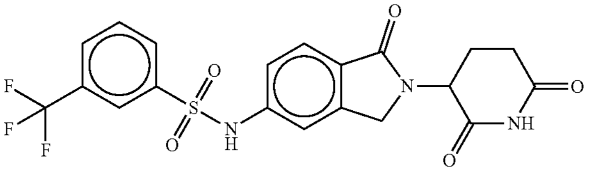 | N-(2-(2,6-dioxo-piperidin-3-yl)-1-oxoisoindolin-5-yl)-3-(trifluoro-methyl)benzene-sulfonamide | FC(F)(F)c1cccc(c1)S(=O)(=O)Nc2ccc3C(=O)N(Cc3c2)C4CCC(=O)NC4=O |
| 51 | 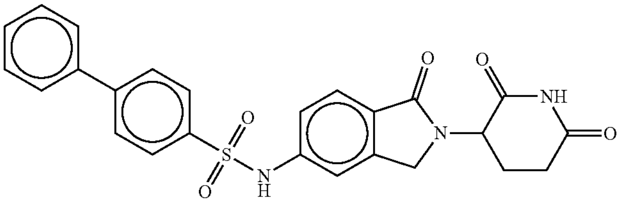 | N-(2-(2,6-dioxo-piperidin-3-yl)-1-oxoisoindolin-5-yl)-[1,1'-biphenyl]-4-sulfonamide | O=C1CCC(N2Cc3cc(NS(=O)(=O)c4ccc(cc4)c5ccccc5)ccc3C2=O)C(=O)N1 |
| 52 | 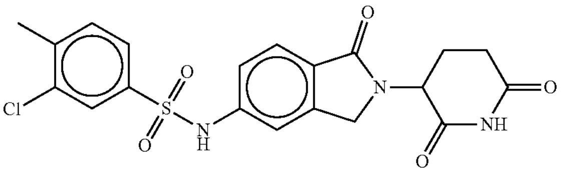 | 3-chloro-N-(2-(2,6-dioxopiperidin-3-yl)-1-oxoisoindolin-5-yl)-4-methyl-benzenesulfonamide | Cc1ccc(cc1Cl)S(=O)(=O)Nc2ccc3C(=O)N(Cc3c2)C4CCC(=O)NC4=O |
| 53 | 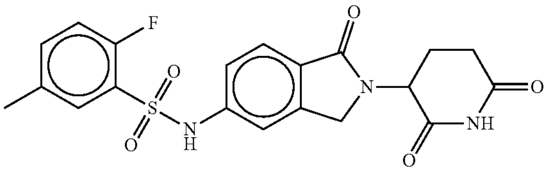 | N-(2-(2,6-dioxo-piperidin-3-yl)-1-oxoisoindolin-5-yl)-2-fluoro-5-methyl-benzenesulfonamide | Cc1ccc(F)c(c1)S(=O)(=O)Nc2ccc3C(=O)N(Cc3c2)C4CCC(=O)NC4=O |
| 54 | 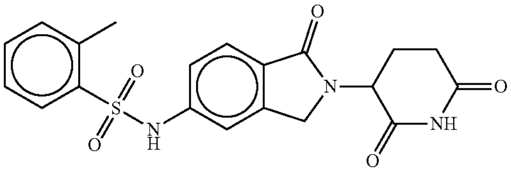 | N-(2-(2,6-dioxo-piperidin-3-yl)-1-oxoisoindolin-5-yl)-2-methyl-benzenesulfonamide | Cc1ccccc1S(=O)(=O)Nc2ccc3C(=O)N(Cc3c2)C4CCC(=O)NC4=O |

TABLE 2-continued

Yield, Purity, and MS Data for Exemplary Disclosed Compounds.

| | | | |
|---|---|---|---|
| 55 | 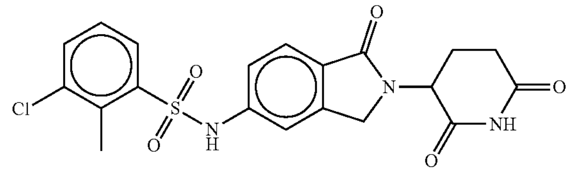 | 3-chloro-N-(2-(2,6-dioxopiperidin-3-yl)-1-oxoisoindolin-5-yl)-2-methyl-benzenesulfonamide | Cc1c(Cl)cccc1S(=O)(=O)Nc2ccc3C(=O)N(Cc3c2)C4CCC(=O)NC4=O |
| 56 | 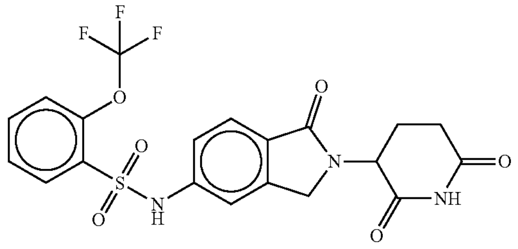 | N-(2-(2,6-dioxo-piperidin-3-yl)-1-oxoisoindolin-5-yl)-2-(trifluoro-methoxy)benzene-sulfonamide | FC(F)(F)Oc1ccccc1S(=O)(=O)Nc2ccc3C(=O)N(Cc3c2)C4CCC(=O)NC4=O |
| 57 | 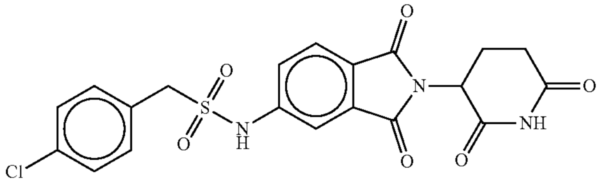 | 1-(4-chlorophenyl)-N-(2-(2,6-dioxo-piperidin-3-yl)-1,3-dioxoisoindolin-5-yl)methane-sulfonamide | O=C(N1C2C(NC(CC2)=O)=O)C3=C(C=CC(NS(CC4=CC=C(Cl)C=C4)(=O)=O)=C3)C1=O |
| 58 | 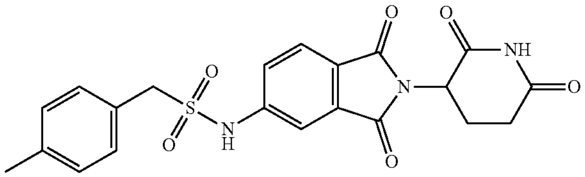 [SMILES: Cc1ccc(CS(=O)(=O)Nc2ccc3c(c2)C(=O)N(C2CCC(=O)NC2=O)C3=O)cc1] | N-(2-(2,6-dioxo-piperidin-3-yl)-1,3-dioxoisoindolin-5-yl)-1-(p-tolyl)methanesulfonamide | O=C(N1C2C(CC2)=O)=O)C3=C(C=CC(NS(CC4=CC=C(C)C=C4)(=O)=O)=C3)C1=O |
| 59 | 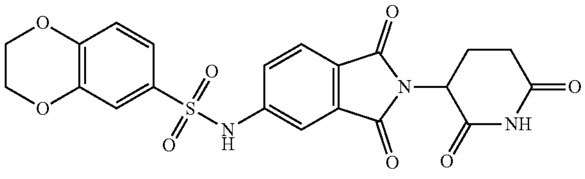 [SMILES: O=C1CCC(N2C(=O)c3ccc(NS(=O)(=O)c4ccc5c(c4)OCCO5)cc3C2=O)C(=O)N1] | N-(2-(2,6-dioxo-piperidin-3-yl)-1,3-dioxoisoindolin-5-yl)-2,3-dihydro-benzo[b][1,4]dioxine-6-sulfonamide | O=C(N1C2C(NC(CC2)=O)=O)C3=C(C=CC(NS(C4=CC(OCCO5)=C5C=C4)(=O)=O)=C3)C1=O |
| 60 | 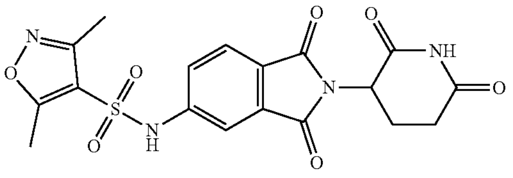 [SMILES: Cc1noc(C)c1S(=O)(=O)Nc1ccc2c(c1)C(=O)N(C1CCC(=O)NC1=O)C2=O] | N-(2-(2,6-dioxo-piperidin-3-yl)-1,3-dioxoisoindolin-5-yl)-3,5-dimethyl-isoxazole-4-sulfonamide | O=C(N1C2C(NC(CC2)=O)=O)C3=C(C=CC(NS(C4=C(C)ON=C4C)(=O)(=O)=C3)C1=O |
| 61 | 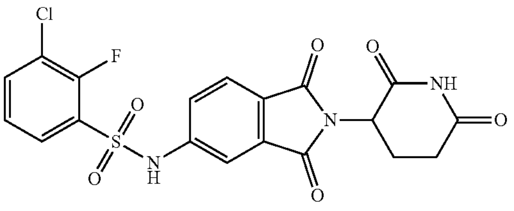 [SMILES: O=C1CCC(N2C(=O)c3ccc(NS(=O)(=O)c4cccc(Cl)c4F)cc3C2=O)C(=O)N1] | 3-chloro-N-(2-(2,6-dioxopiperidin-3-yl)-1,3-dioxoiso-indolin-5-yl)-2-fluorobenzene-sulfonamide | O=C(N1C2C(NC(CC2)=O)=O)C3=CC=CC(NS(C4=CC=CC(Cl)=C4F)(=O)(=O)=C3)C1=O |

TABLE 2-continued

| Yield, Purity, and MS Data for Exemplary Disclosed Compounds. | | | |
|---|---|---|---|
| 62 | 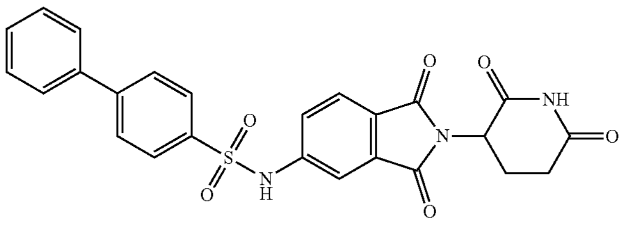 [SMILES: O=C1CCC(N2C(=O)c3ccc(NS(=O)(=O)c4ccc(-c5ccccc5)cc4)cc3C2=O)C(=O)N1] | N-(2-(2,6-dioxo-piperidin-3-yl)-1,3-dioxoisoindolin-5-yl)-[1,1'-biphenyl]-4-sulfonamide | O=C(N1C2C(NC(CC2)=O)=O)C3=C(C=CC(NS(C4=CC=C(C5=CC=CC=C5)C=C4)(=O)=O)=C3)C1=O |
| 63 | 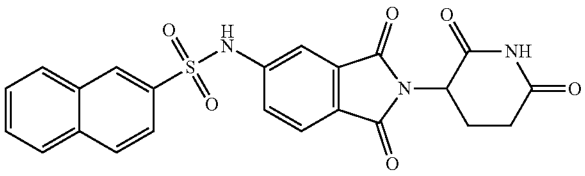 [SMILES: O=C1CCC(N2C(=O)c3ccc(NS(=O)(=O)c4ccc5ccccc5c4)cc3C2=O)C(=O)N1] | N-(2-(2,6-dioxo-piperidin-3-yl)-1,3-dioxoisoindolin-5-yl)naphthalene-2-sulfonamide | O=C(N1C2C(NC(CC2)=O)=O)C3=C(C=CC(NS(C4=CC5=CC=CC=C5C=C4)(=O)=O)=C3)C1=O |
| 64 | 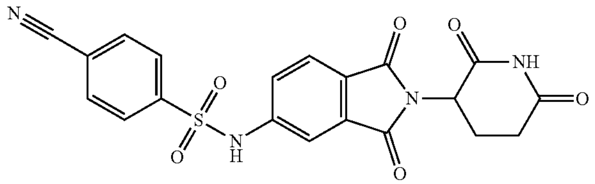 [SMILES: N#Cc1ccc(S(=O)(=O)Nc2ccc3c(c2)C(=O)N(C2CCC(=O)NC2=O)C3=O)cc1] | 4-cyano-N-(2-(2,6-dioxopiperidin-3-yl)-1,3-dioxoiso-indolin-5-yl)benzenesulfonamide | O=C(N1C2C(NC(CC2)=O)=O)C3=C(C=CC(NS(=O)(C(C=C4)=CC=C4C#N)=O)=C3)C1=O |
| 65 | 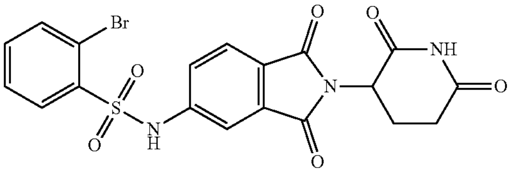 [SMILES: O=C1CCC(N2C(=O)c3ccc(NS(=O)(=O)c4ccccc4Br)cc3C2=O)C(=O)N1] | 2-bromo-N-(2-(2,6-dioxopiperidin-3-yl)-1,3-dioxoiso-indolin-5-yl)benzenesulfonamide | O=C(N1C2C(NC(CC2)=O)=O)C3=C(C=CC(NS(=O)(C4=CC=CC=C4Br)=O)=C3)C1=O |
| 66 | 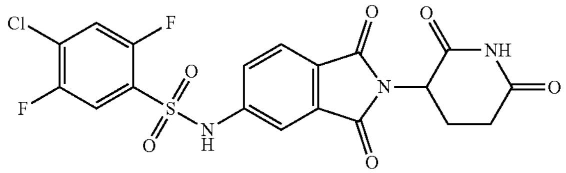 [SMILES: O=C1CCC(N2C(=O)c3ccc(NS(=O)(=O)c4cc(F)c(Cl)cc4F)cc3C2=O)C(=O)N1] | 4-chloro-N-(2-(2,6-dioxopiperidin-3-yl)-1,3-dioxoisoindolin-5-yl)-2,5-difluoro-benzenesulfonamide | O=C(N1C2C(NC(CC2)=O)=O)C3=C(C=CC(NS(C4=CC(F)=C(Cl)C=C4F)(=O)=O)=C3)C1=O |
| 67 | 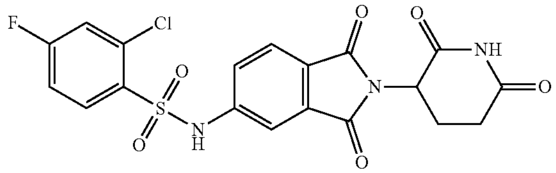 [SMILES: O=C1CCC(N2C(=O)c3ccc(NS(=O)(=O)c4ccc(F)cc4Cl)cc3C2=O)C(=O)N1] | 2-chloro-N-(2-(2,6-dioxopiperidin-3-yl)-1,3-dioxoiso-indolin-5-yl)-4-fluorobenzene-sulfonamide | O=C(N1C2C(NC(CC2)=O)=O)C3=C(C=CC(NS(=O)(C4=CC=C(F)C=C4Cl)=O)=C3)C1=O |
| 68 | 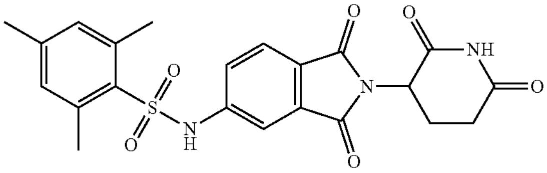 [SMILES: Cc1cc(C)c(S(=O)(=O)Nc2ccc3c(c2)C(=O)N(C2CCC(=O)NC2=O)C3=O)c(C)c1] | N-(2-(2,6-dioxo-piperidin-3-yl)-1,3-dioxoisoindolin-5-yl)-2,4,6-trimethylbenzene-sulfonamide | O=C(N1C2C(NC(CC2)=O)=O)C3=C(C=CC(NS(C4=C(C)C=C(C)C=C4C)(=O)=O)=C3)C1=O |
| 69 | 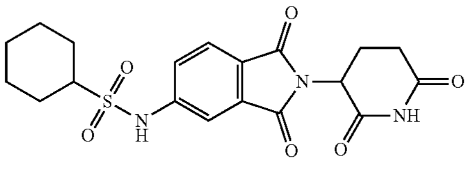 [SMILES: O=C1CCC(N2C(=O)c3ccc(NS(=O)(=O)C4CCCCC4)cc3C2=O)C(=O)N1] | N-(2-(2,6-dioxo-piperidin-3-yl)-1,3-dioxoisoindolin-5-yl)cyclohexane-sulfonamide | O=S(C1CCCCC1)(NC2=CC3=C(C(N(C(CC4)C(NC4=O)=O)C3=O)=O)C=C2)=O |

TABLE 2-continued

Yield, Purity, and MS Data for Exemplary Disclosed Compounds.

| | | | |
|---|---|---|---|
| 70 | 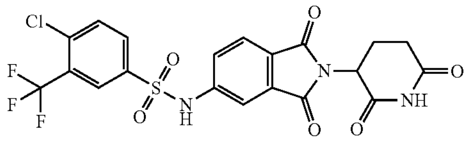 [SMILES: O=C1CCC(N2C(=O)c3ccc(NS(=O)(=O)c4ccc(Cl)c(C(F)(F)F)c4)cc3C2=O)C(=O)N1] | 4-chloro-N-(2-(2,6-dioxopiperidin-3-yl)-1,3-dioxoisoindolin-5-yl)-3-(trifluoromethyl)benzenesulfonamide | O=S(C1=CC=C(Cl)C(C(F)(F)F)=C1)(NC2=CC3=C(C(N(C(CC4)C(NC4=O)=O)C3=O)=O)C=C2)=O |
| 71 | 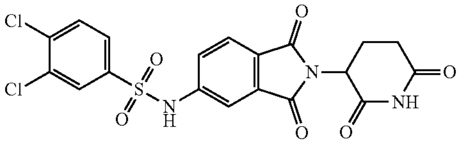 [SMILES: O=C1CCC(N2C(=O)c3ccc(NS(=O)(=O)c4ccc(Cl)c(Cl)c4)cc3C2=O)C(=O)N1] | 3,4-dichloro-N-(2-(2,6-dioxopiperidin-3-yl)-1,3-dioxoisoindolin-5-yl)benzenesulfonamide | O=S(C1=CC=C(Cl)C(Cl)=C1)(NC2=CC3=C(C(N(C(CC4)C(NC4=O)=O)C3=O)=O)C=C2)=O |
| 72 | 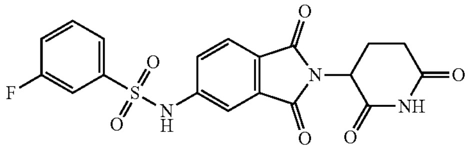 [SMILES: O=C1CCC(N2C(=O)c3ccc(NS(=O)(=O)c4cccc(F)c4)cc3C2=O)C(=O)N1] | N-(2-(2,6-dioxopiperidin-3-yl)-1,3-dioxoisoindolin-5-yl)-3-fluorobenzenesulfonamide | O=S(C1=CC=CC(F)=C1)(NC2=CC3=C(C(N(C(CC4)C(NC4=O)=O)C3=O)=O)C=C2)=O |
| 73 | 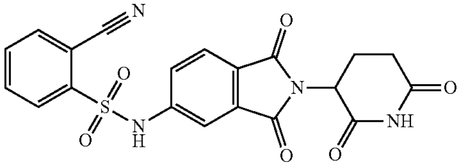 [SMILES: N#Cc1ccccc1S(=O)(=O)Nc1ccc2c(c1)C(=O)N(C1CCC(=O)NC1=O)C2=O] | 2-cyano-N-(2-(2,6-dioxopiperidin-3-yl)-1,3-dioxoisoindolin-5-yl)benzenesulfonamide | O=S(C1=CC=CC=C1C#N)(NC2=CC3=C(C(N(C(CC4)C(NC4=O)=O)C3=O)=O)C=C2)=O |
| 74 | 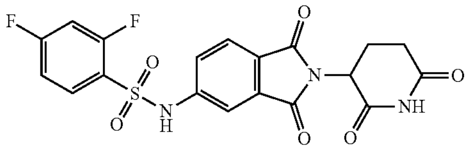 [SMILES: O=C1CCC(N2C(=O)c3ccc(NS(=O)(=O)c4ccc(F)cc4F)cc3C2=O)C(=O)N1] | N-(2-(2,6-dioxopiperidin-3-yl)-1,3-dioxoisoindolin-5-yl)-2,4-difluorobenzenesulfonamide | O=S(C1=CC=C(F)C=C1F)(NC2=CC3=C(C(N(C(CC4)C(NC4=O)=O)C3=O)=O)C=C2)=O |
| 75 | 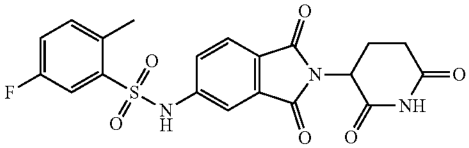 [SMILES: Cc1ccc(F)cc1S(=O)(=O)Nc1ccc2c(c1)C(=O)N(C1CCC(=O)NC1=O)C2=O] | N-(2-(2,6-dioxopiperidin-3-yl)-1,3-dioxoisoindolin-5-yl)-5-fluoro-2-methylbenzenesulfonamide | O=S(C1=CC(F)=CC=C1C)(NC2=CC3=C(C(N(CC4)C(NC4=O)=O)C3=O)=O)C=C2)=O |
| 76 | 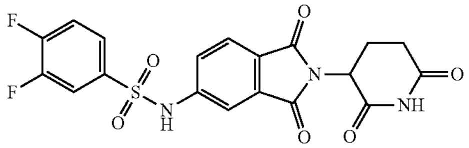 [SMILES: O=C1CCC(N2C(=O)c3ccc(NS(=O)(=O)c4ccc(F)c(F)c4)cc3C2=O)C(=O)N1] | N-(2-(2,6-dioxopiperidin-3-yl)-1,3-dioxoisoindolin-5-yl)-3,4-difluorobenzenesulfonamide | O=S(C1=CC=C(F)C(F)=C1)(NC2=CC3=C(C(N(C(CC4)C(NC4=O)=O)C3=O)=O)C=C2)=O |
| 77 | 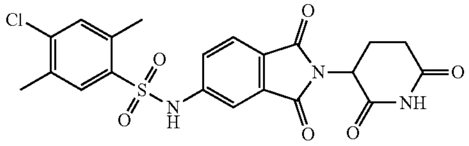 [SMILES: Cc1cc(S(=O)(=O)Nc2ccc3c(c2)C(=O)N(C2CCC(=O)NC2=O)C3=O)c(C)cc1Cl] | 4-chloro-N-(2-(2,6-dioxopiperidin-3-yl)-1,3-dioxoisoindolin-5-yl)-2,5-dimethylbenzenesulfonamide | O=S(C1=CC(C)=C(Cl)C=C1C)(NC2=CC3=C(C(N(C(CC4)C(NC4=O)=O)C3=O)=O)C=C2)=O |
| 78 | 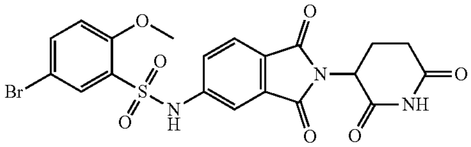 [SMILES: COc1ccc(Br)cc1S(=O)(=O)Nc1ccc2c(c1)C(=O)N(C1CCC(=O)NC1=O)C2=O] | 5-bromo-N-(2-(2,6-dioxopiperidin-3-yl)-1,3-dioxoisoindolin-5-yl)-2-methoxybenzenesulfonamide | O=S(C1=CC(Br)=CC=C1OC)(NC2=CC3=C(C(N(C(CC4)C(NC4=O)=O)C3=O)=O)C=C2)=O |

TABLE 2-continued

| Yield, Purity, and MS Data for Exemplary Disclosed Compounds. | | | |
|---|---|---|---|
| 79 | 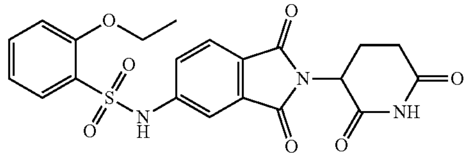 [SMILES: CCOc1ccccc1S(=O)(=O)Nc1ccc2c(c1)C(=O)N(C1CCC(=O)NC1=O)C2=O] | N-(2-(2,6-dioxo-piperidin-3-yl)-1,3-dioxoisoindolin-5-yl)-2-ethoxybenzene-sulfonamide | O=S(C1=CC=CC=C1OOC)(NC2=CC3=C(C(N(C(CC4)C(NC4=O)=O)C3=O)=O)C=C2)=O |
| 80 | 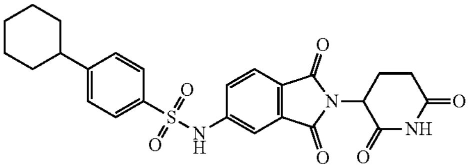 [SMILES: O=C1CCC(N2C(=O)c3ccc(NS(=O)(=O)c4ccc(C5CCCCC5)cc4)cc3C2=O)C(=O)N1] | 4-cyclohexyl-N-(2-(2,6-dioxopiperidin-3-yl)-1,3-dioxoiso-indolin-5-yl)benzene-sulfonamide | O=S(C1=CC=C(C2CCCCC2)C=C1)(NC3=CC4=C(C(N(C(CC5)C(NC5=O)=O)C4=O)=O)C=C3)=O |
| 81 | 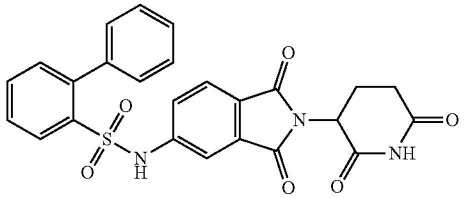 [SMILES: O=C1CCC(N2C(=O)c3ccc(NS(=O)(=O)c4ccccc4-c4ccccc4)cc3C2=O)C(=O)N1] | N-(2-(2,6-dioxo-piperidin-3-yl)-1,3-dioxoisoindolin-5-yl)-[1,1'-biphenyl]-2-sulfonamide | O=S(C1=CC=CC=C1C2=CC=CC=C2)(NC3=CC4=C(C(N(C(CC5)C(NC5=O)=O)C4=O)=O)C=C3)=O |
| 82 | 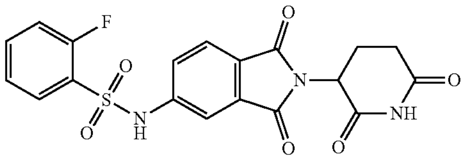 [SMILES: O=C1CCC(N2C(=O)c3ccc(NS(=O)(=O)c4ccccc4F)cc3C2=O)C(=O)N1] | N-(2-(2,6-dioxo-piperidin-3-yl)-1,3-dioxoisoindolin-5-yl)-2-fluorobenzene-sulfonamide | O=S(C1=CC=CC=C1F)(NC2=CC3=C(C(N(C(CC4)(C(NC4=O)=O)C3=O)=O)C=C2)=O |
| 83 | 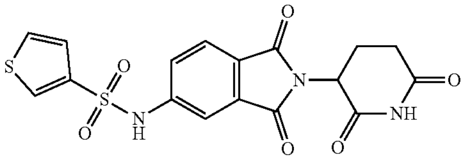 [SMILES: O=C1CCC(N2C(=O)c3ccc(NS(=O)(=O)c4ccsc4)cc3C2=O)C(=O)N1] | N-(2-(2,6-dioxopiperidin-3-yl)-1,3-dioxoisoindolin-5-yl)thiophene-3-sulfonamide | O=S(C1=CSC=C1)(NC2=CC3=C(C(N(C(CC4)C(NC4=O)=O)C3=O)=O)C=C2)=O |
| 84 | 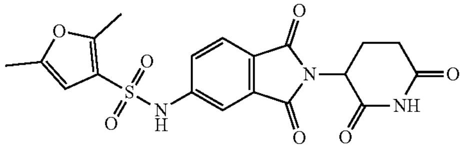 [SMILES: Cc1cc(S(=O)(=O)Nc2ccc3c(c2)C(=O)N(C2CCC(=O)NC2=O)C3=O)c(C)o1] | N-(2-(2,6-dioxo-piperidin-3-yl)-1,3-dioxoisoindolin-5-yl)-2,5-dimethylfuran-3-sulfonamide | O=S(C1=C(C)OC(C)=C1)(NC2=CC3=C(C(N(C(CC4)C(NC4=O)=O)C3=O)=O)C=C2)=O |
| 85 | 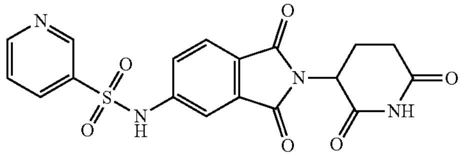 [SMILES: O=C1CCC(N2C(=O)c3ccc(NS(=O)(=O)c4cccnc4)cc3C2=O)C(=O)N1] | N-(2-(2,6-dioxo-piperidin-3-yl)-1,3-dioxoisoindolin-5-yl)pyridine-3-sulfonamide | O=S(C1=CC=CN=C1)(NC2=CC3=C(C(N(C(CC4)C(NC4=O)=O)C3=O)=O)C=C2)=O |
| 86 | 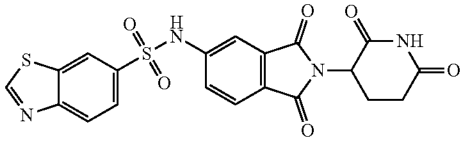 [SMILES: O=C1CCC(N2C(=O)c3ccc(NS(=O)(=O)c4ccc5ncsc5c4)cc3C2=O)C(=O)N1] | N-(2-(2,6-dioxo-piperidin-3-yl)-1,3-dioxoisoindolin-5-yl)-benzo[d]thiazole-6-sulfonamide | O=S(C1=CC=C2N=CSC2=C1)(NC3=CC4=C(C(N(C(CC5)C(NC5=O)=O)C4=O)=O)C=C3)=O |

TABLE 2-continued

Yield, Purity, and MS Data for Exemplary Disclosed Compounds.

| | | | |
|---|---|---|---|
| 87 | 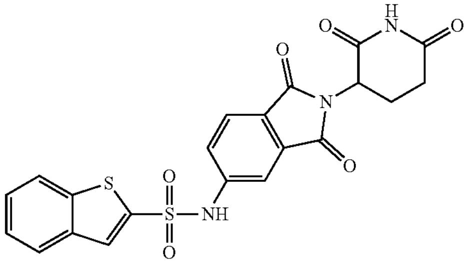 [SMILES: O=C1CCC(N2C(=O)c3ccc(NS(=O)(=O)c4cc5ccccc5s4)cc3C2=O)C(=O)N1] | N-(2-(2,6-dioxo-piperidin-3-yl)-1,3-dioxoisoindolin-5-yl)-benzo[b]thiophene-2-sulfonamide | O=S(C1=CC2=CC=CC=C2S1)(NC3=CC4=C(C(N(C(CC5)C(NC5=O)=O)C4=O)=O)C=C3)=O |
| 88 | 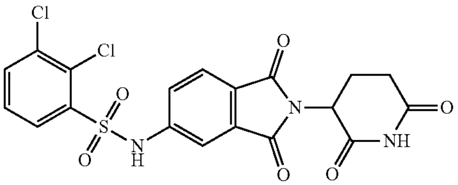 [SMILES: O=C1CCC(N2C(=O)c3ccc(NS(=O)(=O)c4cccc(Cl)c4Cl)cc3C2=O)C(=O)N1] | 2,3-dichloro-N-(2-(2,6-dioxopiperidin-3-yl)-1,3-dioxoisoindolin-5-yl) benzenesulfonamide | O=S(C1=CC=CC(Cl)=C1Cl)(NC2=CC3=C(C(N(C(CC4)C(NC4=O)=O)C3=O)=O)C=C2)=O |
| 89 | 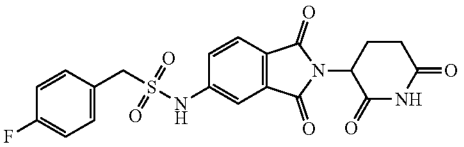 [SMILES: O=C1CCC(N2C(=O)c3ccc(NS(=O)(=O)Cc4ccc(F)cc4)cc3C2=O)C(=O)N1] | N-(2-(2,6-dichloro-piperidin-3-yl)-1,3-dioxoisoindolin-5-yl)-1-(4-fluoro-phenyl)methane-sulfonamide | O=S(CC1=CC=C(F)C=C1)(NC2=CC3=C(C(N(C(CC4)C(NC4=O)=O)C3=O)=O)C=C2)=O |
| 90 | 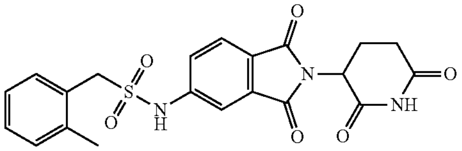 [SMILES: Cc1ccccc1CS(=O)(=O)Nc1ccc2c(c1)C(=O)N(C1CCC(=O)NC1=O)C2=O] | N-(2-(2,6-dioxopiperidin-3-yl)-1,3-dioxoisoindolin-5-yl)-1-(o-tolyl)methane-sulfonamide | O=S(CC1=CC=CC=C1C)(NC2=CC3=C(C(N(C(CC4)C(NC4=O)=O)C3=O)=O)C=C2)=O |
| 91 | 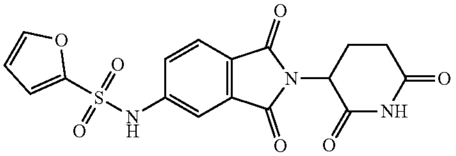 [SMILES: O=C1CCC(N2C(=O)c3ccc(NS(=O)(=O)c4ccco4)cc3C2=O)C(=O)N1] | N-(2-(2,6-dioxopiperidin-3-yl)-1,3-dioxoisoindolin-5-yl)furan-2-sulfonamide | O=S(C1=CC=CO1)(NC2=CC3=C(C(N(C(CC4)C(NC4=O)=O)C3=O)=O)C=C2)=O |
| 92 | 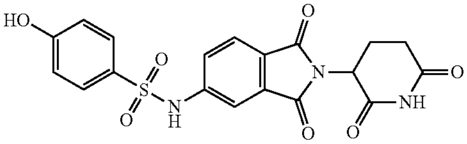 [SMILES: O=C1CCC(N2C(=O)c3ccc(NS(=O)(=O)c4ccc(O)cc4)cc3C2=O)C(=O)N1] | N-(2-(2,6-dioxo-piperidin-3-yl)-1,3-dioxoisoindolin-5-yl)-4-hydroxybenzene-sulfonamide | O=S(C1=CC=C(O)C=C1)(NC2=CC3=C(C(N(C(CC4)C(NC4=O)=O)C3=O)=O)C=C2)=O |
| 93 | 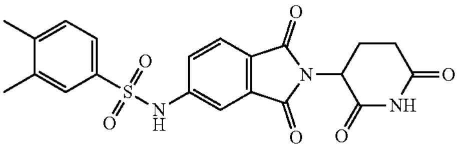 [SMILES: Cc1ccc(S(=O)(=O)Nc2ccc3c(c2)C(=O)N(C2CCC(=O)NC2=O)C3=O)cc1C] | N-(2-(2,6-dioxo-piperidin-3-yl)-1,3-dioxoisoindolin-5-yl)-3,4-dimethylbenzene-sulfonamide | O=S(C1=CC=C(C)C(C)=C1)(NC2=CC3=C(C(N(C(CC4)C(NC4=O)=O)C3=O)=O)C=C2)=O |
| 94 | 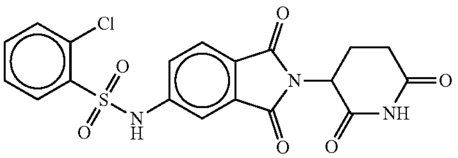 | 2-chloro-N-(2-(2,6-dioxopiperidin-3-yl)-1,3-dioxoiso-indolin-5-yl) benzenesulfonamide | Clc1ccccc1S(=O)(=O)Nc2ccc3C(=O)N(C4CCC(=O)NC4=O)C(=O)c3c2 |
| 95 | 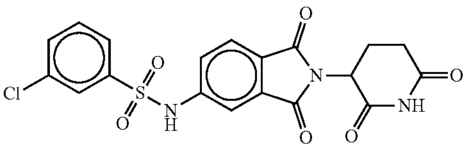 | 3-chloro-N-(2-(2,6-dioxopiperidin-3-yl)-1,3-dioxoisoindolin-5-yl) benzenesulfonamide | Clc1cccc(c1)S(=O)(=O)Nc2ccc3C(=O)N(C4CCC(=O)NC4=O)C(=O)c3c2 |

TABLE 2-continued

Yield, Purity, and MS Data for Exemplary Disclosed Compounds.

| | | | |
|---|---|---|---|
| 96 | 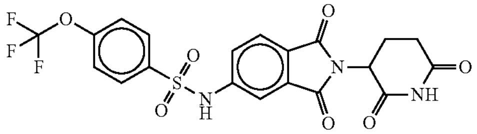 | N-(2-(2,6-dioxo-piperidin-3-yl)-1,3-dioxoisoindolin-5-yl)-4-(trifluoromethoxy) benzenesulfonamide | FC(F)(F)Oc1ccc(cc1)S(=O)(=O) Nc2cc3C(=O)N (C4CCC(=O)NC4=O) C(=O)c3c2 |
| 97 | 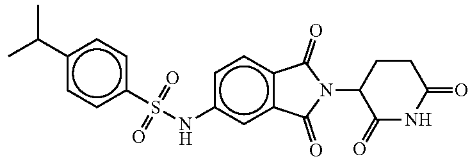 | N-(2-(2,6-dioxo-piperidin-3-yl)-1,3-dioxoisoindolin-5-yl)-4-isopropylbenzene-sulfonamide | CC(C)c1ccc(cc1)S(=O)(=O) Nc2ccc3C(=O)N (C4CCC(=O)NC4=O) C(=O)c3c2 |
| 98 | 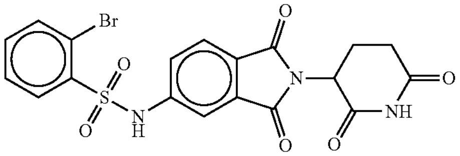 | 2-bromo-N-(2-(2,6-dioxopiperidin-3-yl)-1,3-dioxoiso-indolin-5-yl) benzenesulfonamide | Brc1ccccc1S(=O) (=O)Nc2ccc3C(=O) N(C4CCC(=O) NC4=O)C(=O)c3c2 |
| 99 | 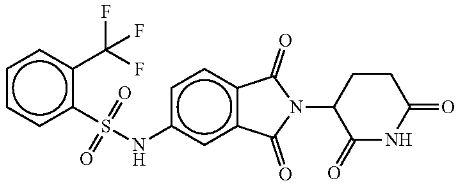 | N-(2-(2,6-dioxopiperidin-3-yl)-1,3-dioxoiso-indolin-5-yl)-2-(trifluoromethyl) benzenesulfonamide | FC(F)(F)c1ccccc1S(=O)(=O) Nc2ccc3C(=O)N(C4CCC(=O) NC4=O)C(=O)c3c2 |
| 100 | 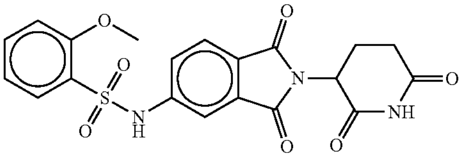 | N-(2-(2,6-dioxopiperidin-3-yl)-1,3-dioxoiso-indolin-5-yl)-2-methoxybenzene-sulfonamide | COc1ccccc1S(=O)(=O) Nc2ccc3C(=O)N (C4CCC(=O)NC4=O) C(=O)c3c2 |
| 101 | 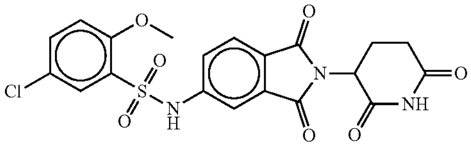 | 5-chloro-N-(2-(2,6-dioxopiperidin-3-yl)-1,3-dioxoiso-indolin-5-yl)-2-methoxybenzene-sulfonamide | COc1ccc(Cl)cc1S(=O)(=O) Nc2ccc3C(=O)N (C4CCC(=O)NC4=O) C(=O)c3c2 |
| 102 | 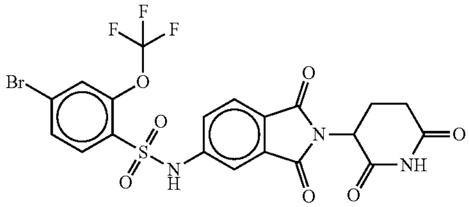 | 4-bromo-N-(2-(2,6-dioxopiperidin-3-yl)-1,3-dioxoiso-indolin-5-yl)-2-(trifluoromethoxy) benzenesulfonamide | FC(F)(F)Oc1cc(Br) ccc1S(=O)(=O) Nc2ccc3C(=O)N (C4CCC(=O) NC4=O) C(=O)c3c2 |
| 103 | 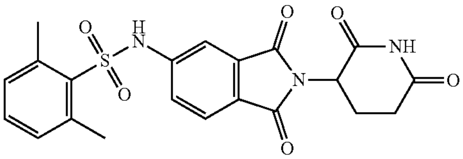 [SMILES: Cc1cccc(C)c1S(=O)(=O)Nc1ccc2c(c1)C(=O)N(C1CCC(=O)NC1=O)C2=O] | N-(2-(2,6-dioxopiperidin-3-yl)-1,3-dioxoiso-indolin-5-yl)-2,6-dimethylbenzene-sulfonamide | O=C1NC(CCC1N2C (C(C=C(NS(C3=C(C) C=CC=C3C)(=O)=O) C=C4)=C4C2=O)=O)=O |

*"Cmpd No." refers to compound number and is used herein throughout.

**Yields based upon the following reactant amounts: 0.1 mmol of 5-amino-2-(2,6-dioxopiperidin-3-yl)isoindoline-1,3-dione and the corresponding sulfonyl chloride (2.0 equiv. 0.2 mmol) for compounds 1-37 and 94-103; and 0.075 mmol of 5-amino-2-(2,6-dioxopiperidin-3-yl)isoindoline-1,3-dione and the corresponding sulfonyl chloride (2.0 equiv, 0.15 mmol) for compounds 38-93 (see synthesis scheme above).0

‡Based on structure shown and generated using ChemDraw® (PerkinElmer Informatics, Inc., Waltham, Massachussetts), version 19.1.0.8.

What is claimed is:

1. A compound having a structure represented by a formula:

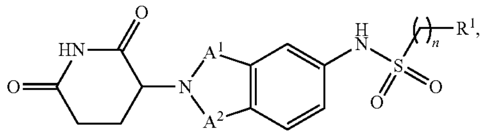

wherein n is an integer selected from 0, 1 and 2;

wherein each of $A^1$ and $A^2$ is independently selected from —(C═O)— and —$CH_2$—, provided that at least one of $A^1$ and $A^2$ is —(C═O)—;

wherein $R^1$ is selected from:

(a) a 5- to 10-membered aryl or heteroaryl optionally substituted with a group selected from halogen, —$SF_5$, —CN, —$N_3$, —$NH_2$, —OH, —CN, —$SCF_3$, $C_1$-$C_3$ alkoxy, $C_1$-$C_3$ haloalkyl, $C_1$-$C_3$ aminoalkyl, $C_1$-$C_3$ alkylamino, $C_1$-$C_3$ hydroxyalkyl, —O—($C_1$-$C_3$ haloalkyl), $C_3$-$C_8$ cycloalkyl, $C_1$-$C_6$ alkyl, and phenyl; and (b) a 5- to 10-membered cycloalkyl optionally substituted with a group selected from halogen, —$SF_5$, —CN, —$N_3$, —$NH_2$, —OH, —CN, —$SCF_3$, $C_1$-$C_3$ alkoxy, $C_1$-$C_3$ haloalkyl, $C_1$-$C_3$ aminoalkyl, $C_1$-$C_3$ alkylamino, $C_1$-$C_3$ hydroxyalkyl, —O—($C_1$-$C_3$ haloalkyl), $C_3$-$C_8$ cycloalkyl, $C_1$-$C_6$ alkyl, and phenyl;

or a pharmaceutically acceptable salt thereof.

2. The compound of claim 1, wherein n is selected from 0 and 1.

3. The compound of claim 1, wherein each of $A^1$ and $A^2$ is —(C═O)—.

4. The compound of claim 1, wherein the compound has a structure represented by a formula

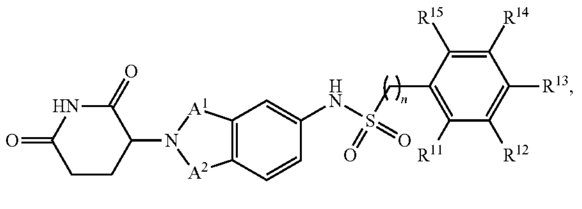

wherein n is an integer selected from 0, 1 and 2;

wherein each of $A^1$ and $A^2$ is independently selected from —(C═O)— and —$CH_2$—, provided that at least one of $A^1$ and $A^2$ is —(C═O)—;

wherein each of $R^{11}$, $R^{12}$, $R^{13}$, $R^{14}$, and $R^{15}$ is independently selected from hydrogen, halogen, —$SF_5$, —CN, —$N_3$, —$NH_2$, —OH, —CN, —$SCF_3$, $C_1$-$C_3$ alkoxy, $C_1$-$C_3$ haloalkyl, $C_1$-$C_3$ aminoalkyl, $C_1$-$C_3$ alkylamino, $C_1$-$C_3$ hydroxyalkyl, —O—($C_1$-$C_3$ haloalkyl), $C_3$-$C_8$ cycloalkyl, $C_1$-$C_6$ alkyl, and phenyl;

or a pharmaceutically acceptable salt thereof.

5. The compound of claim 4, wherein at least one of $R^{11}$ and $R^{15}$ is not hydrogen.

6. The compound of claim 1, wherein the compound has a structure represented by a formula:

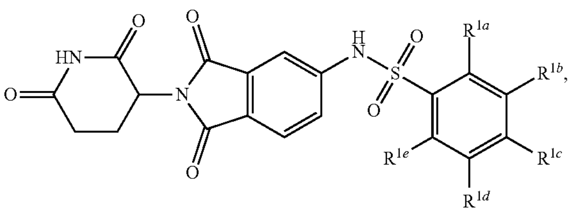

wherein $R^{1a}$ is selected from bromo, methyl, —$CF_3$, and —$OCF_3$;

wherein each of $R^{1b}$, $R^{1d}$, and $R^{1e}$ is independently selected from hydrogen, halogen, and methyl; and wherein $R^{1c}$ is selected from hydrogen, halogen, methyl, and phenyl;

or a pharmaceutically acceptable salt thereof.

7. The compound of claim 6, wherein $R^{1a}$ is selected from —$CF_3$ and —$OCF_3$.

8. The compound of claim 6, wherein each of $R^{1b}$, $R^{1c}$, $R^{1d}$, and $R^{1e}$ is hydrogen.

9. The compound of claim 1, having a structure represented by a formula selected from the group consisting of:

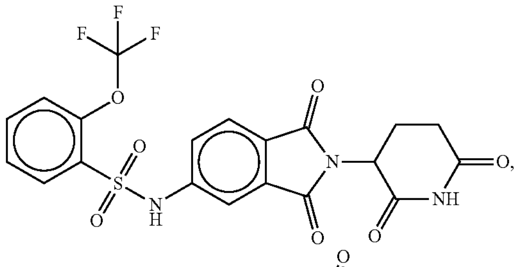

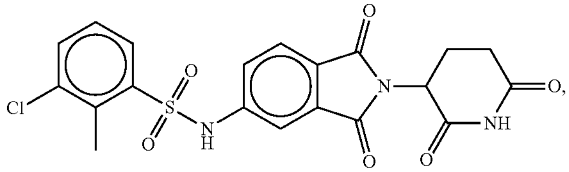

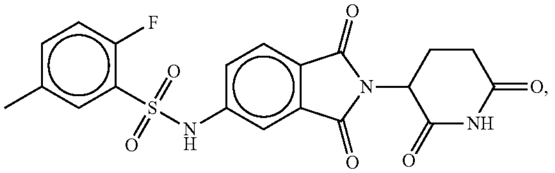

-continued
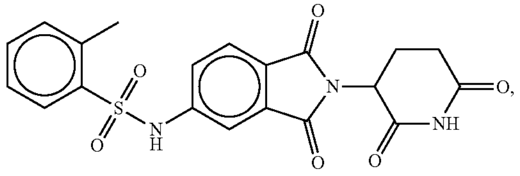
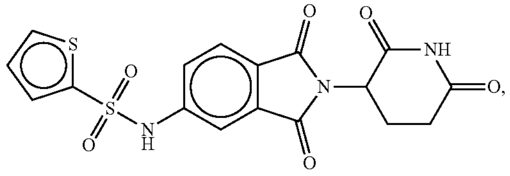
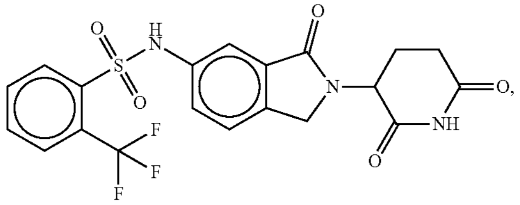
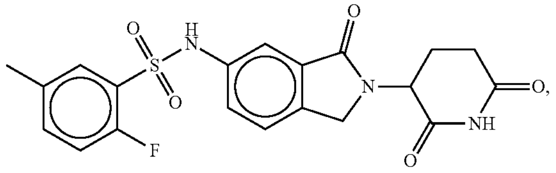
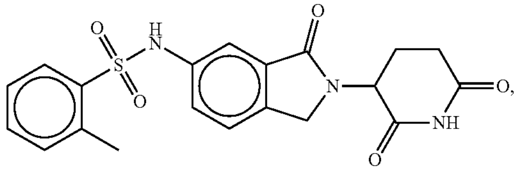
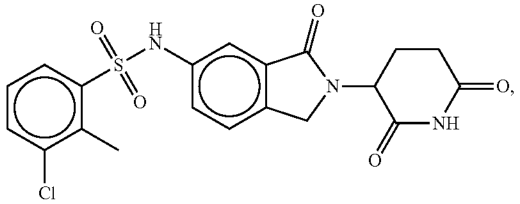
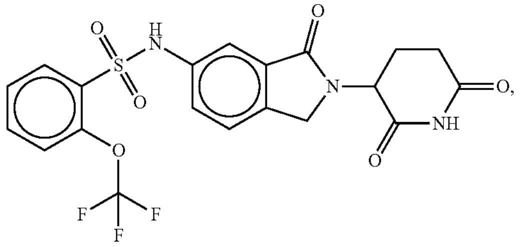
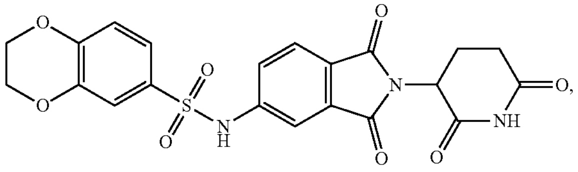
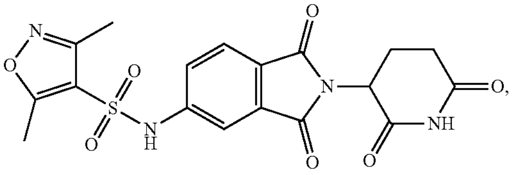
-continued
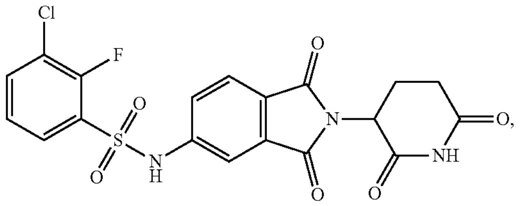
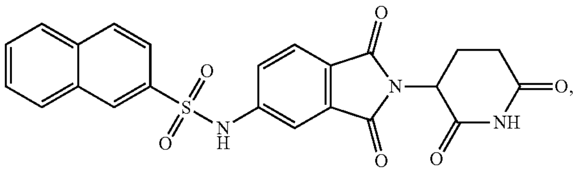
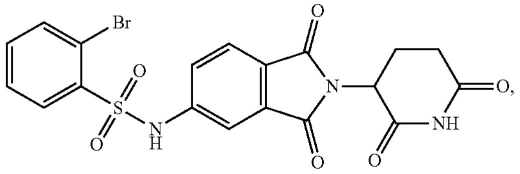
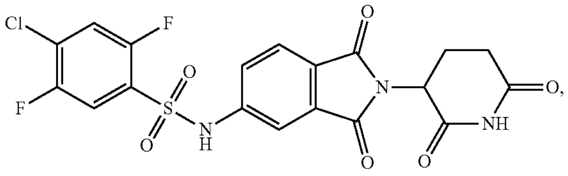
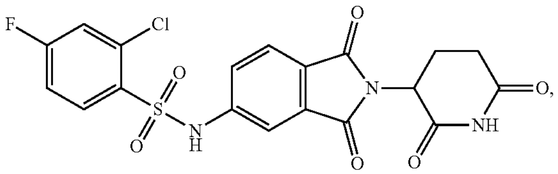
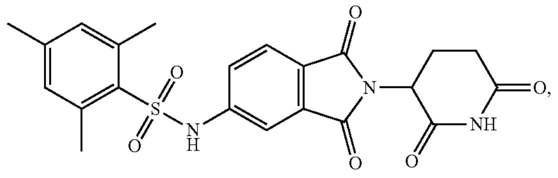
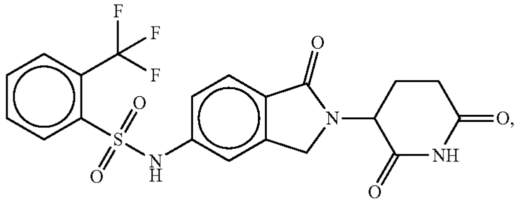
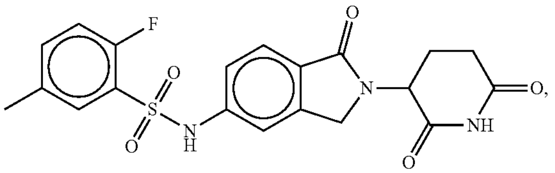
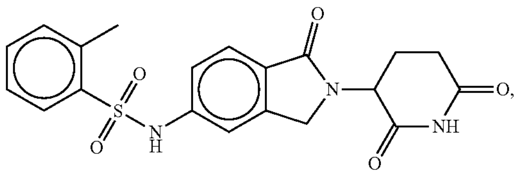

-continued
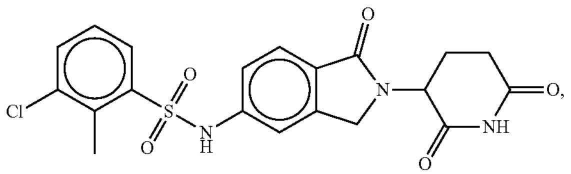
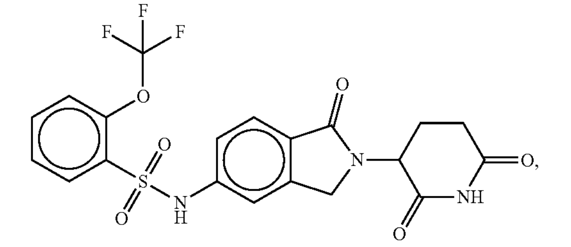
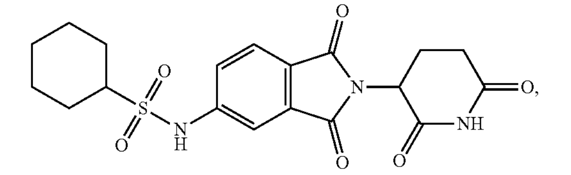
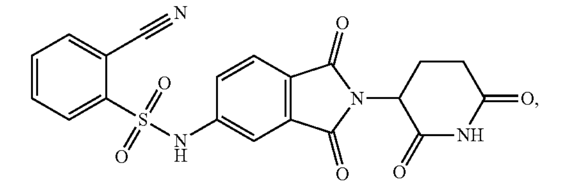
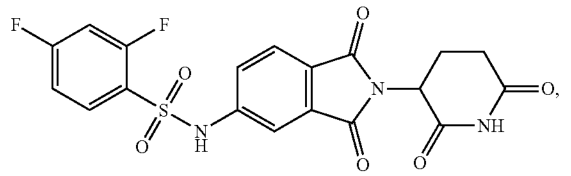
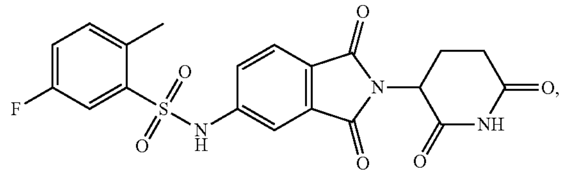
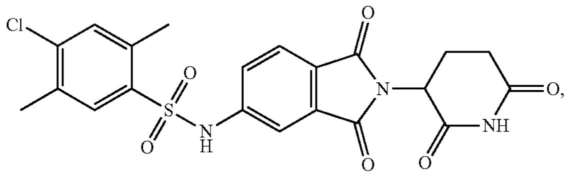
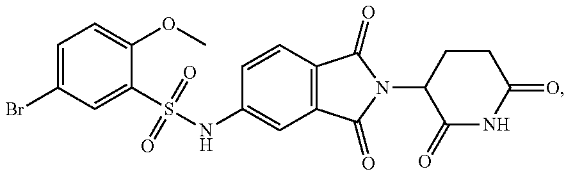
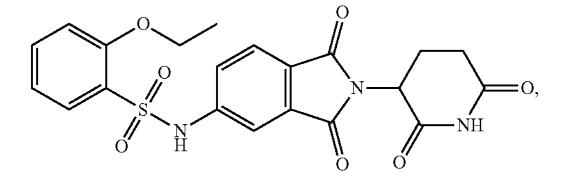
-continued
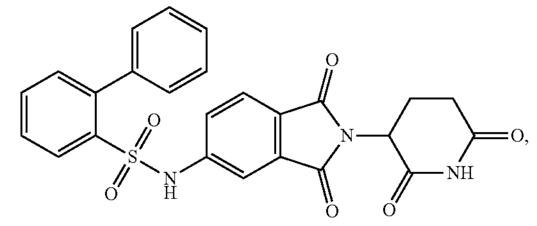
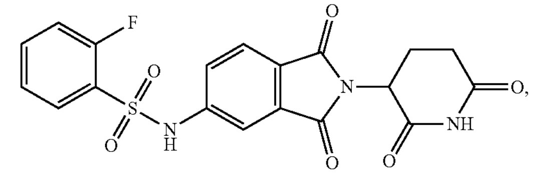
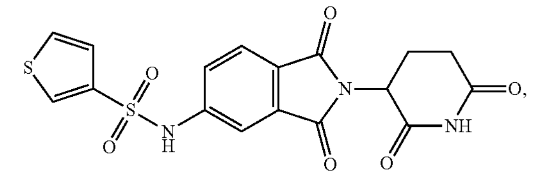
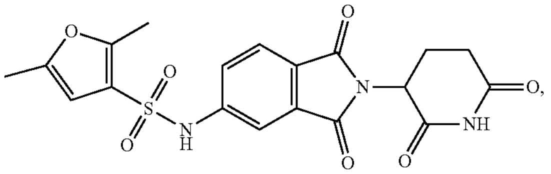
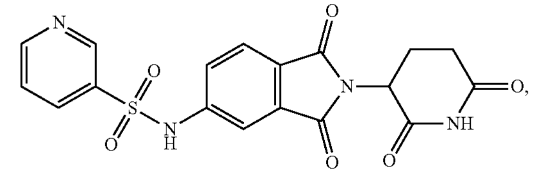
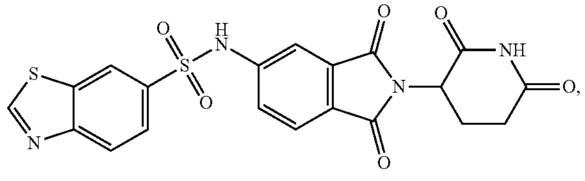
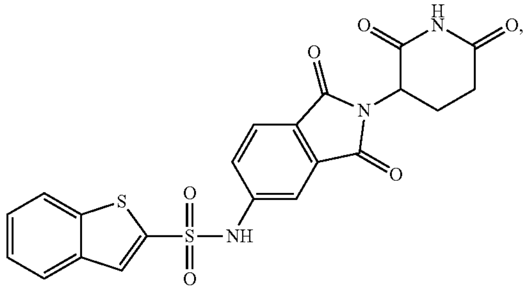
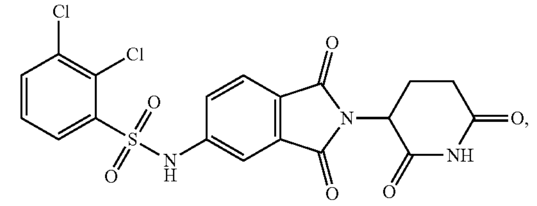

-continued

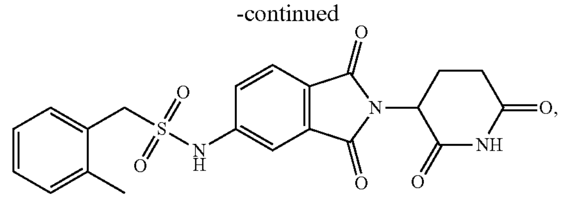,

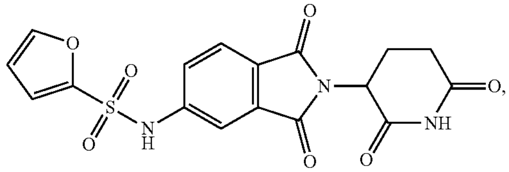,

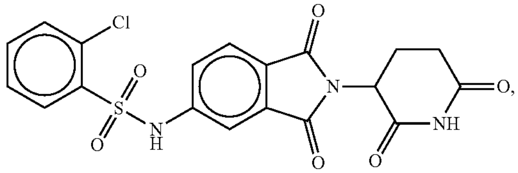,

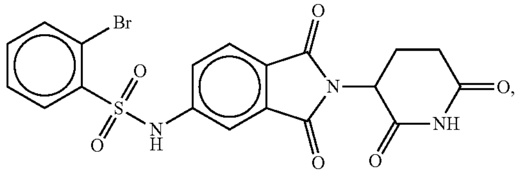,

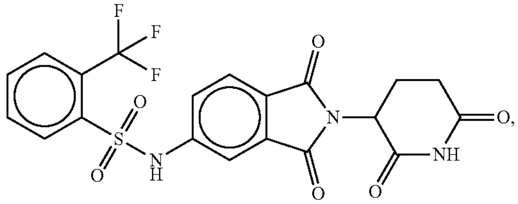,

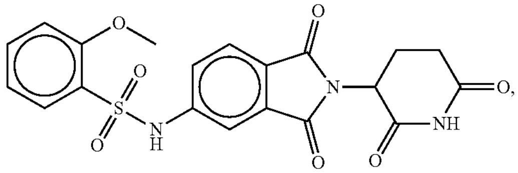,

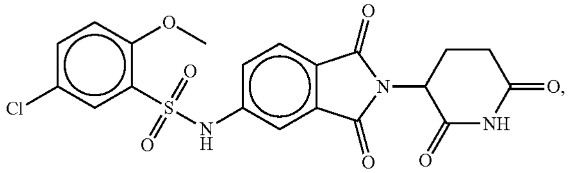,

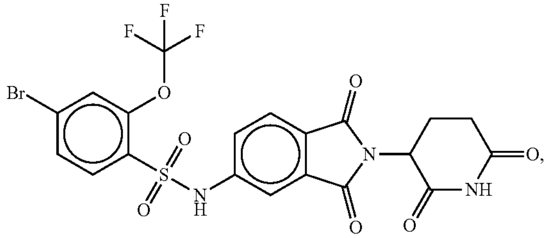, and

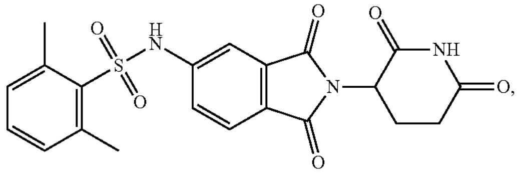, or a pharmaceutically acceptable salt thereof.

10. The compound of claim 9, having a structure represented by a formula selected from the group consisting of:

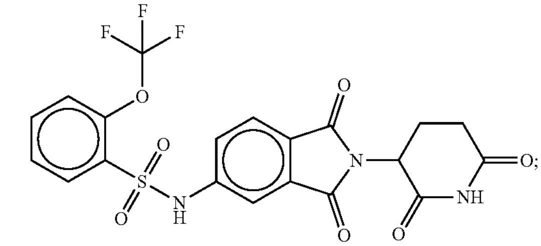;

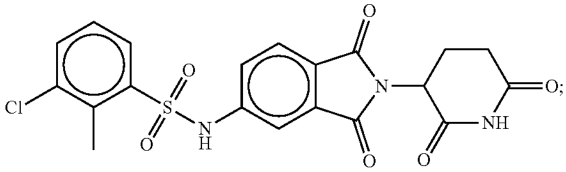;

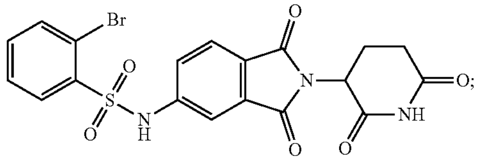;

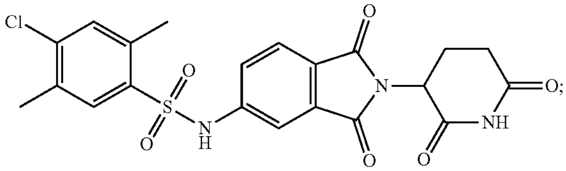;

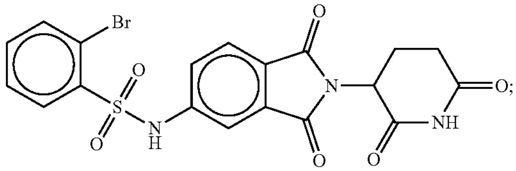;

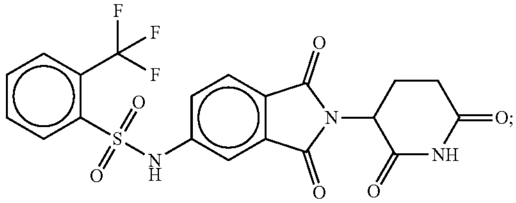;

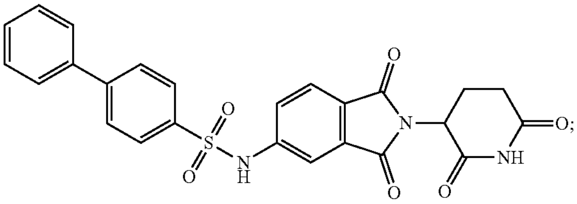;

and or a pharmaceutically acceptable salt thereof.

11. A pharmaceutical composition comprising a therapeutically effective amount of a compound of claim 1, and a pharmaceutically acceptable salt thereof, and a pharmaceutically acceptable carrier.

12. The pharmaceutical composition of claim 11, further comprising at least one agent known to treat a cancer.

13. A method for amelioration or alleviation of a cancer characterized by GSPT1 activity in a mammal comprising a step of administering to the mammal a therapeutically effective amount of at least one compound of claim 1, or a pharmaceutically acceptable salt thereof, thereby ameliorating or alleviating the cancer characterized by GSPT1 activity.

14. The method of claim 13, wherein the mammal has been diagnosed with a need for treatment of the cancer prior to the step of administering to the mammal the therapeutically effective amount of the at least one compound.

15. The method of claim 13, further comprising a step of identifying a mammal in need of treatment of the cancer.

16. The method of claim 13, wherein the cancer is selected from a group consisting of brain cancer, lung cancer, hematological cancer, bladder cancer, colon cancer, cervical cancer, ovarian cancer, squamous cell cancer, kidney cancer, peritoneal cancer, breast cancer, gastric cancer, colorectal cancer, prostate cancer, pancreatic cancer, genitourinary tract cancer, lymphatic system cancer, stomach cancer, larynx cancer, malignant melanoma, endometrial carcinoma, thyroid cancer, rhabdosarcoma, leukemia, and combinations thereof.

17. The method of claim 16, wherein the cancer is selected from a group consisting of leukemia, lung cancer, hematological cancer, bladder cancer, ovarian cancer, squamous cell cancer, breast cancer, prostate cancer, pancreatic cancer, genitourinary tract cancer, malignant melanoma, endometrial carcinoma, and combinations thereof.

18. The method of claim 17, wherein the lung cancer is selected from a group consisting of small-cell lung cancer, non-small cell lung cancer, and combinations thereof;

wherein the bladder cancer is a bladder urothelial carcinoma; and wherein the hematological cancer is selected from a group consisting of a childhood acute leukemia (AL), chronic myeloid leukemia (CML), acute myeloid leukemia (AML), chronic lymphoid leukemia (CLL), acute lymphoid leukemia (ALL), hairy cell leukemia, chronic myelomonocytic leukemia (CMML), juvenile myelomonocyte leukemia (JMML), large granular lymphocytic leukemia (LGL), acute lymphocytic leukemia, acute lymphoblastic leukemia, B-cell lymphoma, T-cell lymphoma, hairy cell lymphoma, Burkett's lymphoma, Hodgkin lymphoma, non-Hodgkin lymphoma, and combinations thereof.

19. The method of claim 13, further comprising a step of administering a therapeutically effective amount of at least one agent known to treat a cancer.

20. The method of claim 19, wherein the at least one agent is selected from a group consisting of uracil mustard, chlormethine, cyclophosphamide, ifosfamide, melphalan, chlorambucil, pipobroman, triethylenemelamine, triethylenethiophosphoramine, busulfan, carmustine, lomustine, streptozocin, dacarbazine, temozolomide, thiotepa, altretamine, methotrexate, 5-fluorouracil, floxuridine, cytarabine, 6-mercaptopurine, 6-thioguanine, fludarabine phosphate, pentostatin, bortezomib, vinblastine, vincristine, vinorelbine, vindesine, bleomycin, dactinomycin, daunorubicin, doxorubicin, epirubicin, dexamethasone, clofarabine, cladribine, pemextresed, idarubicin, paclitaxel, docetaxel, ixabepilone, mithramycin, topotecan, irinotecan, deoxycoformycin, mitomycin-C, L-asparaginase, interferons, etoposide, teniposide 17a-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, cisplatin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, oxaliplatin, gefinitib, capecitabine, erlotinib, azacitidine, temozolomide, gemcitabine, vasostatin, and combinations thereof.

21. The method of claim 19, wherein the at least one agent is selected from a group consisting of a DNA methyltransferase inhibitor, an HDAC-inhibitor, a glucocorticoid, an mTOR inhibitor, a cytotoxic agent, and combinations thereof.

22. The method of claim 21, wherein the DNA methyltransferase inhibitor is selected from a group consisting of 5-aza-2'-deoxycytidine, 5-azacytidine, zebularin, epigallocatechin-3-gallate, procaine, and combinations thereof;

wherein the HDAC-inhibitor is selected from a group consisting of vorinostat, entinostat, pan binostat, trichostatin A, mocetinostat, belinostat, dacinostat, givinostat, tubastatin A, pracinostat, droxinostat, quisinostat, romidepsin, valproic acid, AR-42 (OSU-HDAC42), tacedinaline, rocilinostat, apicidin, and combinations thereof;

wherein the glucocorticoid is selected from a group consisting of dexamethasone, prednisolone, methylprednisolone, betamethasone, triamicinolone, fludrocortisone, beclomethasone, and combinations thereof;

wherein the mTor inhibitor is selected from a group consisting of BEZ235, everolimus, temsirolimus, rapamycin, AZD8055, and combinations thereof; and wherein the cytotoxic agent is selected from a group consisting of an alkylating agent, an antimetabolite agent, an antineoplastic antibiotic agent, a mitotic inhibitor agent, a mTor inhibitor agent, and other chemotherapeutic agent.

23. The method of claim 22, wherein the antineoplastic antibiotic agent is selected from a group consisting of doxorubicin, mitoxantrone, bleomycin, daunorubicin, dactinomycin, epirubicin, idarubicin, plicamycin, mitomycin, pentostatin, valrubicin, and combinations thereof, or a pharmaceutically acceptable salt, hydrate, solvate, or polymorph thereof;

wherein the antimetabolite agent is selected from a group consisting of gemcitabine, 5- fluorouracil, capecitabine, hydroxyurea, mercaptopurine, pemetrexed, fludarabine, nelarabine, cladribine, clofarabine, cytarabine, decitabine, pralatrexate, floxuridine, methotrexate, thioguanine, a combinations thereof, or a pharmaceutically acceptable salt, hydrate, solvate, or polymorph thereof;

wherein the alkylating agent is selected from a group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, streptozocin, and combinations thereof, or a pharmaceutically acceptable salt, hydrate, solvate, or polymorph thereof;

wherein the mitotic inhibitor agent is selected from a group consisting of irinotecan, topotecan, rubitecan, cabazitaxel, docetaxel, paclitaxel, etopside, vincristine, ixabepilone, vinorelbine, vinblastine, teniposide, and combinations thereof, or a pharmaceutically acceptable salt, hydrate, solvate, or polymorph thereof;

wherein the mTor inhibitor is selected from a group consisting of everolimus, sirolimus, temsirolimus, and combinations thereof; and wherein the other chemotherapeutic agent is selected from a group consisting of an anthracycline, cytarabine, a purine analog, sorafenib, gemtuzumab ozogamicin, rituximab, and combinations thereof.

24. The method of claim 19, wherein the at least one agent is administered sequentially or simultaneously.

25. The method of claim 19, wherein the at least one agent is co-formulated or co-packaged.

26. A method for modulating GSPT1 activity in at least one cell, comprising a step of contacting the at least one cell with an effective amount of at least one compound of claim 1, or a pharmaceutically acceptable salt thereof.

27. The method of claim 26, wherein contacting is via administration to a mammal.

28. The method of claim 27, wherein the mammal has been diagnosed with a need for modulating GSPT1 activity or for amelioration or alleviation of a cancer characterized by GSPT1 activity prior to the administering step.

29. The method of claim 27, wherein the compound inhibits cell proliferation with an IC50 of less than about 10 μM when determined in a cell viability assay using MV4-11 cells as described herein;

wherein the compound exhibits cereblon binding with an IC50 of less than about 10 μM using a fluorescence polarization assay as described herein; or wherein the compound inhibits cell proliferation with an IC50 of less than about 20 μM when determined in a cell viability assay using GSPT1 HiBit tagged cell.

* * * * *